United States Patent
Krishna et al.

(10) Patent No.: US 12,275,766 B2
(45) Date of Patent: Apr. 15, 2025

(54) NEOANTIGEN PEPTIDE MIMICS

(71) Applicant: Janssen Biotech, Inc., Horsham, PA (US)

(72) Inventors: Vinod Krishna, Philadelphia, PA (US); Manuel Alejandro Sepulveda, West Windsor, NJ (US); Vipul Bhargava, Warrington, PA (US); Iqbal S. Grewal, Newtown, PA (US); Kurtis Bachman, Wayne, PA (US)

(73) Assignee: Janssen Biotech, Inc., Horsham, PA (US)

( * ) Notice: Subject to any disclaimer, the term of this patent is extended or adjusted under 35 U.S.C. 154(b) by 23 days.

(21) Appl. No.: 17/556,019

(22) Filed: Dec. 20, 2021

(65) Prior Publication Data

US 2022/0194999 A1 Jun. 23, 2022

Related U.S. Application Data

(60) Provisional application No. 63/130,083, filed on Dec. 23, 2020.

(51) Int. Cl.
*C07K 14/47* (2006.01)
*A61K 38/00* (2006.01)
*A61K 39/00* (2006.01)
*C07K 14/725* (2006.01)
*C12N 5/00* (2006.01)
*C12N 5/0783* (2010.01)
*C12N 9/12* (2006.01)
*C12N 9/14* (2006.01)
*C12N 9/16* (2006.01)
*C12N 15/85* (2006.01)

(52) U.S. Cl.
CPC ...... *C07K 14/4703* (2013.01); *A61K 39/0011* (2013.01); *A61K 39/001106* (2018.08); *A61K 39/001151* (2018.08); *C07K 14/47* (2013.01); *C07K 14/4705* (2013.01); *C07K 14/4746* (2013.01); *C07K 14/4748* (2013.01); *C07K 14/7051* (2013.01); *C12N 5/0087* (2013.01); *C12N 5/0638* (2013.01); *C12N 9/12* (2013.01); *C12N 9/1205* (2013.01); *C12N 9/14* (2013.01); *C12N 9/16* (2013.01); *C12N 15/85* (2013.01); *C12Y 207/01153* (2013.01); *C12Y 207/10001* (2013.01); *C12Y 301/03048* (2013.01); *C12Y 306/05002* (2013.01); *A61K 38/00* (2013.01); *C07K 2317/565* (2013.01)

(58) Field of Classification Search
CPC . C07K 14/4748; A61K 38/00; A61K 39/0011
See application file for complete search history.

(56) References Cited

U.S. PATENT DOCUMENTS

| | | |
|---|---|---|
| 5,747,323 A | 5/1998 | Darlix et al. |
| 7,270,811 B2 | 9/2007 | Bout et al. |
| 7,329,731 B2 | 2/2008 | Jakobsen et al. |
| 7,569,664 B2 | 8/2009 | Jakobsen et al. |
| 9,133,264 B2 | 9/2015 | Blankenstein et al. |
| 9,624,292 B2 | 4/2017 | Voss et al. |
| 9,790,256 B2 | 10/2017 | Bunnik et al. |
| 9,884,075 B2 | 2/2018 | Bethune et al. |
| 11,058,751 B1 * | 7/2021 | Gifford .......... C12Y 306/05002 |
| 11,161,892 B1 * | 11/2021 | Gifford ................ G16B 15/20 |
| 11,235,039 B1 * | 2/2022 | Gifford .......... C12Y 306/05002 |
| 11,421,015 B2 * | 8/2022 | Gifford ................ G16B 20/30 |
| 11,464,837 B2 * | 10/2022 | Gifford ............. A61K 39/0011 |
| 11,464,842 B1 * | 10/2022 | Gifford .......... A61K 39/001104 |
| 11,672,850 B2 * | 6/2023 | Gifford .......... A61K 39/001104 424/185.1 |
| 11,673,936 B2 * | 6/2023 | Gifford ................... G16B 5/20 703/11 |
| 2016/0130319 A1 | 5/2016 | Li |
| 2022/0143063 A1 * | 5/2022 | Seidel, III ............... C12N 9/14 |

FOREIGN PATENT DOCUMENTS

| | | | |
|---|---|---|---|
| WO | 95/01447 A1 | 1/1995 | |
| WO | 97/35996 A1 | 10/1997 | |
| WO | 00/70071 A1 | 11/2000 | |
| WO | 2007/104792 A2 | 9/2007 | |
| WO | 2010/086189 A2 | 8/2010 | |
| WO | WO-2016187508 A2 * | 11/2016 | ............. A61K 38/00 |

(Continued)

OTHER PUBLICATIONS

Engelhard, Current Opinion in Immunology vol. 6 p. 13 (1994) (Year: 1994).*
Guo, et al Nature vol. 360 p. 384 (1992) (Year: 1992).*
Rammensee et al, Immunogenetics vol. 41 p. 178 (1995), (Year: 1995).*
Shastri et al J. Immunol. 1995 vol. 155 p. 4339 (Year: 1995).*
Chandrashekara et al, Indian Journal of Pharmacology vol. 44 p. 665 (2012) (Year: 2012).*
Cohen et al., "Isolation of Neoantigen-Specific T Cells from Tumor and Peripheral Lymphocytes", The Journal of Clinical Investigation, Sep. 2015, vol. 125, No. 10, pp. 3981-3991.

(Continued)

*Primary Examiner* — Sheela J. Huff
(74) *Attorney, Agent, or Firm* — BakerHostetler

(57) ABSTRACT

Disclosed herein are polypeptide fragments and polynucleotides based on mutant capicua transcriptional repressor (CIC), catenin beta 1 (CTNNB1), v-erb-b2 erythroblastic leukemia viral oncogene homolog B (ERBB2), kirsten rat sarcoma (KRAS), phosphatidylinositol-4,5-bisphosphate 3-kinase catalytic subunit alpha (PIK3CA), phosphatase and tensin homolog (PTEN), splicing factor 3b subunit 1 (SF3B1), SRY-box transcription factor 17 (SOX17), tumor protein 53 (TP53), and cytomegalovirus (CMV) sequences, vectors, host cells, viruses, methods for generating CD8+ T-cells, and methods of treatment. Also disclosed herein are T-cell receptors (TCRs), polynucleotides, vectors and cells comprising the TCRs, and methods of treatment.

14 Claims, 10 Drawing Sheets

Specification includes a Sequence Listing.

(56) References Cited

FOREIGN PATENT DOCUMENTS

| WO | 2017/220499 A1 | 12/2017 | |
|---|---|---|---|
| WO | 2018/146205 A1 | 8/2018 | |
| WO | 2018/208856 A1 | 11/2018 | |
| WO | WO-2021055594 A1 * | 3/2021 | ......... A61K 31/7088 |
| WO | WO-2022099156 A2 * | 5/2022 | |
| WO | WO-2022099157 A1 * | 5/2022 | |

OTHER PUBLICATIONS

Database Geneseq [Online] Jan. 12, 2017, "Human Derived Tumor-Specific Neoantigenic Peptide, SEQ: 9667.", XP002806351, retrieved from EBI accession No. GSP:BDJ83488, Database accession No. BDJ83488 sequence, p. 1.
Database Geneseq [Online] Apr. 4, 2019 (Apr. 4, 2019), "Human Derived Peptide, SEQ ID 854.", retrieved from EBI accession No. GSP:BGC28101, Database accession No. BGC28101, p. 1.
Pinilla-Ibarz et al., "Improved Human T-Cell Responses Against Synthetic HLA-0201 Analog Peptides Derived from the WT1 Oncoprotein", Leukemia, Nature Publishing Group UK, London, Aug. 2006, vol. 20, No. 11, pp. 2025-2033.
Tourdat et al., "A General Strategy to Enhance Immunogenicity of Low-Affinity HLA-A2. 1-Associated Peptides: Implication in the Identification of Cryptic Tumor Epitopes", European Journal of Immunology, Dec. 2000, vol. 30, Issue 12, pp. 3411-3421.
Tran et al., "Immunogenicity of Somatic Mutations in Human Gastrointestinal Cancers", Science, Dec. 2015, vol. 350, No. 6266, pp. 1387-1390.
Danos et al., "Safe and Efficient Generation of Recombinant Retroviruses with Amphotropic and Ecotropic Host Ranges", Proc. Natl. Acad. Sci. USA, 1988, 85, 6460-6464.
Gilboa et al., Retroviral Gene Transfer: Applications to Human Therapy, Adv. Exp. Med. Biol., 1988, 241, 29-33.
Hoganson et al., "Development of a stable adenoviral vector formulation", Bioprocessing Journal, Mar. 2002, 43-48.
Jurtz et al., "NetMHCpan-4.0: Improved Peptide-MHC Class I Interaction Predictions Integrating Eluted Ligand and Peptide Binding Affinity Data", J. Immunol., 2017, 199(9), 3360-3368.
Markowtiz et al., "Construction of a Safe and Efficient Amphotropic Packaging Cell Line", Virol., 1988, 167, 400-406.
Marty et al., "MHC-I Genotype Restricts the Oncogenic Mutational Landscape", Cell, 2017, 171(6), 1272-1283.
Miller et al., "Improved Retroviral Vectors for Gene Transfer and Expression", BioTechniques, 1989, 7, 980-990.
Vita et al., "The Immune Epitope Database (IEDB): 2018 update", Nucleic Acids Res., Oct. 24, 2018, D339-D343.

* cited by examiner

SEQUENCE LISTING

<160> NUMBER OF SEQ ID NOS: 446

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ile Phe Ser Lys Arg His Trp Ala
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Leu Asp Cys Gly Ile His Ser Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Leu Asp Ser Gly Ile His Phe Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Leu Ser Thr Asp Val Gly Phe Ala
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Val Val Val Gly Ala Ala Gly Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Val Val Val Gly Ala Cys Gly Val
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 7

Leu Val Val Val Gly Ala Val Gly Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Leu Lys Asp Leu Leu Asn Pro Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Leu Asn Arg Glu Ile Asp Phe Ala
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Tyr Val Tyr Tyr Tyr Ser Tyr Leu Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Met Asp Glu Tyr Val His Asn Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Val Ser Asp Ala Ile Ser Ala Val
1               5

<210> SEQ ID NO 13
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Lys Thr Tyr Pro Val Gln Leu Trp Val
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Ala Pro Pro Gln Leu Leu Ile
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Ala Pro Pro Gln Tyr Leu Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Leu Asn Asn Met Phe Cys Gln Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Met Phe Cys Gln Leu Ala Lys Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Leu Trp Val Asp Ser Thr Pro Leu
1               5
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Leu Ile Leu Thr Ile Ile Thr Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Gln Gly Ser Tyr Gly Phe Leu Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Val Thr Cys Thr Tyr Phe Pro Ala
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Leu Gly Arg Asn Ser Phe Glu Met
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Val Pro Cys Glu Pro Pro Glu Val
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 24

Arg Leu Ile His Arg Asp Leu Ala Ala
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Met Phe Ser Lys Arg His Trp Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Leu Phe Ser Lys Arg His Trp Val
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Met Phe Ser Lys Arg His Trp Val
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Met Asp Cys Gly Ile His Ser Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Leu Asp Cys Gly Ile His Ser Val
1               5

<210> SEQ ID NO 30
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Met Asp Cys Gly Ile His Ser Val
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Met Asp Ser Gly Ile His Phe Ile
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Leu Asp Ser Gly Ile His Phe Val
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Met Asp Ser Gly Ile His Phe Val
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Leu Ser Thr Asp Val Gly Phe Val
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Met Ser Thr Asp Val Gly Phe Val
```

```
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Leu Ser Thr Asp Val Gly Phe Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Leu Val Val Gly Ala Ala Gly Val
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Met Val Val Gly Ala Ala Gly Val
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Leu Val Val Gly Ala Cys Gly Val
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Met Val Val Gly Ala Cys Gly Val
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 41

Leu Leu Val Val Gly Ala Val Gly Val
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Met Val Val Gly Ala Val Gly Val
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Leu Lys Asp Leu Leu Asn Pro Val
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Met Lys Asp Leu Leu Asn Pro Val
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Leu Asn Arg Glu Ile Asp Phe Val
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Met Asn Arg Glu Ile Asp Phe Val
1               5

<210> SEQ ID NO 47
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Leu Asn Arg Glu Ile Asp Phe Leu
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Tyr Leu Tyr Tyr Tyr Ser Tyr Leu Leu
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Tyr Leu Tyr Tyr Tyr Ser Tyr Leu Val
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Tyr Met Tyr Tyr Tyr Ser Tyr Leu Val
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Met Asp Glu Tyr Val His Asn Val
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Asn Leu Asp Glu Tyr Val His Asn Val
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asn Met Asp Glu Tyr Val His Asn Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Leu Ser Asp Ala Ile Ser Ala Val
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Met Ser Asp Ala Ile Ser Ala Val
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Leu Ser Asp Ala Ile Ser Ala Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Leu Tyr Pro Val Gln Leu Trp Val
1               5

<210> SEQ ID NO 58
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 58

Lys Met Tyr Pro Val Gln Leu Trp Val
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Met Tyr Pro Val Gln Leu Trp Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Leu Ala Pro Pro Gln Leu Leu Val
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Met Ala Pro Pro Gln Leu Leu Val
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Leu Ala Pro Pro Gln Tyr Leu Val
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Met Ala Pro Pro Gln Tyr Leu Val
1               5

```
<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Leu Asn Asn Met Phe Cys Gln Val
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Leu Phe Cys Gln Leu Ala Lys Val
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Met Asn Asn Met Phe Cys Gln Val
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Leu Trp Val Asp Ser Thr Pro Ile
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Leu Trp Val Asp Ser Thr Pro Val
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69
```

Arg Leu Ile Leu Thr Ile Ile Thr Val
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Gln Gly Ser Tyr Gly Phe Leu Ile
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Gln Gly Ser Tyr Gly Phe Leu Val
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Met Thr Cys Thr Tyr Phe Pro Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Leu Thr Cys Thr Tyr Phe Pro Val
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Met Thr Cys Thr Tyr Phe Pro Val
1               5

<210> SEQ ID NO 75
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 75

Leu Leu Gly Arg Asn Ser Phe Glu Leu
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Leu Gly Arg Asn Ser Phe Glu Ile
1               5

<210> SEQ ID NO 77
<211> LENGTH: 9
<212> TYPE: PRT
<213> ORGANISM: Homo sapiens

<400> SEQUENCE: 77

Leu Leu Gly Arg Asn Ser Phe Glu Val
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Val Leu Pro Cys Glu Pro Pro Glu Val
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Met Pro Cys Glu Pro Pro Glu Val
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Leu Asp Cys Gly Ile His Ser Leu
1               5

<210> SEQ ID NO 81
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Met Asp Ser Gly Ile His Phe Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Tyr Met Ser Thr Asp Val Gly Phe Leu
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Leu Ser Thr Asp Val Gly Phe Ile
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Met Ile His Arg Asp Leu Ala Leu
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Leu Ile His Arg Asp Leu Ala Val
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Met Ile His Arg Asp Leu Ala Val
```

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Tyr Met Tyr Tyr Tyr Ser Tyr Leu Leu
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Tyr Leu Tyr Tyr Tyr Ser Tyr Leu Ile
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Cys Tyr Met Tyr Tyr Tyr Ser Tyr Leu Ile
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asn Leu Asp Glu Tyr Val His Asn Leu
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asn Met Asp Glu Tyr Val His Asn Ile
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 92

Asn Leu Asp Glu Tyr Val His Asn Ile
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val Met Ser Asp Ala Ile Ser Ala Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Lys Leu Tyr Pro Val Gln Leu Trp Ile
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Leu Thr Cys Thr Tyr Phe Pro Leu
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Met Thr Cys Thr Tyr Phe Pro Ile
1               5

<210> SEQ ID NO 97
<211> LENGTH: 9
<212> TYPE: PRT
<213> ORGANISM: Human betaherpesvirus 5

<400> SEQUENCE: 97

Asn Leu Val Pro Met Val Ala Thr Val
1               5

<210> SEQ ID NO 98
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 98

Asn Met Val Pro Met Val Ala Thr Val
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Leu Val Pro Met Val Ala Thr Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asn Met Val Pro Met Val Ala Thr Leu
1               5

<210> SEQ ID NO 101
<211> LENGTH: 9
<212> TYPE: PRT
<213> ORGANISM: Unknown
<220> FEATURE:
<223> OTHER INFORMATION: Description of Unknown:
      Change control negative sequence

<400> SEQUENCE: 101

Ile Val Thr Asp Phe Ser Val Ile Lys
1               5

<210> SEQ ID NO 102
<211> LENGTH: 1608
<212> TYPE: PRT
<213> ORGANISM: Homo sapiens

<400> SEQUENCE: 102

Met Tyr Ser Ala His Arg Pro Leu Met Pro Ala Ser Ser Ala Ser
1               5                   10                  15

Arg Gly Leu Gly Met Phe Val Trp Thr Asn Val Glu Pro Arg Ser Val
                20                  25                  30

Ala Val Phe Pro Trp His Ser Leu Val Pro Phe Leu Ala Pro Ser Gln
            35                  40                  45

Pro Asp Pro Ser Val Gln Pro Ser Glu Ala Gln Gln Pro Ala Ser His
        50                  55                  60

Pro Val Ala Ser Asn Gln Ser Lys Glu Pro Ala Glu Ser Ala Ala Val
65                  70                  75                  80

Ala His Glu Arg Pro Pro Gly Gly Thr Gly Ser Ala Asp Pro Glu Arg
                85                  90                  95

Pro Pro Gly Ala Thr Cys Pro Glu Ser Pro Gly Pro Gly Pro Pro His
                100                 105                 110
```

```
Pro Leu Gly Val Val Glu Ser Gly Lys Gly Pro Pro Thr Thr Glu
        115                 120                 125

Glu Glu Ala Ser Gly Pro Pro Gly Glu Pro Arg Leu Asp Ser Glu Thr
    130                 135                 140

Glu Ser Asp His Asp Asp Ala Phe Leu Ser Ile Met Ser Pro Glu Ile
145                 150                 155                 160

Gln Leu Pro Leu Pro Pro Gly Lys Arg Arg Thr Gln Ser Leu Ser Ala
                165                 170                 175

Leu Pro Lys Glu Arg Asp Ser Ser Glu Lys Asp Gly Arg Ser Pro
            180                 185                 190

Asn Lys Arg Glu Lys Asp His Ile Arg Arg Pro Met Asn Ala Phe Met
        195                 200                 205

Ile Phe Ser Lys Arg His Arg Ala Leu Val His Gln Arg His Pro Asn
    210                 215                 220

Gln Asp Asn Arg Thr Val Ser Lys Ile Leu Gly Glu Trp Trp Tyr Ala
225                 230                 235                 240

Leu Gly Pro Lys Glu Lys Gln Lys Tyr His Asp Leu Ala Phe Gln Val
                245                 250                 255

Lys Glu Ala His Phe Lys Ala His Pro Asp Trp Lys Trp Cys Asn Lys
            260                 265                 270

Asp Arg Lys Lys Ser Ser Ser Glu Ala Lys Pro Thr Ser Leu Gly Leu
        275                 280                 285

Ala Gly Gly His Lys Glu Thr Arg Glu Arg Ser Met Ser Glu Thr Gly
    290                 295                 300

Thr Ala Ala Ala Pro Gly Val Ser Ser Glu Leu Leu Ser Val Ala Ala
305                 310                 315                 320

Gln Thr Leu Leu Ser Ser Asp Thr Lys Ala Pro Gly Ser Ser Ser Cys
                325                 330                 335

Gly Ala Glu Arg Leu His Thr Val Gly Gly Pro Gly Ser Ala Arg Pro
            340                 345                 350

Arg Ala Phe Ser His Ser Gly Val His Ser Leu Asp Gly Gly Glu Val
        355                 360                 365

Asp Ser Gln Ala Leu Gln Glu Leu Thr Gln Met Val Ser Gly Pro Ala
        370                 375                 380

Ser Tyr Ser Gly Pro Lys Pro Ser Thr Gln Tyr Gly Ala Pro Gly Pro
385                 390                 395                 400

Phe Ala Ala Pro Gly Glu Gly Ala Leu Ala Ala Thr Gly Arg Pro
                405                 410                 415

Pro Leu Leu Pro Thr Arg Ala Ser Arg Ser Gln Arg Ala Ala Ser Glu
            420                 425                 430

Asp Met Thr Ser Asp Glu Glu Arg Met Val Ile Cys Glu Glu Glu Gly
        435                 440                 445

Asp Asp Asp Val Ile Ala Asp Asp Gly Phe Gly Thr Thr Asp Ile Asp
450                 455                 460

Leu Lys Cys Lys Glu Arg Val Thr Asp Ser Glu Ser Gly Asp Ser Ser
465                 470                 475                 480

Gly Glu Asp Pro Glu Gly Asn Lys Gly Phe Gly Arg Lys Val Phe Ser
                485                 490                 495

Pro Val Ile Arg Ser Ser Phe Thr His Cys Arg Pro Pro Leu Asp Pro
            500                 505                 510

Glu Pro Pro Gly Pro Asp Pro Pro Val Ala Phe Gly Lys Gly Tyr
        515                 520                 525
```

```
Gly Ser Ala Pro Ser Ser Ala Ser Ser Pro Ala Ser Ser Ala
    530                 535                 540
Ser Ala Ala Thr Ser Phe Ser Leu Gly Ser Gly Thr Phe Lys Ala Gln
545                 550                 555                 560
Glu Ser Gly Gln Gly Ser Thr Ala Gly Pro Leu Arg Pro Pro Pro
                565                 570                 575
Gly Ala Gly Gly Pro Ala Thr Pro Ser Lys Ala Thr Arg Phe Leu Pro
                580                 585                 590
Met Asp Pro Ala Thr Phe Arg Arg Lys Arg Pro Glu Ser Val Gly Gly
        595                 600                 605
Leu Glu Pro Pro Gly Pro Ser Val Ile Ala Ala Pro Ser Gly Gly
    610                 615                 620
Gly Asn Ile Leu Gln Thr Leu Val Leu Pro Asn Lys Glu Glu Gln
625                 630                 635                 640
Glu Gly Gly Gly Ala Arg Val Pro Ser Ala Pro Ala Pro Ser Leu Ala
                645                 650                 655
Tyr Gly Ala Pro Ala Ala Pro Leu Ser Arg Pro Ala Ala Thr Met Val
                660                 665                 670
Thr Asn Val Val Arg Pro Val Ser Ser Thr Pro Val Pro Ile Ala Ser
        675                 680                 685
Lys Pro Phe Pro Thr Ser Gly Arg Ala Glu Ala Ser Pro Asn Asp Thr
    690                 695                 700
Ala Gly Ala Arg Thr Glu Met Gly Thr Gly Ser Arg Val Pro Gly Gly
705                 710                 715                 720
Ser Pro Leu Gly Val Ser Leu Val Tyr Ser Asp Lys Lys Ser Ala Ala
                725                 730                 735
Ala Thr Ser Pro Ala Pro His Leu Val Ala Gly Pro Leu Leu Gly Thr
            740                 745                 750
Val Gly Lys Ala Pro Ala Thr Val Thr Asn Leu Leu Val Gly Thr Pro
        755                 760                 765
Gly Tyr Gly Ala Pro Ala Pro Pro Ala Val Gln Phe Ile Ala Gln Gly
    770                 775                 780
Ala Pro Gly Gly Thr Thr Ala Gly Ser Gly Ala Gly Ala Gly Ser
785                 790                 795                 800
Gly Pro Asn Gly Pro Val Pro Leu Gly Ile Leu Gln Pro Gly Ala Leu
                805                 810                 815
Gly Lys Ala Gly Gly Ile Thr Gln Val Gln Tyr Ile Leu Pro Thr Leu
                820                 825                 830
Pro Gln Gln Leu Gln Val Ala Pro Ala Pro Ala Pro Gly Thr
        835                 840                 845
Lys Ala Ala Ala Pro Ser Gly Pro Ala Pro Thr Thr Ser Ile Arg Phe
    850                 855                 860
Thr Leu Pro Pro Gly Thr Ser Thr Asn Gly Lys Val Leu Ala Ala Thr
865                 870                 875                 880
Ala Pro Thr Pro Gly Ile Pro Ile Leu Gln Ser Val Pro Ser Ala Pro
                885                 890                 895
Pro Pro Lys Ala Gln Ser Val Ser Pro Val Gln Ala Pro Pro Gly
        900                 905                 910
Gly Ser Ala Gln Leu Leu Pro Gly Lys Val Leu Val Pro Leu Ala Ala
                915                 920                 925
Pro Ser Met Ser Val Arg Gly Gly Ala Gly Gln Pro Leu Pro Leu
    930                 935                 940
Val Ser Pro Pro Phe Ser Val Pro Val Gln Asn Gly Ala Gln Pro Pro
```

```
                945                 950                 955                 960
Ser Lys Ile Ile Gln Leu Thr Pro Val Pro Val Ser Thr Pro Ser Gly
                    965                 970                 975
Leu Val Pro Pro Leu Ser Pro Ala Thr Leu Pro Gly Pro Thr Ser Gln
                    980                 985                 990
Pro Gln Lys Val Leu Leu Pro Ser Ser Thr Arg Ile Thr Tyr Val Gln
                    995                 1000                1005
Ser Ala Gly Gly His Ala Leu Pro Leu Gly Thr Ser Pro Ala Ser
    1010                1015                1020
Ser Gln Ala Gly Thr Val Thr Ser Tyr Gly Pro Thr Ser Ser Val
    1025                1030                1035
Ala Leu Gly Phe Thr Ser Leu Gly Pro Ser Gly Pro Ala Phe Val
    1040                1045                1050
Gln Pro Leu Leu Ser Ala Gly Gln Ala Pro Leu Leu Ala Pro Gly
    1055                1060                1065
Gln Val Gly Val Ser Pro Val Pro Ser Pro Gln Leu Pro Pro Ala
    1070                1075                1080
Cys Ala Ala Pro Gly Gly Pro Val Ile Thr Ala Phe Tyr Ser Gly
    1085                1090                1095
Ser Pro Ala Pro Thr Ser Ser Ala Pro Leu Ala Gln Pro Ser Gln
    1100                1105                1110
Ala Pro Pro Ser Leu Val Tyr Thr Val Ala Thr Ser Thr Thr Pro
    1115                1120                1125
Pro Ala Ala Thr Ile Leu Pro Lys Gly Pro Pro Ala Pro Ala Thr
    1130                1135                1140
Ala Thr Pro Ala Pro Thr Ser Pro Phe Pro Ser Ala Thr Ala Gly
    1145                1150                1155
Ser Met Thr Tyr Ser Leu Val Ala Pro Lys Ala Gln Arg Pro Ser
    1160                1165                1170
Pro Lys Ala Pro Gln Lys Val Lys Ala Ala Ile Ala Ser Ile Pro
    1175                1180                1185
Val Gly Ser Phe Glu Ala Gly Ala Ser Gly Arg Pro Gly Pro Ala
    1190                1195                1200
Pro Arg Gln Pro Leu Glu Pro Gly Pro Val Arg Glu Pro Thr Ala
    1205                1210                1215
Pro Glu Ser Glu Leu Glu Gly Gln Pro Thr Pro Pro Ala Pro Pro
    1220                1225                1230
Pro Leu Pro Glu Thr Trp Thr Pro Thr Ala Arg Ser Ser Pro Pro
    1235                1240                1245
Leu Pro Pro Pro Ala Glu Glu Arg Thr Ser Ala Lys Gly Pro Glu
    1250                1255                1260
Thr Met Ala Ser Lys Phe Pro Ser Ser Ser Asp Trp Arg Val
    1265                1270                1275
Pro Gly Gln Gly Leu Glu Asn Arg Gly Glu Pro Thr Pro Pro
    1280                1285                1290
Ser Pro Ala Pro Ala Pro Val Ala Pro Gly Gly Ser Ser Glu
    1295                1300                1305
Ser Ser Ser Gly Arg Ala Ala Gly Asp Thr Pro Glu Arg Lys Glu
    1310                1315                1320
Ala Ala Gly Thr Gly Lys Lys Val Lys Val Arg Pro Pro Pro Leu
    1325                1330                1335
Lys Lys Thr Phe Asp Ser Val Asp Asn Arg Val Leu Ser Glu Val
    1340                1345                1350
```

```
Asp Phe Glu Glu Arg Phe Ala Glu Leu Pro Glu Phe Arg Pro Glu
    1355                1360                1365

Glu Val Leu Pro Ser Pro Thr Leu Gln Ser Leu Ala Thr Ser Pro
    1370                1375                1380

Arg Ala Ile Leu Gly Ser Tyr Arg Lys Lys Arg Lys Asn Ser Thr
    1385                1390                1395

Asp Leu Asp Ser Ala Pro Glu Asp Pro Thr Ser Pro Lys Arg Lys
    1400                1405                1410

Met Arg Arg Arg Ser Ser Cys Ser Ser Glu Pro Asn Thr Pro Lys
    1415                1420                1425

Ser Ala Lys Cys Glu Gly Asp Ile Phe Thr Phe Asp Arg Thr Gly
    1430                1435                1440

Thr Glu Ala Glu Asp Val Leu Gly Glu Leu Glu Tyr Asp Lys Val
    1445                1450                1455

Pro Tyr Ser Ser Leu Arg Arg Thr Leu Asp Gln Arg Arg Ala Leu
    1460                1465                1470

Val Met Gln Leu Phe Gln Asp His Gly Phe Phe Pro Ser Ala Gln
    1475                1480                1485

Ala Thr Ala Ala Phe Gln Ala Arg Tyr Ala Asp Ile Phe Pro Ser
    1490                1495                1500

Lys Val Cys Leu Gln Leu Lys Ile Arg Glu Val Arg Gln Lys Ile
    1505                1510                1515

Met Gln Ala Ala Thr Pro Thr Glu Gln Pro Pro Gly Ala Glu Ala
    1520                1525                1530

Pro Leu Pro Val Pro Pro Thr Gly Thr Ala Ala Ala Pro Ala
    1535                1540                1545

Pro Thr Pro Ser Pro Ala Gly Gly Pro Asp Pro Thr Ser Pro Ser
    1550                1555                1560

Ser Asp Ser Gly Thr Ala Gln Ala Ala Pro Pro Leu Pro Pro Pro
    1565                1570                1575

Pro Glu Ser Gly Pro Gly Gln Pro Gly Trp Glu Gly Ala Pro Gln
    1580                1585                1590

Pro Ser Pro Pro Pro Gly Pro Ser Thr Ala Ala Thr Gly Arg
    1595                1600                1605

<210> SEQ ID NO 103
<211> LENGTH: 781
<212> TYPE: PRT
<213> ORGANISM: Homo sapiens

<400> SEQUENCE: 103

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
                20                  25                  30

Ser Gly Ile His Ser Gly Ala Thr Thr Thr Ala Pro Ser Leu Ser Gly
            35                  40                  45

Lys Gly Asn Pro Glu Glu Glu Asp Val Asp Thr Ser Gln Val Leu Tyr
        50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
```

-continued

```
                100             105             110
Gln Phe Asp Ala Ala His Pro Thr Asn Val Gln Arg Leu Ala Glu Pro
            115                 120                 125
Ser Gln Met Leu Lys His Ala Val Val Asn Leu Ile Asn Tyr Gln Asp
        130                 135                 140
Asp Ala Glu Leu Ala Thr Arg Ala Ile Pro Glu Leu Thr Lys Leu Leu
145                 150                 155                 160
Asn Asp Glu Asp Gln Val Val Val Asn Lys Ala Ala Val Met Val His
                165                 170                 175
Gln Leu Ser Lys Lys Glu Ala Ser Arg His Ala Ile Met Arg Ser Pro
            180                 185                 190
Gln Met Val Ser Ala Ile Val Arg Thr Met Gln Asn Thr Asn Asp Val
        195                 200                 205
Glu Thr Ala Arg Cys Thr Ala Gly Thr Leu His Asn Leu Ser His His
210                 215                 220
Arg Glu Gly Leu Leu Ala Ile Phe Lys Ser Gly Ile Pro Ala Leu
225                 230                 235                 240
Val Lys Met Leu Gly Ser Pro Val Asp Ser Val Leu Phe Tyr Ala Ile
                245                 250                 255
Thr Thr Leu His Asn Leu Leu Leu His Gln Glu Gly Ala Lys Met Ala
            260                 265                 270
Val Arg Leu Ala Gly Gly Leu Gln Lys Met Val Ala Leu Leu Asn Lys
        275                 280                 285
Thr Asn Val Lys Phe Leu Ala Ile Thr Thr Asp Cys Leu Gln Ile Leu
290                 295                 300
Ala Tyr Gly Asn Gln Glu Ser Lys Leu Ile Ile Leu Ala Ser Gly Gly
305                 310                 315                 320
Pro Gln Ala Leu Val Asn Ile Met Arg Thr Tyr Thr Tyr Glu Lys Leu
                325                 330                 335
Leu Trp Thr Thr Ser Arg Val Leu Lys Val Leu Ser Val Cys Ser Ser
            340                 345                 350
Asn Lys Pro Ala Ile Val Glu Ala Gly Gly Met Gln Ala Leu Gly Leu
        355                 360                 365
His Leu Thr Asp Pro Ser Gln Arg Leu Val Gln Asn Cys Leu Trp Thr
370                 375                 380
Leu Arg Asn Leu Ser Asp Ala Ala Thr Lys Gln Glu Gly Met Glu Gly
385                 390                 395                 400
Leu Leu Gly Thr Leu Val Gln Leu Leu Gly Ser Asp Asp Ile Asn Val
                405                 410                 415
Val Thr Cys Ala Ala Gly Ile Leu Ser Asn Leu Thr Cys Asn Asn Tyr
            420                 425                 430
Lys Asn Lys Met Met Val Cys Gln Val Gly Gly Ile Glu Ala Leu Val
        435                 440                 445
Arg Thr Val Leu Arg Ala Gly Asp Arg Glu Asp Ile Thr Glu Pro Ala
450                 455                 460
Ile Cys Ala Leu Arg His Leu Thr Ser Arg His Gln Glu Ala Glu Met
465                 470                 475                 480
Ala Gln Asn Ala Val Arg Leu His Tyr Gly Leu Pro Val Val Val Lys
                485                 490                 495
Leu Leu His Pro Pro Ser His Trp Pro Leu Ile Lys Ala Thr Val Gly
            500                 505                 510
Leu Ile Arg Asn Leu Ala Leu Cys Pro Ala Asn His Ala Pro Leu Arg
        515                 520                 525
```

Glu Gln Gly Ala Ile Pro Arg Leu Val Gln Leu Leu Val Arg Ala His
        530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
        610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
        690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
        770                 775                 780

<210> SEQ ID NO 104
<211> LENGTH: 1255
<212> TYPE: PRT
<213> ORGANISM: Homo sapiens

<400> SEQUENCE: 104

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro

```
              115                 120                 125
Val Thr Gly Ala Ser Pro Gly Gly Leu Arg Glu Leu Gln Leu Arg Ser
            130                 135                 140
Leu Thr Glu Ile Leu Lys Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
                180                 185                 190
His Pro Cys Ser Pro Met Cys Lys Gly Ser Arg Cys Trp Gly Glu Ser
                195                 200                 205
Ser Glu Asp Cys Gln Ser Leu Thr Arg Thr Val Cys Ala Gly Gly Cys
        210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
                275                 280                 285
Tyr Thr Phe Gly Ala Ser Cys Val Thr Ala Cys Pro Tyr Asn Tyr Leu
            290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
            370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
            450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
            530                 535                 540
```

```
Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960
```

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

Ser Gly Gly Gly Asp Leu Thr Leu Gly Leu Glu Pro Ser Glu Glu
        1055                1060                1065

Glu Ala Pro Arg Ser Pro Leu Ala Pro Ser Glu Gly Ala Gly Ser
        1070                1075                1080

Asp Val Phe Asp Gly Asp Leu Gly Met Gly Ala Ala Lys Gly Leu
        1085                1090                1095

Gln Ser Leu Pro Thr His Asp Pro Ser Pro Leu Gln Arg Tyr Ser
        1100                1105                1110

Glu Asp Pro Thr Val Pro Leu Pro Ser Glu Thr Asp Gly Tyr Val
        1115                1120                1125

Ala Pro Leu Thr Cys Ser Pro Gln Pro Glu Tyr Val Asn Gln Pro
        1130                1135                1140

Asp Val Arg Pro Gln Pro Pro Ser Pro Arg Glu Gly Pro Leu Pro
        1145                1150                1155

Ala Ala Arg Pro Ala Gly Ala Thr Leu Glu Arg Pro Lys Thr Leu
        1160                1165                1170

Ser Pro Gly Lys Asn Gly Val Val Lys Asp Val Phe Ala Phe Gly
        1175                1180                1185

Gly Ala Val Glu Asn Pro Glu Tyr Leu Thr Pro Gln Gly Gly Ala
        1190                1195                1200

Ala Pro Gln Pro His Pro Pro Ala Phe Ser Pro Ala Phe Asp
        1205                1210                1215

Asn Leu Tyr Tyr Trp Asp Gln Asp Pro Pro Glu Arg Gly Ala Pro
        1220                1225                1230

Pro Ser Thr Phe Lys Gly Thr Pro Thr Ala Glu Asn Pro Glu Tyr
        1235                1240                1245

Leu Gly Leu Asp Val Pro Val
        1250                1255

<210> SEQ ID NO 105
<211> LENGTH: 189
<212> TYPE: PRT
<213> ORGANISM: Homo sapiens

<400> SEQUENCE: 105

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

```
Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Lys
                165                 170                 175

Thr Pro Gly Cys Val Lys Ile Lys Lys Cys Ile Ile Met
            180                 185

<210> SEQ ID NO 106
<211> LENGTH: 1068
<212> TYPE: PRT
<213> ORGANISM: Homo sapiens

<400> SEQUENCE: 106

Met Pro Pro Arg Pro Ser Ser Gly Glu Leu Trp Gly Ile His Leu Met
  1               5                  10                  15

Pro Pro Arg Ile Leu Val Glu Cys Leu Leu Pro Asn Gly Met Ile Val
             20                  25                  30

Thr Leu Glu Cys Leu Arg Glu Ala Thr Leu Ile Thr Ile Lys His Glu
         35                  40                  45

Leu Phe Lys Glu Ala Arg Lys Tyr Pro Leu His Gln Leu Leu Gln Asp
 50                  55                  60

Glu Ser Ser Tyr Ile Phe Val Ser Val Thr Gln Glu Ala Glu Arg Glu
 65                  70                  75                  80

Glu Phe Phe Asp Glu Thr Arg Arg Leu Cys Asp Leu Arg Leu Phe Gln
                 85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
            115                 120                 125

Asp Met Val Lys Asp Pro Glu Val Gln Asp Phe Arg Arg Asn Ile Leu
130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
            195                 200                 205

Leu Lys Ile Asn His Asp Cys Val Pro Glu Gln Val Ile Ala Glu Ala
            210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
```

```
                245                 250                 255
Cys Asp Glu Tyr Phe Leu Glu Lys Tyr Pro Leu Ser Gln Tyr Lys Tyr
                260                 265                 270

Ile Arg Ser Cys Ile Met Leu Gly Arg Met Pro Asn Leu Met Leu Met
                275                 280                 285

Ala Lys Glu Ser Leu Tyr Ser Gln Leu Pro Met Asp Cys Phe Thr Met
                290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
                340                 345                 350

Lys Ile Tyr Val Arg Thr Gly Ile Tyr His Gly Gly Glu Pro Leu Cys
                355                 360                 365

Asp Asn Val Asn Thr Gln Arg Val Pro Cys Ser Asn Pro Arg Trp Asn
                370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
                420                 425                 430

Thr Asp Thr Leu Val Ser Gly Lys Met Ala Leu Asn Leu Trp Pro Val
                435                 440                 445

Pro His Gly Leu Glu Asp Leu Leu Asn Pro Ile Gly Val Thr Gly Ser
                450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
                500                 505                 510

Leu Ser Asn Arg Leu Ala Arg Asp Asn Glu Leu Arg Glu Asn Asp Lys
                515                 520                 525

Glu Gln Leu Lys Ala Ile Ser Thr Arg Asp Pro Leu Ser Glu Ile Thr
                530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
                580                 585                 590

Ile Lys Pro Glu Gln Ala Met Glu Leu Leu Asp Cys Asn Tyr Pro Asp
                595                 600                 605

Pro Met Val Arg Gly Phe Ala Val Arg Cys Leu Glu Lys Tyr Leu Thr
                610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
                660                 665                 670
```

Ser Glu Met His Asn Lys Thr Val Ser Gln Arg Phe Gly Leu Leu Leu
            675                 680                 685

Glu Ser Tyr Cys Arg Ala Cys Gly Met Tyr Leu Lys His Leu Asn Arg
        690                 695                 700

Gln Val Glu Ala Met Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
                740                 745                 750

Ser Pro Leu Asn Pro Ala His Gln Leu Gly Asn Leu Arg Leu Glu Glu
            755                 760                 765

Cys Arg Ile Met Ser Ser Ala Lys Arg Pro Leu Trp Leu Asn Trp Glu
            770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gly Leu Asp Leu Arg
                820                 825                 830

Met Leu Pro Tyr Gly Cys Leu Ser Ile Gly Asp Cys Val Gly Leu Ile
            835                 840                 845

Glu Val Val Arg Asn Ser His Thr Ile Met Gln Ile Gln Cys Lys Gly
            850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
                900                 905                 910

Ile Gly Asp Arg His Asn Ser Asn Ile Met Val Lys Asp Asp Gly Gln
            915                 920                 925

Leu Phe His Ile Asp Phe Gly His Phe Leu Asp His Lys Lys Lys
            930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
                980                 985                 990

Gln His Ala Asn Leu Phe Ile Asn Leu Phe Ser Met Met Leu Gly Ser
            995                 1000                1005

Gly Met Pro Glu Leu Gln Ser Phe Asp Asp Ile Ala Tyr Ile Arg
    1010                1015                1020

Lys Thr Leu Ala Leu Asp Lys Thr Glu Gln Glu Ala Leu Glu Tyr
    1025                1030                1035

Phe Met Lys Gln Met Asn Asp Ala His His Gly Gly Trp Thr Thr
    1040                1045                1050

Lys Met Asp Trp Ile Phe His Thr Ile Lys Gln His Ala Leu Asn
    1055                1060                1065

<210> SEQ ID NO 107
<211> LENGTH: 403

<212> TYPE: PRT
<213> ORGANISM: Homo sapiens

<400> SEQUENCE: 107

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400
```

Thr Lys Val

<210> SEQ ID NO 108
<211> LENGTH: 1304
<212> TYPE: PRT
<213> ORGANISM: Homo sapiens

<400> SEQUENCE: 108

Met Ala Lys Ile Ala Lys Thr His Glu Asp Ile Glu Ala Gln Ile Arg
1               5                   10                  15

Glu Ile Gln Gly Lys Lys Ala Ala Leu Asp Glu Ala Gln Gly Val Gly
                20                  25                  30

Leu Asp Ser Thr Gly Tyr Tyr Asp Gln Glu Ile Tyr Gly Gly Ser Asp
            35                  40                  45

Ser Arg Phe Ala Gly Tyr Val Thr Ser Ile Ala Ala Thr Glu Leu Glu
50                  55                  60

Asp Asp Asp Asp Tyr Ser Ser Ser Thr Ser Leu Leu Gly Gln Lys
65                  70                  75                  80

Lys Pro Gly Tyr His Ala Pro Val Ala Leu Leu Asn Asp Ile Pro Gln
                85                  90                  95

Ser Thr Glu Gln Tyr Asp Pro Phe Ala Glu His Arg Pro Pro Lys Ile
            100                 105                 110

Ala Asp Arg Glu Asp Glu Tyr Lys Lys His Arg Arg Thr Met Ile Ile
        115                 120                 125

Ser Pro Glu Arg Leu Asp Pro Phe Ala Asp Gly Gly Lys Thr Pro Asp
130                 135                 140

Pro Lys Met Asn Ala Arg Thr Tyr Met Asp Val Met Arg Glu Gln His
145                 150                 155                 160

Leu Thr Lys Glu Glu Arg Glu Ile Arg Gln Gln Leu Ala Glu Lys Ala
                165                 170                 175

Lys Ala Gly Glu Leu Lys Val Val Asn Gly Ala Ala Ala Ser Gln Pro
            180                 185                 190

Pro Ser Lys Arg Lys Arg Arg Trp Asp Gln Thr Ala Asp Gln Thr Pro
        195                 200                 205

Gly Ala Thr Pro Lys Lys Leu Ser Ser Trp Asp Gln Ala Glu Thr Pro
210                 215                 220

Gly His Thr Pro Ser Leu Arg Trp Asp Glu Thr Pro Gly Arg Ala Lys
225                 230                 235                 240

Gly Ser Glu Thr Pro Gly Ala Thr Pro Gly Ser Lys Ile Trp Asp Pro
                245                 250                 255

Thr Pro Ser His Thr Pro Ala Gly Ala Ala Thr Pro Gly Arg Gly Asp
            260                 265                 270

Thr Pro Gly His Ala Thr Pro Gly His Gly Gly Ala Thr Ser Ser Ala
        275                 280                 285

Arg Lys Asn Arg Trp Asp Glu Thr Pro Lys Thr Glu Arg Asp Thr Pro
290                 295                 300

Gly His Gly Ser Gly Trp Ala Glu Thr Pro Arg Thr Asp Arg Gly Gly
305                 310                 315                 320

Asp Ser Ile Gly Glu Thr Pro Thr Pro Gly Ala Ser Lys Arg Lys Ser
                325                 330                 335

Arg Trp Asp Glu Thr Pro Ala Ser Gln Met Gly Gly Ser Thr Pro Val
            340                 345                 350

Leu Thr Pro Gly Lys Thr Pro Ile Gly Thr Pro Ala Met Asn Met Ala
        355                 360                 365

```
Thr Pro Thr Pro Gly His Ile Met Ser Met Thr Pro Glu Gln Leu Gln
    370                 375                 380

Ala Trp Arg Trp Glu Arg Glu Ile Asp Glu Arg Asn Arg Pro Leu Ser
385                 390                 395                 400

Asp Glu Glu Leu Asp Ala Met Phe Pro Glu Gly Tyr Lys Val Leu Pro
                405                 410                 415

Pro Pro Ala Gly Tyr Val Pro Ile Arg Thr Pro Ala Arg Lys Leu Thr
            420                 425                 430

Ala Thr Pro Thr Pro Leu Gly Gly Met Thr Gly Phe His Met Gln Thr
        435                 440                 445

Glu Asp Arg Thr Met Lys Ser Val Asn Asp Gln Pro Ser Gly Asn Leu
    450                 455                 460

Pro Phe Leu Lys Pro Asp Asp Ile Gln Tyr Phe Asp Lys Leu Leu Val
465                 470                 475                 480

Asp Val Asp Glu Ser Thr Leu Ser Pro Glu Glu Gln Lys Glu Arg Lys
                485                 490                 495

Ile Met Lys Leu Leu Leu Lys Ile Lys Asn Gly Thr Pro Pro Met Arg
            500                 505                 510

Lys Ala Ala Leu Arg Gln Ile Thr Asp Lys Ala Arg Glu Phe Gly Ala
        515                 520                 525

Gly Pro Leu Phe Asn Gln Ile Leu Pro Leu Leu Met Ser Pro Thr Leu
    530                 535                 540

Glu Asp Gln Glu Arg His Leu Leu Val Lys Val Ile Asp Arg Ile Leu
545                 550                 555                 560

Tyr Lys Leu Asp Asp Leu Val Arg Pro Tyr Val His Lys Ile Leu Val
                565                 570                 575

Val Ile Glu Pro Leu Leu Ile Asp Glu Asp Tyr Tyr Ala Arg Val Glu
            580                 585                 590

Gly Arg Glu Ile Ile Ser Asn Leu Ala Lys Ala Ala Gly Leu Ala Thr
        595                 600                 605

Met Ile Ser Thr Met Arg Pro Asp Ile Asp Asn Met Asp Glu Tyr Val
    610                 615                 620

Arg Asn Thr Thr Ala Arg Ala Phe Ala Val Val Ala Ser Ala Leu Gly
625                 630                 635                 640

Ile Pro Ser Leu Leu Pro Phe Leu Lys Ala Val Cys Lys Ser Lys Lys
                645                 650                 655

Ser Trp Gln Ala Arg His Thr Gly Ile Lys Ile Val Gln Gln Ile Ala
            660                 665                 670

Ile Leu Met Gly Cys Ala Ile Leu Pro His Leu Arg Ser Leu Val Glu
        675                 680                 685

Ile Ile Glu His Gly Leu Val Asp Glu Gln Gln Lys Val Arg Thr Ile
    690                 695                 700

Ser Ala Leu Ala Ile Ala Ala Leu Ala Glu Ala Thr Pro Tyr Gly
705                 710                 715                 720

Ile Glu Ser Phe Asp Ser Val Leu Lys Pro Leu Trp Lys Gly Ile Arg
                725                 730                 735

Gln His Arg Gly Lys Gly Leu Ala Ala Phe Leu Lys Ala Ile Gly Tyr
            740                 745                 750

Leu Ile Pro Leu Met Asp Ala Glu Tyr Ala Asn Tyr Tyr Thr Arg Glu
        755                 760                 765

Val Met Leu Ile Leu Ile Arg Glu Phe Gln Ser Pro Asp Glu Glu Met
    770                 775                 780
```

```
Lys Lys Ile Val Leu Lys Val Val Lys Gln Cys Cys Gly Thr Asp Gly
785                 790                 795                 800

Val Glu Ala Asn Tyr Ile Lys Thr Glu Ile Leu Pro Pro Phe Phe Lys
                805                 810                 815

His Phe Trp Gln His Arg Met Ala Leu Asp Arg Arg Asn Tyr Arg Gln
            820                 825                 830

Leu Val Asp Thr Thr Val Glu Leu Ala Asn Lys Val Gly Ala Ala Glu
            835                 840                 845

Ile Ile Ser Arg Ile Val Asp Asp Leu Lys Asp Glu Ala Glu Gln Tyr
        850                 855                 860

Arg Lys Met Val Met Glu Thr Ile Glu Lys Ile Met Gly Asn Leu Gly
865                 870                 875                 880

Ala Ala Asp Ile Asp His Lys Leu Glu Glu Gln Leu Ile Asp Gly Ile
                885                 890                 895

Leu Tyr Ala Phe Gln Glu Gln Thr Thr Glu Asp Ser Val Met Leu Asn
                900                 905                 910

Gly Phe Gly Thr Val Val Asn Ala Leu Gly Lys Arg Val Lys Pro Tyr
            915                 920                 925

Leu Pro Gln Ile Cys Gly Thr Val Leu Trp Arg Leu Asn Asn Lys Ser
        930                 935                 940

Ala Lys Val Arg Gln Gln Ala Ala Asp Leu Ile Ser Arg Thr Ala Val
945                 950                 955                 960

Val Met Lys Thr Cys Gln Glu Glu Lys Leu Met Gly His Leu Gly Val
                965                 970                 975

Val Leu Tyr Glu Tyr Leu Gly Glu Glu Tyr Pro Glu Val Leu Gly Ser
            980                 985                 990

Ile Leu Gly Ala Leu Lys Ala Ile  Val Asn Val Ile Gly  Met His Lys
        995                 1000                1005

Met Thr  Pro Pro Ile Lys Asp  Leu Leu Pro Arg Leu  Thr Pro Ile
    1010                1015                1020

Leu Lys  Asn Arg His Glu Lys  Val Gln Glu Asn Cys  Ile Asp Leu
    1025                1030                1035

Val Gly  Arg Ile Ala Asp Arg  Gly Ala Glu Tyr Val  Ser Ala Arg
    1040                1045                1050

Glu Trp  Met Arg Ile Cys Phe  Glu Leu Leu Glu Leu  Leu Lys Ala
    1055                1060                1065

His Lys  Lys Ala Ile Arg Arg  Ala Thr Val Asn Thr  Phe Gly Tyr
    1070                1075                1080

Ile Ala  Lys Ala Ile Gly Pro  His Asp Val Leu Ala  Thr Leu Leu
    1085                1090                1095

Asn Asn  Leu Lys Val Gln Glu  Arg Gln Asn Arg Val  Cys Thr Thr
    1100                1105                1110

Val Ala  Ile Ala Ile Val Ala  Glu Thr Cys Ser Pro  Phe Thr Val
    1115                1120                1125

Leu Pro  Ala Leu Met Asn Glu  Tyr Arg Val Pro Glu  Leu Asn Val
    1130                1135                1140

Gln Asn  Gly Val Leu Lys Ser  Leu Ser Phe Leu Phe  Glu Tyr Ile
    1145                1150                1155

Gly Glu  Met Gly Lys Asp Tyr  Ile Tyr Ala Val Thr  Pro Leu Leu
    1160                1165                1170

Glu Asp  Ala Leu Met Asp Arg  Asp Leu Val His Arg  Gln Thr Ala
    1175                1180                1185

Ser Ala  Val Val Gln His Met  Ser Leu Gly Val Tyr  Gly Phe Gly
```

```
                    1190              1195              1200
    Cys Glu Asp Ser Leu Asn His Leu Leu Asn Tyr Val Trp Pro Asn
            1205              1210              1215
    Val Phe Glu Thr Ser Pro His Val Ile Gln Ala Val Met Gly Ala
            1220              1225              1230
    Leu Glu Gly Leu Arg Val Ala Ile Gly Pro Cys Arg Met Leu Gln
            1235              1240              1245
    Tyr Cys Leu Gln Gly Leu Phe His Pro Ala Arg Lys Val Arg Asp
            1250              1255              1260
    Val Tyr Trp Lys Ile Tyr Asn Ser Ile Tyr Ile Gly Ser Gln Asp
            1265              1270              1275
    Ala Leu Ile Ala His Tyr Pro Arg Ile Tyr Asn Asp Asp Lys Asn
            1280              1285              1290
    Thr Tyr Ile Arg Tyr Glu Leu Asp Tyr Ile Leu
            1295              1300

<210> SEQ ID NO 109
<211> LENGTH: 414
<212> TYPE: PRT
<213> ORGANISM: Homo sapiens

<400> SEQUENCE: 109

Met Ser Ser Pro Asp Ala Gly Tyr Ala Ser Asp Gln Ser Gln Thr
1                5                10                15
Gln Ser Ala Leu Pro Ala Val Met Ala Gly Leu Gly Pro Cys Pro Trp
                20                25                30
Ala Glu Ser Leu Ser Pro Ile Gly Asp Met Lys Val Lys Gly Glu Ala
                35                40                45
Pro Ala Asn Ser Gly Ala Pro Ala Gly Ala Ala Gly Arg Ala Lys Gly
                50                55                60
Glu Ser Arg Ile Arg Arg Pro Met Asn Ala Phe Met Val Trp Ala Lys
65                70                75                80
Asp Glu Arg Lys Arg Leu Ala Gln Gln Asn Pro Asp Leu His Asn Ala
                85                90                95
Glu Leu Ser Lys Met Leu Gly Lys Ser Trp Lys Ala Leu Thr Leu Ala
                100               105               110
Glu Lys Arg Pro Phe Val Glu Glu Ala Glu Arg Leu Arg Val Gln His
                115               120               125
Met Gln Asp His Pro Asn Tyr Lys Tyr Arg Pro Arg Arg Arg Lys Gln
                130               135               140
Val Lys Arg Leu Lys Arg Val Glu Gly Gly Phe Leu His Gly Leu Ala
145               150               155               160
Glu Pro Gln Ala Ala Leu Gly Pro Glu Gly Gly Arg Val Ala Met
                165               170               175
Asp Gly Leu Gly Leu Gln Phe Pro Glu Gln Gly Phe Pro Ala Gly Pro
                180               185               190
Pro Leu Leu Pro Pro His Met Gly Gly His Tyr Arg Asp Cys Gln Ser
                195               200               205
Leu Gly Ala Pro Pro Leu Asp Gly Tyr Pro Leu Pro Thr Pro Asp Thr
                210               215               220
Ser Pro Leu Asp Gly Val Asp Pro Asp Pro Ala Phe Phe Ala Ala Pro
225               230               235               240
Met Pro Gly Asp Cys Pro Ala Ala Gly Thr Tyr Ser Tyr Ala Gln Val
                245               250               255
```

-continued

```
Ser Asp Tyr Ala Gly Pro Pro Glu Pro Pro Ala Gly Pro Met His Pro
            260                 265                 270

Arg Leu Gly Pro Glu Pro Ala Gly Pro Ser Ile Pro Gly Leu Leu Ala
        275                 280                 285

Pro Pro Ser Ala Leu His Val Tyr Tyr Gly Ala Met Gly Ser Pro Gly
    290                 295                 300

Ala Gly Gly Gly Arg Gly Phe Gln Met Gln Pro Gln His Gln His Gln
305                 310                 315                 320

His Gln His Gln His His Pro Pro Gly Pro Gly Gln Pro Ser Pro Pro
                325                 330                 335

Pro Glu Ala Leu Pro Cys Arg Asp Gly Thr Asp Pro Ser Gln Pro Ala
        340                 345                 350

Glu Leu Leu Gly Glu Val Asp Arg Thr Glu Phe Glu Gln Tyr Leu His
    355                 360                 365

Phe Val Cys Lys Pro Glu Met Gly Leu Pro Tyr Gln Gly His Asp Ser
370                 375                 380

Gly Val Asn Leu Pro Asp Ser His Gly Ala Ile Ser Ser Val Val Ser
385                 390                 395                 400

Asp Ala Ser Ser Ala Val Tyr Tyr Cys Asn Tyr Pro Asp Val
                405                 410

<210> SEQ ID NO 110
<211> LENGTH: 393
<212> TYPE: PRT
<213> ORGANISM: Homo sapiens

<400> SEQUENCE: 110

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
        100                 105                 110

Phe Leu His Ser Gly Thr Ala Lys Ser Val Thr Cys Thr Tyr Ser Pro
    115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
    195                 200                 205

Arg Asn Thr Phe Arg His Ser Val Val Val Pro Tyr Glu Pro Pro Glu
210                 215                 220
```

```
Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
        260                 265                 270

Arg Val Cys Ala Cys Pro Gly Arg Asp Arg Thr Glu Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Gly Gln Ser Thr Ser Arg His Lys Lys Leu Met
370                 375                 380

Phe Lys Thr Glu Gly Pro Asp Ser Asp
385                 390

<210> SEQ ID NO 111
<211> LENGTH: 561
<212> TYPE: PRT
<213> ORGANISM: Human betaherpesvirus 5

<400> SEQUENCE: 111

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
```

```
                195                 200                 205
Glu Asn Thr Arg Ala Thr Lys Met Gln Val Ile Gly Asp Gln Tyr Val
210                 215                 220
Lys Val Tyr Leu Glu Ser Phe Cys Glu Asp Val Pro Ser Gly Lys Leu
225                 230                 235                 240
Phe Met His Val Thr Leu Gly Ser Asp Val Glu Glu Asp Leu Thr Met
                245                 250                 255
Thr Arg Asn Pro Gln Pro Phe Met Arg Pro His Glu Arg Asn Gly Phe
            260                 265                 270
Thr Val Leu Cys Pro Lys Asn Met Ile Ile Lys Pro Gly Lys Ile Ser
            275                 280                 285
His Ile Met Leu Asp Val Ala Phe Thr Ser His Glu His Phe Gly Leu
            290                 295                 300
Leu Cys Pro Lys Ser Ile Pro Gly Leu Ser Ile Ser Gly Asn Leu Leu
305                 310                 315                 320
Met Asn Gly Gln Gln Ile Phe Leu Glu Val Gln Ala Ile Arg Glu Thr
                325                 330                 335
Val Glu Leu Arg Gln Tyr Asp Pro Val Ala Ala Leu Phe Phe Phe Asp
            340                 345                 350
Ile Asp Leu Leu Leu Gln Arg Gly Pro Gln Tyr Ser Glu His Pro Thr
            355                 360                 365
Phe Thr Ser Gln Tyr Arg Ile Gln Gly Lys Leu Glu Tyr Arg His Thr
            370                 375                 380
Trp Asp Arg His Asp Glu Gly Ala Ala Gln Gly Asp Asp Val Trp
385                 390                 395                 400
Thr Ser Gly Ser Asp Ser Asp Glu Glu Leu Val Thr Thr Glu Arg Lys
                405                 410                 415
Thr Pro Arg Val Thr Gly Gly Gly Ala Met Ala Gly Ala Ser Thr Ser
            420                 425                 430
Ala Gly Arg Lys Arg Lys Ser Ala Ser Ser Ala Thr Ala Cys Thr Ser
            435                 440                 445
Gly Val Met Thr Arg Gly Arg Leu Lys Ala Glu Ser Thr Val Ala Pro
450                 455                 460
Glu Glu Asp Thr Asp Glu Asp Ser Asp Asn Glu Ile His Asn Pro Ala
465                 470                 475                 480
Val Phe Thr Trp Pro Pro Trp Gln Ala Gly Ile Leu Ala Arg Asn Leu
                485                 490                 495
Val Pro Met Val Ala Thr Val Gln Gly Gln Asn Leu Lys Tyr Gln Glu
            500                 505                 510
Phe Phe Trp Asp Ala Asn Asp Ile Tyr Arg Ile Phe Ala Glu Leu Glu
            515                 520                 525
Gly Val Trp Gln Pro Ala Ala Gln Pro Lys Arg Arg His Arg Gln
            530                 535                 540
Asp Ala Leu Pro Gly Pro Cys Ile Ala Ser Thr Pro Lys Lys His Arg
545                 550                 555                 560
Gly

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 112

Cys Val Leu Leu His Lys Lys Thr Thr Gly Lys Leu Ile Phe
1               5                   10

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tgtgtactac tgcataaaaa acaacaggc aaactaatct tt                         42

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Ala Ser Ser Phe Ser Thr Cys Ser Ala Asn Tyr Gly Tyr Thr Phe
1               5                   10                  15

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgtgccagca gtttctcgac ctgttcggct aactatggct acaccttc                  48

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Ala Glu Ser Pro Ser Gly Tyr Ala Leu Asn Phe
1               5                   10

<210> SEQ ID NO 117
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tgtgcagaga gtccttccgg gtatgcactc aacttc                              36

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Cys Ala Leu Ser Glu Asp Arg Gly Ser Thr Leu Gly Arg Leu Tyr Phe
1               5                   10                  15

<210> SEQ ID NO 119
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tgtgctctga gtgaagacag aggctcaacc ctggggaggc tatacttt                48

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Ala Gly Leu Ile Gly Thr Ala Leu Ile Phe
1               5                   10

<210> SEQ ID NO 121
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgtgccgggt taataggaac tgctctgatc ttt                                33

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ala Leu Ser Arg Asp Ser Gly Tyr Ala Leu Asn Phe
1               5                   10

<210> SEQ ID NO 123
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tgtgctctaa gtagggattc cgggtatgca ctcaacttc                          39

<210> SEQ ID NO 124
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 124

Cys Ser Ala Gln Gly Leu Ala Gly Glu Pro Ile Tyr Glu Gln Tyr Phe
1               5                   10                  15

<210> SEQ ID NO 125
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgcagtgccc agggactagc gggtgaacca atctacgagc agtacttc                   48

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Cys Ala Gln Ser Arg Asp Ser Gly Tyr Ala Leu Asn Phe
1               5                   10

<210> SEQ ID NO 127
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tgtgctcaaa gtagggattc cgggtatgca ctcaacttc                             39

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Cys Ala Ser Ser Leu Lys Leu Ala Pro Tyr Glu Gln Tyr Phe
1               5                   10

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tgtgccagca gcttgaaact agcccctac gagcagtact tc                          42

<210> SEQ ID NO 130
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Cys Thr Phe Pro Leu Pro Arg Pro Gln Thr Gln Ala Phe Ile Ser Val
1               5                   10                  15

Leu Ser Arg Thr Ser Ala Ser Asn Thr Gly Lys Leu Ile Phe
            20                  25                  30

<210> SEQ ID NO 131
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgtacatttc ctcttcccag accacagact caggcgttta tttctgtgct gtcccgaact    60
tcagctagca acacaggcaa actaatcttt                                     90

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Cys Ala Ser Ser Glu Ser Thr Tyr Glu Gln Tyr Phe
1               5                   10

<210> SEQ ID NO 133
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tgtgccagca gcgagagtac ctacgagcag tacttc                              36

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Ala Thr Ser Phe Pro Asp Leu Tyr Gly Tyr Thr Phe
1               5                   10

<210> SEQ ID NO 135
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 135
tgtgccacca gcttcccgga cctctatggc tacaccttc    39

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Ala Arg Asn Thr Gly Asn Gln Phe Tyr Phe
1               5                   10

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tgtgcccgga acaccggtaa ccagttctat ttt    33

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Cys Ala Ser Arg Ser Gly Val Leu Leu Ala Lys Asn Ile Gln Tyr Phe
1               5                   10                  15

<210> SEQ ID NO 139
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tgtgccagca gatcgggtgt actactagcc aaaaacattc agtacttc    48

<210> SEQ ID NO 140
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Cys Leu Val Gly Asp Arg Gly Leu Met Phe Ser Gly Gly Tyr Asn Lys
1               5                   10                  15

Leu Ile Phe

<210> SEQ ID NO 141
<211> LENGTH: 57
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 141
tgcctcgtgg gtgacagggg actcatgttt tctggtggct acaataagct gattttt      57

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Ala Ser Ser Ser Leu Ser Asn Gln Pro Gln His Phe
1               5                   10

<210> SEQ ID NO 143
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tgtgccagca gctcgttgag caatcagccc cagcatttt                          39

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Ala Ala Arg Gly Gly Ala Asp Gly Leu Thr Phe
1               5                   10

<210> SEQ ID NO 145
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tgtgcagcac gaggaggtgc tgacggactc acctttt                            36

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Ala Ser Ser Tyr Tyr Gly Gln Gly Gly Glu Lys Leu Phe Phe
1               5                   10                  15

<210> SEQ ID NO 147
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tgtgccagca gttactatgg acagggggga gaaaaactgt ttttt                          45

<210> SEQ ID NO 148
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Cys Thr Phe Pro Leu Pro Arg Pro Gln Thr Gln Ala Phe Ile Ser Val
1               5                   10                  15

Leu Ser Arg Thr Ala Ala Ser Asn Thr Gly Lys Leu Ile Phe
            20                  25                  30

<210> SEQ ID NO 149
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tgtacatttc ctcttcccag accacagact caggcgttta tttctgtgct gtcccgaact         60
gcagctagca acacaggcaa actaatcttt                                          90

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Ala Ser Ser Ser Asp Arg Val Tyr Glu Gln Tyr Phe
1               5                   10

<210> SEQ ID NO 151
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tgtgccagca gttccgaccg agtttacgag cagtacttc                                39

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152
```

Cys Ala Val Ser Asp Leu Glu Pro Asn Ser Ser Ala Ser Lys Ile Ile
1               5                   10                  15

Phe

<210> SEQ ID NO 153
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tgtgctgtga gtgatctcga accgaacagc agtgcttcca agataatctt t          51

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Cys Ala Leu Arg Glu Asp Arg Gly Ser Thr Leu Gly Arg Leu Tyr Phe
1               5                   10                  15

<210> SEQ ID NO 155
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tgtgctctgc gtgaagacag aggctcaacc ctggggaggc tatacttt              48

<210> SEQ ID NO 156
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Cys Lys Pro Ile Ser Gly His Asn Ser Leu Phe Trp Tyr Arg Gln Thr
1               5                   10                  15

Met Met Arg Gly Leu Glu Leu Leu Ile Tyr Phe Asn Asn Asn Val Pro
            20                  25                  30

Ile Asp Asp Ser Gly Met Pro Glu Asp Arg Phe Ser Ala Lys Met Pro
        35                  40                  45

Asn Ala Ser Phe Ser Thr Leu Lys Ile Gln Pro Ser Glu Pro Arg Asp
    50                  55                  60

Ser Ala Val Tyr Phe Tyr Ala Ser Ser Phe Ser Thr Cys Ser Ala Asn
65                  70                  75                  80

Tyr Gly Tyr Thr Phe
                85

<210> SEQ ID NO 157
<211> LENGTH: 255
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 157

```
tgtaaaccaa tttcaggcca caactcccett ttctggtaca gacagaccat gatgcgggga    60
ctggagttgc tcatttactt taacaacaac gttccgatag atgattcagg gatgcccgag   120
gatcgattct cagctaagat gcctaatgca tcattctcca ctctgaagat ccagccctca   180
gaacccaggg actcagctgt gtacttctat gccagcagtt tctcgacctg ttcggctaac   240
tatggctaca ccttc                                                    255
```

<210> SEQ ID NO 158
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Cys Lys Pro Ile Ser Gly His Asn Ser Leu Phe Trp Tyr Arg Gln Thr
1               5                   10                  15

Met Met Arg Gly Leu Glu Leu Leu Ile Tyr Phe Asn Asn Asn Val Pro
                20                  25                  30

Ile Asp Asp Ser Gly Met Pro Glu Asp Arg Phe Ser Ala Lys Met Pro
            35                  40                  45

Asn Ala Ser Phe Ser Thr Leu Lys Ile Gln Pro Ser Glu Pro Arg Asp
        50                  55                  60

Ser Ala Val Tyr Phe Gly Ala Ser Ser Phe Ser Thr Cys Ser Ala Asn
65                  70                  75                  80

Tyr Gly Tyr Thr Phe
                85

<210> SEQ ID NO 159
<211> LENGTH: 255
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

```
tgtaaaccaa tttcaggcca caactcccett ttctggtaca gacagaccat gatgcgggga    60
ctggagttgc tcatttactt taacaacaac gttccgatag atgattcagg gatgcccgag   120
gatcgattct cagctaagat gcctaatgca tcattctcca ctctgaagat ccagccctca   180
gaacccaggg actcagctgt gtacttcggt gccagcagtt tctcgacctg ttcggctaac   240
tatggctaca ccttc                                                    255
```

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Ala Thr Leu Ala Gly Ser Thr Asn Thr Gly Glu Leu Phe Phe

<210> SEQ ID NO 161
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tgtgccaccc ttgccgggtc tacgaacacc ggggagctgt ttttt              45

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Ala Ser Ser Leu Ser Met Asn Arg Val Lys Asn Glu Gln Phe Phe
1               5                   10                  15

<210> SEQ ID NO 163
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tgtgccagca gtttatccat gaacagggtt aagaatgagc agttcttc              48

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Val Val Ser Glu Arg Thr Ser Gly Thr Tyr Lys Tyr Ile Phe
1               5                   10                  15

<210> SEQ ID NO 165
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tgtgtggtga gcgaaaggac ctcaggaacc tacaaataca tcttt              45

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Ala Ser Ser Leu Gly Gly Pro Gly Glu Leu Phe Phe
1               5                   10

<210> SEQ ID NO 167
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgtgccagca gcctaggggg acccggggag ctgttttt                            39

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Arg Glu His Gly Asp Asp Met Arg Phe
1               5                   10

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tgccgtgaac atggcgatga catgcgcttt                                    30

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Cys Ala Ser Ser Pro Leu Arg Asp Asn Thr Glu Ala Phe Phe
1               5                   10

<210> SEQ ID NO 171
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tgtgccagct caccacttcg ggacaacacc gaagctttct tt                       42

<210> SEQ ID NO 172
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys Lys Leu Gln Leu Leu Asn Leu Glu Thr Gln Leu Ser Thr Phe Val
1               5                   10                  15

Pro Glu Asn Thr Gly Gly Phe Lys Thr Ile Phe
            20                  25

<210> SEQ ID NO 173
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tgcaaattgc agctactcaa cctggagact cagctgtcta cttttgtgcc tgaaatact      60 ggaggcttca aaactatctt t                                               81

<210> SEQ ID NO 174
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Cys Lys Leu Gln Leu Leu Asn Leu Glu Thr Gln Leu Ser Thr Phe Val
1               5                   10                  15

Gln Arg Gln Thr Gln Asn Gln Ala Gly Thr Ala Leu Ile Phe
            20                  25                  30

<210> SEQ ID NO 175
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tgcaaattgc agctactcaa cctggagact cagctgtcta cttttgtgca gagacaaacg      60
caaaaccagg caggaactgc tctgatcttt                                       90

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Ala Ser His Leu Gly Thr Gly Ala Tyr Asn Glu Gln Phe Phe
1               5                   10                  15

<210> SEQ ID NO 177
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tgtgccagcc atttagggac aggggcttac aatgagcagt cttc                45

<210> SEQ ID NO 178
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Ala Ser Ser Leu Asp Pro Glu Ser Trp Gly Pro Ser Tyr Glu Gln
1               5                   10                  15

Tyr Phe

<210> SEQ ID NO 179
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tgcgccagca gcttggatcc cgagagctgg ggaccctcct acgagcagta cttc         54

<210> SEQ ID NO 180
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Cys Ala Ser Ser Phe Gly Ser Tyr His Asn Glu Gln Phe Phe
1               5                   10

<210> SEQ ID NO 181
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tgtgccagca gttttggctc ttatcacaat gagcagttct tc                    42

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Ser Val Val Gly Gly Val Thr Tyr Glu Gln Tyr Phe
1               5                   10

<210> SEQ ID NO 183
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tgcagcgttg taggggggcgt tacctacgag cagtacttc                              39

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Gly Glu Arg Arg Asn Ser Gly Tyr Ser Thr Leu Thr Phe
1               5                   10

<210> SEQ ID NO 185
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tgtggtgagc gcaggaattc aggatacagc accctcacct tt                           42

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Ala Leu Gly Gly Phe Lys Thr Ile Phe
1               5                   10

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tgtgccttgg gaggcttcaa aactatcttt                                        30

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Ala Ser Ser Gln Asp Arg Glu Thr Gln Tyr Phe
1               5                   10

<210> SEQ ID NO 189
<211> LENGTH: 36

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tgtgccagca gccaagatag ggagacccag tacttc                              36

<210> SEQ ID NO 190
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Cys Ala Gly His Ala Ile Thr Arg Pro Met Asp Ser Ser Tyr Lys Leu
1               5                   10                  15

Ile Phe

<210> SEQ ID NO 191
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tgtgcagggc acgcgataac ccgaccgatg gatagcagct ataaattgat cttc          54

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Cys Ala Ser Ser Tyr Gly Ser Pro Ala Gln Asp Glu Gln Tyr Phe
1               5                   10                  15

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tgtgccagca gttacgggtc ccccgctcag gacgagcagt acttc                    45

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Gly Glu Arg Arg Asn Ser Gly Tyr Ser Asn Leu Thr Phe
1               5                   10
```

<210> SEQ ID NO 195
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tgtggtgagc gcaggaattc aggatacagc aacctcacct tt                          42

<210> SEQ ID NO 196
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
tgtttccctg acaatcatga ctttcagtga aacacaaag tcgaacggaa gagatacagc         60
aacactggag gaagacacaa agcaaagatc aaggcacaac acagcctccc agctcagcga       120
tagagcctcc tacatctggg tgatgagcga aggaatagag ggtacagcaa cctcatcttt      180

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Cys Ala Ser Ser Tyr Gly Gln Leu Ala Asp Thr Gln Tyr Phe
1               5                   10

<210> SEQ ID NO 198
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tgtgccagca gttacggcca gttggccgat acgcagtatt tt                          42

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Cys Ala Ser Ser Ser Thr Gly Thr Gly Asn Thr Gly Glu Leu Phe Phe
1               5                   10                  15

<210> SEQ ID NO 200
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
tgtgccagca gttcaaccgg gacagggaac accggggagc tgttttttt        48

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Cys Ile Val Gly Arg Asp Phe Gly Asn Glu Lys Leu Thr Phe
1               5                   10

<210> SEQ ID NO 202
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tgcatcgtgg gccgggactt tggaaatgag aaattaacct tt        42

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Cys Ala Ser Ser Leu Glu Arg Ala Gly Ala Tyr Glu Gln Tyr Phe
1               5                   10                  15

<210> SEQ ID NO 204
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tgtgccagca gcttagagcg ggcagggggcc tacgagcagt acttc        45

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Ala Ala Ser Ile Pro Ala Arg Ser Asn Thr Gly Lys Leu Ile Phe
1               5                   10                  15

<210> SEQ ID NO 206
<211> LENGTH: 48
<212> TYPE: DNA
<213> ORGANISM: Artificial Sequence -continued
<220> FEATURE:
<223> OTHER INFORMATION: Description of Artificial Sequence: Synthetic
      oligonucleotide

<400> SEQUENCE: 206
tgtgcagcaa gtatacccgc caggagcaac acaggcaaac taatcttt                48

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Cys Ala Leu Gln Ala Gly Gly Gly Ala Asn Ser Lys Leu Thr Phe
1               5                   10                  15

<210> SEQ ID NO 208
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tgtgctctgc aagcgggagg tggagccaat agtaagctga cattt                45

<210> SEQ ID NO 209
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tgtgctgtga gtgatctgga accgaacagc agtgcttcca agataatctt t          51

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Cys Ala Val Ser Asp Glu Asp Thr Gly Phe Gln Lys Leu Val Phe
1               5                   10                  15

<210> SEQ ID NO 211
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tgtgctgtga gtgacgagga cacaggcttt cagaaacttg tattt                45

<210> SEQ ID NO 212
<211> LENGTH: 210
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 212
tgcaataccc caaccaagga ctccagcttc tcctgaagta cacatcagcg gccaccctgg      60
ttaaaggcat caacggtttt gaggctgaat ttaagaagag tgaaacctcc ttccacctga     120
cgaaaccctc agcccatatg agcgacgcgg ctgagtactt ctgtgctgag tgatctcgaa     180
ccgaacagca gtgcttccaa gataatcttt                                      210

<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Ala Ser Ser Gln Gly Asp Arg Gly Pro Ser Asn Thr Glu Ala Phe
1               5                   10                  15

Phe

<210> SEQ ID NO 214
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tgtgccagca gccaagggga caggggccg tcgaacactg aagctttctt t                51

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Cys Ala Pro Glu Glu Asn Tyr Gly Lys Asn Phe Val Phe
1               5                   10

<210> SEQ ID NO 216
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tgtgctcccg aggagaacta tggtaagaat tttgtcttt                             39

<210> SEQ ID NO 217
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 217

Cys Ala Ala Ile Gly Tyr Gly Glu Asn Phe Val Phe
1               5                   10

<210> SEQ ID NO 218
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tgtgcagcaa tcggctatgg tgagaatttt gtcttt                          36

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Cys Ala Met Thr Arg Ser Ser Asn Thr Gly Lys Leu Ile Phe
1               5                   10

<210> SEQ ID NO 220
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tgtgcaatga cccgttctag caacacaggc aaactaatct tt                    42

<210> SEQ ID NO 221
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Cys Ala Ser Ser Arg Asp Arg Val Gly Gln Tyr Phe
1               5                   10

<210> SEQ ID NO 222
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tgtgccagca gccgggacag ggtcgggcag tacttc                          36

<210> SEQ ID NO 223
<211> LENGTH: 16
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 223

Cys Ala Leu Asp Met Asn Tyr Gly Gly Ala Thr Asn Lys Leu Ile Phe
1               5                   10                  15

<210> SEQ ID NO 224
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tgtgctctag acatgaatta tggtggtgct acaaacaagc tcatctttt          48

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than isoleucine
<220> FEATURE:
<221> NAME/KEY: MOD_RES
<222> LOCATION: (9)..(9)
<223> OTHER INFORMATION: Any amino acid other than alanine
<220> FEATURE:
<223> OTHER INFORMATION: See specification as filed for detailed
      description of substitutions and preferred embodiments

<400> SEQUENCE: 225

Met Xaa Phe Ser Lys Arg His Trp Xaa
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
<222> LOCATION: (9)..(9)
<223> OTHER INFORMATION: Any amino acid other than glycine
<220> FEATURE:
<223> OTHER INFORMATION: See specification as filed for detailed
      description of substitutions and preferred embodiments

<400> SEQUENCE: 226

Tyr Xaa Asp Cys Gly Ile His Ser Xaa
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
<222> LOCATION: (9)..(9)
<223> OTHER INFORMATION: Any amino acid other than glycine
<220> FEATURE:
<223> OTHER INFORMATION: See specification as filed for detailed
      description of substitutions and preferred embodiments

<400> SEQUENCE: 227

Tyr Xaa Asp Ser Gly Ile His Phe Xaa
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than valine
<220> FEATURE:
<223> OTHER INFORMATION: See specification as filed for detailed
      description of substitutions and preferred embodiments

<400> SEQUENCE: 228

Leu Xaa Val Val Gly Ala Ala Gly Val
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than valine
<220> FEATURE:
<223> OTHER INFORMATION: See specification as filed for detailed
      description of substitutions and preferred embodiments

<400> SEQUENCE: 229

Leu Xaa Val Val Gly Ala Cys Gly Val
1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than valine
<220> FEATURE:
<223> OTHER INFORMATION: See specification as filed for detailed
      description of substitutions and preferred embodiments

<400> SEQUENCE: 230

Leu Xaa Val Val Gly Ala Val Gly Val
1               5
```

```
<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
<222> LOCATION: (9)..(9)
<223> OTHER INFORMATION: Any amino acid other than isoleucine
<220> FEATURE:
<223> OTHER INFORMATION: See specification as filed for detailed
      description of substitutions and preferred embodiments

<400> SEQUENCE: 231

Gly Xaa Lys Asp Leu Leu Asn Pro Xaa
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
<222> LOCATION: (9)..(9)
<223> OTHER INFORMATION: Any amino acid other than alanine
<220> FEATURE:
<223> OTHER INFORMATION: See specification as filed for detailed
      description of substitutions and preferred embodiments

<400> SEQUENCE: 232

Ile Xaa Asn Arg Glu Ile Asp Phe Xaa
1               5

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid other than valine
<220> FEATURE:
<221> NAME/KEY: MOD_RES
<222> LOCATION: (10)..(10)
<223> OTHER INFORMATION: Any amino acid other than leucine
<220> FEATURE:
<223> OTHER INFORMATION: See specification as filed for detailed
      description of substitutions and preferred embodiments

<400> SEQUENCE: 233

Cys Tyr Xaa Tyr Tyr Tyr Ser Tyr Leu Xaa
1               5                   10

<210> SEQ ID NO 234
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than methionine
<220> FEATURE:
<221> NAME/KEY: MOD_RES
<222> LOCATION: (9)..(9)
<223> OTHER INFORMATION: Any amino acid other than threonine
<220> FEATURE:
<223> OTHER INFORMATION: See specification as filed for detailed
      description of substitutions and preferred embodiments

<400> SEQUENCE: 234

Asn Xaa Asp Glu Tyr Val His Asn Xaa
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than valine
<220> FEATURE:
<221> NAME/KEY: MOD_RES
<222> LOCATION: (9)..(9)
<223> OTHER INFORMATION: Any amino acid other than valine
<220> FEATURE:
<223> OTHER INFORMATION: See specification as filed for detailed
      description of substitutions and preferred embodiments

<400> SEQUENCE: 235

Val Xaa Ser Asp Ala Ile Ser Ala Xaa
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
<222> LOCATION: (9)..(9)
<223> OTHER INFORMATION: Any amino acid other than isoleucine
<220> FEATURE:
<223> OTHER INFORMATION: See specification as filed for detailed
      description of substitutions and preferred embodiments

<400> SEQUENCE: 236

Gly Xaa Ala Pro Pro Gln Tyr Leu Xaa
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
<222> LOCATION: (9)..(9)
<223> OTHER INFORMATION: Any amino acid other than leucine
<220> FEATURE:
<223> OTHER INFORMATION: See specification as filed for detailed
      description of substitutions and preferred embodiments

<400> SEQUENCE: 237

Ala Xaa Asn Asn Met Phe Cys Gln Xaa
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than methionine
<220> FEATURE:
<221> NAME/KEY: MOD_RES
<222> LOCATION: (9)..(9)
<223> OTHER INFORMATION: Any amino acid other than threonine
<220> FEATURE:
<223> OTHER INFORMATION: See specification as filed for detailed
      description of substitutions and preferred embodiments

<400> SEQUENCE: 238

Asn Xaa Phe Cys Gln Leu Ala Lys Xaa
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid other than leucine
<220> FEATURE:
<223> OTHER INFORMATION: See specification as filed for detailed
      description of substitutions and preferred embodiments

<400> SEQUENCE: 239

Gln Leu Trp Val Asp Ser Thr Pro Xaa
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid other than leucine
<220> FEATURE:
<223> OTHER INFORMATION: See specification as filed for detailed
      description of substitutions and preferred embodiments
```

```
<400> SEQUENCE: 240

Arg Leu Ile Leu Thr Ile Ile Thr Xaa
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid other than leucine
<220> FEATURE:
<223> OTHER INFORMATION: See specification as filed for detailed
      description of substitutions and preferred embodiments

<400> SEQUENCE: 241

Tyr Gln Gly Ser Tyr Gly Phe Leu Xaa
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than valine
<220> FEATURE:
<221> NAME/KEY: MOD_RES
<222> LOCATION: (9)..(9)
<223> OTHER INFORMATION: Any amino acid other than alanine
<220> FEATURE:
<223> OTHER INFORMATION: See specification as filed for detailed
      description of substitutions and preferred embodiments

<400> SEQUENCE: 242

Ser Xaa Thr Cys Thr Tyr Phe Pro Xaa
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than valine
<220> FEATURE:
<223> OTHER INFORMATION: See specification as filed for detailed
      description of substitutions and preferred embodiments

<400> SEQUENCE: 243

Val Xaa Pro Cys Glu Pro Pro Glu Val
1               5

<210> SEQ ID NO 244
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than threonine
<220> FEATURE:
<221> NAME/KEY: MOD_RES
<222> LOCATION: (9)..(9)
<223> OTHER INFORMATION: Any amino acid other than valine
<220> FEATURE:
<223> OTHER INFORMATION: See specification as filed for detailed
      description of substitutions and preferred embodiments

<400> SEQUENCE: 244

Lys Xaa Tyr Pro Val Gln Leu Trp Xaa
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
<222> LOCATION: (9)..(9)
<223> OTHER INFORMATION: Any amino acid other than isoleucine
<220> FEATURE:
<223> OTHER INFORMATION: See specification as filed for detailed
      description of substitutions and preferred embodiments

<400> SEQUENCE: 245

Gly Xaa Ala Pro Pro Gln Leu Leu Xaa
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid other than methionine
<220> FEATURE:
<223> OTHER INFORMATION: See specification as filed for detailed
      description of substitutions and preferred embodiments

<400> SEQUENCE: 246

Leu Leu Gly Arg Asn Ser Phe Glu Xaa
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than leucine
<220> FEATURE:
<221> NAME/KEY: MOD_RES
```

```
<222> LOCATION: (9)..(9)
<223> OTHER INFORMATION: Any amino acid other than alanine
<220> FEATURE:
<223> OTHER INFORMATION: See specification as filed for detailed
      description of substitutions and preferred embodiments

<400> SEQUENCE: 247

Arg Xaa Ile His Arg Asp Leu Ala Xaa
1               5

<210> SEQ ID NO 248
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Ile Leu Asp Asn Asn Asn Asp Met Arg Phe
1               5                   10

<210> SEQ ID NO 249
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tgcatccttg acaataacaa tgacatgcgc ttt                                33

<210> SEQ ID NO 250
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Ala Ser Ser Leu Ala Pro Gly Ala Thr Asn Glu Lys Leu Phe Phe
1               5                   10                  15

<210> SEQ ID NO 251
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tgtgccagca gcttagcgcc gggtgcaact aatgaaaaac tgttttttt               48

<210> SEQ ID NO 252
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Cys Ala Thr Ser Arg Asp Leu Pro Leu Ala Gly Gly Arg Gly Glu Gln
1               5                   10                  15
```

Phe Phe

<210> SEQ ID NO 253
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tgtgccacca gcagagatct cccgctagcg ggggggcgag gtgagcagtt cttc        54

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Cys Leu Val Val Tyr Asp Tyr Lys Leu Ser Phe
1               5                   10

<210> SEQ ID NO 255
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tgcctcgtgg tctacgacta caagctcagc ttt        33

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Cys Ala Ser Ser His Leu Thr Gly Leu Ala Glu Ala Phe Phe
1               5                   10

<210> SEQ ID NO 257
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tgcgccagca gccatctgac agggttggct gaagctttct tt        42

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Ala Ser Ser Leu Leu Gly Asn Ser Pro Leu His Phe
1               5                   10

<210> SEQ ID NO 259
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tgcgccagca gtctgctggg taattcaccc ctccacttt                        39

<210> SEQ ID NO 260
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
tgttcatcag agactcacag cccagtgatt cagccaccta cctctgtgca atgacctgcc    60
actgaccttc agggagccca gaagctggta ttt                               93

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Ala Ser Ser Gly Leu Ala Gly Ala Tyr Asn Glu Gln Phe Phe
1               5                   10                  15

<210> SEQ ID NO 262
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tgcgccagca gcgggctagc gggggcctac aatgagcagt tcttc                 45

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Cys Ala Ala Thr His Ser Asn Ser Gly Tyr Ala Leu Asn Phe
1               5                   10

<210> SEQ ID NO 264
<211> LENGTH: 42
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 264
tgtgcagcaa cccactcaaa ttccgggtat gcactcaact tc                              42

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Cys Ala Ser Ser Leu Trp Val Met Asn Thr Glu Ala Phe Phe
1               5                   10

<210> SEQ ID NO 266
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tgtgccagca gcttgtgggt tatgaacact gaagctttct tt                              42

<210> SEQ ID NO 267
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Cys Ala Val Tyr Gly Gly Ala Thr Asn Lys Leu Ile Phe
1               5                   10

<210> SEQ ID NO 268
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
tgtgctgttt atggtggtgc tacaaacaag ctcatctttt                                 39

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Cys Ala Ser Ser Ile Gly Glu Ala Phe Phe
1               5                   10

<210> SEQ ID NO 270
<211> LENGTH: 30
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 270
tgtgccagca gtattgggga agctttcttt                                           30

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Cys Ala Ser Thr Pro Gly Thr Gly Ala Tyr Glu Gln Tyr Phe
1               5                   10

<210> SEQ ID NO 272
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tgtgccagca cccccgggac aggggcgtac gagcagtact tc                             42

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Cys Ala Val Arg Ala Leu Val Pro Gly Ala Gly Ser Tyr Gln Leu Thr
1               5                   10                  15

Phe

<210> SEQ ID NO 274
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tgtgctgtga gagccctcgt ccctggggct gggagttacc aactcacttt c                   51

<210> SEQ ID NO 275
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Cys Ala Ser Asn Asp Tyr Ser Ser Pro Leu His Phe
1               5                   10
```

```
<210> SEQ ID NO 276
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tgtgccagca acgactatag ttcaccccte cactttt                                36

<210> SEQ ID NO 277
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Cys Ala Val Asn Arg Gly Gly Gly Asn Lys Leu Thr Phe
1               5                   10

<210> SEQ ID NO 278
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tgtgccgtga accggggagg aggaaacaaa ctcacctttt                             39

<210> SEQ ID NO 279
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Cys Ala Ser Ser Tyr Gly Gly Ala Tyr Glu Gln Tyr Phe
1               5                   10

<210> SEQ ID NO 280
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tgtgccagca gttatggggg agcctacgag cagtacttc                              39

<210> SEQ ID NO 281
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Cys Ile Ser Trp Ile Pro Ser Leu Glu Thr Gln Pro Pro Pro Leu Arg
```

-continued

```
1               5                  10                 15
Ser Gln Leu Ile Phe
            20

<210> SEQ ID NO 282
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tgcatatcat ggattcccag cctggagact cagccacccc ccttgaggtc gcaactcatc    60
ttt                                                                 63

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Cys Ala Ser Ser Pro Val Gln Gly Val Tyr Asn Glu Gln Phe Phe
1               5                   10                  15

<210> SEQ ID NO 284
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
tgtgccagca gcccagtcca gggggtttac aatgagcagt tcttc                    45

<210> SEQ ID NO 285
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Cys Ala Thr Pro Arg Tyr Phe
1               5

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tgtgcaaccc cgcgctattt t                                              21

<210> SEQ ID NO 287
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 287

Cys Ala Ser Ser Leu Ala Gly Glu Thr Gln Tyr Phe
1               5                   10

<210> SEQ ID NO 288
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tgtgccagca gcctcgcggg agagacccag tacttc                                  36

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Cys Ala Ala Ser Leu Ile Gly Lys Leu Thr Phe
1               5                   10

<210> SEQ ID NO 290
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
tgtgcagcaa gccttatagg gaaactgaca ttt                                     33

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Cys Ala Ser Ser Gln Leu Gln Ser Ser Tyr Asn Glu Gln Phe Phe
1               5                   10                  15

<210> SEQ ID NO 292
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
tgtgccagca gccaattaca gagctcctac aatgagcagt tcttc                        45

<210> SEQ ID NO 293
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ser Gly His Asn Ser
1               5

<210> SEQ ID NO 294
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tcaggccaca actcc                                                    15

<210> SEQ ID NO 295
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Phe Asn Asn Asn Val Pro
1               5

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
tttaacaaca acgttccg                                                 18

<210> SEQ ID NO 297
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Asp Phe Gln Ala Thr Thr
1               5

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gactttcagg ccacaact                                                 18
```

```
<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ser Asn Glu Gly Ser Lys Ala
1               5

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
tccaatgagg gctccaaggc c                                              21

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Tyr Ser Gly Ser Pro Glu
1               5

<210> SEQ ID NO 302
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tattctggga gtcctgaa                                                  18

<210> SEQ ID NO 303
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

His Ile Ser Arg
1

<210> SEQ ID NO 304
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
cacatctcta ga                                                        12
```

```
<210> SEQ ID NO 305
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ser Gly His Ala Thr
1               5

<210> SEQ ID NO 306
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
tctggccatg ctacc                                                    15

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Phe Gln Asp Glu Ser Val
1               5

<210> SEQ ID NO 308
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tttcaggatg agagtgta                                                 18

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Asp Ser Ser Ser Thr Tyr
1               5

<210> SEQ ID NO 310
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
```
gacagctcct ccacctac                                                  18

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ile Phe Ser Asn Met Asp Met
1               5

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312 atttttcaa atatggacat g                                               21

<210> SEQ ID NO 313
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ser Gly His Asp Thr
1               5

<210> SEQ ID NO 314
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tctgggcatg acact                                                     15

<210> SEQ ID NO 315
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Tyr Tyr Glu Glu Glu Glu
1               5

<210> SEQ ID NO 316
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 316
tattatgagg aggaagag                                              18

<210> SEQ ID NO 317
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Leu Asn His Asn Val
1               5

<210> SEQ ID NO 318
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
ttgaaccata acgtc                                                 15

<210> SEQ ID NO 319
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Tyr Tyr Asp Lys Asp Phe
1               5

<210> SEQ ID NO 320
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tactatgaca aagatttt                                              18

<210> SEQ ID NO 321
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ser Ser Asn Phe Tyr Ala
1               5

<210> SEQ ID NO 322
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 322
tccagcaatt tttatgcc                                                  18

<210> SEQ ID NO 323
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Met Thr Leu Asn Gly Asp Glu
1               5

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
atgactttaa atggggatga a                                              21

<210> SEQ ID NO 325
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ser Asn His Leu Tyr
1               5

<210> SEQ ID NO 326
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tctaatcact tatac                                                     15

<210> SEQ ID NO 327
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Phe Tyr Asn Asn Glu Ile
1               5

<210> SEQ ID NO 328
<211> LENGTH: 18
<212> TYPE: DNA

<213> ORGANISM: Artificial Sequence
<220> FEATURE:
<223> OTHER INFORMATION: Description of Artificial Sequence: Synthetic
       oligonucleotide

<400> SEQUENCE: 328
ttttataata atgaaatc                                                   18

<210> SEQ ID NO 329
<211> LENGTH: 5
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 329

Ser Gly His Val Ser
1               5

<210> SEQ ID NO 330
<211> LENGTH: 15
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 330
tcgggtcatg tatcc                                                      15

<210> SEQ ID NO 331
<211> LENGTH: 6
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 331

Phe Gln Asn Glu Ala Gln
1               5

<210> SEQ ID NO 332
<211> LENGTH: 18
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 332
ttccagaatg aagctcaa                                                   18

<210> SEQ ID NO 333
<211> LENGTH: 6
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 333

Ser Ser Val Pro Pro Tyr
1               5

<210> SEQ ID NO 334

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tcgtctgttc caccatat                                                    18

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Tyr Thr Ser Ala Ala Thr Leu Val
1               5

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tacacatcag cggccaccct ggtt                                             24

<210> SEQ ID NO 337
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ala Thr Gly Tyr Pro Ser
1               5

<210> SEQ ID NO 338
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gccacaggat acccttcc                                                    18

<210> SEQ ID NO 339
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ala Thr Lys Ala Asp Asp Lys
1               5
```

```
<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gccacgaagg ctgatgacaa g                                              21

<210> SEQ ID NO 341
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asp Ser Ala Ser Asn Tyr
1               5

<210> SEQ ID NO 342
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gacagtgcct caaactac                                                  18

<210> SEQ ID NO 343
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ile Arg Ser Asn Val Gly Glu
1               5

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
attcgttcaa atgtgggcga a                                              21

<210> SEQ ID NO 345
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Met Asn His Asn Tyr
```

<210> SEQ ID NO 346
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
atgaaccata actac                                                     15

<210> SEQ ID NO 347
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ser Val Gly Ala Gly Ile
1               5

<210> SEQ ID NO 348
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tcagttggtg ctggtatc                                                  18

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Tyr Thr Ser Ala Ala Thr Leu Ala
1               5

<210> SEQ ID NO 350
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
tacacatcag cggccaccct ggct                                           24

<210> SEQ ID NO 351
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asn Ile Ala Thr Asn Asp Tyr
1               5

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
aacattgcta caaatgatta t                                              21

<210> SEQ ID NO 353
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Gly Tyr Lys Thr Lys
1               5

<210> SEQ ID NO 354
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
ggatacaaga caaaa                                                     15

<210> SEQ ID NO 355
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Met Asn His Glu Tyr
1               5

<210> SEQ ID NO 356
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
atgaaccatg aatac                                                     15

<210> SEQ ID NO 357
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 357

Ser Val Gly Glu Gly Thr
1               5

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tcagttggtg agggtaca                                                 18

<210> SEQ ID NO 359
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
atgaaccatg agtat                                                    15

<210> SEQ ID NO 360
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ser Met Asn Val Glu Val
1               5

<210> SEQ ID NO 361
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tcaatgaatg ttgaggtg                                                 18

<210> SEQ ID NO 362
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Gly His Asp Tyr
1               5

<210> SEQ ID NO 363
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 363
tcaggacacg actac                                                    15

<210> SEQ ID NO 364
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ser Glu His Asn Arg
1               5

<210> SEQ ID NO 365
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tctgaacaca accgc                                                    15

<210> SEQ ID NO 366
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ala Gln Lys Val Thr Gln Ala Gln Ser Ser Val Ser Met Pro Val Arg
1               5                  10                  15

Lys Ala Val Thr Leu Asn Cys Leu Tyr Glu
            20                  25

<210> SEQ ID NO 367
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
acaagttggt ggtcatatta t                                             21

<210> SEQ ID NO 368
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gln Gly Ser
1
```

```
<210> SEQ ID NO 369
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369 cagggttct                                                                 9

<210> SEQ ID NO 370
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Phe Gln Asn Asn Gly Val
1               5

<210> SEQ ID NO 371
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tttcagaata acggtgta                                                      18

<210> SEQ ID NO 372
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ser Gly His Arg Ser
1               5

<210> SEQ ID NO 373
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
tctgggcata ggagt                                                         15

<210> SEQ ID NO 374
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Tyr Phe Ser Glu Thr Gln
1               5
```

<210> SEQ ID NO 375
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tacttcagtg agacacag                                                 18

<210> SEQ ID NO 376
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Ile Asn Ala Glu Tyr Gln Ile Gly Ser His Val Ser Val Ser Glu Gly
1               5                  10                  15

Ala Leu Val Leu Leu Arg Cys Asn Tyr Ser
            20                  25

<210> SEQ ID NO 377
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Lys Asn Gln Val Glu Gln Ser Pro Gln Ser Leu Ile Ile Leu Glu Gly
1               5                  10                  15

Lys Asn Cys Thr Leu Gln Cys Asn Tyr Thr
            20                  25

<210> SEQ ID NO 378
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gtgagcccct tcagcaac                                                 18

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Met Thr Phe Ser Glu Asn Thr
1               5

<210> SEQ ID NO 380
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 380
atgactttca gtgagaacac a                                              21

<210> SEQ ID NO 381
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ser Gln Val Thr Met
1               5

<210> SEQ ID NO 382
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
agccaagtca ccatg                                                     15

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Asn Gln Gly Ser Glu Ala
1               5

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gcaaatcagg gctctgaggc c                                              21

<210> SEQ ID NO 385
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Trp Ser His Ser Tyr
1               5

<210> SEQ ID NO 386

<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
tggagccaca gctat                                                      15

<210> SEQ ID NO 387
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Ala Ala Ala Asp Ile
1               5

<210> SEQ ID NO 388
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
tcagcagctg ctgatatt                                                   18

<210> SEQ ID NO 389
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gly Gln Gln Val Met Gln Ile Pro Gln Tyr Gln His Val Gln Glu Gly
1               5                   10                  15

Glu Asp Phe Thr Thr Tyr Cys Asn Ser Ser
            20                  25

<210> SEQ ID NO 390
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
actactttaa gcaat                                                      15

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Leu Val Lys Ser Gly Glu Val
1               5

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
ttagtgaaga gtggagaagt g                                        21

<210> SEQ ID NO 393
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ile Asn Ala Glu Tyr Arg Cys Gly Ser His Val Ser Val Ser Glu Gly
1               5                   10                  15

Ala Leu Val Leu Leu Arg Cys Asn Tyr Ser
            20                  25

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Thr Ile Ser Gly Asn Glu Tyr
1               5

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
accatcagtg gaaatgagta t                                        21

<210> SEQ ID NO 396
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gly Leu Lys Asn Asn
1               5

<210> SEQ ID NO 397
<211> LENGTH: 15
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 397
ggtctaaaaa acaat                                                          15

<210> SEQ ID NO 398
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Pro Arg His Asp Thr
1               5

<210> SEQ ID NO 399
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cctagacacg acact                                                          15

<210> SEQ ID NO 400
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Phe Tyr Glu Lys Met Gln
1               5

<210> SEQ ID NO 401
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
ttttatgaaa agatgcag                                                       18

<210> SEQ ID NO 402
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Phe Asn Asn Asn Val Ser
1               5

<210> SEQ ID NO 403
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tttaacaaca acgtttcg                                                    18

<210> SEQ ID NO 404
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Leu Gly His Asp Thr
1               5

<210> SEQ ID NO 405
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
ctgggccatg atact                                                       15

<210> SEQ ID NO 406
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Tyr Asn Asn Lys Glu Leu
1               5

<210> SEQ ID NO 407
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
tacaataata aggagctc                                                    18

<210> SEQ ID NO 408
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Asn Ser Ala Phe Gln Tyr
1               5
```

```
<210> SEQ ID NO 409
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
aacagtgctt ttcaatac                                                 18

<210> SEQ ID NO 410
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Thr Tyr Ser Ser Gly Asn
1               5

<210> SEQ ID NO 411
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
acatactcca gtggtaac                                                 18

<210> SEQ ID NO 412
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Ser Gly His Asp Asn
1               5

<210> SEQ ID NO 413
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tctggacatg ataat                                                    15

<210> SEQ ID NO 414
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Phe Val Lys Glu Ser Lys
1               5
```

<210> SEQ ID NO 415
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
tttgtgaaag agtctaaa                                                     18

<210> SEQ ID NO 416
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Leu Gly His Asn Ala
1               5

<210> SEQ ID NO 417
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
ctgggtcata acgct                                                        15

<210> SEQ ID NO 418
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Tyr Ser Leu Glu Glu Arg
1               5

<210> SEQ ID NO 419
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
tacagtcttg aagaacgg                                                     18

<210> SEQ ID NO 420
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Met Gly His Arg Ala
1               5

<210> SEQ ID NO 421
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
atggggcaca gggct                                                    15

<210> SEQ ID NO 422
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Tyr Ser Tyr Glu Lys Leu
1               5

<210> SEQ ID NO 423
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
tacagctatg agaaactc                                                 18

<210> SEQ ID NO 424
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Thr Ile Ser Gly Thr Asp Tyr
1               5

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
acaatcagtg gaactgatta c                                             21

<210> SEQ ID NO 426
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 426

Gly Leu Thr Ser Asn
1               5

<210> SEQ ID NO 427
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ggtcttacaa gcaat                                                     15

<210> SEQ ID NO 428
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Phe Asn Tyr Glu Ala Gln
1               5

<210> SEQ ID NO 429
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
ttcaattatg aagcccaa                                                  18

<210> SEQ ID NO 430
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Asp Ser Val Asn Asn
1               5

<210> SEQ ID NO 431
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
gactctgtga acaat                                                     15

<210> SEQ ID NO 432
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 432

Ile Pro Ser Gly Thr
1               5

<210> SEQ ID NO 433
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
attccctcag ggaca                                                    15

<210> SEQ ID NO 434
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
tcgtctgttc caccgtat                                                 18

<210> SEQ ID NO 435
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Thr Ser Gly Phe Asn Gly
1               5

<210> SEQ ID NO 436
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
acatctgggt tcaacggg                                                 18

<210> SEQ ID NO 437
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Asn Val Leu Asp Gly Leu
1               5

<210> SEQ ID NO 438
<211> LENGTH: 18
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 438
aatgttctgg atggtttg                                                 18

<210> SEQ ID NO 439
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Asp Arg Gly Ser Gln Ser
1               5

<210> SEQ ID NO 440
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
gaccgaggtt cccagtcc                                                 18

<210> SEQ ID NO 441
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Ile Tyr Ser Asn Gly Asp
1               5

<210> SEQ ID NO 442
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
atatactcca atggtgac                                                 18

<210> SEQ ID NO 443
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Asn Ser Met Phe Asp Tyr
1               5

<210> SEQ ID NO 444
<211> LENGTH: 18

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
aacagcatgt ttgattat                                                        18

<210> SEQ ID NO 445
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ile Ser Ser Ile Lys Asp Lys
1               5

<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
ataagttcca ttaaggataa a                                                    21
```

NEOANTIGEN PEPTIDE MIMICS

SEQUENCE LISTING

The instant application contains a Sequence Listing which has been submitted electronically in ASCII format and is hereby incorporated by reference in its entirety. Said ASCII copy, created on Jan. 3, 2022, is named 103693_002689_SL.txt and is 181,053 bytes in size.

CROSS REFERENCE TO RELATED APPLICATIONS

This application claims priority to U.S. Provisional Patent Application No. 63/130,083, filed Dec. 23, 2020, the contents of which is incorporated herein by reference in its entirety.

TECHNICAL FIELD

Provided are polypeptide fragments and polynucleotides based on mutant capicua transcriptional repressor (CIC), catenin beta 1 (CTNNB1), v-erb-b2 erythroblastic leukemia viral oncogene homolog B (ERBB2), kirsten rat sarcoma (KRAS), phosphatidylinositol-4,5-bisphosphate 3-kinase catalytic subunit alpha (PIK3CA), phosphatase and tensin homolog (PTEN), splicing factor 3b subunit 1 (SF3B1), SRY-box transcription factor 17 (SOX17), tumor protein 53 (TP53), and cytomegalovirus (CMV), as well as vectors, host cells, viruses, methods for generating CD8+ T-cells, and methods of treatment. Also provided are T-cell receptors (TCRs), polynucleotides and vectors that encode the TCRs, cells comprising the TCRs, and methods of treatment.

BACKGROUND

Clinical evidence demonstrates the central role for neoantigen-specific T cell responses in cancer. For example, neoantigen load is associated with better clinical outcomes, neoantigen-specific T cells have shown clinical evidence of anti-tumor activity, and neoantigen-specific T cells kill tumor cell in vitro and in vivo. However, recurrent oncogenic mutations are expected to be poor binders to class I HLA alleles.

SUMMARY

Described herein are capicua transcriptional repressor (CIC) polypeptide fragments comprising: an arginine to tryptophan amino acid substitution at a position corresponding to position 215 of SEQ ID NO: 102 (R215W), and an amino acid substitution at amino acid position 2 of the fragment, amino acid position 9 of the fragment, or both, wherein the fragment is at least nine amino acids in length, and wherein the fragment binds to HLA-A*02:01. In some embodiments, the CIC polypeptide fragment has greater affinity for HLA-A*02:01 than a cognate native polypeptide fragment. In certain embodiments, the R215W substitution is at amino acid position 8 of the fragment. In further embodiments, the CIC polypeptide fragment is selected from the group consisting of SEQ ID NO: 25, SEQ ID NO: 26 and SEQ ID NO: 27.

Described herein are catenin beta 1 (CTNNB1) polypeptide fragments comprising: (i) a serine to cysteine amino acid substitution at a position corresponding to position 33 of SEQ ID NO: 103 (S33C), or (i) a serine to phenylalanine amino acid substitution at a position corresponding to position 37 of SEQ ID NO: 103 (S37F), and an amino acid substitution at amino acid position 2 of the fragment, amino acid position 9 of the fragment, or both, wherein the fragment is at least nine amino acids in length, and wherein the fragment binds to HLA-A*02:01. In certain embodiments, the CTNNB1 polypeptide fragment has greater affinity for HLA-A*02:01 than a cognate native polypeptide fragment. In some embodiments, the S33C substitution is at amino acid position 4 of the fragment. In further embodiments, the S37F substitution is at amino acid position 8 of the fragment. In still further embodiments, the CTNNB1 polypeptide fragment is selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 80, and SEQ ID NO: 81.

Described herein are v-erb-b2 erythroblastic leukemia viral oncogene homolog B (ERBB2) polypeptide fragments comprising a valine to isoleucine amino acid substitution at a position corresponding to position 842 of SEQ ID NO: 104 (V842I), and an amino acid substitution at amino acid position 2 of the fragment, amino acid position 9 of the fragment, or both, wherein the fragment is at least nine amino acids in length, and wherein the fragment binds to HLA-A*02:01. In some embodiments, the ERBB2 polypeptide fragment has greater affinity for HLA-A*02:01 than a cognate native polypeptide fragment. In certain embodiments, the V842I substitution at amino acid position 3 of the fragment. In still further embodiments, the ERBB2 polypeptide fragment is selected from the group consisting of SEQ ID NO: 84, SEQ ID NO: 85, and SEQ ID NO: 86.

Described herein are kirsten rat sarcoma (KRAS) polypeptide fragments comprising: (i) a glycine to alanine amino acid substitution at a position corresponding to position 12 of SEQ ID NO: 105 (G12A), (ii) a glycine to cysteine amino acid substitution at a position corresponding to position 12 of SEQ ID NO: 105 (G12C), or (iii) a glycine to valine amino acid substitution at a position corresponding to at position 12 of SEQ ID NO: 105 (G12V), and an amino acid substitution at amino acid position 2 of the fragment, amino acid position 9 of the fragment, or both, wherein the fragment is at least nine amino acids in length, and wherein the fragment binds to HLA-A*02:01. In some embodiments, the KRAS polypeptide fragment has greater affinity for HLA-A*02:01 than a cognate native polypeptide fragment. In certain embodiments, the G12A substitution is at amino acid position 7 of the fragment. In further embodiments, the G12C substitution is at amino acid position 7 of the fragment. In still further embodiments, the G12V substitution is at amino acid position 7 of the fragment. In some embodiments, the KRAS polypeptide fragment is selected from the group consisting of SEQ ID NO: 37, SEQ ID NO: 38, SEQ ID NO: 39, SEQ ID NO: 40, SEQ ID NO: 41, and SEQ ID NO: 42.

Described herein are phosphatidylinositol-4,5-bisphosphate 3-kinase catalytic subunit alpha (PIK3CA) polypeptide fragments comprising: (i) a glutamic acid to lysine amino acid substitution at a position corresponding to position 453 of SEQ ID NO: 106 (E453K), or (ii) a glycine to aspartic acid amino acid substitution at a position corresponding to position 118 of SEQ ID NO: 106 (G118D), and an amino acid substitution at amino acid position 2 of the fragment, amino acid position 9 of the fragment, or both, wherein the fragment is at least nine amino acids in length, and wherein the fragment binds to HLA-A*02:01. In some embodiments, the PIK3CA polypeptide fragment has greater affinity for HLA-A*02:01 than a cognate native polypeptide fragment. In certain embodiments, the E453K substitution is at amino acid position 3 of the fragment. In further embodiments, the G118D substitution is at amino acid position 7 of the fragment. In still further embodiments, the PIK3CA polypeptide fragment is selected from the group consisting of SEQ ID NO: 43, SEQ ID NO: 44, SEQ ID NO: 45, SEQ ID NO: 46, and SEQ ID NO: 47.

Described herein are phosphatase and tensin homolog (PTEN) polypeptide fragments comprising: an arginine to cysteine amino acid substitution at a position corresponding to position 173 of SEQ ID NO: 107 (R173C), and an amino acid substitution at amino acid position 3 of the fragment, amino acid position 10 of the fragment, or both, wherein the fragment is ten amino acids in length, and wherein the fragment binds to HLA-A*02:01. In some embodiments, the PTEN polypeptide fragment has greater affinity for HLA-A*02:01 than a cognate native polypeptide fragment. In certain embodiments, the R173C substitution is at amino acid position 1 of the fragment. In further embodiments, the PTEN polypeptide fragment is selected from the group consisting of SEQ ID NO: 48, SEQ ID NO: 49, and SEQ ID NO: 88.

Described herein are splicing factor 3b subunit 1 (SF3B1) polypeptide fragments comprising: an arginine to histidine amino acid substitution at a position corresponding to position 625 of SEQ ID NO: 108 (R625H), and an amino acid substitution at amino acid position 2 of the fragment, amino acid position 9 of the fragment, or both, wherein the fragment is at least nine amino acids in length, and wherein the fragment binds to HLA-A*02:01. In certain embodiments, the SF3B1 polypeptide fragment has greater affinity for HLA-A*02:01 than a cognate native epitope. In some embodiments, the R625H substitution is at amino acid position 7 of the fragment. In further embodiments, the SF3B1 polypeptide fragment is selected from the group consisting of SEQ ID NO: 51, SEQ ID NO: 52, SEQ ID NO: 53, SEQ ID NO: 90, SEQ ID NO: 91 and SEQ ID NO: 92.

Described herein are SRY-box transcription factor 17 (SOX17) polypeptide fragments comprising: a serine to isoleucine amino acid substitution at a position corresponding to position 403 of SEQ ID NO: 109 (S403I), and an amino acid substitution at amino acid position 2 of the fragment, amino acid position 9 of the fragment, or both, wherein the fragment is at least nine amino acids in length, and wherein the fragment binds to HLA-A*02:01. In certain embodiments, the SOX17 polypeptide fragment has greater affinity for HLA-A*02:01 than a cognate native polypeptide fragment. In some embodiments, the S403I substitution is at amino acid position 6 of the fragment. In further embodiments, the SOX17 polypeptide fragment is selected from the group consisting of SEQ ID NO: 54, SEQ ID NO: 55, SEQ ID NO: 56, and SEQ ID NO: 93.

Described herein are tumor protein 53 (TP53) polypeptide fragments comprising: (i) an arginine to leucine amino acid substitution at a position corresponding to position 110 of SEQ ID NO: 110 (R110L), (ii) a serine to phenylalanine amino acid substitution at a position corresponding to position 127 of SEQ ID NO: 110 (S127F), (iii) a lysine to asparagine amino acid substitution at a position corresponding to position 132 of SEQ ID NO: 110 (K132N), (iv) a cysteine to tyrosine amino acid substitution at a position corresponding to position 141 of SEQ ID NO: 110 (C141Y), (v) a proline to leucine amino acid substitution at a position corresponding to position 152 of SEQ ID NO: 110 (P152L), (vi) a histidine to leucine amino acid substitution at a position corresponding to position 193 of SEQ ID NO: 110 (H193L), (vii) a histidine to tyrosine amino acid substitution at a position corresponding to position 193 of SEQ ID NO: 110 (H193Y), (viii) a tyrosine to cysteine amino acid substitution at a position corresponding to position 220 of SEQ ID NO: 110 (Y220C), or (ix) a valine to methionine amino acid substitution at a position corresponding to position 272 of SEQ ID NO: 110 (V272M), and an amino acid substitution at amino acid position 2 of the fragment, amino acid position 9 of the fragment, or both, wherein the fragment is at least nine amino acids in length, and wherein the fragment binds to HLA-A*02:01. In certain embodiments, the TP53 polypeptide fragment has greater affinity for HLA-A*02:01 than a cognate native polypeptide fragment. In some embodiments, the R110L substitution is at amino acid position 8 of the fragment. In further embodiments, the S127F substitution is at amino acid position 7 of the fragment. In still further embodiments, the K132N substitution is at amino acid position 4 of the fragment. In certain embodiments, the C141Y substitution is at amino acid position 3 of the fragment. In further embodiments, the P152L substitution is at amino acid position 9 of the fragment. In still further embodiments, the H193L substitution is at amino acid position 7 of the fragment. In some embodiments, the Y220C substitution is at amino acid position 4 of the fragment. In further embodiments, the V272M substitution is at amino acid position 9 of the fragment. In still further embodiments, the TP53 polypeptide fragment is selected from the group consisting of SEQ ID NO: 57, SEQ ID NO: 58, SEQ ID NO: 59, SEQ ID NO: 60, SEQ ID NO: 61, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 94, SEQ ID NO: 95, and SEQ ID NO: 96.

Described herein is a polypeptide fragment selected from the group consisting of SEQ ID NO: 25, SEQ ID NO: 26 and SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 66, SEQ ID NO: 67, SEQ ID NO: 68, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81; SEQ ID NO: 84, SEQ ID NO: 85, and SEQ ID NO: 86, SEQ ID NO: 88, SEQ ID NO: 90, SEQ ID NO: 91, SEQ ID NO: 92, SEQ ID NO: 93, SEQ ID NO: 94, SEQ ID NO: 95, and SEQ ID NO: 96.

Described herein is a polypeptide fragment selected from the group consisting of SEQ ID NO: 29, SEQ ID NO: 32, SEQ ID NO: 45, SEQ ID NO: 59, SEQ ID NO: 64, SEQ ID NO: 68, SEQ ID NO: 75 and SEQ ID NO: 78.

Described herein are polynucleotides encoding at least one or more polypeptide fragments provided herein. In certain embodiments, the polynucleotide is cDNA.

Described herein are vectors comprising one or more polynucleotides provided herein. In certain embodiments, the vector is selected from an adenovirus vector, an alphaviral vector, a poxvirus vector, an adeno-associated virus vector, a retrovirus vector, a self-replicating RNA molecule, and a combination thereof. In certain embodiments, the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3. In some embodiments, the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Described herein are pharmaceutical compositions comprising at least one or more polypeptide fragments provided herein.

Described herein are pharmaceutical compositions comprising at least one or more polynucleotides provided herein.

Described herein are pharmaceutical compositions comprising at least one or more vectors provided herein.

Described herein are methods of treating cancer in a subject comprising administering to the subject in need thereof the polypeptide fragments, the polynucleotides encoding the polypeptide fragments, the vectors comprising the polynucleotides, or the pharmaceutical compositions described herein.

Described herein are methods of inducing an immune response in a subject comprising administering to the subject in need thereof the polypeptide fragments, the polynucleotides encoding the polypeptide fragments, the vectors comprising the polynucleotides, or the pharmaceutical compositions described herein.

Described herein are methods of treating, preventing, reducing a risk of onset or delaying the onset of a clinical condition characterized by expression of CTNNB1 mutant comprising a serine to cysteine amino acid substitution at a position corresponding to position 33 of SEQ ID NO: 103 (S33C) in a subject, the method comprising administering to the subject in need thereof a) a polynucleotide encoding a polypeptide fragment comprising SEQ ID NO: 2, b) a polynucleotide encoding a polypeptide fragment comprising SEQ ID NO: 29, or c) a combination thereof in an amount effective to treat, prevent, reduce the risk of onset or delay the onset of the clinical condition.

Described herein are methods of treating, preventing, reducing a risk of onset or delaying the onset of a clinical condition characterized by expression of a catenin beta 1 (CTNNB1) mutant comprising a serine to phenylalanine amino acid substitution at a position corresponding to position 37 of SEQ ID NO: 103 (S37F) in a subject, the method comprising administering to the subject in need thereof a) a polynucleotide encoding a polypeptide fragment comprising SEQ ID NO: 3, b) a polynucleotide encoding a polypeptide fragment comprising SEQ ID NO: 32, or c) a combination thereof in an amount effective to treat, prevent, reduce the risk of onset or delay the onset of the clinical condition.

Described herein are methods of treating, preventing, reducing a risk of onset or delaying the onset of a clinical condition characterized by expression of a phosphatidylinositol-4,5-bisphosphate 3-kinase catalytic subunit alpha (PIK3CA) mutant comprising a glycine to aspartic acid amino acid substitution at a position corresponding to position 118 of SEQ ID NO: 106 (G118D) in a subject, the method comprising administering to the subject in need thereof a) a polynucleotide encoding a polypeptide fragment comprising SEQ ID NO: 9, b) a polynucleotide encoding a polypeptide fragment comprising SEQ ID NO: 45, or c) a combination thereof in an amount effective to treat, prevent, reduce the risk of onset or delay the onset of the clinical condition.

Described herein are methods of treating, preventing, reducing a risk of onset or delaying the onset of a clinical condition characterized by expression of a tumor protein 53 (TP53) mutant comprising a cysteine to tyrosine amino acid substitution at a position corresponding to position 141 of SEQ ID NO: 110 (C141Y) in a subject, the method comprising administering to the subject in need thereof a) a polynucleotide encoding a polypeptide fragment comprising SEQ ID NO: 13, b) a polynucleotide encoding a polypeptide fragment comprising SEQ ID NO: 59, or c) a combination thereof in an amount effective to treat, prevent, reduce the risk of onset or delay the onset of the clinical condition.

Described herein are methods of treating, preventing, reducing a risk of onset or delaying the onset of a clinical condition characterized by expression of a tumor protein 53 (TP53) mutant comprising a lysine to asparagine amino acid substitution at a position corresponding to position 132 of SEQ ID NO: 110 (K132N) in a subject, the method comprising administering to the subject in need thereof a) a polynucleotide encoding a polypeptide fragment comprising SEQ ID NO: 16, b) a polynucleotide encoding a polypeptide fragment comprising SEQ ID NO: 64, or c) a combination thereof in an amount effective to treat, prevent, reduce the risk of onset or delay the onset of the clinical condition.

Described herein are methods of treating, preventing, reducing a risk of onset or delaying the onset of a clinical condition characterized by expression of a tumor protein 53 (TP53) mutant comprising a proline to leucine amino acid substitution at a position corresponding to position 152 of SEQ ID NO: 110 (P152L) in a subject, the method comprising administering to the subject in need thereof a) a polynucleotide encoding a polypeptide fragment comprising SEQ ID NO: 18, b) a polynucleotide encoding a polypeptide fragment comprising SEQ ID NO: 68, or c) a combination thereof in an amount effective to treat, prevent, reduce the risk of onset or delay the onset of the clinical condition.

Described herein are methods of treating, preventing, reducing a risk of onset or delaying the onset of a clinical condition characterized by expression of a tumor protein 53 (TP53) mutant comprising a valine to methionine amino acid substitution at a position corresponding to position 272 of SEQ ID NO: 110 (V272M) in a subject, the method comprising administering to the subject in need thereof a) a polynucleotide encoding a polypeptide fragment comprising SEQ ID NO: 22, b) a polynucleotide encoding a polypeptide fragment comprising SEQ ID NO: 75, or c) a combination thereof in an amount effective to treat, prevent, reduce the risk of onset or delay the onset of the clinical condition.

Described herein are methods of treating, preventing, reducing a risk of onset or delaying the onset of a clinical condition characterized by expression of a tumor protein 53 (TP53) mutant comprising a tyrosine to cysteine amino acid substitution at a position corresponding to position 220 of SEQ ID NO: 110 (Y220C) in a subject, the method comprising administering to the subject in need thereof a) a polynucleotide encoding a polypeptide fragment comprising SEQ ID NO: 23, b) a polynucleotide encoding a polypeptide fragment comprising SEQ ID NO: 78, or c) a combination thereof in an amount effective to treat, prevent, reduce the risk of onset or delay the onset of the clinical condition.

In certain embodiments the methods of treatment comprise administering the polynucleotide in part a) prior to administering the polynucleotide in part b). In certain embodiments the methods of treatment comprise administering the polynucleotide in part b) prior to administering the polynucleotide in part a). In certain embodiments the methods of treatment comprise administering the polynucleotide in part a) concurrently with the polynucleotide in part b).

In certain embodiments the methods of treatment comprise administering a vector encoding the polynucleotide of part a) and a vector encoding the polynucleotide of part b). In some embodiments, the vectors are independently selected from an adenovirus vector, an alphaviral vector, a poxvirus vector, an adeno-associated virus vector, a retrovirus vector, and a self-replicating RNA molecule. In further embodiments, the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3. In further embodiments, the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Described herein are kits of parts comprising a pair of polypeptide fragments selected from the group consisting of: (a) SEQ ID NO: 2 and SEQ ID NO: 29; (b) SEQ ID NO: 3 and SEQ ID NO: 32; (c) SEQ ID NO: 9 and SEQ ID NO: 45; (d) SEQ ID NO: 13 and SEQ ID NO: 59; (e) SEQ ID NO: 16 and SEQ ID NO: 64; (f) SEQ ID NO: 18 and SEQ ID NO 68; (g) SEQ ID NO: 22 and SEQ ID NO: 75; and (h) SEQ ID NO: 23 and SEQ ID NO: 78.

Described herein are kits of parts comprising a pair of polypeptide fragments selected from the group consisting of: (a) SEQ ID NO: 9 and SEQ ID NO: 45; (b) SEQ ID NO: 13 and SEQ ID NO: 59; and (c) SEQ ID NO: 18 and SEQ ID NO 68.

Described herein are methods for generating CD8+ T-cells that are positive for an HLA-A*02:01-restricted polypeptide fragment and a cognate native polypeptide fragment, comprising exposing CD8+ T-cells to the HLA-A*02:01-restricted polypeptide fragment and cognate native polypeptide fragment selected from the group consisting of: (a) SEQ ID NO: 2 and SEQ ID NO: 29; (b) SEQ ID NO: 3 and SEQ ID NO: 32; (c) SEQ ID NO: 9 and SEQ ID NO: 45; (d) SEQ ID NO: 13 and SEQ ID NO: 59; (e) SEQ ID NO: 16 and SEQ ID NO: 64; (f) SEQ ID NO: 18 and SEQ ID NO 68; (g) SEQ ID NO: 22 and SEQ ID NO: 75; and (h) SEQ ID NO: 23 and SEQ ID NO: 78; and selecting CD8+ T cells that are positive to both the HLA-A*02:01-restricted polypeptide fragment and a cognate neoantigen polypeptide fragment.

Described herein are methods for generating CD8+ T-cells that are positive for an HLA-A*02:01-restricted polypeptide fragment and a cognate native polypeptide fragment, comprising exposing CD8+ T-cells to the HLA-A*02:01-restricted polypeptide fragment and cognate native polypeptide fragment selected from the group consisting of: (a) SEQ ID NO: 9 and SEQ ID NO: 45; (b) SEQ ID NO: 13 and SEQ ID NO: 59; and (c) SEQ ID NO: 18 and SEQ ID NO 68; and selecting CD8+ T cells that are positive to both the HLA-A*02:01-restricted polypeptide fragment and a cognate neoantigen polypeptide fragment.

Described herein are T-cell receptors (TCRs) comprising an alpha chain and a beta chain, wherein: (a) the alpha chain comprises a complementarity determining region 3 (CDR3) comprising an amino acid sequence provided in Table 14, Table 15, Table 16, Table 17 or Table 18, and (b) the beta chain comprises a CDR3 comprising a corresponding amino acid sequence provided in Table 14, Table 15, Table 16, Table 17 or Table 18. An alpha chain CDR3 corresponds to a beta chain CDR3 if they appear in the same row in Table 14, Table 15, Table 16, Table 17, or Table 18.

Described herein are T-cell receptors (TCRs) comprising an alpha chain and a beta chain, wherein: (a) the alpha chain comprises a complementarity determining region 1 (CDR1) comprising an amino acid sequence provided in Table 19, Table 20, Table 21, Table 22, or Table 23, a complementarity determining region 2 (CDR2) comprising an amino acid sequence provided in Table 19, Table 20, Table 21, Table 22, or Table 23, and a complementarity determining region 3 (CDR3) comprising an amino acid sequence provided in Table 14, Table 15, Table 16, Table 17, or Table 18, and (b) the beta chain comprises a CDR1 comprising an amino acid sequence provided in Table 19, Table 20, Table 21, Table 22, or Table 23, a CDR2 comprising an amino acid sequence provided in Table 19, Table 20, Table 21, Table 22, or Table 23, and a CDR3 comprising a corresponding amino acid sequence provided in Table 14, Table 15, Table 16, Table 17 or Table 18. An alpha chain CDR1 or CDR2 corresponds to a beta chain CDR1 or CDR2 if they appear in the same row in Table 19, Table 20, Table 21, Table 22, or Table 23. An alpha chain CDR3 corresponds to a beta chain CDR3 if they appear in the same row in Table 14, Table 15, Table 16, Table 17, or Table 18. An alpha and beta chain CDR1 and CDR2 provided in Table 19, Table 20, Table 21, Table 22, or Table 23 correspond to an alpha and beta chain CDR3 provided in the same row in Table 14, Table 15, Table 16, Table 17 or Table 18.

Described herein are polynucleotides encoding the TCRs provided herein.

Described herein are vectors comprising the polynucleotides provided herein.

Described herein are cells transformed to express the polynucleotides provided herein.

Described herein are cells comprising the vectors provided herein. In certain embodiments, the cell is a CD8+ T cell.

Described herein are pharmaceutical compositions comprising the TCRs, polynucleotides, the vectors, or the cells provided herein.

Described herein are methods of treating cancer in a subject comprising administering to the subject in need thereof a pharmaceutical composition comprising a TCR described herein.

Described herein are methods of inducing an immune response in a subject comprising administering to the subject in need thereof a pharmaceutical composition comprising a TCR described herein.

Described herein are methods of treating, preventing, reducing a risk of onset or delaying the onset of a clinical condition characterized by expression of a phosphatidylinositol-4,5-bisphosphate 3-kinase catalytic subunit alpha (PIK3CA) mutant comprising a glycine to aspartic acid amino acid substitution at a position corresponding to position 118 of SEQ ID NO: 106 (G118D) in a subject comprising administering to the subject in need thereof a TCRs described herein.

Described herein are methods of treating, preventing, reducing a risk of onset or delaying the onset of a clinical condition characterized by expression of a tumor protein 53 (TP53) mutant comprising a cysteine to tyrosine amino acid substitution at a position corresponding to position 141 of SEQ ID NO: 110 (C141Y) in a subject comprising administering to the subject in need thereof a TCR described herein.

Described herein are methods of treating, preventing, reducing a risk of onset or delaying the onset of a clinical condition characterized by expression of a tumor protein 53 (TP53) mutant comprising a proline to leucine amino acid substitution at a position corresponding to position 152 of SEQ ID NO: 110 (P152L) in a subject comprising administering to the subject in need thereof a TCR described herein.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF ILLUSTRATIVE EMBODIMENTS

Figure 1:
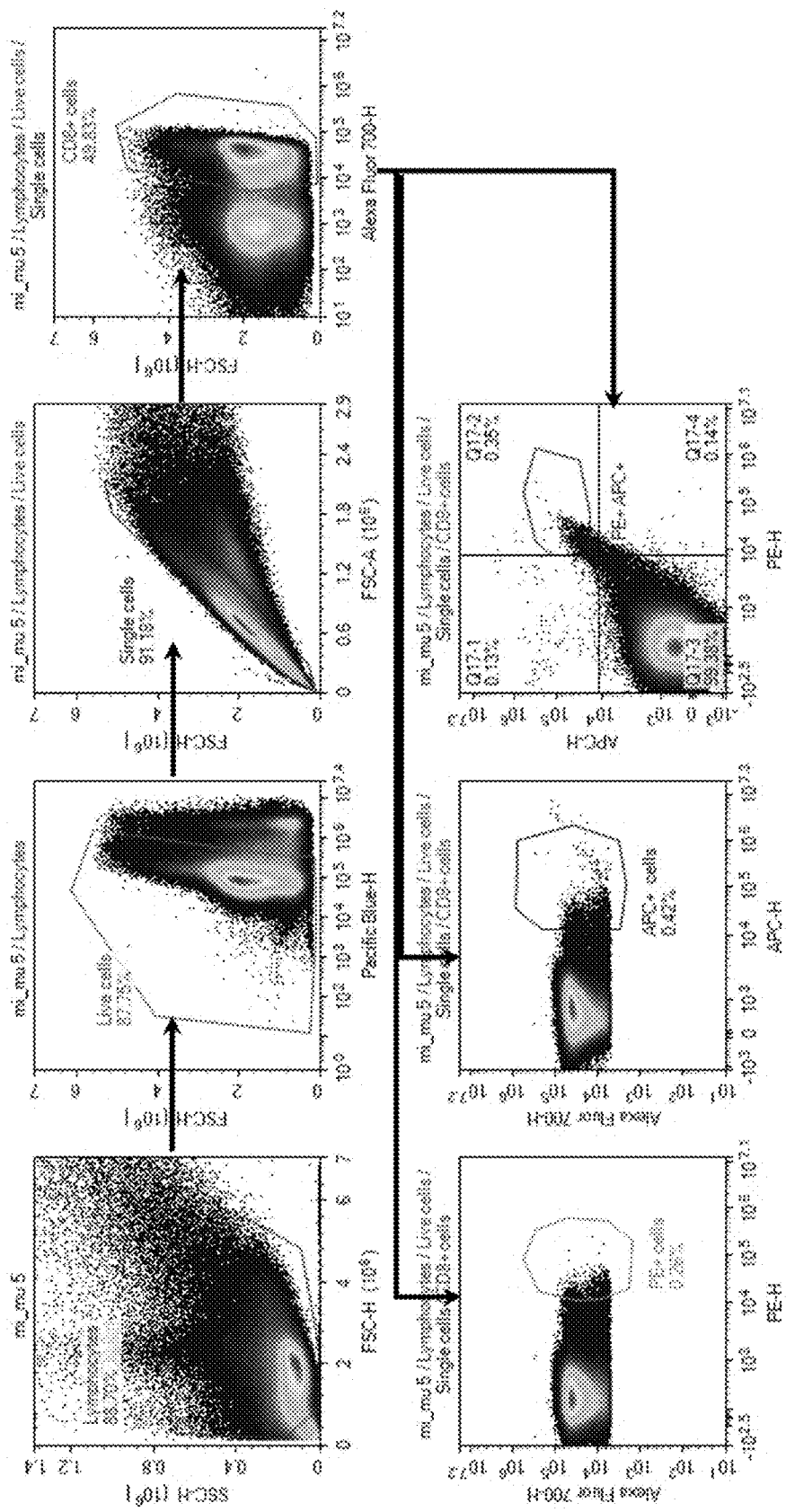
FIG. 1 illustrates exemplary FACS plots used to determine the frequency of dual positive T cells for tetramers specific for mutant and mimic peptides represented by SEQ ID NO: 9 and SEQ ID NO: 45. The donor used was Lot #19054445 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.
Figure 2:
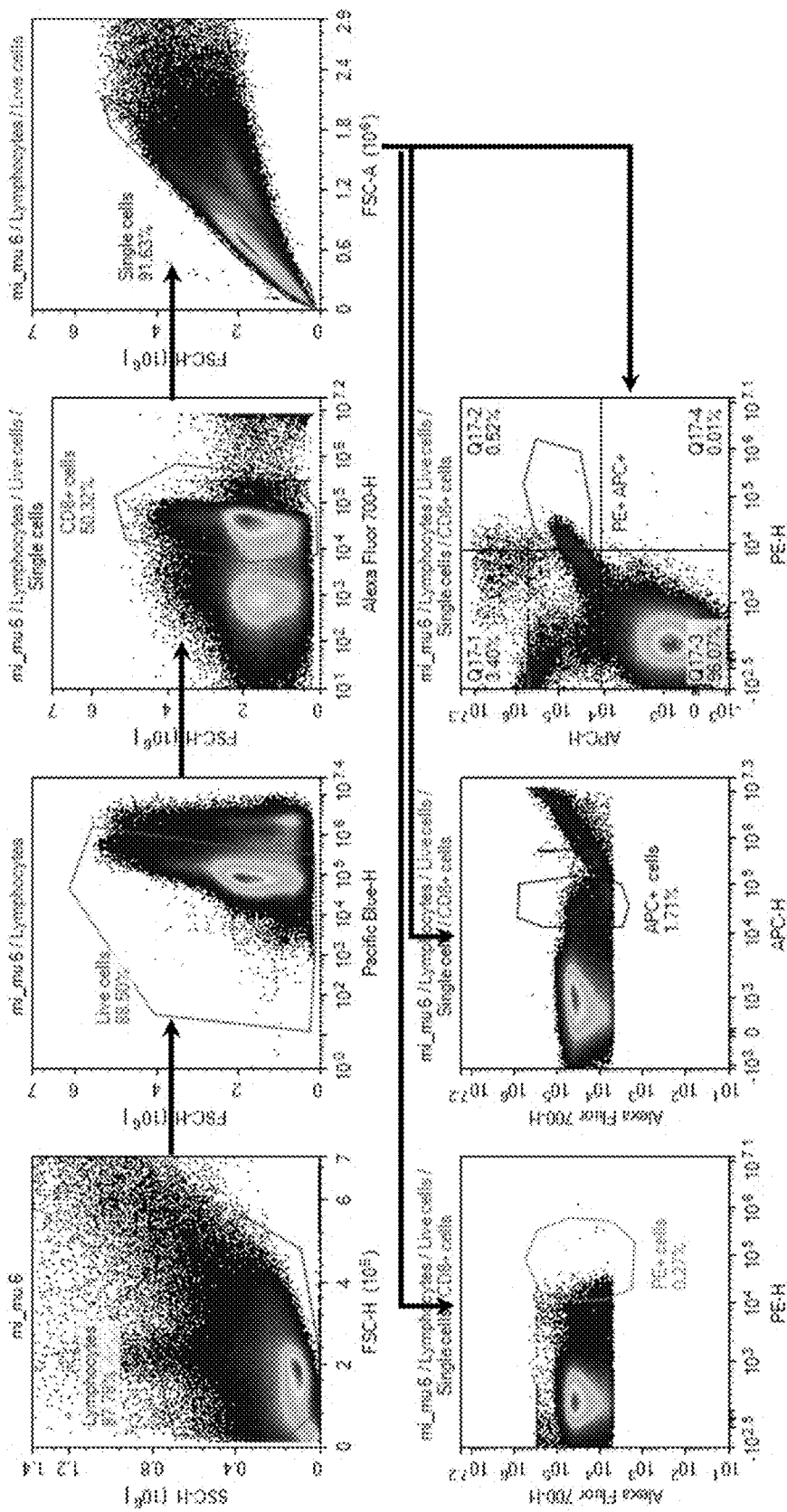
FIG. 2 illustrates exemplary FACS plots used to determine the frequency of dual positive T cells for tetramers specific for mutant and mimic peptides represented by SEQ ID NO: 13 and SEQ ID NO: 59. The donor used was Lot #19054445 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.
Figure 3:
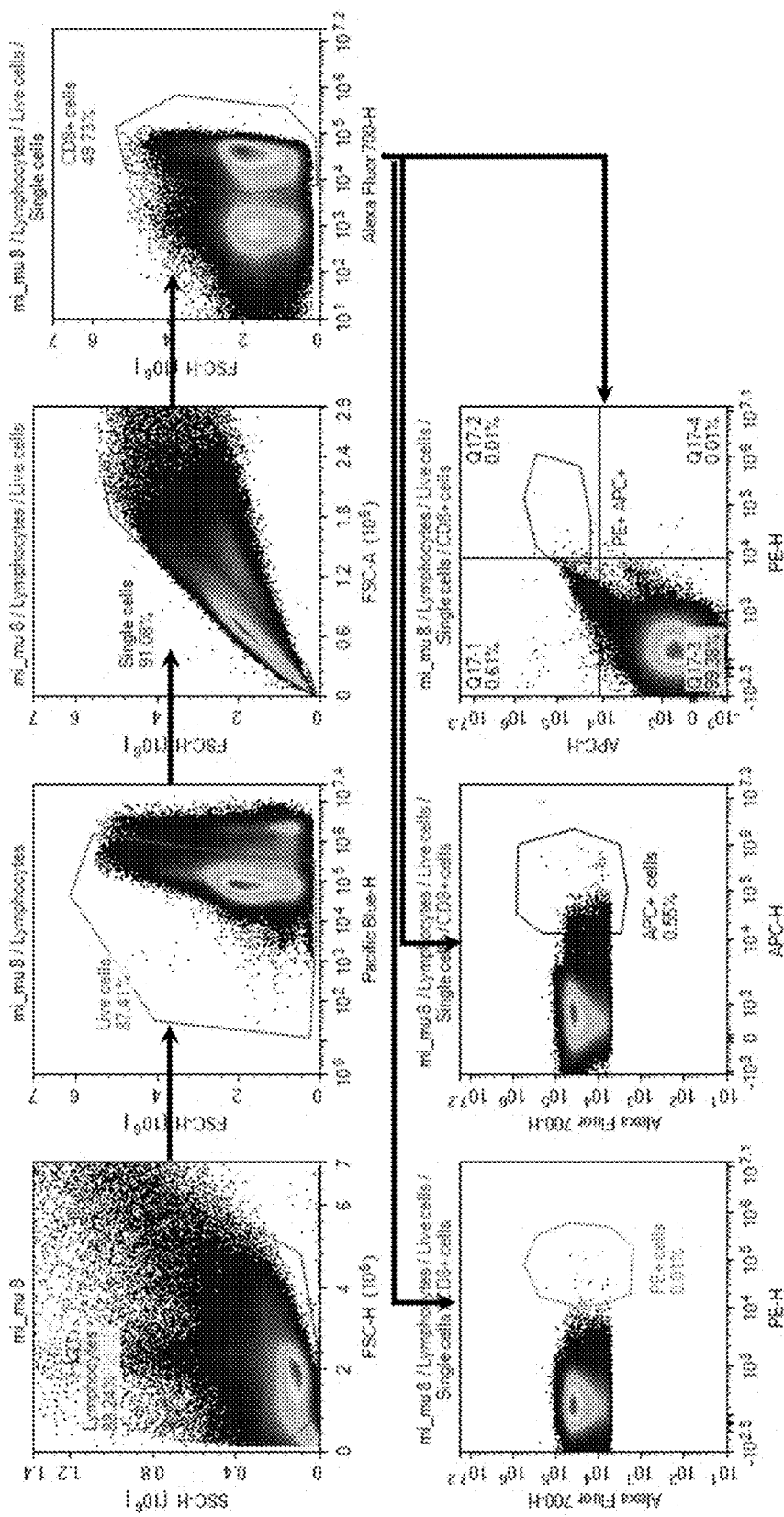
FIG. 3 illustrates exemplary FACS plots used to determine the frequency of dual positive T cells for tetramers specific for mutant and mimic peptides represented by SEQ ID NO: 18 and SEQ ID NO 68. The donor used was Lot #19054445 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.
Figure 4:
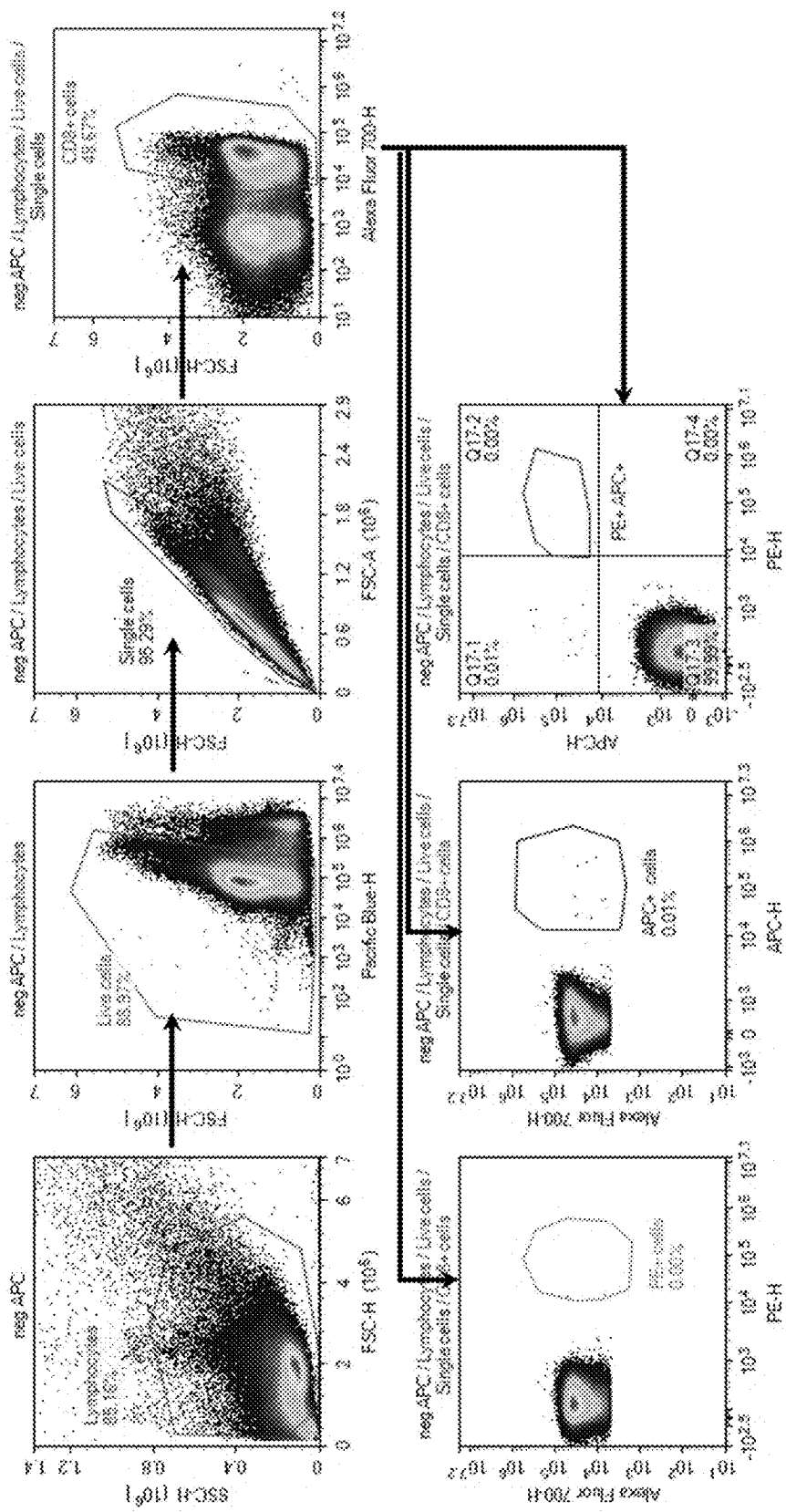
FIG. 4 illustrates exemplary FACS plots used to determine the frequency of T cells staining positive for negative tetramer on APC fluorescence channel. The negative tetramer is loaded with a non-specific peptide with no known reactivity. The negative tetramer was used as a control to gate on the cells. The donor used was Lot #19054445 from Hemacare. The gating strategy is mentioned in the figure. Lymphocytes derived from the donor were gated to remove dead cells. Live cells were further gated to remove doublets and other cell aggregates. Finally, CD8+ T cells were gated to exclude background signal arising from the negative tetramer. Neg APC refers to a sample in which negative tetramer for APC was used for staining.
Figure 5:
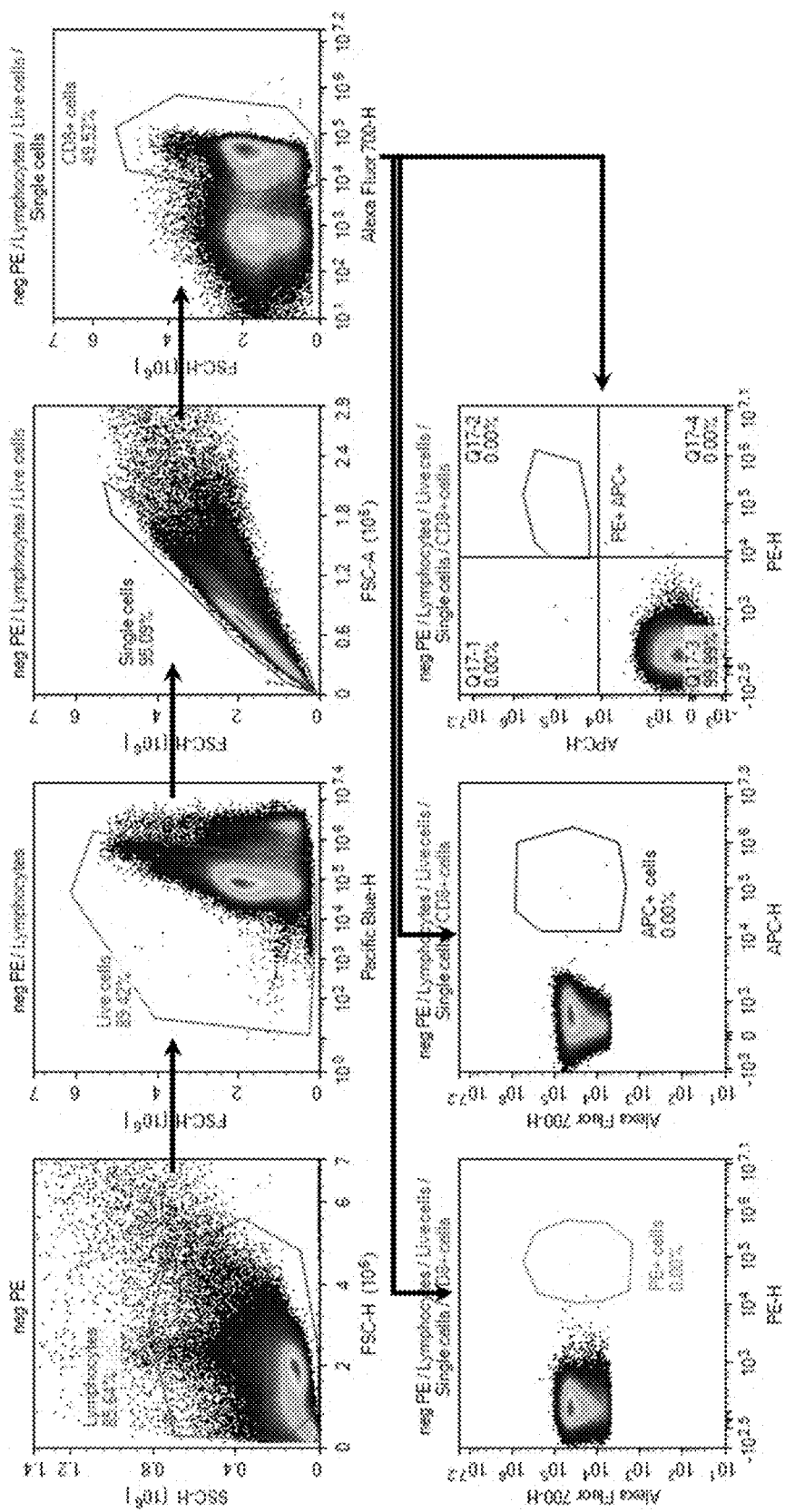
FIG. 5 illustrates exemplary FACS plots used to determine the frequency of T cells staining positive for negative tetramer on PE fluorescence channel. The negative tetramer is loaded with a non-specific peptide with no known reactivity. The negative tetramer was used as a control to gate on the cells. The donor used was Lot #19054445 from Hemacare. The gating strategy is mentioned in the figure. Lymphocytes derived from the donor were gated to remove dead cells. Live cells were further gated to remove doublets and other cell aggregates. Finally, CD8+ T cells were gated to exclude background signal arising from the negative tetramer. Neg PE refers to a sample in which negative tetramer for PE was used for staining.
Figure 6:
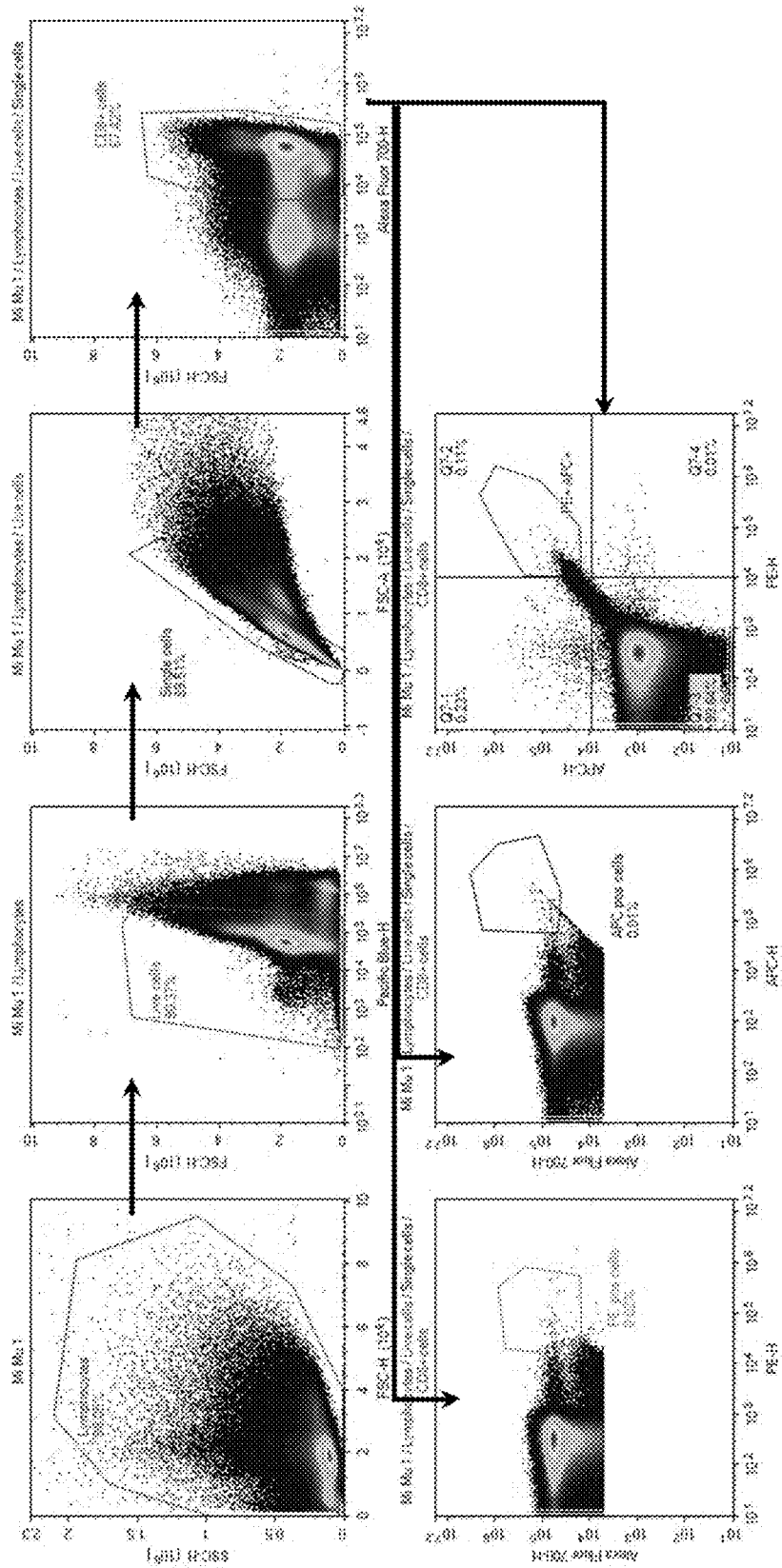
FIG. 6 illustrates exemplary FACS plots used to determine the frequency of dual positive T cells for tetramers specific for mutant and mimic peptides represented by SEQ ID NO: 2 and SEQ ID NO: 29. The donor used was Lot #20061357 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.
Figure 7:
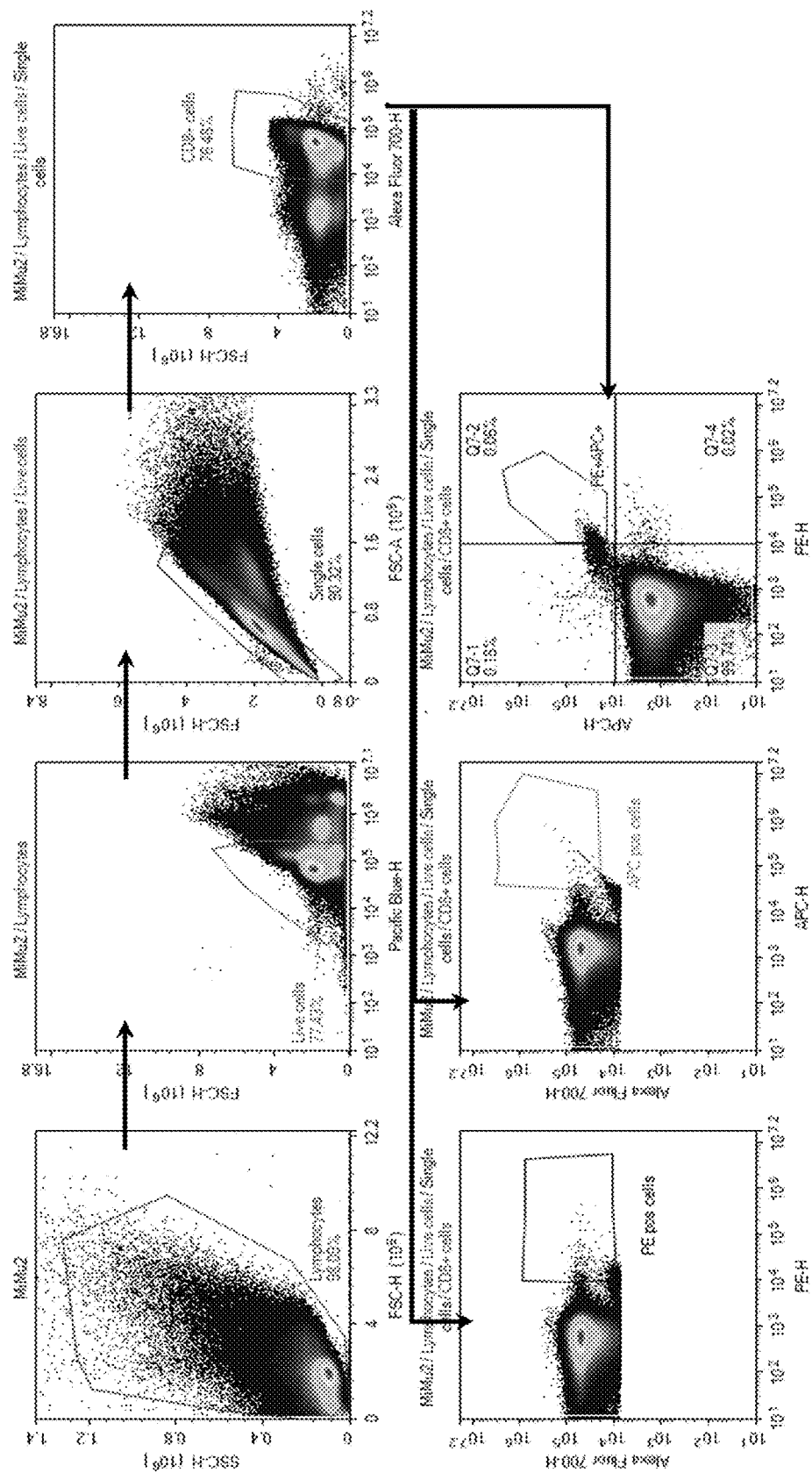
FIG. 7 illustrates exemplary FACS plots used to determine the frequency of dual positive T cells for tetramers specific for mutant and mimic peptides represented by SEQ ID NO: 3 and SEQ ID NO: 32. The donor used was Lot #20001476 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.
Figure 8:
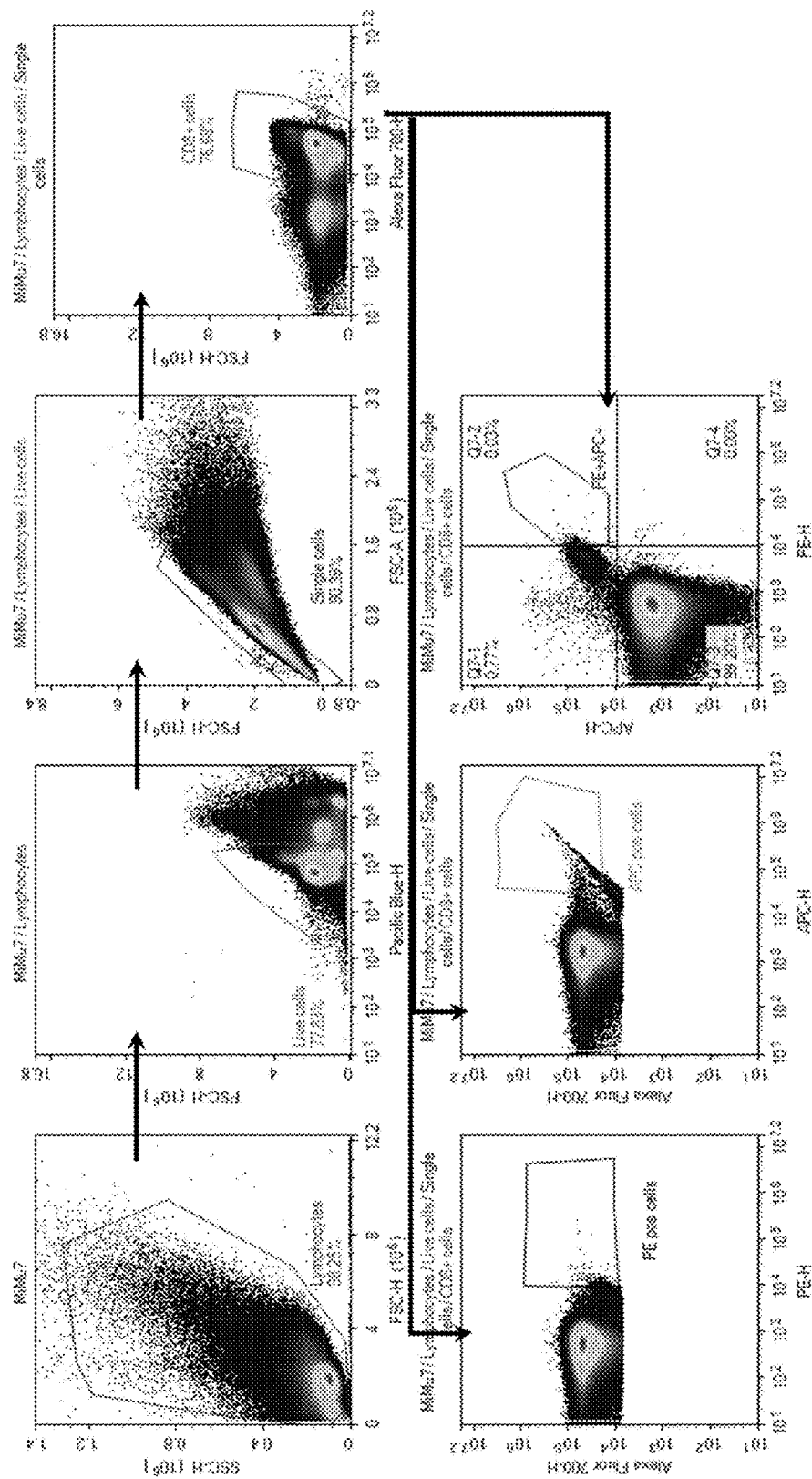
FIG. 8 illustrates exemplary FACS plots used to determine the frequency of dual positive T cells for tetramers specific for mutant and mimic peptides represented by SEQ ID NO: 16 and SEQ ID NO: 64. The donor used was Lot #20001476 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.
Figure 9:
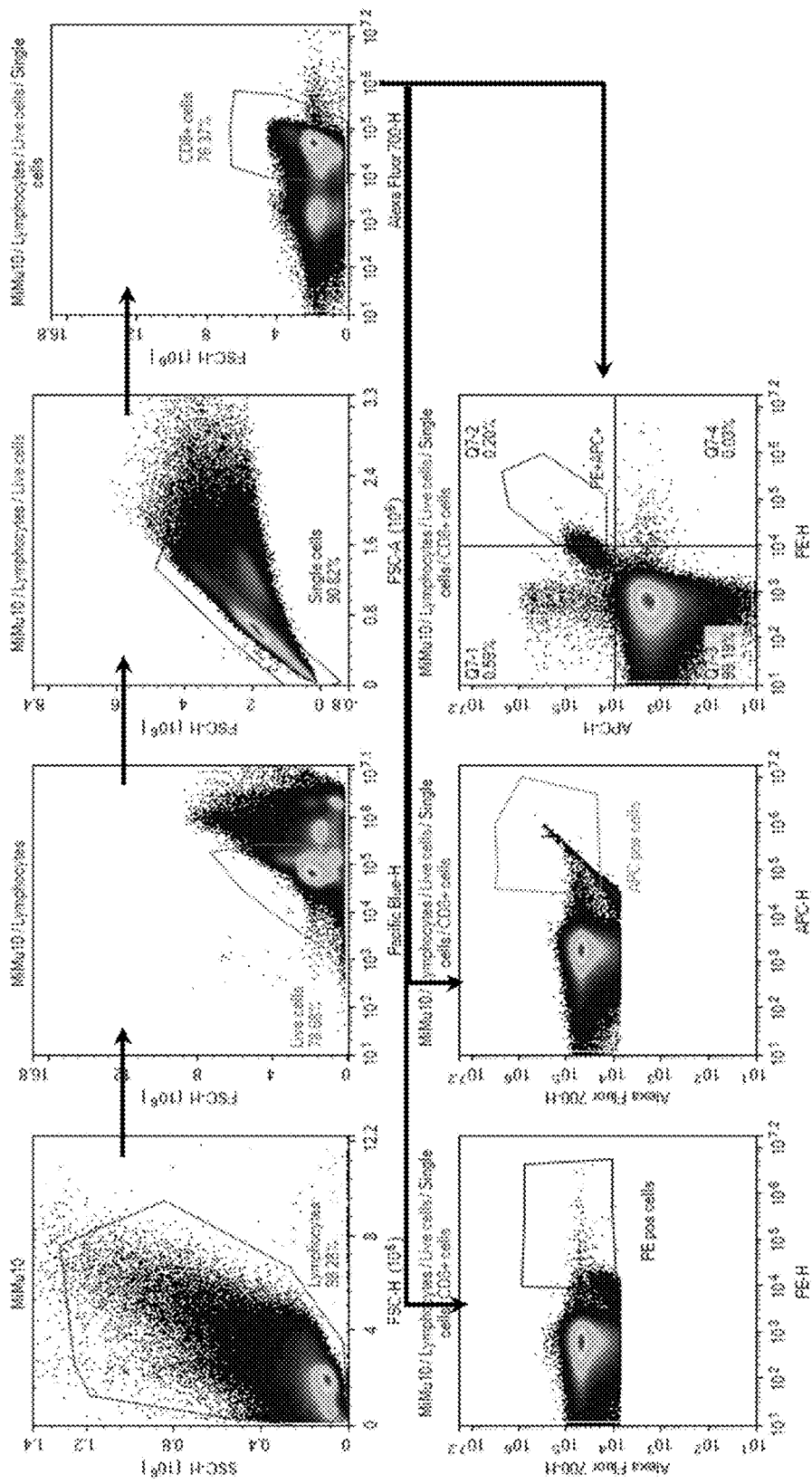
FIG. 9 illustrates exemplary FACS plots used to determine the frequency of dual positive T cells for tetramers specific for mutant and mimic peptides represented by SEQ ID NO: 23 and SEQ ID NO: 78. The donor used was Lot #20001476 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.

The disclosed polypeptide fragments, polynucleotides, vectors, compositions, kits, methods, T-cell receptors (TCRs), and cells may be understood more readily by reference to the following detailed description taken in connection with the accompanying figures, which form a part of this disclosure. It is to be understood that the disclosed polypeptide fragments, polynucleotides, vectors, compositions, kits, methods, T-cell receptors (TCRs), and cells are not limited to those specifically described and/or shown herein, and that the terminology used herein is for the purpose of describing particular embodiments by way of example only and is not intended to be limiting of the claimed polypeptide fragments, polynucleotides, vectors, compositions, kits, methods, T-cell receptors (TCRs), and cells.

Unless specifically stated otherwise, any description as to a possible mechanism or mode of action or reason for improvement is meant to be illustrative only, and the disclosed polypeptide fragments, polynucleotides, vectors, compositions, kits, methods, T-cell receptors (TCRs), and cells are not to be constrained by the correctness or incorrectness of any such suggested mechanism or mode of action or reason for improvement.

Throughout this text, the descriptions refer to polypeptide fragments and methods of using said polypeptide fragments. Where the disclosure describes or claims a feature or embodiment associated with a polypeptide fragment, such a feature or embodiment is equally applicable to the methods of using said polypeptide fragment. Likewise, where the disclosure describes or claims a feature or embodiment associated with a method of using a polypeptide fragment, such a feature or embodiment is equally applicable to the polypeptide fragment.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of."

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about". In other cases, the gradations used in a series of values may be used to determine the intended range available to the term "about" for each value. Where present, all ranges are inclusive and combinable. That is, references to values stated in ranges include every value within that range.

If not otherwise specified, the term "about" signifies a variance of ±10% of the associated value. Thus, the term "about" is used to encompass variations of ±10% or less, variations of ±5% or less, variations of ±1% or less, variations of ±0.5% or less, or variations of ±0.1% or less from the specified value.

When a list is presented, unless stated otherwise, it is to be understood that each individual element of that list, and every combination of that list, is a separate embodiment. For example, a list of embodiments presented as "A, B, or C" is to be interpreted as including the embodiments, "A", "B", "C", "A or B", "A or C", "B or C", or "A, B, or C".

As used herein, the singular forms "a", "an", and "the" include the plural.

As used herein, the term "at least one" means "one or more."

The terms "kit" and "article of manufacture" are used as synonyms.

"Neoantigen" refers to a mutated antigen which is expressed in tumor cells but not in normal cells. Neoantigens include antigens which arise from, for example, amino acid substitutions, frame shift mutation, fusion polypeptides, in-frame deletion, insertion, expression of endogenous retroviral polypeptides, and tumor-specific overexpression of polypeptides.

"9-mer" or "9mer" refers to a polypeptide that is nine amino acids in length.

"10-mer" or "10mer" refers to a polypeptide that is ten amino acids in length.

"Corresponding" refers to residues that occur at aligned loci. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure. In other instances, corresponding regions can be identified.

"Immunogenic fragment" refers to a polypeptide that is recognized by cytotoxic T lymphocytes, helper T lymphocytes or B cells when the fragment is in complex with MHC class I or MHC class II molecules.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"CIC" refers to human capicua transcriptional repressor. Human CIC protein comprises an amino acid sequence as shown for example in UniProt accession number Q96RK0.

"CTNNB1" refers to human catenin beta 1. Human CTTNB1 protein comprises an amino acid sequence as shown for example in UniProt accession number P35222.

"ERBB2" refers to human v-erb-b2 erythroblastic leukemia viral oncogene homolog B. Human ERBB2 protein comprises an amino acid sequence as shown for example in UniProt accession number P04626.

"KRAS" refers to human kirsten rat sarcoma. Human KRAS protein comprises an amino acid sequence as shown for example in UniProt accession number P01116.

"PIK3CA" refers to human phosphatidylinositol-4,5-bisphosphate 3-kinase catalytic subunit alpha. Human PIK3CA protein comprises an amino acid sequence as shown for example in UniProt accession number P42336.

"PTEN" refers to human phosphatase and tensin homolog. Human PTEN comprises an amino acid sequence as shown for example in UniProt accession number P60484.

"SF3B1" refers to human splicing factor 3b subunit 1. Human SF3B1 comprises an amino acid sequence as shown for example in UniProt accession number O75533.

"SOX17" refers to human SRY-box transcription factor 17. Human SOX17 comprises an amino acid sequence as shown for example in UniProt accession number Q9H6I2.

"TP53" refers to human tumor protein 53. Human TP53 comprises an amino acid sequence as shown for example in UniProt accession number P04637.

"CMV" refers to human cytomegalovirus. Human CMV pp65 protein comprises an amino acid sequence as shown for example in UniProt accession number P18139.

Polypeptides

Provided herein are optimized MHC-binding polypeptide fragments comprising, consisting of, or consisting essentially of an amino acid modification relative to a cognate native MHC-binding polypeptide fragment. Exemplary modifications include, but are not limited to, substitutions, deletions or additions of amino acids. In certain embodiments, the MHC-binding polypeptides are neoantigens. In certain embodiments, the optimized immunogenic MHC-binding epitope has greater affinity for MHC than a cognate native MHC-binding polypeptide fragment. Peptide to MHC affinity (pMHC affinity) may range, for example, from >1 nM to <20.00 nM, with the strength of binding characterized as equilibrium dissociation constant, Kd (low dissociation constant represents high binding affinity)

Cognate native MHC-binding polypeptide fragments may be characterized by an absence of certain residues at critical anchor positions involved in MCH binding. Optimized MHC-binding polypeptide fragments may be generated by modifying amino acids at certain positions to improve MHC binding, for example as described in Slansky et al, Immunity, 2000 Oct. 13(4):529-38. In certain embodiments, the optimized MHC-binding polypeptide fragments is nine amino acids in length and comprises an amino acid substitution at amino acid position 2, amino acid position 9, or both. In certain embodiments, the optimized MHC-binding polypeptide fragments is ten amino acids in length and comprises an amino acid substitution at amino acid position 3, amino acid position 10, or both.

Positional numbering used herein (e.g. amino acid position 9) refers to the amino acid position starting at the N-terminus and moving toward the C-terminus. For purposes of illustration, taking the hypothetical peptide ABCDEFG, letter "A" is in amino acid position 1, letter "B" is in amino acid position 2, and so forth.

In some embodiments, the MHC-binding epitope binds to an MHC Class I or Class II molecule.

Preferred MHC Class I molecules include a heavy chain (e.g., an α chain) and a β2-microglobin. Such an MHC Class I molecule may be either a full-length molecule or an extracellular portion of a full-length molecule, such extracellular portion lacking complete transmembrane or cytoplasmic domains, or lacking both complete transmembrane and cytoplasmic domains. The MHC Class I molecule is preferably capable of binding a selected peptide. Exemplary MHC Class I molecules that may be employed in the present invention include, for example, molecules that are encoded by human leukocyte antigen (HLA)-A, HLA-B, HLA-C, HLA-E, HLA-F, or HLA-G loci. Preferably, the MHC Class I molecule is selected from molecules encoded by HLA-A, HLA-B, and HLA-C loci. Techniques, methods, and reagents useful for selection, cloning, preparation, and expression of β2-microglobin molecules, MHC Class I molecules such as HLA molecules, and portions thereof, are exemplified in U.S. Pat. Nos. 6,225,042, 6,355,479, and 6,362,001.

In certain embodiments, MHC Class I molecules include, but are not limited to, HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07:02, HLA-B*44:02, and HLA-B*35:01. In preferred embodiments, MHC Class I molecule is HLA-A*02:01.

Preferred MHC Class II molecules include an alpha (a) chain and a beta (p) chain which associate together to form an MHC class II heterodimer. Such an MHC Class II heterodimer may be either a full-length molecule or an extracellular portion of a full-length a chain, an extracellular portion of a full-length p chain, or extracellular portions of both α and β chains, such extracellular portion or portions lacking complete transmembrane or cytoplasmic domains. Exemplary MHC Class II molecules that may be employed in the present invention include molecules that are encoded by HLA-DP, HLA-DQ HLA-DR, HLA-DO, HLA-DN, or HLA-DZ loci. Techniques, methods, and reagents useful for selection, cloning, preparation, and expression of MHC Class II α chains, β chains, and αβ heterodimers, and extracellular portions thereof, are exemplified in U.S. Pat. Nos. 5,583,031, and 6,355,479.

In certain embodiments, the neoantigen is encoded by a mutant variant of a gene selected from the group consisting of CIC, CTNNB1, ERBB2, KRAS, PIK3CA, PTEN, SF3B1, SOX17, TP53, and CMV.

In certain embodiments, the polypeptide fragment is selected from the group consisting of SEQ ID NO: 25, SEQ ID NO: 26 and SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 66, SEQ ID NO: 67, SEQ ID NO: 68, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81; SEQ ID NO: 84, SEQ ID NO: 85, and SEQ ID NO: 86, SEQ ID NO: 88, SEQ ID NO: 90, SEQ ID NO: 91, SEQ ID NO: 92, SEQ ID NO: 93, SEQ ID NO: 94, SEQ ID NO: 95, SEQ ID NO: 96, and any combination thereof.

In certain embodiments, the polypeptide fragment is selected from the group consisting of SEQ ID NO: 29, SEQ ID NO: 32, SEQ ID NO: 45, SEQ ID NO: 59, SEQ ID NO: 64, SEQ ID NO: 68, SEQ ID NO: 75, SEQ ID NO: 78, and any combination thereof.

CIC Polypeptides

Described herein are CIC polypeptide fragments comprising, consisting of, or consisting essentially of an amino acid modification relative to SEQ ID NO: 102, and an amino acid substitution at amino acid position 2 of the fragment, amino acid position 9 of the fragment, or both, wherein the fragment is at least nine amino acids in length. Described herein are CIC polypeptide fragments comprising, consisting of, or consisting essentially of an amino acid modification relative to SEQ ID NO: 102, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In more preferred embodiments, the modification comprises an arginine to tryptophan amino acid substitution at a position corresponding to position 215 of SEQ ID NO: 102 (R215W).

Described herein are CIC polypeptide fragments comprising, consisting of, or consisting essentially of an arginine to tryptophan amino acid substitution at a position corresponding to position 215 of SEQ ID NO: 102 (R215W), and an amino acid substitution at amino acid position 2 of the fragment, amino acid position 9 of the fragment, or both, wherein the fragment is nine amino acids in length. In certain embodiments, the CIC polypeptide fragments comprise, consist of, or consist essentially of an arginine to tryptophan amino acid substitution at a position corresponding to position 215 of SEQ ID NO: 102 (R215W), and an amino acid substitution at amino acid position 2 of the fragment. In certain embodiments, the CIC polypeptide fragments comprise, consist of, or consist essentially of an arginine to tryptophan amino acid substitution at a position corresponding to position 215 of SEQ ID NO: 102 (R215W), and an amino acid substitution at amino acid position 9 of the fragment. In certain embodiments, the CIC polypeptide fragments comprise, consist of, or consist essentially of an arginine to tryptophan amino acid substitution at a position corresponding to position 215 of SEQ ID NO: 102 (R215W), and an amino acid substitution at amino acid position 2 of the fragment and at position 9 of the fragment.

In certain embodiments, the CIC polypeptide fragment binds to HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07:02, HLA-B*44:02, or HLA-B*35:01. In preferred embodiments, the CIC polypeptide fragment binds to HLA-A*02:01.

In some embodiments, the CIC polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the CIC polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the R215W substitution is at amino acid position 1 of the fragment. In certain embodiments, the R215W substitution is at amino acid position 2 of the fragment. In certain embodiments, the R215W substitution is at amino acid position 3 of the fragment. In certain embodiments, the R215W substitution is at amino acid position 4 of the fragment. In certain embodiments, the R215W substitution is at amino acid position 5 of the fragment. In certain embodiments, the R215W substitution is at amino acid position 6 of the fragment. In certain embodiments, the R215W substitution is at amino acid position 7 of the fragment. In certain embodiments, the R215W substitution is at amino acid position 8 of the fragment. In certain embodiments, the R215W substitution is at amino acid position 9 of the fragment. In certain embodiments, the R215W substitution is at amino acid position 10 of the fragment. In preferred embodiments, the R215W substitution is at amino acid position 8 of the fragment.

In further embodiments, the CIC polypeptide fragment is selected from the group consisting of SEQ ID NO: 25, SEQ ID NO: 26 and SEQ ID NO: 27. In certain embodiments, the CIC polypeptide fragment is SEQ ID NO: 25 or a sequence having at least 90% sequence identity, at least 95% sequence identity or at least 99% sequence identity to SEQ ID NO: 25. In certain embodiments, the CIC polypeptide fragment is SEQ ID NO: 26 or a sequence having at least 90% sequence identity, at least 95% sequence identity or at least 99% sequence identity to SEQ ID NO: 26. In certain embodiments, the CIC polypeptide fragment is SEQ ID NO: 27 or a sequence having at least 90% sequence identity, at least 95% sequence identity or at least 99% sequence identity to SEQ ID NO: 27.

In some embodiments, the CIC polypeptide fragment has the sequence $MX_2FSKRHWX_9$(SEQ ID NO: 225), wherein $X_2$ is any amino acid other than isoleucine, and preferably methionine or leucine, and $X_9$ is any amino acid other than alanine, and preferably isoleucine or valine.

CTNNB1 Polypeptides

Described herein are CTNNB1 polypeptide fragments comprising, consisting of, or consisting essentially of an amino acid modification relative to SEQ ID NO: 103, and an amino acid substitution at amino acid position 2 of the fragment, amino acid position 9 of the fragment, or both, wherein the fragment is at least nine amino acids in length. Described herein are CTNNB1 polypeptide fragments comprising, consisting of, or consisting essentially of an amino acid modification relative to SEQ ID NO: 103, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises a serine to cysteine amino acid substitution at a position corresponding to position 33 of SEQ ID NO: 103 (S33C). In further preferred embodiments, the modification comprises a serine to phenylalanine amino acid substitution at a position corresponding to position 37 of SEQ ID NO: 103 (S37F).

Described herein are CTNNB1 polypeptide fragments comprising, consisting of, or consisting essentially of a serine to cysteine amino acid substitution at a position corresponding to position 33 of SEQ ID NO: 103 (S33C), and an amino acid substitution at amino acid position 2 of the fragment, amino acid position 9 of the fragment, or both, wherein the fragment is nine amino acids in length. In certain embodiments, the CTNNB1 polypeptide fragments comprise, consist of, or consist essentially of a serine to cysteine amino acid substitution at a position corresponding to position 33 of SEQ ID NO: 103 (S33C), and an amino acid substitution at amino acid position 2 of the fragment. In certain embodiments, the CTNNB1 polypeptide fragments comprise, consist of, or consist essentially of a serine to cysteine amino acid substitution at a position corresponding to position 33 of SEQ ID NO: 103 (S33C), and an amino acid substitution at amino acid position 9 of the fragment. In certain embodiments, the CTNNB1 polypeptide fragments comprise, consist of, or consist essentially of a serine to cysteine amino acid substitution at a position corresponding to position 33 of SEQ ID NO: 103 (S33C), and an amino acid substitution at amino acid position 2 of the fragment and at position 9 of the fragment.

Described herein are CTNNB1 polypeptide fragments comprising, consisting of, or consisting essentially of a serine to phenylalanine amino acid substitution at a position corresponding to position 37 of SEQ ID NO: 103 (S37F), and an amino acid substitution at amino acid position 2 of the fragment, amino acid position 9 of the fragment, or both, wherein the fragment is nine amino acids in length. In certain embodiments, the CTNNB1 polypeptide fragments comprise, consist of, or consist essentially of a serine to phenylalanine amino acid substitution at a position corresponding to position 37 of SEQ ID NO: 103 (S37F), and an amino acid substitution at amino acid position 2 of the fragment. In certain embodiments, the CTNNB1 polypeptide fragments comprise, consist of, or consist essentially of a serine to phenylalanine amino acid substitution at a position corresponding to position 37 of SEQ ID NO: 103 (S37F), and an amino acid substitution at amino acid position 9 of the fragment. In certain embodiments, the CTNNB1 polypeptide fragments comprise, consist of, or consist essentially of a serine to phenylalanine acid substitution at a position corresponding to position 37 of SEQ ID NO: 103 (S37F), and an amino acid substitution at amino acid position 2 of the fragment and at position 9 of the fragment.

In certain embodiments, the CTNNB1 polypeptide fragment binds to HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07:02, HLA-B*44:02, or HLA-B*35:01. In preferred embodiments, the CTNNB1 polypeptide fragment binds to HLA-A*02:01.

In some embodiments, the CTNNB1 polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the CTNNB1 polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the S33C substitution is at amino acid position 1 of the fragment. In certain embodiments, the S33C substitution is at amino acid position 2 of the fragment. In certain embodiments, the S33C substitution is at amino acid position 3 of the fragment. In certain embodiments, the S33C substitution is at amino acid position 4 of the fragment. In certain embodiments, the S33C substitution is at amino acid position 5 of the fragment. In certain embodiments, the S33C substitution is at amino acid position 6 of the fragment. In certain embodiments, the S33C substitution is at amino acid position 7 of the fragment. In certain embodiments, the S33C substitution is at amino acid position 8 of the fragment. In certain embodiments, the S33C substitution is at amino acid position 9 of the fragment. In certain embodiments, the S33C substitution is at amino acid position 10 of the fragment. In preferred embodiments, the S33C substitution is at amino acid position 4 of the fragment.

In certain embodiments, the S37F substitution is at amino acid position 1 of the fragment. In certain embodiments, the S37F substitution is at amino acid position 2 of the fragment. In certain embodiments, the S37F substitution is at amino acid position 3 of the fragment. In certain embodiments, the S37F substitution is at amino acid position 4 of the fragment. In certain embodiments, the S37F substitution is at amino acid position 5 of the fragment. In certain embodiments, the S37F substitution is at amino acid position 6 of the fragment. In certain embodiments, the S37F substitution is at amino acid position 7 of the fragment. In certain embodiments, the S37F substitution is at amino acid position 8 of the fragment. In certain embodiments, the S37F substitution is at amino acid position 9 of the fragment. In certain embodiments, the S37F substitution is at amino acid position 10 of the fragment. In preferred embodiments, the S37F substitution is at amino acid position 8 of the fragment.

In still further embodiments, the CTNNB1 polypeptide fragment is selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 80, and SEQ ID NO: 81. In still further embodiments, the CTNNB1 polypeptide fragment is SEQ ID NO: 28 or a sequence having at least 90% sequence identity, at least 95% sequence identity or at least 99% sequence identity to SEQ ID NO: 28. In still further embodiments, the CTNNB1 polypeptide fragment is SEQ ID NO: 29 or a sequence having at least 90% sequence identity, at least 95% sequence identity or at least 99% sequence identity to SEQ ID NO: 29. In still further embodiments, the CTNNB1 polypeptide fragment is SEQ ID NO: 30 or a sequence having at least 90% sequence identity, at least 95% sequence identity or at least 99% sequence identity to SEQ ID NO: 30. In still further embodiments, the CTNNB1 polypeptide fragment is SEQ ID NO: 31 or a sequence having at least 90% sequence identity, at least 95% sequence identity or at least 99% sequence identity to SEQ ID NO: 31. In still further embodiments, the CTNNB1 polypeptide fragment is SEQ ID NO: 32 or a sequence having at least 90% sequence identity, at least 95% sequence identity or at least 99% sequence identity to SEQ ID NO: 32. In still further embodiments, the CTNNB1 polypeptide fragment is SEQ ID NO: 33 or a sequence having at least 90% sequence identity, at least 95% sequence identity or at least 99% sequence identity to SEQ ID NO: 33. In still further embodiments, the CTNNB1 polypeptide fragment is SEQ ID NO: 80 or a sequence having at least 90% sequence identity, at least 95% sequence identity or at least 99% sequence identity to SEQ ID NO: 80. In still further embodiments, the CTNNB1 polypeptide fragment is SEQ ID NO: 81 or a sequence having at least 90% sequence identity, at least 95% sequence identity or at least 99% sequence identity to SEQ ID NO: 81.

In some embodiments, the CTNNB1 polypeptide fragment has the sequence $YX_2DCGIHSX_9$ (SEQ ID NO: 226), wherein $X_2$ is any amino acid other than leucine, and preferably methionine, and $X_9$ is any amino acid other than glycine, and preferably leucine or valine.

In some embodiments, the CTNNB1 polypeptide fragment has the sequence $YX_2DSGIHFX_9$ (SEQ ID NO: 227), wherein $X_2$ is any amino acid other than leucine, and preferably methionine, and $X_9$ is any amino acid other than glycine, and preferably isoleucine, leucine or valine.

KRAS Polypeptides

Described herein are KRAS polypeptide fragments comprising, consisting of, or consisting essentially of an amino acid modification relative to SEQ ID NO: 105, and an amino acid substitution at amino acid position 2 of the fragment, amino acid position 9 of the fragment, or both, wherein the fragment is at least nine amino acids in length. Described herein are KRAS polypeptide fragments comprising, consisting of, or consisting essentially of an amino acid modification relative to SEQ ID NO: 105, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises a glycine to alanine amino acid substitution at a position corresponding to position 12 of SEQ ID NO: 105 (G12A). In further preferred embodiments, the modification comprises a glycine to cysteine amino acid substitution at a position corresponding to position 12 of SEQ ID NO: 105 (G12C). In further preferred embodiments, the modification comprises a glycine to valine amino acid substitution at a position corresponding to position 12 of SEQ ID NO: 105 (G12V).

Described herein are KRAS polypeptide fragments comprising, consisting of, or consisting essentially of a glycine to alanine amino acid substitution at a position corresponding to position 12 of SEQ ID NO: 105 (G12A), and an amino acid substitution at amino acid position 2 of the fragment, amino acid position 9 of the fragment, or both, wherein the fragment is nine amino acids in length. In certain embodiments, the KRAS polypeptide fragments comprise, consist of, or consist essentially of a glycine to alanine amino acid substitution at a position corresponding to position 12 of SEQ ID NO: 105 (G12A), and an amino acid substitution at amino acid position 2 of the fragment. In certain embodiments, the KRAS polypeptide fragments comprise, consist of, or consist essentially of a glycine to alanine amino acid substitution at a position corresponding to position 12 of SEQ ID NO: 105 (G12A), and an amino acid substitution at amino acid position 9 of the fragment. In certain embodiments, the KRAS polypeptide fragments comprise, consist of, or consist essentially of a glycine to alanine amino acid substitution at a position corresponding to position 12 of SEQ ID NO: 105 (G12A), and an amino acid substitution at amino acid position 2 of the fragment and at position 9 of the fragment.

Described herein are KRAS polypeptide fragments comprising, consisting of, or consisting essentially of a glycine to cysteine amino acid substitution at a position corresponding to position 12 of SEQ ID NO: 105 (G12C), and an amino acid substitution at amino acid position 2 of the fragment, amino acid position 9 of the fragment, or both, wherein the fragment is nine amino acids in length. In certain embodiments, the KRAS polypeptide fragments comprise, consist of, or consist essentially of a glycine to cysteine amino acid substitution at a position corresponding to position 12 of SEQ ID NO: 105 (G12C), and an amino acid substitution at amino acid position 2 of the fragment. In certain embodiments, the KRAS polypeptide fragments comprise, consist of, or consist essentially of a glycine to cysteine amino acid substitution at a position corresponding to position 12 of SEQ ID NO: 105 (G12C), and an amino acid substitution at amino acid position 9 of the fragment. In certain embodiments, the KRAS polypeptide fragments comprise, consist of, or consist essentially of a glycine to cysteine amino acid substitution at a position corresponding to position 12 of SEQ ID NO: 105 (G12C), and an amino acid substitution at amino acid position 2 of the fragment and at position 9 of the fragment.

Described herein are KRAS polypeptide fragments comprising, consisting of, or consisting essentially of a glycine to valine amino acid substitution at a position corresponding to at position 12 of SEQ ID NO: 105 (G12V), and an amino acid substitution at amino acid position 2 of the fragment, amino acid position 9 of the fragment, or both, wherein the fragment is nine amino acids in length. In certain embodiments, the KRAS polypeptide fragments comprise, consist of, or consist essentially of a glycine to valine amino acid substitution at a position corresponding to at position 12 of SEQ ID NO: 105 (G12V), and an amino acid substitution at amino acid position 2 of the fragment. In certain embodiments, the KRAS polypeptide fragments comprise, consist of, or consist essentially of a glycine to valine amino acid substitution at a position corresponding to at position 12 of SEQ ID NO: 105 (G12V), and an amino acid substitution at amino acid position 9 of the fragment. In certain embodiments, the KRAS polypeptide fragments comprise, consist of, or consist essentially of a glycine to valine amino acid substitution at a position corresponding to at position 12 of SEQ ID NO: 105 (G12V), and an amino acid substitution at amino acid position 2 of the fragment and at position 9 of the fragment.

In certain embodiments, the KRAS polypeptide fragment binds to HLA 2.1 (HLA-A*02:01), HLA-A*01:01, HLA-A*03:01, HLA-A*1 1:01, HLA-A*24:02, HLA-A*33:03, HLA-C*07:01, HLA-C*07:02, HLA-C*04:01, HLA-B*07: 02, HLA-B*44:02, or HLA-B*35:01. In preferred embodiments, the KRAS polypeptide fragment binds to HLA-A*02:01.

In some embodiments, the KRAS polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the KRAS polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the G12A substitution is at amino acid position 1 of the fragment. In certain embodiments, the G12A substitution is at amino acid position 2 of the fragment. In certain embodiments, the G12A substitution is at amino acid position 3 of the fragment. In certain embodiments, the G12A substitution is at amino acid position 4 of the fragment. In certain embodiments, the G12A substitution is at amino acid position 5 of the fragment. In certain embodiments, the G12A substitution is at amino acid position 6 of the fragment. In certain embodiments, the G12A substitution is at amino acid position 7 of the fragment. In certain embodiments, the G12A substitution is at amino acid position 8 of the fragment. In certain embodiments, the G12A substitution is at amino acid position 9 of the fragment. In certain embodiments, the G12A substitution is at amino acid position 10 of the fragment. In preferred embodiments, the G12A substitution is at amino acid position 7 of the fragment.

In certain embodiments, the G12C substitution is at amino acid position 1 of the fragment. In certain embodiments, the G12C substitution is at amino acid position 2 of the fragment. In certain embodiments, the G12C substitution is at amino acid position 3 of the fragment. In certain embodiments, the G12C substitution is at amino acid position 4 of the fragment. In certain embodiments, the G12C substitution is at amino acid position 5 of the fragment. In certain embodiments, the G12C substitution is at amino acid position 6 of the fragment. In certain embodiments, the G12C substitution is at amino acid position 7 of the fragment. In certain embodiments, the G12C substitution is at amino acid position 8 of the fragment. In certain embodiments, the G12C substitution is at amino acid position 9 of the fragment. In certain embodiments, the G12C substitution is at amino acid position 10 of the fragment. In preferred embodiments, the G12C substitution is at amino acid position 7 of the fragment.

In certain embodiments, the G12V substitution is at amino acid position 1 of the fragment. In certain embodiments, the G12V substitution is at amino acid position 2 of the fragment. In certain embodiments, the G12V substitution is at amino acid position 3 of the fragment. In certain embodiments, the G12V substitution is at amino acid position 4 of the fragment. In certain embodiments, the G12V substitution is at amino acid position 5 of the fragment. In certain embodiments, the G12V substitution is at amino acid position 6 of the fragment. In certain embodiments, the G12V substitution is at amino acid position 7 of the fragment. In certain embodiments, the G12V substitution is at amino acid position 8 of the fragment. In certain embodiments, the G12V substitution is at amino acid position 9 of the fragment. In certain embodiments, the G12V substitution is at amino acid position 10 of the fragment. In preferred embodiments, the G12V substitution is at amino acid position 7 of the fragment.

In some embodiments, the KRAS polypeptide fragment is selected from the group consisting of SEQ ID NO: 37, SEQ ID NO: 38, SEQ ID NO: 39, SEQ ID NO: 40, SEQ ID NO: 41, and SEQ ID NO: 42. In certain embodiments, the KRAS polypeptide fragment is SEQ ID NO: 37 or a sequence having at least 90% sequence identity, at least 95% sequence identity or at least 99% sequence identity to SEQ ID NO: 37. In certain embodiments, the KRAS polypeptide fragment is SEQ ID NO: 38 or a sequence having at least 90% sequence identity, at least 95% sequence identity or at least 99% sequence identity to SEQ ID NO: 38. In certain embodiments, the KRAS polypeptide fragment is SEQ ID NO: 39 or a sequence having at least 90% sequence identity, at least 95% sequence identity or at least 99% sequence identity to SEQ ID NO: 39. In certain embodiments, the KRAS polypeptide fragment is SEQ ID NO: 40 or a sequence having at least 90% sequence identity, at least 95% sequence identity or at least 99% sequence identity to SEQ ID NO: 40. In certain embodiments, the KRAS polypeptide fragment is SEQ ID NO: 41 or a sequence having at least 90% sequence identity, at least 95% sequence identity or at least 99% sequence identity to SEQ ID NO: 41. In certain embodiments, the KRAS polypeptide fragment is SEQ ID NO: 42 or a sequence having at least 90% sequence identity, at least 95% sequence identity or at least 99% sequence identity to SEQ ID NO: 42.

In some embodiments, the KRAS polypeptide fragment has the sequence LX2VVGAAGV (SEQ ID NO: 228), wherein $X_2$ is any amino acid other than valine, and preferably methionine or leucine.

In some embodiments, the KRAS polypeptide fragment has the sequence LX2VVGACGV (SEQ ID NO: 229), wherein $X_2$ is any amino acid other than valine, and preferably methionine or leucine.

In some embodiments, the KRAS polypeptide fragment has the sequence LX2VVGAVGV (SEQ ID NO: 230), wherein $X_2$ is any amino acid other than valine, and preferably methionine or leucine.

PIK3CA Polypeptides

Described herein are PIK3CA polypeptide fragments comprising, consisting of, or consisting essentially of an amino acid modification relative to SEQ ID NO: 106, and an amino acid substitution at amino acid position 2 of the fragment, amino acid position 9 of the fragment, or both, wherein the fragment is at least nine amino acids in length. Described herein are PIK3CA polypeptide fragments comprising, consisting of, or consisting essentially of an amino acid modification relative to SEQ ID NO: 106, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises a glutamic acid to lysine amino acid substitution at a position corresponding to position 453 of SEQ ID NO: 106 (E453K). In further preferred embodiments, the modification comprises a glycine to aspartic acid amino acid substitution at a position corresponding to position 118 of SEQ ID NO: 106 (G118D).

Described herein are PIK3CA polypeptide fragments comprising, consisting of, or consisting essentially of a glutamic acid to lysine amino acid substitution at a position corresponding to position 453 of SEQ ID NO: 106 (E453K), and an amino acid substitution at amino acid position 2 of the fragment, amino acid position 9 of the fragment, or both, wherein the fragment is nine amino acids in length. In certain embodiments, the PIK3CA polypeptide fragments comprise, consist of, or consist essentially of a glutamic acid to lysine amino acid substitution at a position corresponding to position 453 of SEQ ID NO: 106 (E453K), and an amino acid substitution at amino acid position 2 of the fragment. In certain embodiments, the PIK3CA polypeptide fragments comprise, consist of, or consist essentially of a glutamic acid to lysine amino acid substitution at a position corresponding to position 453 of SEQ ID NO: 106 (E453K), and an amino acid substitution at amino acid position 9 of the fragment. In certain embodiments, the PIK3CA polypeptide fragments comprise, consist of, or consist essentially of a glutamic acid to lysine amino acid substitution at a position corresponding to position 453 of SEQ ID NO: 106 (E453K), and an amino acid substitution at amino acid position 2 of the fragment and at position 9 of the fragment.

Described herein are PIK3CA polypeptide fragments comprising, consisting of, or consisting essentially of a glycine to aspartic acid amino acid substitution at a position corresponding to position 118 of SEQ ID NO: 106 (G118D), and an amino acid substitution at amino acid position 2 of the fragment, amino acid position 9 of the fragment, or both, wherein the fragment is nine amino acids in length. In certain embodiments, the PIK3CA polypeptide fragments comprise, consist of, or consist essentially of a glycine to aspartic acid amino acid substitution at a position corresponding to position 118 of SEQ ID NO: 106 (G118D), and an amino acid substitution at amino acid position 2 of the fragment. In certain embodiments, the PIK3CA polypeptide fragments comprise, consist of, or consist essentially of a glycine to aspartic acid amino acid substitution at a position corresponding to position 118 of SEQ ID NO: 106 (G118D), and an amino acid substitution at amino acid position 9 of the fragment. In certain embodiments, the PIK3CA polypeptide fragments comprise, consist of, or consist essentially of a glycine to aspartic acid amino acid substitution at a position corresponding to position 118 of SEQ ID NO: 106 (G118D), and an amino acid substitution at amino acid position 2 of the fragment and at position 9 of the fragment.

In certain embodiments, the PIK3CA polypeptide fragment binds to HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07:02, HLA-B*44:02, or HLA-B*35:01. In preferred embodiments, the PIK3CA polypeptide fragment binds to HLA-A*02:01.

In some embodiments, the PIK3CA polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the PIK3CA polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the E453K substitution is at amino acid position 1 of the fragment. In certain embodiments, the E453K substitution is at amino acid position 2 of the fragment. In certain embodiments, the E453K substitution is at amino acid position 3 of the fragment. In certain embodiments, the E453K substitution is at amino acid position 4 of the fragment. In certain embodiments, the E453K substitution is at amino acid position 5 of the fragment. In certain embodiments, the E453K substitution is at amino acid position 6 of the fragment. In certain embodiments, the E453K substitution is at amino acid position 7 of the fragment. In certain embodiments, the E453K substitution is at amino acid position 8 of the fragment. In certain embodiments, the E453K substitution is at amino acid position 9 of the fragment. In certain embodiments, the E453K substitution is at amino acid position 10 of the fragment. In preferred embodiments, the E453K substitution is at amino acid position 3 of the fragment.

In certain embodiments, the G118D substitution is at amino acid position 1 of the fragment. In certain embodiments, the G118D substitution is at amino acid position 2 of the fragment. In certain embodiments, the G118D substitution is at amino acid position 3 of the fragment. In certain embodiments, the G118D substitution is at amino acid position 4 of the fragment. In certain embodiments, the G118D substitution is at amino acid position 5 of the fragment. In certain embodiments, the G118D substitution is at amino acid position 6 of the fragment. In certain embodiments, the G118D substitution is at amino acid position 7 of the fragment. In certain embodiments, the G118D substitution is at amino acid position 8 of the fragment. In certain embodiments, the G118D substitution is at amino acid position 9 of the fragment. In certain embodiments, the G118D substitution is at amino acid position 10 of the fragment. In preferred embodiments, the G118D substitution is at amino acid position 7 of the fragment.

In still further embodiments, the PIK3CA polypeptide fragment is selected from the group consisting of SEQ ID NO: 43, SEQ ID NO: 44, SEQ ID NO: 45, SEQ ID NO: 46, and SEQ ID NO: 47. In certain embodiments, the PIK3CA polypeptide fragment is SEQ ID NO: 43 or a sequence having at least 90% sequence identity, at least 95% sequence identity or at least 99% sequence identity to SEQ ID NO: 43. In certain embodiments, the PIK3CA polypeptide fragment is SEQ ID NO: 44 or a sequence having at least 90% sequence identity, at least 95% sequence identity or at least 99% sequence identity to SEQ ID NO: 44. In certain embodiments, the PIK3CA polypeptide fragment is SEQ ID NO: 45 or a sequence having at least 90% sequence identity, at least 95% sequence identity or at least 99% sequence identity to SEQ ID NO: 45. In certain embodiments, the PIK3CA polypeptide fragment is SEQ ID NO: 46 or a sequence having at least 90% sequence identity, at least 95% sequence identity or at least 99% sequence identity to SEQ ID NO: 46. In certain embodiments, the PIK3CA polypeptide fragment is SEQ ID NO: 47 or a sequence having at least 90% sequence identity, at least 95% sequence identity or at least 99% sequence identity to SEQ ID NO: 47.

In some embodiments, the PIK3CA polypeptide fragment has the sequence $GX_2KDLLNPX_9$ (SEQ ID NO: 231), wherein $X_2$ is any amino acid other than leucine, and preferably methionine, and $X_9$ is any amino acid other than isoleucine, and preferably valine.

In some embodiments, the PIK3CA polypeptide fragment has the sequence $IX_2NREIDFX_9$ (SEQ ID NO: 232), wherein $X_2$ is any amino acid other than leucine, and preferably methionine, and $X_9$ is any amino acid other than alanine, and preferably valine or leucine.

PTEN Polypeptides

Described herein are PTEN polypeptide fragments comprising, consisting of, or consisting essentially of an amino acid modification relative to SEQ ID NO: 107, and an amino acid substitution at amino acid position 2 of the fragment, amino acid position 9 of the fragment, or both, wherein the fragment is at least nine amino acids in length. Described herein are PTEN polypeptide fragments comprising, consisting of, or consisting essentially of an amino acid modification relative to SEQ ID NO: 107, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises an arginine to cysteine amino acid substitution at a position corresponding to position 173 of SEQ ID NO: 107 (R173C).

Described herein are PTEN polypeptide fragments comprising, consisting of, or consisting essentially of an arginine to cysteine amino acid substitution at a position corresponding to position 173 of SEQ ID NO: 107 (R173C), and an amino acid substitution at amino acid position 3 of the fragment, amino acid position 10 of the fragment, or both, wherein the fragment is ten amino acids in length. In certain embodiments, the PTEN polypeptide fragments comprise, consist of, or consist essentially of an arginine to cysteine amino acid substitution at a position corresponding to position 173 of SEQ ID NO: 107 (R173C), and an amino acid substitution at amino acid position 3 of the fragment. In certain embodiments, the PTEN polypeptide fragments comprise, consist of, or consist essentially of an arginine to cysteine amino acid substitution at a position corresponding to position 173 of SEQ ID NO: 107 (R173C), and an amino acid substitution at amino acid position 10 of the fragment. In certain embodiments, the PTEN polypeptide fragments comprise, consist of, or consist essentially of an arginine to cysteine amino acid substitution at a position corresponding to position 173 of SEQ ID NO: 107 (R173C), and an amino acid substitution at amino acid position 3 of the fragment and at position 10 of the fragment.

In certain embodiments, the PTEN polypeptide fragment binds to HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07:02, HLA-B*44:02, or HLA-B*35:01. In preferred embodiments, the PTEN polypeptide fragment binds to HLA-A*02:01.

In some embodiments, the PTEN polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the PTEN polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the R173C substitution is at amino acid position 1 of the fragment. In certain embodiments, the R173C substitution is at amino acid position 2 of the fragment. In certain embodiments, the R173C substitution is at amino acid position 3 of the fragment. In certain embodiments, the R173C substitution is at amino acid position 4 of the fragment. In certain embodiments, the R173C substitution is at amino acid position 5 of the fragment. In certain embodiments, the R173C substitution is at amino acid position 6 of the fragment. In certain embodiments, the R173C substitution is at amino acid position 7 of the fragment. In certain embodiments, the R173C substitution is at amino acid position 8 of the fragment. In certain embodiments, the R173C substitution is at amino acid position 9 of the fragment. In certain embodiments, the R173C substitution is at amino acid position 10 of the fragment. In preferred embodiments, the R173C substitution is at amino acid position 1 of the fragment.

In further embodiments, the PTEN polypeptide fragment is selected from the group consisting of SEQ ID NO: 48, SEQ ID NO: 49, and SEQ ID NO: 88. In certain embodiments, the PTEN polypeptide fragment is SEQ ID NO: 48 or a sequence having at least 90% sequence identity, at least 95% sequence identity or at least 99% sequence identity to SEQ ID NO: 48. In certain embodiments, the PTEN polypeptide fragment is SEQ ID NO: 49 or a sequence having at least 90% sequence identity, at least 95% sequence identity or at least 99% sequence identity to SEQ ID NO: 49. In certain embodiments, the PTEN polypeptide fragment is SEQ ID NO: 88 or a sequence having at least 90% sequence identity, at least 95% sequence identity or at least 99% sequence identity to SEQ ID NO: 88.

In some embodiments, the PTEN polypeptide fragment has the sequence $CYX_3YYYSYLX_{10}$ (SEQ ID NO: 233), wherein $X_3$ is any amino acid other than valine, and preferably methionine or leucine, and $X_{10}$ is any amino acid other than leucine, and preferably valine or isoleucine.

SF3B1 Polypeptides

Described herein are SF3B1 polypeptide fragments comprising, consisting of, or consisting essentially of an amino acid modification relative to SEQ ID NO: 108, and an amino acid substitution at amino acid position 2 of the fragment, amino acid position 9 of the fragment, or both, wherein the fragment is at least nine amino acids in length. Described herein are SF3B1 polypeptide fragments comprising, consisting of, or consisting essentially of an amino acid modification relative to SEQ ID NO: 108, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises an arginine to histidine amino acid substitution at a position corresponding to position 625 of SEQ ID NO: 108 (R625H).

Described herein are SF3B1 polypeptide fragments comprising, consisting of, or consisting essentially of an arginine to histidine amino acid substitution at a position corresponding to position 625 of SEQ ID NO: 108 (R625H), and an amino acid substitution at amino acid position 2 of the fragment, amino acid position 9 of the fragment, or both, wherein the fragment is nine amino acids in length. In certain embodiments, the SF3B1 polypeptide fragments comprise, consist of, or consist essentially of an arginine to histidine amino acid substitution at a position corresponding to position 625 of SEQ ID NO: 108 (R625H), and an amino acid substitution at amino acid position 2 of the fragment. In certain embodiments, the SF3B1 polypeptide fragments comprise, consist of, or consist essentially of an arginine to histidine amino acid substitution at a position corresponding to position 625 of SEQ ID NO: 108 (R625H), and an amino acid substitution at amino acid position 9 of the fragment. In certain embodiments, the SF3B1 polypeptide fragments comprise, consist of, or consist essentially of an arginine to histidine amino acid substitution at a position corresponding to position 625 of SEQ ID NO: 108 (R625H), and an amino acid substitution at amino acid position 2 of the fragment and at position 9 of the fragment.

In certain embodiments, the SF3B1 polypeptide fragment binds to HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07: 02, HLA-B*44:02, or HLA-B*35:01. In preferred embodiments, the SF3B1 polypeptide fragment binds to HLA-A*02:01.

In some embodiments, the SF3B1 polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the SF3B1 polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the R625H substitution is at amino acid position 1 of the fragment. In certain embodiments, the R625H substitution is at amino acid position 2 of the fragment. In certain embodiments, the R625H substitution is at amino acid position 3 of the fragment. In certain embodiments, the R625H substitution is at amino acid position 4 of the fragment. In certain embodiments, the R625H substitution is at amino acid position 5 of the fragment. In certain embodiments, the R625H substitution is at amino acid position 6 of the fragment. In certain embodiments, the R625H substitution is at amino acid position 7 of the fragment. In certain embodiments, the R625H substitution is at amino acid position 8 of the fragment. In certain embodiments, the R625H substitution is at amino acid position 9 of the fragment. In certain embodiments, the R625H substitution is at amino acid position 10 of the fragment. In preferred embodiments, the R625H substitution is at amino acid position 7 of the fragment.

In further embodiments, the SF3B1 polypeptide fragment is selected from the group consisting of SEQ ID NO: 51, SEQ ID NO: 52, SEQ ID NO: 53, SEQ ID NO: 90, SEQ ID NO: 91 and SEQ ID NO: 92. In certain embodiments, the SF3B1 polypeptide fragment is SEQ ID NO: 51 or a sequence having at least 90% sequence identity, at least 95% sequence identity or at least 99% sequence identity to SEQ ID NO: 51. In certain embodiments, the SF3B1 polypeptide fragment is SEQ ID NO: 52 or a sequence having at least 90% sequence identity, at least 95% sequence identity or at least 99% sequence identity to SEQ ID NO: 52. In certain embodiments, the SF3B1 polypeptide fragment is SEQ ID NO: 53 or a sequence having at least 90% sequence identity, at least 95% sequence identity or at least 99% sequence identity to SEQ ID NO: 53. In certain embodiments, the SF3B1 polypeptide fragment is SEQ ID NO: 90 or a sequence having at least 90% sequence identity, at least 95% sequence identity or at least 99% sequence identity to SEQ ID NO: 90. In certain embodiments, the SF3B1 polypeptide fragment is SEQ ID NO: 91 or a sequence having at least 90% sequence identity, at least 95% sequence identity or at least 99% sequence identity to SEQ ID NO: 91. In certain embodiments, the SF3B1 polypeptide fragment is SEQ ID NO: 92 or a sequence having at least 90% sequence identity, at least 95% sequence identity or at least 99% sequence identity to SEQ ID NO: 92.

In some embodiments, the SF3B1 polypeptide fragment has the sequence $NX_2DEYVHNX_9$ (SEQ ID NO: 234), wherein $X_2$ is any amino acid other than methionine, and preferably leucine, and $X_9$ is any amino acid other than threonine, and preferably valine, leucine, or isoleucine.

SOX17 Polypeptides

Described herein are SOX17 polypeptide fragments comprising, consisting of, or consisting essentially of an amino acid modification relative to SEQ ID NO: 109, and an amino acid substitution at amino acid position 2 of the fragment, amino acid position 9 of the fragment, or both, wherein the fragment is at least nine amino acids in length. Described herein are SOX17 polypeptide fragments comprising, consisting of, or consisting essentially of an amino acid modification relative to SEQ ID NO: 109, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises a serine to isoleucine amino acid substitution at a position corresponding to position 403 of SEQ ID NO: 109 (S403I).

Described herein are SOX17 polypeptide fragments comprising, consisting of, or consisting essentially of a serine to isoleucine amino acid substitution at a position corresponding to position 403 of SEQ ID NO: 109 (S403I), and an amino acid substitution at amino acid position 2 of the fragment, amino acid position 9 of the fragment, or both, wherein the fragment is nine amino acids in length. In certain embodiments, the SOX17 polypeptide fragments comprise, consist of, or consist essentially of a serine to isoleucine amino acid substitution at a position corresponding to position 403 of SEQ ID NO: 109 (S403I), and an amino acid substitution at amino acid position 2 of the fragment. In certain embodiments, the SOX17 polypeptide fragments comprise, consist of, or consist essentially of a serine to isoleucine amino acid substitution at a position corresponding to position 403 of SEQ ID NO: 109 (S403I), and an amino acid substitution at amino acid position 9 of the fragment. In certain embodiments, the SOX17 polypeptide fragments comprise, consist of, or consist essentially of a serine to isoleucine amino acid substitution at a position corresponding to position 403 of SEQ ID NO: 109 (S403I), and an amino acid substitution at amino acid position 2 of the fragment and at position 9 of the fragment.

In certain embodiments, the SOX17 polypeptide fragment binds to HLA 2.1 (HLA-A*02:01), HLA-A*01:01, HLA-A*03:01, HLA-A*1 1:01, HLA-A*24:02, HLA-A*33:03, HLA-C*07:01, HLA-C*07:02, HLA-C*04:01, HLA-B*07:02, HLA-B*44:02, or HLA-B*35:01. In preferred embodiments, the SOX17 polypeptide fragment binds to HLA-A*02:01.

In some embodiments, the SOX17 polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the SOX17 polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the S403I substitution is at amino acid position 1 of the fragment. In certain embodiments, the S403I substitution is at amino acid position 2 of the fragment. In certain embodiments, the S403I substitution is at amino acid position 3 of the fragment. In certain embodiments, the S403I substitution is at amino acid position 4 of the fragment. In certain embodiments, the S403I substitution is at amino acid position 5 of the fragment. In certain embodiments, the S403I substitution is at amino acid position 6 of the fragment. In certain embodiments, the S403I substitution is at amino acid position 7 of the fragment. In certain embodiments, the S403I substitution is at amino acid position 8 of the fragment. In certain embodiments, the S403I substitution is at amino acid position 9 of the fragment. In certain embodiments, the S403I substitution is at amino acid position 10 of the fragment. In preferred embodiments, the S403I substitution is at amino acid position 6 of the fragment.

In further embodiments, the SOX17 polypeptide fragment is selected from the group consisting of SEQ ID NO: 54, SEQ ID NO: 55, SEQ ID NO: 56, and SEQ ID NO: 93. In certain embodiments, the SOX17 polypeptide fragment is SEQ ID NO: 54 or a sequence having at least 90% sequence identity, at least 95% sequence identity or at least 99% sequence identity to SEQ ID NO: 54. In certain embodiments, the SOX17 polypeptide fragment is SEQ ID NO: 55 or a sequence having at least 90% sequence identity, at least 95% sequence identity or at least 99% sequence identity to SEQ ID NO: 55. In certain embodiments, the SOX17 polypeptide fragment is SEQ ID NO: 56 or a sequence having at least 90% sequence identity, at least 95% sequence identity or at least 99% sequence identity to SEQ ID NO: 56. In certain embodiments, the SOX17 polypeptide fragment is SEQ ID NO: 93 or a sequence having at least 90% sequence identity, at least 95% sequence identity or at least 99% sequence identity to SEQ ID NO: 93.

In some embodiments, the SOX17 polypeptide fragment has the sequence $VX_2SDAISAX_9$ (SEQ ID NO: 235), wherein $X_2$ is any amino acid other than valine, and preferably leucine or methionine, and $X_9$ is any amino acid other than valine, and preferably leucine.

TP53 Polypeptides

Described herein are TP53 polypeptide fragments comprising, consisting of, or consisting essentially of an amino acid modification relative to SEQ ID NO: 110, and an amino acid substitution at amino acid position 2 of the fragment, amino acid position 9 of the fragment, or both, wherein the fragment is at least nine amino acids in length. Described herein are TP53 polypeptide fragments comprising, consisting of, or consisting essentially of an amino acid modification relative to SEQ ID NO: 110, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises an arginine to leucine amino acid substitution at a position corresponding to position 110 of SEQ ID NO: 110 (R110L). In further preferred embodiments, the modification comprises a serine to phenylalanine amino acid substitution at a position corresponding to position 127 of SEQ ID NO: 110 (S127F). In further preferred embodiments, the modification comprises a lysine to asparagine amino acid substitution at a position corresponding to position 132 of SEQ ID NO: 110 (K132N). In further preferred embodiments, the modification comprises a cysteine to tyrosine amino acid substitution at a position corresponding to position 141 of SEQ ID NO: 110 (C141Y). In further preferred embodiments, the modification comprises a proline to leucine amino acid substitution at a position corresponding to position 152 of SEQ ID NO: 110 (P152L). In further preferred embodiments, the modification comprises a histidine to leucine amino acid substitution at a position corresponding to position 193 of SEQ ID NO: 110 (H193L). In further preferred embodiments, the modification comprises a histidine to tyrosine amino acid substitution at a position corresponding to position 193 of SEQ ID NO: 110 (H193Y). In further preferred embodiments, the modification comprises a tyrosine to cysteine amino acid substitution at a position corresponding to position 220 of SEQ ID NO: 110 (Y220C). In further preferred embodiments, the modification comprises a valine to methionine amino acid substitution at a position corresponding to position 272 of SEQ ID NO: 110 (V272M).

Described herein are TP53 polypeptide fragments comprising, consisting of, or consisting essentially of an arginine to leucine amino acid substitution at a position corresponding to position 110 of SEQ ID NO: 110 (R110L), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of an arginine to leucine amino acid substitution at a position corresponding to position 110 of SEQ ID NO: 110 (R110L), and an amino acid substitution at amino acid position 2 of the fragment. In certain embodiments, the TP53 polypeptide fragments comprise, consist of, or consist essentially of an arginine to leucine amino acid substitution at a position corresponding to position 110 of SEQ ID NO: 110 (R110L), and an amino acid substitution at amino acid position 9 of the fragment. In certain embodiments, the TP53 polypeptide fragments comprise, consist of, or consist essentially of an arginine to leucine amino acid substitution at a position corresponding to position 110 of SEQ ID NO: 110 (R110L), and an amino acid substitution at amino acid position 2 of the fragment and at position 9 of the fragment.

Described herein are TP53 polypeptide fragments comprising, consisting of, or consisting essentially of a serine to phenylalanine amino acid substitution at a position corresponding to position 127 of SEQ ID NO: 110 (S127F), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a serine to phenylalanine amino acid substitution at a position corresponding to position 127 of SEQ ID NO: 110 (S127F), and an amino acid substitution at amino acid position 2 of the fragment. In certain embodiments, the TP53 polypeptide fragments comprise, consist of, or consist essentially of a serine to phenylalanine amino acid substitution at a position corresponding to position 127 of SEQ ID NO: 110 (S127F), and an amino acid substitution at amino acid position 9 of the fragment. In certain embodiments, the TP53 polypeptide fragments comprise, consist of, or consist essentially of a serine to phenylalanine amino acid substitution at a position corresponding to position 127 of SEQ ID NO: 110 (S127F), and an amino acid substitution at amino acid position 2 of the fragment and at position 9 of the fragment.

Described herein are TP53 polypeptide fragments comprising, consisting of, or consisting essentially of a lysine to asparagine amino acid substitution at a position corresponding to position 132 of SEQ ID NO: 110 (K132N), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a lysine to asparagine amino acid substitution at a position corresponding to position 132 of SEQ ID NO: 110 (K132N), and an amino acid substitution at amino acid position 2 of the fragment. In certain embodiments, the TP53 polypeptide fragments comprise, consist of, or consist essentially of a lysine to asparagine amino acid substitution at a position corresponding to position 132 of SEQ ID NO: 110 (K132N), and an amino acid substitution at amino acid position 9 of the fragment. In certain embodiments, the TP53 polypeptide fragments comprise, consist of, or consist essentially of a lysine to asparagine amino acid substitution at a position corresponding to position 132 of SEQ ID NO: 110 (K132N), and an amino acid substitution at amino acid position 2 of the fragment and at position 9 of the fragment.

Described herein are TP53 polypeptide fragments comprising, consisting of, or consisting essentially of a cysteine to tyrosine amino acid substitution at a position corresponding to position 141 of SEQ ID NO: 110 (C141Y), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a cysteine to tyrosine amino acid substitution at a position corresponding to position 141 of SEQ ID NO: 110 (C141Y), and an amino acid substitution at amino acid position 2 of the fragment. In certain embodiments, the TP53 polypeptide fragments comprise, consist of, or consist essentially of a cysteine to tyrosine amino acid substitution at a position corresponding to position 141 of SEQ ID NO: 110 (C141Y), and an amino acid substitution at amino acid position 9 of the fragment. In certain embodiments, the TP53 polypeptide fragments comprise, consist of, or consist essentially of a cysteine to tyrosine amino acid substitution at a position corresponding to position 141 of SEQ ID NO: 110 (C141Y), and an amino acid substitution at amino acid position 2 of the fragment and at position 9 of the fragment.

Described herein are TP53 polypeptide fragments comprising, consisting of, or consisting essentially of a proline to leucine amino acid substitution at a position corresponding to position 152 of SEQ ID NO: 110 (P152L), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a proline to leucine amino acid substitution at a position corresponding to position 152 of SEQ ID NO: 110 (P152L), and an amino acid substitution at amino acid position 2 of the fragment. In certain embodiments, the TP53 polypeptide fragments comprise, consist of, or consist essentially of a proline to leucine amino acid substitution at a position corresponding to position 152 of SEQ ID NO: 110 (P152L), and an amino acid substitution at amino acid position 9 of the fragment. In certain embodiments, the TP53 polypeptide fragments comprise, consist of, or consist essentially of a proline to leucine amino acid substitution at a position corresponding to position 152 of SEQ ID NO: 110 (P152L), and an amino acid substitution at amino acid position 2 of the fragment and at position 9 of the fragment.

Described herein are TP53 polypeptide fragments comprising, consisting of, or consisting essentially of a histidine to leucine amino acid substitution at a position corresponding to position 193 of SEQ ID NO: 110 (H193L), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a histidine to leucine amino acid substitution at a position corresponding to position 193 of SEQ ID NO: 110 (H193L), and an amino acid substitution at amino acid position 2 of the fragment. In certain embodiments, the TP53 polypeptide fragments comprise, consist of, or consist essentially of a histidine to leucine amino acid substitution at a position corresponding to position 193 of SEQ ID NO: 110 (H193L), and an amino acid substitution at amino acid position 9 of the fragment. In certain embodiments, the TP53 polypeptide fragments comprise, consist of, or consist essentially of a histidine to leucine amino acid substitution at a position corresponding to position 193 of SEQ ID NO: 110 (H193L), and an amino acid substitution at amino acid position 2 of the fragment and at position 9 of the fragment.

Described herein are TP53 polypeptide fragments comprising, consisting of, or consisting essentially of a histidine to tyrosine amino acid substitution at a position corresponding to position 193 of SEQ ID NO: 110 (H193Y), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a histidine to tyrosine amino acid substitution at a position corresponding to position 193 of SEQ ID NO: 110 (H193Y), and an amino acid substitution at amino acid position 2 of the fragment. In certain embodiments, the TP53 polypeptide fragments comprise, consist of, or consist essentially of a histidine to tyrosine amino acid substitution at a position corresponding to position 193 of SEQ ID NO: 110 (H193Y), and an amino acid substitution at amino acid position 9 of the fragment. In certain embodiments, the TP53 polypeptide fragments comprise, consist of, or consist essentially of a histidine to tyrosine amino acid substitution at a position corresponding to position 193 of SEQ ID NO: 110 (H193Y), and an amino acid substitution at amino acid position 2 of the fragment and at position 9 of the fragment.

Described herein are TP53 polypeptide fragments comprising, consisting of, or consisting essentially of a tyrosine to cysteine amino acid substitution at a position corresponding to position 220 of SEQ ID NO: 110 (Y220C), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a tyrosine to cysteine amino acid substitution at a position corresponding to position 220 of SEQ ID NO: 110 (Y220C), and an amino acid substitution at amino acid position 2 of the fragment. In certain embodiments, the TP53 polypeptide fragments comprise, consist of, or consist essentially of a tyrosine to cysteine amino acid substitution at a position corresponding to position 220 of SEQ ID NO: 110 (Y220C), and an amino acid substitution at amino acid position 9 of the fragment. In certain embodiments, the TP53 polypeptide fragments comprise, consist of, or consist essentially of a tyrosine to cysteine amino acid substitution at a position corresponding to position 220 of SEQ ID NO: 110 (Y220C), and an amino acid substitution at amino acid position 2 of the fragment and at position 9 of the fragment.

Described herein are TP53 polypeptide fragments comprising, consisting of, or consisting essentially of a valine to methionine amino acid substitution at a position corresponding to position 272 of SEQ ID NO: 110 (V272M), and an amino acid substitution at amino acid position 2 of the fragment, amino acid position 9 of the fragment, or both, wherein the fragment is nine amino acids in length. In certain embodiments, the TP53 polypeptide fragments comprise, consist of, or consist essentially of a valine to methionine amino acid substitution at a position corresponding to position 272 of SEQ ID NO: 110 (V272M), and an amino acid substitution at amino acid position 2 of the fragment. In certain embodiments, the TP53 polypeptide fragments comprise, consist of, or consist essentially of a valine to methionine amino acid substitution at a position corresponding to position 272 of SEQ ID NO: 110 (V272M), and an amino acid substitution at amino acid position 9 of the fragment. In certain embodiments, the TP53 polypeptide fragments comprise, consist of, or consist essentially of a valine to methionine amino acid substitution at a position corresponding to position 272 of SEQ ID NO: 110 (V272M), and an amino acid substitution at amino acid position 2 of the fragment and at position 9 of the fragment.

In certain embodiments, the TP53 polypeptide fragment binds to HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07:02, HLA-B*44:02, or HLA-B*35:01. In preferred embodiments, the SOX17 polypeptide fragment binds to HLA-A*02:01.

In some embodiments, the TP53 polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the TP53 polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the R110L substitution is at amino acid position 1 of the fragment. In certain embodiments, the R110L substitution is at amino acid position 2 of the fragment. In certain embodiments, the R110L substitution is at amino acid position 3 of the fragment. In certain embodiments, the R110L substitution is at amino acid position 4 of the fragment. In certain embodiments, the R110L substitution is at amino acid position 5 of the fragment. In certain embodiments, the R110L substitution is at amino acid position 6 of the fragment. In certain embodiments, the R110L substitution is at amino acid position 7 of the fragment. In certain embodiments, the R110L substitution is at amino acid position 8 of the fragment. In certain embodiments, the RI OL substitution is at amino acid position 9 of the fragment. In certain embodiments, the R110L substitution is at amino acid position 10 of the fragment. In preferred embodiments, the R110L substitution is at amino acid position 8 of the fragment.

In certain embodiments, the S127F substitution is at amino acid position 1 of the fragment. In certain embodiments, the Si27F substitution is at amino acid position 2 of the fragment. In certain embodiments, the Si27F substitution is at amino acid position 3 of the fragment. In certain embodiments, the S127F substitution is at amino acid position 4 of the fragment. In certain embodiments, the S127F substitution is at amino acid position 5 of the fragment. In certain embodiments, the S127F substitution is at amino acid position 6 of the fragment. In certain embodiments, the S127F substitution is at amino acid position 7 of the fragment. In certain embodiments, the Si27F substitution is at amino acid position 8 of the fragment. In certain embodiments, the Si27F substitution is at amino acid position 9 of the fragment. In certain embodiments, the S127F substitution is at amino acid position 10 of the fragment. In preferred embodiments, the S127F substitution is at amino acid position 7 of the fragment.

In certain embodiments, the K132N substitution is at amino acid position 1 of the fragment. In certain embodiments, the K132N substitution is at amino acid position 2 of the fragment. In certain embodiments, the K132N substitution is at amino acid position 3 of the fragment. In certain embodiments, the K132N substitution is at amino acid position 4 of the fragment. In certain embodiments, the K132N substitution is at amino acid position 5 of the fragment. In certain embodiments, the K132N substitution is at amino acid position 6 of the fragment. In certain embodiments, the K132N substitution is at amino acid position 7 of the fragment. In certain embodiments, the K132N substitution is at amino acid position 8 of the fragment. In certain embodiments, the K132N substitution is at amino acid position 9 of the fragment. In certain embodiments, the K132N substitution is at amino acid position 10 of the fragment. In preferred embodiments, the K132N substitution is at amino acid position 4 of the fragment. In preferred embodiments, the K132N substitution is at amino acid position 1 of the fragment In certain embodiments, the C141Y substitution is at amino acid position 1 of the fragment. In certain embodiments, the C141Y substitution is at amino acid position 2 of the fragment. In certain embodiments, the C141Y substitution is at amino acid position 3 of the fragment. In certain embodiments, the C141Y substitution is at amino acid position 4 of the fragment. In certain embodiments, the C141Y substitution is at amino acid position 5 of the fragment. In certain embodiments, the C141Y substitution is at amino acid position 6 of the fragment. In certain embodiments, the C141Y substitution is at amino acid position 7 of the fragment. In certain embodiments, the C141Y substitution is at amino acid position 8 of the fragment. In certain embodiments, the C141Y substitution is at amino acid position 9 of the fragment. In certain embodiments, the C141Y substitution is at amino acid position 10 of the fragment. In preferred embodiments, the C141Y substitution is at amino acid position 3 of the fragment.

In certain embodiments, the P152L substitution is at amino acid position 1 of the fragment. In certain embodiments, the P152L substitution is at amino acid position 2 of the fragment. In certain embodiments, the P152L substitution is at amino acid position 3 of the fragment. In certain embodiments, the P152L substitution is at amino acid position 4 of the fragment. In certain embodiments, the P152L substitution is at amino acid position 5 of the fragment. In certain embodiments, the P152L substitution is at amino acid position 6 of the fragment. In certain embodiments, the P152L substitution is at amino acid position 7 of the fragment. In certain embodiments, the P152L substitution is at amino acid position 8 of the fragment. In certain embodiments, the P152L substitution is at amino acid position 9 of the fragment. In certain embodiments, the P152L substitution is at amino acid position 10 of the fragment. In preferred embodiments, the P152L substitution is at amino acid position 9 of the fragment.

In certain embodiments, the H193L substitution is at amino acid position 1 of the fragment. In certain embodiments, the H193L substitution is at amino acid position 2 of the fragment. In certain embodiments, the H193L substitution is at amino acid position 3 of the fragment. In certain embodiments, the H193L substitution is at amino acid position 4 of the fragment. In certain embodiments, the H193L substitution is at amino acid position 5 of the fragment. In certain embodiments, the H193L substitution is at amino acid position 6 of the fragment. In certain embodiments, the H193L substitution is at amino acid position 7 of the fragment. In certain embodiments, the H193L substitution is at amino acid position 8 of the fragment. In certain embodiments, the H193L substitution is at amino acid position 9 of the fragment. In certain embodiments, the H193L substitution is at amino acid position 10 of the fragment. In preferred embodiments, the H193L substitution is at amino acid position 7 of the fragment.

In certain embodiments, the H193Y substitution is at amino acid position 1 of the fragment. In certain embodiments, the H193Y substitution is at amino acid position 2 of the fragment. In certain embodiments, the H193Y substitution is at amino acid position 3 of the fragment. In certain embodiments, the H193Y substitution is at amino acid position 4 of the fragment. In certain embodiments, the H193Y substitution is at amino acid position 5 of the fragment. In certain embodiments, the H193Y substitution is at amino acid position 6 of the fragment. In certain embodiments, the H193Y substitution is at amino acid position 7 of the fragment. In certain embodiments, the H193Y substitution is at amino acid position 8 of the fragment. In certain embodiments, the H193Y substitution is at amino acid position 9 of the fragment. In certain embodiments, the H193Y substitution is at amino acid position 10 of the fragment. In preferred embodiments, the H193Y substitution is at amino acid position 7 of the fragment.

In certain embodiments, the Y220C substitution is at amino acid position 1 of the fragment. In certain embodiments, the Y220C substitution is at amino acid position 2 of the fragment. In certain embodiments, the Y220C substitution is at amino acid position 3 of the fragment. In certain embodiments, the Y220C substitution is at amino acid position 4 of the fragment. In certain embodiments, the Y220C substitution is at amino acid position 5 of the fragment. In certain embodiments, the Y220C substitution is at amino acid position 6 of the fragment. In certain embodiments, the Y220C substitution is at amino acid position 7 of the fragment. In certain embodiments, the Y220C substitution is at amino acid position 8 of the fragment. In certain embodiments, the Y220C substitution is at amino acid position 9 of the fragment. In certain embodiments, the Y220C substitution is at amino acid position 10 of the fragment. In preferred embodiments, the Y220C substitution is at amino acid position 4 of the fragment.

In certain embodiments, the V272M substitution is at amino acid position 1 of the fragment. In certain embodiments, the V272M substitution is at amino acid position 2 of the fragment. In certain embodiments, the V272M substitution is at amino acid position 3 of the fragment. In certain embodiments, the V272M substitution is at amino acid position 4 of the fragment. In certain embodiments, the V272M substitution is at amino acid position 5 of the fragment. In certain embodiments, the V272M substitution is at amino acid position 6 of the fragment. In certain embodiments, the V272M substitution is at amino acid position 7 of the fragment. In certain embodiments, the V272M substitution is at amino acid position 8 of the fragment. In certain embodiments, the V272M substitution is at amino acid position 9 of the fragment. In certain embodiments, the V272M substitution is at amino acid position 10 of the fragment. In preferred embodiments, the V272M substitution is at amino acid position 9 of the fragment.

In still further embodiments, the TP53 polypeptide fragment is selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 66, SEQ ID NO: 67, SEQ ID NO: 68, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 94, SEQ ID NO: 95, and SEQ ID NO: 96. In certain embodiments, the TP53 polypeptide fragment is SEQ ID NO: 57 or a sequence having at least 90% sequence identity, at least 95% sequence identity or at least 99% sequence identity to SEQ ID NO: 57. In certain embodiments, the TP53 polypeptide fragment is SEQ ID NO: 58 or a sequence having at least 90% sequence identity, at least 95% sequence identity or at least 99% sequence identity to SEQ ID NO: 58. In certain embodiments, the TP53 polypeptide fragment is SEQ ID NO: 59 or a sequence having at least 90% sequence identity, at least 95% sequence identity or at least 99% sequence identity to SEQ ID NO: 59. In certain embodiments, the TP53 polypeptide fragment is SEQ ID NO: 60 or a sequence having at least 90% sequence identity, at least 95% sequence identity or at least 99% sequence identity to SEQ ID NO: 60. In certain embodiments, the TP53 polypeptide fragment is SEQ ID NO: 61 or a sequence having at least 90% sequence identity, at least 95% sequence identity or at least 99% sequence identity to SEQ ID NO: 61. In certain embodiments, the TP53 polypeptide fragment is SEQ ID NO: 62 or a sequence having at least 90% sequence identity, at least 95% sequence identity or at least 99% sequence identity to SEQ ID NO: 62. In certain embodiments, the TP53 polypeptide fragment is SEQ ID NO: 63 or a sequence having at least 90% sequence identity, at least 95% sequence identity or at least 99% sequence identity to SEQ ID NO: 63. In certain embodiments, the TP53 polypeptide fragment is SEQ ID NO: 64 or a sequence having at least 90% sequence identity, at least 95% sequence identity or at least 99% sequence identity to SEQ ID NO: 64. In certain embodiments, the TP53 polypeptide fragment is SEQ ID NO: 66 or a sequence having at least 90% sequence identity, at least 95% sequence identity or at least 99% sequence identity to SEQ ID NO: 66. In certain embodiments, the TP53 polypeptide fragment is SEQ ID NO: 67 or a sequence having at least 90% sequence identity, at least 95% sequence identity or at least 99% sequence identity to SEQ ID NO: 67. In certain embodiments, the TP53 polypeptide fragment is SEQ ID NO: 68 or a sequence having at least 90% sequence identity, at least 95% sequence identity or at least 99% sequence identity to SEQ ID NO: 68. In certain embodiments, the TP53 polypeptide fragment is SEQ ID NO: 70 or a sequence having at least 90% sequence identity, at least 95% sequence identity or at least 99% sequence identity to SEQ ID NO: 70. In certain embodiments, the TP53 polypeptide fragment is SEQ ID NO: 71 or a sequence having at least 90% sequence identity, at least 95% sequence identity or at least 99% sequence identity to SEQ ID NO: 71. In certain embodiments, the TP53 polypeptide fragment is SEQ ID NO: 72 or a sequence having at least 90% sequence identity, at least 95% sequence identity or at least 99% sequence identity to SEQ ID NO: 72. In certain embodiments, the TP53 polypeptide fragment is SEQ ID NO: 73 or a sequence having at least 90% sequence identity, at least 95% sequence identity or at least 99% sequence identity to SEQ ID NO: 73. In certain embodiments, the TP53 polypeptide fragment is SEQ ID NO: 74 or a sequence having at least 90% sequence identity, at least 95% sequence identity or at least 99% sequence identity to SEQ ID NO: 74. In certain embodiments, the TP53 polypeptide fragment is SEQ ID NO: 75 or a sequence having at least 90% sequence identity, at least 95% sequence identity or at least 99% sequence identity to SEQ ID NO: 75. In certain embodiments, the TP53 polypeptide fragment is SEQ ID NO: 76 or a sequence having at least 90% sequence identity, at least 95% sequence identity or at least 99% sequence identity to SEQ ID NO: 76. In certain embodiments, the TP53 polypeptide fragment is SEQ ID NO: 78 or a sequence having at least 90% sequence identity, at least 95% sequence identity or at least 99% sequence identity to SEQ ID NO: 78. In certain embodiments, the TP53 polypeptide fragment is SEQ ID NO: 79 or a sequence having at least 90% sequence identity, at least 95% sequence identity or at least 99% sequence identity to SEQ ID NO: 79. In certain embodiments, the TP53 polypeptide fragment is SEQ ID NO: 94 or a sequence having at least 90% sequence identity, at least 95% sequence identity or at least 99% sequence identity to SEQ ID NO: 94. In certain embodiments, the TP53 polypeptide fragment is SEQ ID NO: 95 or a sequence having at least 90% sequence identity, at least 95% sequence identity or at least 99% sequence identity to SEQ ID NO: 95. In certain embodiments, the TP53 polypeptide fragment is SEQ ID NO: 96 or a sequence having at least 90% sequence identity, at least 95% sequence identity or at least 99% sequence identity to SEQ ID NO: 96.

In some embodiments, the TP53 polypeptide fragment has the sequence $GX_2APPQYLX_9$ (SEQ ID NO: 236), wherein $X_2$ is any amino acid other than leucine, and preferably methionine, and $X_9$ is any amino acid other than isoleucine, and preferably valine.

In some embodiments, the TP53 polypeptide fragment has the sequence $AX2NNMFCQX_9$ (SEQ ID NO: 237), wherein $X_2$ is any amino acid other than leucine, and preferably methionine, and $X_9$ is any amino acid other than leucine, and preferably valine.

In some embodiments, the TP53 polypeptide fragment has the sequence $NX_2FCQLAKX_9$ (SEQ ID NO: 238), wherein $X_2$ is any amino acid other than methionine, and preferably leucine, and $X_9$ is any amino acid other than threonine, and preferably valine.

In some embodiments, the TP53 polypeptide fragment has the sequence QLWVDSTP$X_9$ (SEQ ID NO: 239), wherein $X_9$ is any amino acid other than leucine, and preferably isoleucine or valine.

In some embodiments, the TP53 polypeptide fragment has the sequence RLILTIIT$X_9$ (SEQ ID NO: 240), wherein $X_9$ is any amino acid other than leucine, and preferably valine.

In some embodiments, the TP53 polypeptide fragment has the sequence YQGSYGFL$X_9$ (SEQ ID NO: 241), wherein $X_9$ is any amino acid other than leucine, and preferably isoleucine or valine.

In some embodiments, the TP53 polypeptide fragment has the sequence S$X_2$TCTYFP$X_9$ (SEQ ID NO: 242), wherein $X_2$ is any amino acid other than valine, and preferably leucine or methionine, and $X_9$ is any amino acid other than alanine, and preferably leucine, isoleucine, or valine.

In some embodiments, the TP53 polypeptide fragment has the sequence V$X_2$PCEPPEV (SEQ ID NO: 243), wherein $X_2$ is any amino acid other than valine, and preferably leucine or methionine.

In some embodiments, the TP53 polypeptide fragment has the sequence K$X_2$YPVQLW$X_9$ (SEQ ID NO: 244); wherein $X_2$ is any amino acid other than threonine, and preferably leucine or methionine, and $X_9$ is any amino acid other than valine, and preferably leucine or isoleucine.

In some embodiments, the TP53 polypeptide fragment has the sequence G$X_2$APPQLL$X_9$ (SEQ ID NO: 245), wherein $X_2$ is any amino acid other than leucine, and preferably methionine, and $X_9$ is any amino acid other than isoleucine, and preferably valine.

In some embodiments, the TP53 polypeptide fragment has the sequence LLGRNSFE$X_9$ (SEQ ID NO: 246), wherein $X_9$ is any amino acid other than methionine, and preferably leucine or isoleucine.

ERBB2 Polypeptides

Described herein are ERBB2 polypeptide fragments comprising, consisting of, or consisting essentially of an amino acid modification relative to SEQ ID NO: 104, and an amino acid substitution at amino acid position 2 of the fragment, amino acid position 9 of the fragment, or both, wherein the fragment is at least nine amino acids in length. Described herein are ERBB2 polypeptide fragments comprising, consisting of, or consisting essentially of an amino acid modification relative to SEQ ID NO: 104, and an amino acid substitution at amino acid position 3 of the fragment, amino acid position 10 of the fragment, or both, wherein the fragment is at least ten amino acids in length.

In certain embodiments, the modification comprises a deletion, insertion, and/or substitution. In preferred embodiments, the modification comprises a substitution. In further preferred embodiments, the modification comprises valine to isoleucine amino acid substitution at a position corresponding to position 842 of SEQ ID NO: 104 (V842I).

Described herein are ERBB2 polypeptide fragments comprising, consisting of, or consisting essentially of a valine to isoleucine amino acid substitution at a position corresponding to position 842 of SEQ ID NO: 104 (V842I), and an amino acid substitution at amino acid position 2 of the fragment, amino acid position 9 of the fragment, or both, wherein the fragment is nine amino acids in length. In certain embodiments, the ERBB2 polypeptide fragments comprise, consist of, or consist essentially of a valine to isoleucine amino acid substitution at a position corresponding to position 842 of SEQ ID NO: 104 (V842I), and an amino acid substitution at amino acid position 2 of the fragment. In certain embodiments, the ERBB2 polypeptide fragments comprise, consist of, or consist essentially of a valine to isoleucine amino acid substitution at a position corresponding to position 842 of SEQ ID NO: 104 (V842I), and an amino acid substitution at amino acid position 9 of the fragment. In certain embodiments, the ERBB2 polypeptide fragments comprise, consist of, or consist essentially of a valine to isoleucine amino acid substitution at a position corresponding to position 842 of SEQ ID NO: 104 (V842I), and an amino acid substitution at amino acid position 2 of the fragment and at position 9 of the fragment.

In certain embodiments, the ERBB2 polypeptide fragment binds to HLA 2.1 (HLA-A*02:01), HLA-A*01:01, HLA-A*03:01, HLA-A*11:01, HLA-A*24:02, HLA-A*33:03, HLA-C*07:01, HLA-C*07:02, HLA-C*04:01, HLA-B*07:02, HLA-B*44:02, or HLA-B*35:01. In preferred embodiments, the ERBB2 polypeptide fragment binds to HLA-A*02:01.

In some embodiments, the ERBB2 polypeptide fragment has greater affinity for HLA-A*02:01 than a cognate native polypeptide fragment. In certain embodiments, binding affinity for HLA-A*02:01 is a measurement of average relative binding to a positive 9-mer polypeptide control, expressed as a percent (%) binding affinity. In certain embodiments, the ERBB2 polypeptide fragment has a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% greater affinity for HLA-A*02:01 than a cognate native polypeptide fragment, wherein binding affinity for HLA-A*02:01 is a measurement of average relative binding to a positive 9-mer polypeptide control.

In certain embodiments, the V842I substitution is at amino acid position 1 of the fragment. In certain embodiments, the V842I substitution is at amino acid position 2 of the fragment. In certain embodiments, the V842I substitution is at amino acid position 3 of the fragment. In certain embodiments, the V842I substitution is at amino acid position 4 of the fragment. In certain embodiments, the V842I substitution is at amino acid position 5 of the fragment. In certain embodiments, the V842I substitution is at amino acid position 6 of the fragment. In certain embodiments, the V842I substitution is at amino acid position 7 of the fragment. In certain embodiments, the V842I substitution is at amino acid position 8 of the fragment. In certain embodiments, the V842I substitution is at amino acid position 9 of the fragment. In certain embodiments, the V842I substitution is at amino acid position 10 of the fragment. In preferred embodiments, the V842I substitution at amino acid position 3 of the fragment.

In still further embodiments, the ERBB2 polypeptide fragment is selected from the group consisting of SEQ ID NO: 84, SEQ ID NO: 85, and SEQ ID NO: 86. In certain embodiments, the ERBB2 polypeptide fragment is SEQ ID NO: 84 or a sequence having at least 90% sequence identity, at least 95% sequence identity or at least 99% sequence identity to SEQ ID NO: 84. In certain embodiments, the ERBB2 polypeptide fragment is SEQ ID NO: 85 or a sequence having at least 90% sequence identity, at least 95% sequence identity or at least 99% sequence identity to SEQ ID NO: 85. In certain embodiments, the ERBB2 polypeptide fragment is SEQ ID NO: 86 or a sequence having at least 90% sequence identity, at least 95% sequence identity or at least 99% sequence identity to SEQ ID NO: 86.

In some embodiments, the ERBB2 polypeptide fragment has the sequence RX$_2$IHRDLAX$_9$ (SEQ ID NO: 247), wherein X$_2$ is any amino acid other than leucine, and preferably methionine, and X$_9$ is any amino acid other than alanine, and preferably leucine or valine.

T-Cell Receptors

TCRs may be generated that bind the polypeptide fragments of the disclosure. The TCRs may be identified based on T-cell binding to the polypeptide fragments, followed by sequencing of the TCR. The identified TCR may be identified from αβ T cells. The identified TCRs may be further engineered to improve their affinity, stability, solubility or the like. For example, TCRs may be cysteine stabilized, expressed as soluble TCRs, as single chain TCRs, as fusion with N-terminal or C-terminal epitope tags, engineered to improve stability with mutations in hydrophobic core, such as positions 11, 13, 19, 21, 53, 76, 89, 91 or 94 of the a chain, domain swapped with α and β chain variable and/or constant domains swapped as described in U.S. Pat. Nos. 7,329,731, 7,569,664, 9,133,264, 9,624,292, US2016/0130319 and U.S. Pat. No. 9,884,075.

Described herein are TCRs comprising an alpha chain and a beta chain, wherein: (a) the alpha chain comprises a CDR3 comprising an amino acid sequence provided in Table 14, Table 15, Table 16, Table 17 or Table 18, and (b) the beta chain comprises a CDR3 comprising a corresponding amino acid sequence provided in Table 14, Table 15, Table 16, Table 17, or Table 18. An alpha chain CDR3 corresponds to a beta chain CDR3 if they appear in the same row in Table 14, Table 15, Table 16, Table 17 or Table 18.

Also described herein are TCRs comprising an alpha chain and a beta chain, wherein: (a) the alpha chain comprises a CDR1 comprising an amino acid sequence provided in Table 19, Table 20, Table 21, Table 22, or Table 23, a CDR2 comprising an amino acid sequence provided in Table 19, Table 20, Table 21, Table 22, or Table 23, and a CDR3 comprising an amino acid sequence provided in Table 14, Table 15, Table 16, Table 17, or Table 18, and (b) the beta chain comprises a CDR1 comprising an amino acid sequence provided in Table 19, Table 20, Table 21, Table 22, or Table 23, a CDR2 comprising an amino acid sequence provided in Table 19, Table 20, Table 21, Table 22, or Table 23, and a CDR3 comprising a corresponding amino acid sequence provided in Table 14, Table 15, Table 16, Table 17 or Table 18. An alpha chain CDR1 or CDR2 corresponds to a beta chain CDR1 or CDR2 if they appear in the same row in Table 19, Table 20, Table 21, Table 22, or Table 23. An alpha chain CDR3 corresponds to a beta chain CDR3 if they appear in the same row in Table 14, Table 15, Table 16, Table 17, or Table 18. An alpha and beta chain CDR1 and CDR2 provided in Table 19, Table 20, Table 21, Table 22, or Table 23 correspond to an alpha and beta chain CDR3 provided in the same row in Table 14, Table 15, Table 16, Table 17 or Table 18.

Described herein are TCRs comprising an alpha chain and a beta chain, wherein: (a) the alpha chain comprises a CDR3 comprising an amino acid sequence provided in Table 14, and (b) the beta chain comprises a CDR3 comprising a corresponding amino acid sequence provided in Table 14. In certain embodiments, the TCRs provided in Table 14 recognize the PIK3CA mutant-mimic fragments SEQ ID NO: 9 and SEQ ID NO: 45.

Also described herein are TCRs comprising an alpha chain and a beta chain, wherein: (a) the alpha chain comprises a CDR1 comprising an amino acid sequence provided in Table 19, a CDR2 comprising an amino acid sequence provided in Table 19, and a CDR3 comprising an amino acid sequence provided in Table 14, and (b) the beta chain comprises a CDR1 comprising an amino acid sequence provided in Table 19, a CDR2 comprising an amino acid sequence provided in Table 19, and a CDR3 comprising a corresponding amino acid sequence provided in Table 14. In certain embodiments, the TCRs provided in Table 19 and Table 14 recognize the PIK3CA mutant-mimic fragments SEQ ID NO: 9 and SEQ ID NO: 45. An alpha and beta chain CDR1 and CDR2 provided in Table 19 correspond to and alpha and beta chain CDR3 provided in the same row in Table 14.

In certain embodiments, described herein are TCRs comprising an alpha chain and a beta chain, wherein: (a) the alpha chain comprises a CDR3 comprising the amino acid sequence of SEQ ID NO: 120 or having at least 90% sequence identity to SEQ ID NO: 120 and the beta chain comprises a CDR3 comprising the amino acid sequence of SEQ ID NO: 114 or having at least 90% sequence identity to SEQ ID NO: 114; (b) the alpha chain comprises a CDR3 comprising the amino acid sequence of SEQ ID NO: 118 or having at least 90% sequence identity to SEQ ID NO: 118 and the beta chain comprises a CDR3 comprising the amino acid sequence of SEQ ID NO: 114 or having at least 90% sequence identity to SEQ ID NO: 114; (c) the alpha chain comprises a CDR3 comprising the amino acid sequence of SEQ ID NO: 122 or having at least 90% sequence identity to SEQ ID NO: 122 and the beta chain comprises a CDR3 comprising the amino acid sequence of SEQ ID NO: 114 or having at least 90% sequence identity to SEQ ID NO: 114; (d) the alpha chain comprises a CDR3 comprising the amino acid sequence of SEQ ID NO: 122 or having at least 90% sequence identity to SEQ ID NO: 122 and the beta chain comprises a CDR3 comprising the amino acid sequence of SEQ ID NO: 124 or having at least 90% sequence identity to SEQ ID NO: 124; (e) the alpha chain comprises a CDR3 comprising the amino acid sequence of SEQ ID NO: 122 or having at least 90% sequence identity to SEQ ID NO: 122 and the beta chain comprises a CDR3 comprising the amino acid sequence of SEQ ID NO: 134 or having at least 90% sequence identity to SEQ ID NO: 134; (f) the alpha chain comprises a CDR3 comprising the amino acid sequence of SEQ ID NO: 112 or having at least 90% sequence identity to SEQ ID NO: 112 and the beta chain comprises a CDR3 comprising the amino acid sequence of SEQ ID NO: 114 or having at least 90% sequence identity to SEQ ID NO: 114; (g) the alpha chain comprises a CDR3 comprising the amino acid sequence of SEQ ID NO: 116 or having at least 90% sequence identity to SEQ ID NO: 116 and the beta chain comprises a CDR3 comprising the amino acid sequence of SEQ ID NO: 114 or having at least 90% sequence identity to SEQ ID NO: 114; (h) the alpha chain comprises a CDR3 comprising the amino acid sequence of SEQ ID NO: 116 or having at least 90% sequence identity to SEQ ID NO: 116 and the beta chain comprises a CDR3 comprising the amino acid sequence of SEQ ID NO: 128 or having at least 90% sequence identity to SEQ ID NO: 128; (i) the alpha chain comprises a CDR3 comprising the amino acid sequence of SEQ ID NO: 126 or having at least 90% sequence identity to SEQ ID NO: 126 and the beta chain comprises a CDR3 comprising the amino acid sequence of SEQ ID NO: 114 or having at least 90% sequence identity to SEQ ID NO: 114; (j) the alpha chain comprises a CDR3 comprising the amino acid sequence of SEQ ID NO: 130 or having at least 90% sequence identity to SEQ ID NO: 130 and the beta chain comprises a CDR3 comprising the amino acid sequence of SEQ ID NO: 114 or having at least 90% sequence identity to SEQ ID NO: 114; (k) the alpha chain comprises a CDR3 comprising the amino acid sequence of SEQ ID NO: 130 or having at least 90% sequence identity to SEQ ID NO: 130 and the beta chain comprises a CDR3 comprising the amino acid sequence of SEQ ID NO: 132 or having at least 90% sequence identity to SEQ ID NO: 132; or (1) the alpha chain comprises a CDR3 comprising the amino acid sequence of SEQ ID NO: 130 or having at least 90% sequence identity to SEQ ID NO: 130 and the beta chain comprises a CDR3 comprising the amino acid sequence of SEQ ID NO: 134 or having at least 90% sequence identity to SEQ ID NO: 134.

Described herein are TCRs comprising an alpha chain and a beta chain, wherein: (a) the alpha chain comprises a CDR3 comprising an amino acid sequence provided in Table 15, and the beta chain comprises a CDR3 comprising a corresponding amino acid sequence provided in Table 15. In certain embodiments, the TCRs provided in Table 15 recognize the TP53 mutant-mimic fragments SEQ ID NO: 13 and SEQ ID NO: 59.

Also described herein are TCRs comprising an alpha chain and a beta chain, wherein: (a) the alpha chain comprises a CDR1 comprising an amino acid sequence provided in Table 20, a CDR2 comprising an amino acid sequence provided in Table 20, and a CDR3 comprising an amino acid sequence provided in Table 15, and (b) the beta chain comprises a CDR1 comprising an amino acid sequence provided in Table 20, a CDR2 comprising an amino acid sequence provided in Table 20, and a CDR3 comprising a corresponding amino acid sequence provided in Table 15. In certain embodiments, the TCRs provided in Table 20 and Table 15 recognize the TP53 mutant-mimic fragments SEQ ID NO: 13 and SEQ ID NO: 59. An alpha and beta chain CDR1 and CDR2 provided in Table 20 correspond to and alpha and beta chain CDR3 provided in the same row in Table 15.

In certain embodiments, described herein are TCRs comprising an alpha chain and a beta chain, wherein: (a) the alpha chain comprises a CDR3 comprising the amino acid sequence of SEQ ID NO: 118 or having at least 90% sequence identity to SEQ ID NO: 118 and the beta chain comprises a CDR3 comprising the amino acid sequence of SEQ ID NO: 114 or having at least 90% sequence identity to SEQ ID NO: 114; (b) the alpha chain comprises a CDR3 comprising the amino acid sequence of SEQ ID NO: 118 or having at least 90% sequence identity to SEQ ID NO: 118 and the beta chain comprises a CDR3 comprising the amino acid sequence of SEQ ID NO: 142 or having at least 90% sequence identity to SEQ ID NO: 142; (c) the alpha chain comprises a CDR3 comprising the amino acid sequence of SEQ ID NO: 207 or having at least 90% sequence identity to SEQ ID NO: 207 and the beta chain comprises a CDR3 comprising the amino acid sequence of SEQ ID NO: 114 or having at least 90% sequence identity to SEQ ID NO: 114; (d) the alpha chain comprises a CDR3 comprising the amino acid sequence of SEQ ID NO: 112 or having at least 90% sequence identity to SEQ ID NO: 112 and the beta chain comprises a CDR3 comprising the amino acid sequence of SEQ ID NO: 114 or having at least 90% sequence identity to SEQ ID NO: 114; (e) the alpha chain comprises a CDR3 comprising the amino acid sequence of SEQ ID NO: 205 or having at least 90% sequence identity to SEQ ID NO: 205 and the beta chain comprises a CDR3 comprising the amino acid sequence of SEQ ID NO: 114 or having at least 90% sequence identity to SEQ ID NO: 114; (f) the alpha chain comprises a CDR3 comprising the amino acid sequence of SEQ ID NO: 172 or having at least 90% sequence identity to SEQ ID NO: 172 and the beta chain comprises a CDR3 comprising the amino acid sequence of SEQ ID NO: 114 or having at least 90% sequence identity to SEQ ID NO: 114; (g) the alpha chain comprises a CDR3 comprising the amino acid sequence of SEQ ID NO: 172 or having at least 90% sequence identity to SEQ ID NO: 172 and the beta chain comprises a CDR3 comprising the amino acid sequence of SEQ ID NO: 166 or having at least 90% sequence identity to SEQ ID NO: 166; (h) the alpha chain comprises a CDR3 comprising the amino acid sequence of SEQ ID NO: 186 or having at least 90% sequence identity to SEQ ID NO: 186 and the beta chain comprises a CDR3 comprising the amino acid sequence of SEQ ID NO: 114 or having at least 90% sequence identity to SEQ ID NO: 114; (i) the alpha chain comprises a CDR3 comprising the amino acid sequence of SEQ ID NO: 152 or having at least 90% sequence identity to SEQ ID NO: 152 and the beta chain comprises a CDR3 comprising the amino acid sequence of SEQ ID NO: 114 or having at least 90% sequence identity to SEQ ID NO: 114; (j) the alpha chain comprises a CDR3 comprising the amino acid sequence of SEQ ID NO: 130 or having at least 90% sequence identity to SEQ ID NO: 130 and the beta chain comprises a CDR3 comprising the amino acid sequence of SEQ ID NO: 114 or having at least 90% sequence identity to SEQ ID NO: 114; (k) the alpha chain comprises a CDR3 comprising the amino acid sequence of SEQ ID NO: 130 or having at least 90% sequence identity to SEQ ID NO: 130 and the beta chain comprises a CDR3 comprising the amino acid sequence of SEQ ID NO: 142 or having at least 90% sequence identity to SEQ ID NO: 142; (1) the alpha chain comprises a CDR3 comprising the amino acid sequence of SEQ ID NO: 130 or having at least 90% sequence identity to SEQ ID NO: 130 and the beta chain comprises a CDR3 comprising the amino acid sequence of SEQ ID NO: 150 or having at least 90% sequence identity to SEQ ID NO: 150; (m) the alpha chain comprises a CDR3 comprising the amino acid sequence of SEQ ID NO: 130 or having at least 90% sequence identity to SEQ ID NO: 130 and the beta chain comprises a CDR3 comprising the amino acid sequence of SEQ ID NO: 162 or having at least 90% sequence identity to SEQ ID NO: 162; (n) the alpha chain comprises a CDR3 comprising the amino acid sequence of SEQ ID NO: 136 or having at least 90% sequence identity to SEQ ID NO: 136 and the beta chain comprises a CDR3 comprising the amino acid sequence of SEQ ID NO: 114 or having at least 90% sequence identity to SEQ ID NO: 114; (o) the alpha chain comprises a CDR3 comprising the amino acid sequence of SEQ ID NO: 136 or having at least 90% sequence identity to SEQ ID NO: 136 and the beta chain comprises a CDR3 comprising the amino acid sequence of SEQ ID NO: 138 or having at least 90% sequence identity to SEQ ID NO: 138; (p) the alpha chain comprises a CDR3 comprising the amino acid sequence of SEQ ID NO: 136 or having at least 90% sequence identity to SEQ ID NO: 136 and the beta chain comprises a CDR3 comprising the amino acid sequence of SEQ ID NO: 142 or having at least 90% sequence identity to SEQ ID NO: 142; (q) the alpha chain comprises a CDR3 comprising the amino acid sequence of SEQ ID NO: 140 or having at least 90% sequence identity to SEQ ID NO: 140 and the beta chain comprises a CDR3 comprising the amino acid sequence of SEQ ID NO: 114 or having at least 90% sequence identity to SEQ ID NO: 114; (r) the alpha chain comprises a CDR3 comprising the amino acid sequence of SEQ ID NO: 140 or having at least 90% sequence identity to SEQ ID NO: 140 and the beta chain comprises a CDR3 comprising the amino acid sequence of SEQ ID NO: 160 or having at least 90% sequence identity to SEQ ID NO: 160; (s) the alpha chain comprises a CDR3 comprising the amino acid sequence of SEQ ID NO: 144 or having at least 90% sequence identity to SEQ ID NO: 144 and the beta chain comprises a CDR3 comprising the amino acid sequence of SEQ ID NO: 114 or having at least 90% sequence identity to SEQ ID NO: 114; (t) the alpha chain comprises a CDR3 comprising the amino acid sequence of SEQ ID NO: 144 or having at least 90% sequence identity to SEQ ID NO: 144 and the beta chain comprises a CDR3 comprising the amino acid sequence of SEQ ID NO: 146 or having at least 90% sequence identity to SEQ ID NO: 146; (u) the alpha chain comprises a CDR3 comprising the amino acid sequence of SEQ ID NO: 144 or having at least 90% sequence identity to SEQ ID NO: 144 and the beta chain comprises a CDR3 comprising the amino acid sequence of SEQ ID NO: 158 or having at least 90% sequence identity to SEQ ID NO: 158; (v) the alpha chain comprises a CDR3 comprising the amino acid sequence of SEQ ID NO: 148 or having at least 90% sequence identity to SEQ ID NO: 148 and the beta chain comprises a CDR3 comprising the amino acid sequence of SEQ ID NO: 114 or having at least 90% sequence identity to SEQ ID NO: 114; (w) the alpha chain comprises a CDR3 comprising the amino acid sequence of SEQ ID NO: 148 or having at least 90% sequence identity to SEQ ID NO: 148 and the beta chain comprises a CDR3 comprising the amino acid sequence of SEQ ID NO: 150 or having at least 90% sequence identity to SEQ ID NO: 150; (x) the alpha chain comprises a CDR3 comprising the amino acid sequence of SEQ ID NO: 154 or having at least 90% sequence identity to SEQ ID NO: 154 and the beta chain comprises a CDR3 comprising the amino acid sequence of SEQ ID NO: 156 or having at least 90% sequence identity to SEQ ID NO: 156; (y) the alpha chain comprises a CDR3 comprising the amino acid sequence of SEQ ID NO: 164 or having at least 90% sequence identity to SEQ ID NO: 164 and the beta chain comprises a CDR3 comprising the amino acid sequence of SEQ ID NO: 114 or having at least 90% sequence identity to SEQ ID NO: 114; (z) the alpha chain comprises a CDR3 comprising the amino acid sequence of SEQ ID NO: 164 or having at least 90% sequence identity to SEQ ID NO: 164 and the beta chain comprises a CDR3 comprising the amino acid sequence of SEQ ID NO: 166 or having at least 90% sequence identity to SEQ ID NO: 166; (aa) the alpha chain comprises a CDR3 comprising the amino acid sequence of SEQ ID NO: 164 or having at least 90% sequence identity to SEQ ID NO: 164 and the beta chain comprises a CDR3 comprising the amino acid sequence of SEQ ID NO: 180 or having at least 90% sequence identity to SEQ ID NO: 180; (bb) the alpha chain comprises a CDR3 comprising the amino acid sequence of SEQ ID NO: 164 or having at least 90% sequence identity to SEQ ID NO: 164 and the beta chain comprises a CDR3 comprising the amino acid sequence of SEQ ID NO: 182 or having at least 90% sequence identity to SEQ ID NO: 182; (cc) the alpha chain comprises a CDR3 comprising the amino acid sequence of SEQ ID NO: 164 or having at least 90% sequence identity to SEQ ID NO: 164 and the beta chain comprises a CDR3 comprising the amino acid sequence of SEQ ID NO: 197 or having at least 90% sequence identity to SEQ ID NO: 197; (dd) the alpha chain comprises a CDR3 comprising the amino acid sequence of SEQ ID NO: 168 or having at least 90% sequence identity to SEQ ID NO: 168 and the beta chain comprises a CDR3 comprising the amino acid sequence of SEQ ID NO: 114 or having at least 90% sequence identity to SEQ ID NO: 114; (ee) the alpha chain comprises a CDR3 comprising the amino acid sequence of SEQ ID NO: 168 or having at least 90% sequence identity to SEQ ID NO: 168 and the beta chain comprises a CDR3 comprising the amino acid sequence of SEQ ID NO: 170 or having at least 90% sequence identity to SEQ ID NO: 170; (ff) the alpha chain comprises a CDR3 comprising the amino acid sequence of SEQ ID NO: 168 or having at least 90% sequence identity to SEQ ID NO: 168 and the beta chain comprises a CDR3 comprising the amino acid sequence of SEQ ID NO: 199 or having at least 90% sequence identity to SEQ ID NO: 199; (gg) the alpha chain comprises a CDR3 comprising the amino acid sequence of SEQ ID NO: 174 or having at least 90% sequence identity to SEQ ID NO: 174 and the beta chain comprises a CDR3 comprising the amino acid sequence of SEQ ID NO: 176 or having at least 90% sequence identity to SEQ ID NO: 176; (hh) the alpha chain comprises a CDR3 comprising the amino acid sequence of SEQ ID NO: 174 or having at least 90% sequence identity to SEQ ID NO: 174 and the beta chain comprises a CDR3 comprising the amino acid sequence of SEQ ID NO: 178 or having at least 90% sequence identity to SEQ ID NO: 178; (ii) the alpha chain comprises a CDR3 comprising the amino acid sequence of SEQ ID NO: 184 or having at least 90% sequence identity to SEQ ID NO: 184 and the beta chain comprises a CDR3 comprising the amino acid sequence of SEQ ID NO: 114 or having at least 90% sequence identity to SEQ ID NO: 114; (jj) the alpha chain comprises a CDR3 comprising the amino acid sequence of SEQ ID NO: 184 or having at least 90% sequence identity to SEQ ID NO: 184 and the beta chain comprises a CDR3 comprising the amino acid sequence of SEQ ID NO: 188 or having at least 90% sequence identity to SEQ ID NO: 188; (kk) the alpha chain comprises a CDR3 comprising the amino acid sequence of SEQ ID NO: 190 or having at least 90% sequence identity to SEQ ID NO: 190 and the beta chain comprises a CDR3 comprising the amino acid sequence of SEQ ID NO: 192 or having at least 90% sequence identity to SEQ ID NO: 192; (ll) the alpha chain comprises a CDR3 comprising the amino acid sequence of SEQ ID NO: 194 or having at least 90% sequence identity to SEQ ID NO: 194 and the beta chain comprises a CDR3 comprising the amino acid sequence of SEQ ID NO: 114 or having at least 90% sequence identity to SEQ ID NO: 114; (mm) the alpha chain comprises a CDR3 comprising the amino acid sequence of SEQ ID NO: 201 or having at least 90% sequence identity to SEQ ID NO: 201 and the beta chain comprises a CDR3 comprising the amino acid sequence of SEQ ID NO: 203 or having at least 90% sequence identity to SEQ ID NO: 203; or (nn) the alpha chain comprises a CDR3 comprising the amino acid sequence of SEQ ID NO: 210 or having at least 90% sequence identity to SEQ ID NO: 210 and the beta chain comprises a CDR3 comprising the amino acid sequence of SEQ ID NO: 114 or having at least 90% sequence identity to SEQ ID NO: 114.

Described herein are T-cell receptors (TCRs) comprising an alpha chain and a beta chain, wherein: (a) the alpha chain comprises a complementarity determining region 3 (CDR3) comprising an amino acid sequence provided in Table 16, and the beta chain comprises a CDR3 comprising a corresponding amino acid sequence provided in Table 16. In certain embodiments, the TCRs provided in Table 16 recognize the TP53 mutant-mimic fragments SEQ ID NO: 18 and SEQ ID NO: 68.

Also described herein are TCRs comprising an alpha chain and a beta chain, wherein: (a) the alpha chain comprises a CDR1 comprising an amino acid sequence provided in Table 21, a CDR2 comprising an amino acid sequence provided in Table 21, and a CDR3 comprising an amino acid sequence provided in Table 16, and (b) the beta chain comprises a CDR1 comprising an amino acid sequence provided in Table 21, a CDR2 comprising an amino acid sequence provided in Table 21, and a CDR3 comprising a corresponding amino acid sequence provided in Table 16. In certain embodiments, the TCRs provided in Table 21 and Table 16 recognize the TP53 mutant-mimic fragments SEQ ID NO: 18 and SEQ ID NO: 68. An alpha and beta chain CDR1 and CDR2 provided in Table 21 correspond to and alpha and beta chain CDR3 provided in the same row in Table 16.

In certain embodiments, described herein are TCRs comprising an alpha chain and a beta chain, wherein: (a) the alpha chain comprises a CDR3 comprising the amino acid sequence of SEQ ID NO: 172 or having at least 90% sequence identity to SEQ ID NO: 172 and the beta chain comprises a CDR3 comprising the amino acid sequence of SEQ ID NO: 114 or having at least 90% sequence identity to SEQ ID NO: 114; (b) the alpha chain comprises a CDR3 comprising the amino acid sequence of SEQ ID NO: 172 or having at least 90% sequence identity to SEQ ID NO: 172 and the beta chain comprises a CDR3 comprising the amino acid sequence of SEQ ID NO: 170 or having at least 90% sequence identity to SEQ ID NO: 170; (c) the alpha chain comprises a CDR3 comprising the amino acid sequence of SEQ ID NO: 172 or having at least 90% sequence identity to SEQ ID NO: 172 and the beta chain comprises a CDR3 comprising the amino acid sequence of SEQ ID NO: 213 or having at least 90% sequence identity to SEQ ID NO: 213; (d) the alpha chain comprises a CDR3 comprising the amino acid sequence of SEQ ID NO: 152 or having at least 90% sequence identity to SEQ ID NO: 152 and the beta chain comprises a CDR3 comprising the amino acid sequence of SEQ ID NO: 114 or having at least 90% sequence identity to SEQ ID NO: 114; (e) the alpha chain comprises a CDR3 comprising the amino acid sequence of SEQ ID NO: 168 or having at least 90% sequence identity to SEQ ID NO: 168 and the beta chain comprises a CDR3 comprising the amino acid sequence of SEQ ID NO: 170 or having at least 90% sequence identity to SEQ ID NO: 170; (f) the alpha chain comprises a CDR3 comprising the amino acid sequence of SEQ ID NO: 215 or having at least 90% sequence identity to SEQ ID NO: 215 and the beta chain comprises a CDR3 comprising the amino acid sequence of SEQ ID NO: 114 or having at least 90% sequence identity to SEQ ID NO: 114; (g) the alpha chain comprises a CDR3 comprising the amino acid sequence of SEQ ID NO: 217 or having at least 90% sequence identity to SEQ ID NO: 217 and the beta chain comprises a CDR3 comprising the amino acid sequence of SEQ ID NO: 114 or having at least 90% sequence identity to SEQ ID NO: 114; (h) the alpha chain comprises a CDR3 comprising the amino acid sequence of SEQ ID NO: 219 or having at least 90% sequence identity to SEQ ID NO: 219 and the beta chain comprises a CDR3 comprising the amino acid sequence of SEQ ID NO: 114 or having at least 90% sequence identity to SEQ ID NO: 114; (i) the alpha chain comprises a CDR3 comprising the amino acid sequence of SEQ ID NO: 219 or having at least 90% sequence identity to SEQ ID NO: 219 and the beta chain comprises a CDR3 comprising the amino acid sequence of SEQ ID NO: 221 or having at least 90% sequence identity to SEQ ID NO: 221; or (j) the alpha chain comprises a CDR3 comprising the amino acid sequence of SEQ ID NO: 223 or having at least 90% sequence identity to SEQ ID NO: 223 and the beta chain comprises a CDR3 comprising the amino acid sequence of SEQ ID NO: 221 or having at least 90% sequence identity to SEQ ID NO: 221.

Described herein are TCRs comprising an alpha chain and a beta chain, wherein: (a) the alpha chain comprises a CDR3 comprising an amino acid sequence provided in Table 17, and the beta chain comprises a CDR3 comprising a corresponding amino acid sequence provided in Table 17. In certain embodiments, the TCRs provided in Table 17 recognize the CTNNB1 mutant-mimic fragments SEQ ID NO: 3 and SEQ ID NO: 32.

Also described herein are TCRs comprising an alpha chain and a beta chain, wherein: (a) the alpha chain comprises a CDR1 comprising an amino acid sequence provided in Table 22, a CDR2 comprising an amino acid sequence provided in Table 22, and a CDR3 comprising an amino acid sequence provided in Table 17, and (b) the beta chain comprises a CDR1 comprising an amino acid sequence provided in Table 22, a CDR2 comprising an amino acid sequence provided in Table 22, and a CDR3 comprising a corresponding amino acid sequence provided in Table 17. In certain embodiments, the TCRs provided in Table 22 and Table 17 recognize the CTNNB1 mutant-mimic fragments SEQ ID NO: 3 and SEQ ID NO: 32. An alpha and beta chain CDR1 and CDR2 provided in Table 22 correspond to and alpha and beta chain CDR3 provided in the same row in Table 17.

In certain embodiments, described herein are TCRs comprising an alpha chain and a beta chain, wherein: (a) the alpha chain comprises a CDR3 comprising the amino acid sequence of SEQ ID NO: 152 or having at least 90% sequence identity to SEQ ID NO: 152 and the beta chain comprises a CDR3 comprising the amino acid sequence of SEQ ID NO: 252 or having at least 90% sequence identity to SEQ ID NO: 252; (b) the alpha chain comprises a CDR3 comprising the amino acid sequence of SEQ ID NO: 152 or having at least 90% sequence identity to SEQ ID NO: 152 and the beta chain comprises a CDR3 comprising the amino acid sequence of SEQ ID NO: 114 or having at least 90% sequence identity to SEQ ID NO: 114; (c) the alpha chain comprises a CDR3 comprising the amino acid sequence of SEQ ID NO: 248 or having at least 90% sequence identity to SEQ ID NO: 248 and the beta chain comprises a CDR3 comprising the amino acid sequence of SEQ ID NO: 250 or having at least 90% sequence identity to SEQ ID NO: 250; (d) the alpha chain comprises a CDR3 comprising the amino acid sequence of SEQ ID NO: 248 or having at least 90% sequence identity to SEQ ID NO: 248 and the beta chain comprises a CDR3 comprising the amino acid sequence of SEQ ID NO: 258 or having at least 90% sequence identity to SEQ ID NO: 258; (e) the alpha chain comprises a CDR3 comprising the amino acid sequence of SEQ ID NO: 254 or having at least 90% sequence identity to SEQ ID NO: 254 and the beta chain comprises a CDR3 comprising the amino acid sequence of SEQ ID NO: 256 or having at least 90% sequence identity to SEQ ID NO: 256; (f) the alpha chain comprises a CDR3 comprising the amino acid sequence of SEQ ID NO: 254 or having at least 90% sequence identity to SEQ ID NO: 254 and the beta chain comprises a CDR3 comprising the amino acid sequence of SEQ ID NO: 114 or having at least 90% sequence identity to SEQ ID NO: 114; (g) the alpha chain comprises a CDR3 comprising the amino acid sequence of SEQ ID NO: 263 or having at least 90% sequence identity to SEQ ID NO: 263 and the beta chain comprises a CDR3 comprising the amino acid sequence of SEQ ID NO: 265 or having at least 90% sequence identity to SEQ ID NO: 265; (h) the alpha chain comprises a CDR3 comprising the amino acid sequence of SEQ ID NO: 267 or having at least 90% sequence identity to SEQ ID NO: 267 and the beta chain comprises a CDR3 comprising the amino acid sequence of SEQ ID NO: 269 or having at least 90% sequence identity to SEQ ID NO: 269; (i) the alpha chain comprises a CDR3 comprising the amino acid sequence of SEQ ID NO: 267 or having at least 90% sequence identity to SEQ ID NO: 267 and the beta chain comprises a CDR3 comprising the amino acid sequence of SEQ ID NO: 271 or having at least 90% sequence identity to SEQ ID NO: 271; or (j) the alpha chain comprises a CDR3 comprising the amino acid sequence of SEQ ID NO: 273 or having at least 90% sequence identity to SEQ ID NO: 273 and the beta chain comprises a CDR3 comprising the amino acid sequence of SEQ ID NO: 275 or having at least 90% sequence identity to SEQ ID NO: 275; or (k) the alpha chain comprises a CDR3 comprising the amino acid sequence of SEQ ID NO: 277 or having at least 90% sequence identity to SEQ ID NO: 277 and the beta chain comprises a CDR3 comprising the amino acid sequence of SEQ ID NO: 279 or having at least 90% sequence identity to SEQ ID NO: 279; or (l) the alpha chain comprises a CDR3 comprising the amino acid sequence of SEQ ID NO: 281 or having at least 90% sequence identity to SEQ ID NO: 281 and the beta chain comprises a CDR3 comprising the amino acid sequence of SEQ ID NO: 283 or having at least 90% sequence identity to SEQ ID NO: 283; or (m) the alpha chain comprises a CDR3 comprising the amino acid sequence of SEQ ID NO: 285 or having at least 90% sequence identity to SEQ ID NO: 285 and the beta chain comprises a CDR3 comprising the amino acid sequence of SEQ ID NO: 287 or having at least 90% sequence identity to SEQ ID NO: 287.

Described herein are TCRs comprising an alpha chain and a beta chain, wherein: (a) the alpha chain comprises a CDR3 comprising an amino acid sequence provided in Table 18, and the beta chain comprises a CDR3 comprising a corresponding amino acid sequence provided in Table 18. In certain embodiments, the TCRs provided in Table 18 recognize the TP53 mutant-mimic fragments SEQ ID NO: 23 and SEQ ID NO: 78.

Also described herein are TCRs comprising an alpha chain and a beta chain, wherein: (a) the alpha chain comprises a CDR1 comprising an amino acid sequence provided in Table 23, a CDR2 comprising an amino acid sequence provided in Table 23, and a CDR3 comprising an amino acid sequence provided in Table 18, and (b) the beta chain comprises a CDR1 comprising an amino acid sequence provided in Table 23, a CDR2 comprising an amino acid sequence provided in Table 23, and a CDR3 comprising a corresponding amino acid sequence provided in Table 18. In certain embodiments, the TCRs provided in Table 23 and Table 18 recognize the TP53 mutant-mimic fragments SEQ ID NO: 23 and SEQ ID NO: 78. An alpha and beta chain CDR1 and CDR2 provided in Table 23 correspond to and alpha and beta chain CDR3 provided in the same row in Table 18.

In certain embodiments, described herein are TCRs comprising an alpha chain and a beta chain, wherein: (a) the alpha chain comprises a CDR3 comprising the amino acid sequence of SEQ ID NO: 248 or having at least 90% sequence identity to SEQ ID NO: 248 and the beta chain comprises a CDR3 comprising the amino acid sequence of SEQ ID NO: 114 or having at least 90% sequence identity to SEQ ID NO: 114; (b) the alpha chain comprises a CDR3 comprising the amino acid sequence of SEQ ID NO: 289 or having at least 90% sequence identity to SEQ ID NO: 289 and the beta chain comprises a CDR3 comprising the amino acid sequence of SEQ ID NO: 114 or having at least 90% sequence identity to SEQ ID NO: 114; (c) the alpha chain comprises a CDR3 comprising the amino acid sequence of SEQ ID NO: 289 or having at least 90% sequence identity to SEQ ID NO: 289 and the beta chain comprises a CDR3 comprising the amino acid sequence of SEQ ID NO: 291 or having at least 90% sequence identity to SEQ ID NO: 291.

Polynucleotides

The disclosure also provides polynucleotides that encode any of the polypeptide fragments or TCRs disclosed herein.

In some embodiments, the polynucleotide encodes a polypeptide fragment selected from the group consisting of SEQ ID NO: 25 or a sequence having at least 90% identity, at least 95% identity, or at least 99% identity to SEQ ID NO: 25, SEQ ID NO: 26 or a sequence having at least 90% identity, at least 95% identity, or at least 99% identity to SEQ ID NO: 26, SEQ ID NO: 27 or a sequence having at least 90% identity, at least 95% identity, or at least 99% identity to SEQ ID NO: 27, SEQ ID NO: 28 or a sequence having at least 90% identity, at least 95% identity, or at least 99% identity to SEQ ID NO: 28, SEQ ID NO: 29 or a sequence having at least 90% identity, at least 95% identity, or at least 99% identity to SEQ ID NO: 29, SEQ ID NO: 30 or a sequence having at least 90% identity, at least 95% identity, or at least 99% identity to SEQ ID NO: 30, SEQ ID NO: 31 or a sequence having at least 90% identity, at least 95% identity, or at least 99% identity to SEQ ID NO: 31, SEQ ID NO: 32 or a sequence having at least 90% identity, at least 95% identity, or at least 99% identity to SEQ ID NO: 32, SEQ ID NO: 33 or a sequence having at least 90% identity, at least 95% identity, or at least 99% identity to SEQ ID NO: 33, SEQ ID NO: 37 or a sequence having at least 90% identity, at least 95% identity, or at least 99% identity to SEQ ID NO: 37, SEQ ID NO: 38 or a sequence having at least 90% identity, at least 95% identity, or at least 99% identity to SEQ ID NO: 38, SEQ ID NO: 39 or a sequence having at least 90% identity, at least 95% identity, or at least 99% identity to SEQ ID NO: 39, SEQ ID NO: 40 or a sequence having at least 90% identity, at least 95% identity, or at least 99% identity to SEQ ID NO: 40, SEQ ID NO: 41 or a sequence having at least 90% identity, at least 95% identity, or at least 99% identity to SEQ ID NO: 41, SEQ ID NO: 42 or a sequence having at least 90% identity, at least 95% identity, or at least 99% identity to SEQ ID NO: 42, SEQ ID NO: 43 or a sequence having at least 90% identity, at least 95% identity, or at least 99% identity to SEQ ID NO: 43, SEQ ID NO: 44 or a sequence having at least 90% identity, at least 95% identity, or at least 99% identity to SEQ ID NO: 44, SEQ ID NO: 45 or a sequence having at least 90% identity, at least 95% identity, or at least 99% identity to SEQ ID NO: 45, SEQ ID NO: 46 or a sequence having at least 90% identity, at least 95% identity, or at least 99% identity to SEQ ID NO: 46, SEQ ID NO: 47 or a sequence having at least 90% identity, at least 95% identity, or at least 99% identity to SEQ ID NO: 47, SEQ ID NO: 48 or a sequence having at least 90% identity, at least 95% identity, or at least 99% identity to SEQ ID NO: 48, SEQ ID NO: 49 or a sequence having at least 90% identity, at least 95% identity, or at least 99% identity to SEQ ID NO: 49, SEQ ID NO: 51 or a sequence having at least 90% identity, at least 95% identity, or at least 99% identity to SEQ ID NO: 51, SEQ ID NO: 52 or a sequence having at least 90% identity, at least 95% identity, or at least 99% identity to SEQ ID NO: 52, SEQ ID NO: 53 or a sequence having at least 90% identity, at least 95% identity, or at least 99% identity to SEQ ID NO: 53, SEQ ID NO: 54 or a sequence having at least 90% identity, at least 95% identity, or at least 99% identity to SEQ ID NO: 54, SEQ ID NO: 55 or a sequence having at least 90% identity, at least 95% identity, or at least 99% identity to SEQ ID NO: 55, SEQ ID NO: 56 or a sequence having at least 90% identity, at least 95% identity, or at least 99% identity to SEQ ID NO: 56, SEQ ID NO: 57 or a sequence having at least 90% identity, at least 95% identity, or at least 99% identity to SEQ ID NO: 57, SEQ ID NO: 58 or a sequence having at least 90% identity, at least 95% identity, or at least 99% identity to SEQ ID NO: 58, SEQ ID NO: 59 or a sequence having at least 90% identity, at least 95% identity, or at least 99% identity to SEQ ID NO: 59, SEQ ID NO: 60 or a sequence having at least 90% identity, at least 95% identity, or at least 99% identity to SEQ ID NO: 60, SEQ ID NO: 61 or a sequence having at least 90% identity, at least 95% identity, or at least 99% identity to SEQ ID NO: 61, SEQ ID NO: 62 or a sequence having at least 90% identity, at least 95% identity, or at least 99% identity to SEQ ID NO: 62, SEQ ID NO: 63 or a sequence having at least 90% identity, at least 95% identity, or at least 99% identity to SEQ ID NO: 63, SEQ ID NO: 64 or a sequence having at least 90% identity, at least 95% identity, or at least 99% identity to SEQ ID NO: 64, SEQ ID NO: 66 or a sequence having at least 90% identity, at least 95% identity, or at least 99% identity to SEQ ID NO: 66, SEQ ID NO: 67 or a sequence having at least 90% identity, at least 95% identity, or at least 99% identity to SEQ ID NO: 67, SEQ ID NO: 68 or a sequence having at least 90% identity, at least 95% identity, or at least 99% identity to SEQ ID NO: 68, SEQ ID NO: 70 or a sequence having at least 90% identity, at least 95% identity, or at least 99% identity to SEQ ID NO: 70, SEQ ID NO: 71 or a sequence having at least 90% identity, at least 95% identity, or at least 99% identity to SEQ ID NO: 71, SEQ ID NO: 72 or a sequence having at least 90% identity, at least 95% identity, or at least 99% identity to SEQ ID NO: 72, SEQ ID NO: 73 or a sequence having at least 90% identity, at least 95% identity, or at least 99% identity to SEQ ID NO: 73, SEQ ID NO: 74 or a sequence having at least 90% identity, at least 95% identity, or at least 99% identity to SEQ ID NO: 74, SEQ ID NO: 75 or a sequence having at least 90% identity, at least 95% identity, or at least 99% identity to SEQ ID NO: 75, SEQ ID NO: 76 or a sequence having at least 90% identity, at least 95% identity, or at least 99% identity to SEQ ID NO: 76, SEQ ID NO: 78 or a sequence having at least 90% identity, at least 95% identity, or at least 99% identity to SEQ ID NO: 78, SEQ ID NO: 79 or a sequence having at least 90% identity, at least 95% identity, or at least 99% identity to SEQ ID NO: 79, SEQ ID NO: 80 or a sequence having at least 90% identity, at least 95% identity, or at least 99% identity to SEQ ID NO: 80, SEQ ID NO: 81 or a sequence having at least 90% identity, at least 95% identity, or at least 99% identity to SEQ ID NO: 81, SEQ ID NO: 84 or a sequence having at least 90% identity, at least 95% identity, or at least 99% identity to SEQ ID NO: 84, SEQ ID NO: 85 or a sequence having at least 90% identity, at least 95% identity, or at least 99% identity to SEQ ID NO: 85, SEQ ID NO: 86 or a sequence having at least 90% identity, at least 95% identity, or at least 99% identity to SEQ ID NO: 86, SEQ ID NO: 88 or a sequence having at least 90% identity, at least 95% identity, or at least 99% identity to SEQ ID NO: 88, SEQ ID NO: 90 or a sequence having at least 90% identity, at least 95% identity, or at least 99% identity to SEQ ID NO: 90, SEQ ID NO: 91 or a sequence having at least 90% identity, at least 95% identity, or at least 99% identity to SEQ ID NO: 91, SEQ ID NO: 92 or a sequence having at least 90% identity, at least 95% identity, or at least 99% identity to SEQ ID NO: 92, SEQ ID NO: 93 or a sequence having at least 90% identity, at least 95% identity, or at least 99% identity to SEQ ID NO: 93, SEQ ID NO: 94 or a sequence having at least 90% identity, at least 95% identity, or at least 99% identity to SEQ ID NO: 94, SEQ ID NO: 95 or a sequence having at least 90% identity, at least 95% identity, or at least 99% identity to SEQ ID NO: 95, SEQ ID NO: 96 or a sequence having at least 90% identity, at least 95% identity, or at least 99% identity to SEQ ID NO: 96, and any combination thereof.

In some embodiments, the polynucleotide encodes a polypeptide fragment selected from the group consisting of SEQ ID NO: 29 or a sequence having at least 90% identity, at least 95% identity, or at least 99% identity to SEQ ID NO: 29, SEQ ID NO: 32 or a sequence having at least 90% identity, at least 95% identity, or at least 99% identity to SEQ ID NO: 32, SEQ ID NO: 45 or a sequence having at least 90% identity, at least 95% identity, or at least 99% identity to SEQ ID NO: 45, SEQ ID NO: 59 or a sequence having at least 90% identity, at least 95% identity, or at least 99% identity to SEQ ID NO: 59, SEQ ID NO: 64 or a sequence having at least 90% identity, at least 95% identity, or at least 99% identity to SEQ ID NO: 64, SEQ ID NO: 68 or a sequence having at least 90% identity, at least 95% identity, or at least 99% identity to SEQ ID NO: 68, SEQ ID NO: 75 or a sequence having at least 90% identity, at least 95% identity, or at least 99% identity to SEQ ID NO: 75, SEQ ID NO: 78 or a sequence having at least 90% identity, at least 95% identity, or at least 99% identity to SEQ ID NO: 78, and any combination thereof.

In some embodiments, the polynucleotide encodes a TCR polypeptide comprising an alpha chain and a beta chain, wherein: (a) the alpha chain comprises a complementarity determining region 3 (CDR3) comprising an amino acid sequence provided in Table 14, Table 15, Table 16, Table 17 or Table 18, and the beta chain comprises a CDR3 comprising a corresponding amino acid sequence provided in Table 14, Table 15, Table 16, Table 17, or Table 18.

In some embodiments, the polynucleotide encodes a TCR polypeptide comprising an alpha chain and a beta chain, wherein: (a) the alpha chain comprises a complementarity determining region 3 (CDR3) that is encoded by a nucleic acid sequence provided in Table 14, Table 15, Table 16, Table 17, or Table 18, and the beta chain comprises a CDR3 that is encoded by a corresponding nucleic acid sequence provided in Table 14, Table 15, Table 16, Table 17 or Table 18.

In some embodiments, the polynucleotide comprises DNA.

In some embodiments, the polynucleotide comprises RNA.

In some embodiments, RNA is mRNA.

In some embodiments, the polynucleotide comprises a promoter, an enhancer, a polyadenylation site, a Kozak sequence, a stop codon, or any combination thereof.

Methods of generating polynucleotides of the disclosure are known in the art and include chemical synthesis, enzymatic synthesis (e.g. in vitro transcription), enzymatic or chemical cleavage of a longer precursor, chemical synthesis of smaller fragments of the polynucleotides followed by ligation of the fragments or known PCR methods. The polynucleotide sequence to be synthesized may be designed with the appropriate codons for the desired amino acid sequence. In general, preferred codons may be selected for the intended host in which the sequence will be used for expression

Vectors

The disclosure also provides vectors comprising any of the polynucleotides disclosed herein. The disclosure also provides vectors comprising a polynucleotide encoding for any of the polypeptides disclosed herein.

In some embodiments, vector comprises a polynucleotide that encodes a polypeptide fragment selected from the group consisting of SEQ ID NO: 25 or a sequence having at least 90% identity, at least 95% identity, or at least 99% identity to SEQ ID NO: 25, SEQ ID NO: 26 or a sequence having at least 90% identity, at least 95% identity, or at least 99% identity to SEQ ID NO: 26, SEQ ID NO: 27 or a sequence having at least 90% identity, at least 95% identity, or at least 99% identity to SEQ ID NO: 27, SEQ ID NO: 28 or a sequence having at least 90% identity, at least 95% identity, or at least 99% identity to SEQ ID NO: 28, SEQ ID NO: 29 or a sequence having at least 90% identity, at least 95% identity, or at least 99% identity to SEQ ID NO: 29, SEQ ID NO: 30 or a sequence having at least 90% identity, at least 95% identity, or at least 99% identity to SEQ ID NO: 30, SEQ ID NO: 31 or a sequence having at least 90% identity, at least 95% identity, or at least 99% identity to SEQ ID NO: 31, SEQ ID NO: 32 or a sequence having at least 90% identity, at least 95% identity, or at least 99% identity to SEQ ID NO: 32, SEQ ID NO: 33 or a sequence having at least 90% identity, at least 95% identity, or at least 99% identity to SEQ ID NO: 33, SEQ ID NO: 37 or a sequence having at least 90% identity, at least 95% identity, or at least 99% identity to SEQ ID NO: 37, SEQ ID NO: 38 or a sequence having at least 90% identity, at least 95% identity, or at least 99% identity to SEQ ID NO: 38, SEQ ID NO: 39 or a sequence having at least 90% identity, at least 95% identity, or at least 99% identity to SEQ ID NO: 39, SEQ ID NO: 40 or a sequence having at least 90% identity, at least 95% identity, or at least 99% identity to SEQ ID NO: 40, SEQ ID NO: 41 or a sequence having at least 90% identity, at least 95% identity, or at least 99% identity to SEQ ID NO: 41, SEQ ID NO: 42 or a sequence having at least 90% identity, at least 95% identity, or at least 99% identity to SEQ ID NO: 42, SEQ ID NO: 43 or a sequence having at least 90% identity, at least 95% identity, or at least 99% identity to SEQ ID NO: 43, SEQ ID NO: 44 or a sequence having at least 90% identity, at least 95% identity, or at least 99% identity to SEQ ID NO: 44, SEQ ID NO: 45 or a sequence having at least 90% identity, at least 95% identity, or at least 99% identity to SEQ ID NO: 45, SEQ ID NO: 46 or a sequence having at least 90% identity, at least 95% identity, or at least 99% identity to SEQ ID NO: 46, SEQ ID NO: 47 or a sequence having at least 90% identity, at least 95% identity, or at least 99% identity to SEQ ID NO: 47, SEQ ID NO: 48 or a sequence having at least 90% identity, at least 95% identity, or at least 99% identity to SEQ ID NO: 48, SEQ ID NO: 49 or a sequence having at least 90% identity, at least 95% identity, or at least 99% identity to SEQ ID NO: 49, SEQ ID NO: 51 or a sequence having at least 90% identity, at least 95% identity, or at least 99% identity to SEQ ID NO: 51, SEQ ID NO: 52 or a sequence having at least 90% identity, at least 95% identity, or at least 99% identity to SEQ ID NO: 52, SEQ ID NO: 53 or a sequence having at least 90% identity, at least 95% identity, or at least 99% identity to SEQ ID NO: 53, SEQ ID NO: 54 or a sequence having at least 90% identity, at least 95% identity, or at least 99% identity to SEQ ID NO: 54, SEQ ID NO: 55 or a sequence having at least 90% identity, at least 95% identity, or at least 99% identity to SEQ ID NO: 55, SEQ ID NO: 56 or a sequence having at least 90% identity, at least 95% identity, or at least 99% identity to SEQ ID NO: 56, SEQ ID NO: 57 or a sequence having at least 90% identity, at least 95% identity, or at least 99% identity to SEQ ID NO: 57, SEQ ID NO: 58 or a sequence having at least 90% identity, at least 95% identity, or at least 99% identity to SEQ ID NO: 58, SEQ ID NO: 59 or a sequence having at least 90% identity, at least 95% identity, or at least 99% identity to SEQ ID NO: 59, SEQ ID NO: 60 or a sequence having at least 90% identity, at least 95% identity, or at least 99% identity to SEQ ID NO: 60, SEQ ID NO: 61 or a sequence having at least 90% identity, at least 95% identity, or at least 99% identity to SEQ ID NO: 61, SEQ ID NO: 62 or a sequence having at least 90% identity, at least 95% identity, or at least 99% identity to SEQ ID NO: 62, SEQ ID NO: 63 or a sequence having at least 90% identity, at least 95% identity, or at least 99% identity to SEQ ID NO: 63, SEQ ID NO: 64 or a sequence having at least 90% identity, at least 95% identity, or at least 99% identity to SEQ ID NO: 64, SEQ ID NO: 66 or a sequence having at least 90% identity, at least 95% identity, or at least 99% identity to SEQ ID NO: 66, SEQ ID NO: 67 or a sequence having at least 90% identity, at least 95% identity, or at least 99% identity to SEQ ID NO: 67, SEQ ID NO: 68 or a sequence having at least 90% identity, at least 95% identity, or at least 99% identity to SEQ ID NO: 68, SEQ ID NO: 70 or a sequence having at least 90% identity, at least 95% identity, or at least 99% identity to SEQ ID NO: 70, SEQ ID NO: 71 or a sequence having at least 90% identity, at least 95% identity, or at least 99% identity to SEQ ID NO: 71, SEQ ID NO: 72 or a sequence having at least 90% identity, at least 95% identity, or at least 99% identity to SEQ ID NO: 72, SEQ ID NO: 73 or a sequence having at least 90% identity, at least 95% identity, or at least 99% identity to SEQ ID NO: 73, SEQ ID NO: 74 or a sequence having at least 90% identity, at least 95% identity, or at least 99% identity to SEQ ID NO: 74, SEQ ID NO: 75 or a sequence having at least 90% identity, at least 95% identity, or at least 99% identity to SEQ ID NO: 75, SEQ ID NO: 76 or a sequence having at least 90% identity, at least 95% identity, or at least 99% identity to SEQ ID NO: 76, SEQ ID NO: 78 or a sequence having at least 90% identity, at least 95% identity, or at least 99% identity to SEQ ID NO: 78, SEQ ID NO: 79 or a sequence having at least 90% identity, at least 95% identity, or at least 99% identity to SEQ ID NO: 79, SEQ ID NO: 80 or a sequence having at least 90% identity, at least 95% identity, or at least 99% identity to SEQ ID NO: 80, SEQ ID NO: 81 or a sequence having at least 90% identity, at least 95% identity, or at least 99% identity to SEQ ID NO: 81, SEQ ID NO: 84 or a sequence having at least 90% identity, at least 95% identity, or at least 99% identity to SEQ ID NO: 84, SEQ ID NO: 85 or a sequence having at least 90% identity, at least 95% identity, or at least 99% identity to SEQ ID NO: 85, SEQ ID NO: 86 or a sequence having at least 90% identity, at least 95% identity, or at least 99% identity to SEQ ID NO: 86, SEQ ID NO: 88 or a sequence having at least 90% identity, at least 95% identity, or at least 99% identity to SEQ ID NO: 88, SEQ ID NO: 90 or a sequence having at least 90% identity, at least 95% identity, or at least 99% identity to SEQ ID NO: 90, SEQ ID NO: 91 or a sequence having at least 90% identity, at least 95% identity, or at least 99% identity to SEQ ID NO: 91, SEQ ID NO: 92 or a sequence having at least 90% identity, at least 95% identity, or at least 99% identity to SEQ ID NO: 92, SEQ ID NO: 93 or a sequence having at least 90% identity, at least 95% identity, or at least 99% identity to SEQ ID NO: 93, SEQ ID NO: 94 or a sequence having at least 90% identity, at least 95% identity, or at least 99% identity to SEQ ID NO: 94, SEQ ID NO: 95 or a sequence having at least 90% identity, at least 95% identity, or at least 99% identity to SEQ ID NO: 95, SEQ ID NO: 96 or a sequence having at least 90% identity, at least 95% identity, or at least 99% identity to SEQ ID NO: 96, and any combination thereof.

In some embodiments, vector comprises a polynucleotide that encodes a polypeptide fragment selected from the group consisting of SEQ ID NO: 29 or a sequence having at least 90% identity, at least 95% identity, or at least 99% identity to SEQ ID NO: 29, SEQ ID NO: 32 or a sequence having at least 90% identity, at least 95% identity, or at least 99% identity to SEQ ID NO: 32, SEQ ID NO: 45 or a sequence having at least 90% identity, at least 95% identity, or at least 99% identity to SEQ ID NO: 45, SEQ ID NO: 59 or a sequence having at least 90% identity, at least 95% identity, or at least 99% identity to SEQ ID NO: 59, SEQ ID NO: 64 or a sequence having at least 90% identity, at least 95% identity, or at least 99% identity to SEQ ID NO: 64, SEQ ID NO: 68 or a sequence having at least 90% identity, at least 95% identity, or at least 99% identity to SEQ ID NO: 68, SEQ ID NO: 75 or a sequence having at least 90% identity, at least 95% identity, or at least 99% identity to SEQ ID NO: 75, SEQ ID NO: 78 or a sequence having at least 90% identity, at least 95% identity, or at least 99% identity to SEQ ID NO: 78, and any combination thereof.

In some embodiments, the vector comprises a polynucleotide that encodes a TCR polypeptide comprising an alpha chain and a beta chain, wherein: (a) the alpha chain comprises a complementarity determining region 3 (CDR3) comprising an amino acid sequence provided in Table 14, Table 15, Table 16, Table 17 or Table 18, and the beta chain comprises a CDR3 comprising a corresponding amino acid sequence provided in Table 14, Table 15, Table 16, Table 17 or Table 18.

In some embodiments, the vector comprises a polynucleotide that encodes a TCR polypeptide comprising an alpha chain and a beta chain, wherein: (a) the alpha chain comprises a CDR1 comprising an amino acid sequence provided in Table 19, Table 20, Table 21, Table 22, or Table 23, a CDR2 comprising an amino acid sequence provided in Table 19, Table 20, Table 21, Table 22, or Table 23, and a CDR3 comprising an amino acid sequence provided in Table 14, Table 15, Table 16, Table 17, or Table 18, and (b) the beta chain comprises a CDR1 comprising an amino acid sequence provided in Table 19, Table 20, Table 21, Table 22, or Table 23, a CDR2 comprising an amino acid sequence provided in Table 19, Table 20, Table 21, Table 22, or Table 23, and a CDR3 comprising a corresponding amino acid sequence provided in Table 14, Table 15, Table 16, Table 17 or Table 18. An alpha chain CDR1 or CDR2 corresponds to a beta chain CDR1 or CDR2 if they appear in the same row in Table 19, Table 20, Table 21, Table 22, or Table 23. An alpha chain CDR3 corresponds to a beta chain CDR3 if they appear in the same row in Table 14, Table 15, Table 16, Table 17, or Table 18. An alpha and beta chain CDR1 and CDR2 provided in Table 19, Table 20, Table 21, Table 22, or Table 23 correspond to an alpha and beta chain CDR3 provided in the same row in Table 14, Table 15, Table 16, Table 17 or Table 18.

In some embodiments, the vector comprises a polynucleotide that encodes a TCR polypeptide comprising an alpha chain and a beta chain, wherein: (a) the alpha chain comprises a complementarity determining region 3 (CDR3) that is encoded by a nucleic acid sequence provided in Table 14, Table 15, Table 16, Table 17 or Table 18, and the beta chain comprises a CDR3 that is encoded by a corresponding nucleic acid sequence provided in Table 14, Table 15, Table 16, Table 17 or Table 18.

In some embodiments, the vector comprises a polynucleotide that encodes a TCR polypeptide comprising an alpha chain and a beta chain, wherein: (a) the alpha chain comprises a CDR1 that is encoded by a nucleic acid sequence provided in Table 19, Table 20, Table 21, Table 22, or Table 23, a CDR2 that is encoded by a nucleic acid sequence provided in Table 19, Table 20, Table 21, Table 22, or Table 23, and a CDR3 that is encoded by a nucleic acid sequence provided in Table 14, Table 15, Table 16, Table 17, or Table 18, and (b) the beta chain comprises a CDR1 that is encoded by a nucleic acid sequence provided in Table 19, Table 20, Table 21, Table 22, or Table 23, a CDR2 that is encoded by a nucleic acid sequence provided in Table 19, Table 20, Table 21, Table 22, or Table 23, and a CDR3 that is encoded by a nucleic acid sequence provided in Table 14, Table 15, Table 16, Table 17 or Table 18. An alpha chain CDR1 or CDR2 corresponds to a beta chain CDR1 or CDR2 if they appear in the same row in Table 19, Table 20, Table 21, Table 22, or Table 23. An alpha chain CDR3 corresponds to a beta chain CDR3 if they appear in the same row in Table 14, Table 15, Table 16, Table 17, or Table 18. An alpha and beta chain CDR1 and CDR2 provided in Table 19, Table 20, Table 21, Table 22, or Table 23 correspond to and alpha and beta chain CDR3 provided in the same row in Table 14, Table 15, Table 16, Table 17 or Table 18.

The vector may be a vector intended for expression of the polynucleotide of the disclosure in any host, such as bacteria, yeast or a mammal. Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed or transduced with the desired DNA sequences. Exemplary vectors are plasmids, cosmids, phages, viral vectors or artificial chromosomes.

Suitable vectors that may be used are—Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene), pSVK3, pBPV, pMSG and pSVL (Pharmacia).

The disclosure provides an expression vector comprising the polynucleotide of the disclosure. The disclosure also provides an expression vector comprising the polynucleotide encoding for the polypeptide of the disclosure.

Other Viral Vectors and Recombinant Viruses

The disclosure also provides a viral vector comprising any of the polynucleotides of the disclosure.

The disclosure also provides a viral vector comprising a polynucleotide encoding any of the polypeptides of the disclosure.

Viral vectors are derived from naturally occurring virus genomes, which typically are modified to be replication incompetent, e.g. non-replicating. Non-replicating viruses require the provision of proteins in trans for replication. Typically, those proteins are stably or transiently expressed in a viral producer cell line, thereby allowing replication of the virus. The viral vectors are, thus, typically infectious and non-replicating. Viral vectors may be adenovirus vectors, adeno-associated virus (AAV) vectors (e.g., AAV type 5 and type 2), Great ape adenovirus vectors (GAd), alphavirus vectors (e.g., Venezuelan equine encephalitis virus (VEE), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus vectors, lentivirus vectors, viral like particles, and bacterial spores.

In some embodiments, the viral vector is derived from adenovirus, poxvirus, alphavirus, adeno-associated virus, retrovirus, or a self-replicating RNA molecule.

In some embodiments, the viral vector is derived from an adenovirus. In certain embodiments, the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

Adenovirus vectors may be derived from human adenovirus (Ad) but also from adenoviruses that infect other species, such as bovine adenovirus (e.g. bovine adenovirus 3, BAdV3), a canine adenovirus (e.g. CAdV2), a porcine adenovirus (e.g. PAdV3 or 5), or great apes, such as Chimpanzee (Pan), Gorilla (Gorilla), Orangutan (Pongo), Bonobo (Pan paniscus) and common chimpanzee (Pan troglodytes). Typically, naturally occurring great ape adenoviruses are isolated from stool samples of the respective great ape.

Human adenovirus vectors may be derived from various adenovirus serotypes, for example from human adenovirus serotypes hAd5, hAd7, hAd11, hAd26, hAd34, hAd35, hAd48, hAd49 or hAd50 (the serotypes are also referred to as Ad5, Ad7, Adl 1, Ad26, Ad34, Ad35, Ad48, Ad49 or Ad50).

Great ape adenovirus (GAd) vectors may be derived from various adenovirus serotypes, for example from great ape adenovirus serotypes GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, or PanAd3.

Adenovirus vectors are known in the art. The sequences of most of the human and non-human adenoviruses are known, and for others can be obtained using routine procedures. An exemplary genome sequence of Ad26 is found in GenBank Accession number EF153474 and in Int. Pat. Publ. No. WO2007/104792. An exemplary genome sequence of Ad35 is found in Int. Pat. Publ. No. WO2000/70071. Vectors based on Ad26 are described for example, in Int. Pat. Publ. No. WO2007/104792. Vectors based on Ad35 are described for example in U.S. Pat. No. 7,270,811 and Int. Pat. Publ. No. WO2000/70071. Vectors based on ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in WO2005/071093. Vectors based on PanAd1, PanAd2, PanAd3, ChAd55, ChAd73, ChAd83, ChAd146, and ChAd147 are described in Int. Pat. Publ. No. WO2010/086189.

In some embodiments, the viral vector is a poxvirus. In some embodiments, the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Poxvirus (Poxviridae) vectors may be derived from smallpox virus (variola), vaccinia virus, cowpox virus or monkeypox virus. Exemplary vaccinia viruses are the Copenhagen vaccinia virus (W), New York Attenuated Vaccinia Virus (NYVAC), ALVAC, TROVAC or Modified Vaccinia Ankara (MVA).

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

In some embodiments, the viral vector is an adeno-associated virus. The viral vector comprising the polynucleotides of the disclosure may be derived from human adeno-associated viruses, such as AAV-2 (adeno-associated virus type 2). An attractive feature of AAV vectors is that they do not express any viral genes. The only viral DNA sequences included in the AAV vectors are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{n}$ particles or copies of DNA in contrast to naked DNA doses of 50 gg or about $10^{15}$ copies. AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay).

The viral vector comprising the polynucleotide of the disclosure also include Retroviral vectors. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (Int. Pat. Publ. No. WO1995/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323).

The polynucleotides encoding the polypeptide of the disclosure may be inserted downstream of the encapsidation sequence, such as in opposite direction relative to the retroviral genome. Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, Bio-Techniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. Packaging cell line, such as the PA317 cells (ATCC CRL 9078) or 293EI6 (WO97/35996) containing an amphotropic envelope protein may therefore be used to allow infection of human and other species' target cells. The retroviral particles are recovered from the culture supernatant and may optionally be further purified according to standard techniques (e.g. chromatography, ultracentrifugation).

Self-Replicating RNA Molecules

Provided herein is a viral vector comprising any of the polynucleotides of the disclosure, wherein the vector is a self-replicating RNA molecule.

Self-replicating RNA may be derived from alphavirus. Alphaviruses may belong to the VEEV/EEEV group, or the SF group, or the SIN group. Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S. A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV).

The self-replicating RNA molecules can be derived from alphavirus genomes, meaning that they have some of the structural characteristics of alphavirus genomes, or similar to them. The self-replicating RNA molecules can be derived from modified alphavirus genomes.

Self-replicating RNA molecules may be derived from Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. Virulent and avirulent alphavirus strains are both suitable. In some embodiments, the alphavirus RNA replicon is of a Sindbis virus (SIN), a Semliki Forest virus (SFV), a Ross River virus (RRV), a Venezuelan equine encephalitis virus (VEEV), or an Eastern equine encephalitis virus (EEEV).

In some embodiments, the alphavirus-derived self-replicating RNA molecule is a Venezuelan equine encephalitis virus (VEEV).

The self-replicating RNA molecules can contain RNA sequences from (or amino acid sequences encoded by) a wild-type New World or Old World alphavirus genome. Any of the self-replicating RNA molecules disclosed herein can contain RNA sequences "derived from" or "based on" wild type alphavirus genome sequences, meaning that they have at least 60% or at least 65% or at least 68% or at least 70% or at least 80% or at least 85% or at least 90% or at least 95% or at least 97% or at least 98% or at least 99% or 100% or 80-99% or 90-100% or 95-99% or 95-100% or 97-99% or 98-99% sequence identity with an RNA sequence (which can be a corresponding RNA sequence) from a wild type RNA alphavirus genome, which can be a New World or Old World alphavirus genome.

Self-replicating RNA molecules contain all of the genetic information required for directing their own amplification or self-replication within a permissive cell. To direct their own replication, self-replicating RNA molecules encode polymerase, replicase, or other proteins which may interact with viral or host cell-derived proteins, nucleic acids or ribonucleoproteins to catalyze the RNA amplification process; and contain cis-acting RNA sequences required for replication and transcription of the replicon-encoded RNA. Thus, RNA replication leads to the production of multiple daughter RNAs. These daughter RNAs, as well as collinear subgenomic transcripts, can be translated to provide in situ expression of a gene of interest, or can be transcribed to provide further transcripts with the same sense as the delivered RNA which are translated to provide in situ expression of the gene of interest. The overall results of this sequence of transcriptions is a huge amplification in the number of the introduced replicon RNAs and so the encoded gene of interest becomes a major polypeptide product of the cells.

There are two open reading frames (ORF's) in the genome of alphaviruses, non-structural (ns) and structural genes. The ns ORF encodes proteins (nsP1-nsP4) necessary for transcription and replication of viral RNA and are produced as a polyprotein and are the virus replication machinery. The structural ORF encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion. The four ns protein genes are encoded by genes in the 5' two-thirds of the genome, while the three structural proteins are translated from a subgenomic mRNA colinear with the 3' one-third of the genome.

Self-replicating RNA molecules can be used as basis of introducing foreign sequences to host cells by replacing viral sequences encoding structural genes or inserting the foreign sequences 5' or 3' of the sequences encoding the structural genes. They can be engineered to replace the viral structural genes downstream of the replicase, which are under control of a subgenomic promoter, by genes of interest (GOI), e.g. the polynucleotide encoding for the polypeptide of the disclosure. Upon transfection, the replicase which is translated immediately, interacts with the 5' and 3' termini of the genomic RNA, and synthesizes complementary genomic RNA copies. Those act as templates for the synthesis of novel positive-stranded, capped, and poly-adenylated genomic copies, and subgenomic transcripts. Amplification eventually leads to very high RNA copy numbers of up to $2 \times 10^5$ copies per cell. The result is a uniform and/or enhanced expression of a GOI (e.g. the polynucleotide encoding for the polypeptide of the disclosure) that can affect vaccine efficacy or therapeutic impact of a treatment. Vaccines based on self-replicating RNA molecules can therefore be dosed at very low levels due to the very high copies of RNA generated compared to conventional viral vector. One of the significant values of the compositions and methods disclosed herein is that vaccine efficacy can be increased in individuals that are in a chronic or acute state of immune activation.

The disclosure provides a self-replicating RNA molecule containing all of the genetic information required for directing its own amplification or self-replication within a permissive cell.

The disclosure also provides a self-replicating RNA molecule that can be used as the basis of introducing foreign sequences to host cells (e.g. the polypeptides of the disclosure) by replacing viral sequences encoding structural genes.

In some embodiments, the self-replicating RNA molecule comprises an RNA sequence encoding a protein or peptide; 5' and 3' alphavirus untranslated regions; RNA sequences encoding amino acid sequences derived from New World alphavirus VEEV nonstructural proteins nsP1, nsP2, nsP3 and nsP4; a sub-genomic promoter that is operably linked to and regulates translation of the RNA sequence encoding the protein; a 5' cap and a 3' poly-A tail; positive sense, single-stranded RNA; a DLP from Sindbis virus upstream of the non-structural protein 1(nsP1); a 2A ribosome skipping element; and a nsp1 nucleotide repeat downstream of the 5'-UTR and upstream of the DLP.

In some embodiments, the self-replicating RNA molecules may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size.

Any of the above-disclosed self-replicating RNA molecules can further include a coding sequence for an autoprotease peptide (e.g., autocatalytic self-cleaving peptide).

In some embodiments, the autoprotease peptide comprises, or consists of, a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the autoprotease peptide includes a peptide sequence of porcine teschovirus-1 2A (P2A).

Regulatory Elements

The polynucleotides encoding the polypeptides of the disclosure may be operably linked to one or more regulatory elements in the vector. The regulatory elements may comprise promoters, enhancers, polyadenylation signals, repressors and the like. As used herein, the term "operably linked" is to be taken in its broadest reasonable context and refers to a linkage of polynucleotide elements in a functional relationship. A polynucleotide is "operably linked" when it is placed into a functional relationship with another polynucleotide. For instance, a promoter is operably linked to a coding sequence if it affects the transcription of the coding sequence.

Some of the commonly used enhancer and promoter sequences in expression vectors and viral vectors are, for example, human cytomegalovirus (hCMV), vaccinia P7.5 early/late promoter, CAG, SV40, mouse CMV (mCMV), EF-1 and hPGK promoters. Due to its high potency and moderate size of ca. 0.8 kB, the hCMV promoter is one of the most commonly used of these promoters. The hPGK promoter is characterized by a small size (ca. 0.4 kB), but it is less potent than the hCMV promoter. On the other hand, the CAG promoter consisting of a cytomegalovirus early enhancer element, promoter, first exon and intron of chicken beta-actin gene, and splice acceptor of the rabbit beta-globin gene, can direct very potent gene expression that is comparable to the hCMV promoter, but its large size makes it less suitable in viral vectors where space constraints can be a significant concern, e.g., in adenoviral vectors (AdV), adeno-associated viral vectors (AAV) or lentiviral vectors (LVs).

Additional promoters that may be used are Aotine Herpesvirus 1 major immediate early promoter (AoHV-1 promoter) described in Int. Pat. Publ. No. WO2018/146205. The promoter may be operably coupled to a repressor operator sequence, to which a repressor protein can bind in order to repress expression of the promoter in the presence of the repressor protein. In certain embodiments, the repressor operator sequence is a TetO sequence or a CuO sequence (see e.g. U.S. Pat. No. 9,790,256).

In certain cases, it may be desirable to express at least two separate polypeptides from the same vector. In this case each polynucleotide may be operably linked to the same or different promoter and/or enhancer sequences, or well-known bicistronic expression systems for example by utilizing internal ribosome entry site (IRES) from encephalomyocarditis virus may be used. Alternatively, bidirectional synthetic promoters may be used, such as a hCMV-rhCMV promoter and other promoters described in Int. Pat. Publ. No. WO2017/220499. Polyadenylation signals may be derived from SV40 or bovine growth hormone (BGH).

The vectors comprising the polynucleotide encoding the polypeptide of the disclosure can further comprise any regulatory elements to establish conventional function(s) of the vector, including but not limited to replication and expression of the polypeptide of the disclosure encoded by the polynucleotide sequence of the vector. Regulatory elements include, but are not limited to, a promoter, an enhancer, a polyadenylation signal, translation stop codon, a ribosome binding element, a transcription terminator, selection markers, origin of replication, etc. A vector can comprise one or more expression cassettes. An "expression cassette" is part of a vector that directs the cellular machinery to make RNA and protein. An expression cassette typically comprises three components: a promoter sequence, an open reading frame, and a 3'-untranslated region (UTR) optionally comprising a polyadenylation signal. An open reading frame (ORF) is a reading frame that contains a coding sequence of a protein of interest (e.g., the polypeptides of the disclosure) from a start codon to a stop codon. Regulatory elements of the expression cassette can be operably linked to a polynucleotide sequence encoding the polypeptides of interest. Any components suitable for use in an expression cassette described herein can be used in any combination and in any order to prepare vectors of the application.

The vector can comprise a promoter sequence, preferably within an expression cassette, to control expression of the polypeptides of the disclosure. The term "promoter" is used in its conventional sense and refers to a nucleotide sequence that initiates the transcription of an operably linked nucleotide sequence. A promoter is located on the same strand near the nucleotide sequence it transcribes. Promoters can be a constitutive, inducible, or repressible. Promoters can be naturally occurring or synthetic. A promoter can be derived from sources including viral, bacterial, fungal, plants, insects, and animals. A promoter can be a homologous promoter (i.e., derived from the same genetic source as the vector) or a heterologous promoter (i.e., derived from a different vector or genetic source). Preferably, the promoter is located upstream of the polynucleotide encoding the polypeptides of the disclosure within an expression cassette. For example, in a self-replicating RNA, the promoter can be a subgenomic promoter for the alphavirus.

In a self-replicating RNA, the vector can further comprise additional polynucleotide sequences that stabilize the expressed transcript, enhance nuclear export of the RNA transcript, and/or improve transcriptional-translational coupling. Examples of such sequences include polyadenylation signals and enhancer sequences. A polyadenylation signal is typically located downstream of the coding sequence for a protein of interest (e.g., the polypeptides of the disclosure) within an expression cassette of the vector. Enhancer sequences are regulatory DNA sequences that, when bound by transcription factors, enhance the transcription of an associated gene. An enhancer sequence is preferably located upstream of the polynucleotide sequence encoding the polypeptides of the disclosure, but downstream of a promoter sequence within an expression cassette of the vector.

Any enhancer sequence known to those skilled in the art in view of the present disclosure can be used.

Any of the components or sequences of the vector of the disclosure can be functionally or operably linked to any other of the components or sequences. The components or sequences of the polypeptide fragments described herein can be operably linked for the expression of the at least one protein or peptide (or biotherapeutic) in a host cell or treated organism and/or for the ability of the replicon to self-replicate.

A promoter or UTR operably linked to a coding sequence is capable of effecting the transcription and expression of the coding sequence when the proper enzymes are present. The promoter need not be contiguous with the coding sequence, so long as it functions to direct the expression thereof. Thus, an operable linkage between an RNA sequence encoding a protein or peptide and a regulatory sequence (for example, a promoter or UTR) is a functional link that allows for expression of the polynucleotide of interest. Operably linked can also refer to sequences such as the sequences encoding the RdRp (e.g. nsP4), nsP1-4, the UTRs, promoters, and other sequences encoding in the RNA replicon, are linked so that they enable transcription and translation of the biotherapeutic molecule and/or replication of the replicon. The UTRs can be operably linked by providing sequences and spacing necessary for recognition and translation by a ribosome of other encoded sequences.

Host Cells

The disclosure also provides a host cell comprising any of the above vectors of the disclosure.

In some embodiments, the host cell comprising any of the polynucleotides encoding the polypeptide fragments described herein is prokaryotic or eukaryotic host cell. In some embodiments, the host cell is PER.C6, PER.C6 TetO, a chicken embryo fibroblast (CEF), CHO, HEK293, HT-1080, HKB-11, CAP, HuH-7, or Age1 cell line.

In certain embodiments, the host cell comprising any of the polynucleotides encoding the TCRs described herein is a CD8+ T cell.

Compositions

The disclosure also provides compositions comprising any of the polynucleotides, any of the polypeptides, and any of the vectors disclosed herein. In some embodiments, the compositions may comprise a vector comprising any of the nucleotides disclosed herein.

Any of the compositions described above may comprise or may be formulated into a pharmaceutical composition comprising the composition and a pharmaceutically acceptable excipient. "Pharmaceutically acceptable" refers to the excipient that at the dosages and concentrations employed, will not cause unwanted or harmful effects in the subjects to which they are administered and include carrier, buffers, stabilizers or other materials well known to those skilled in the art. The precise nature of the carrier or other material may depend on the route of administration, e.g., intramuscular, subcutaneous, oral, intravenous, cutaneous, intramucosal (e.g., gut), intranasal or intraperitoneal routes. Liquid carriers such as water, petroleum, animal or vegetable oils, mineral oil or synthetic oil may be included. Physiological saline solution, dextrose or other saccharide solution or glycols such as ethylene glycol, propylene glycol or polyethylene glycol may be included. Exemplary formulation are the Adenovirus World Standard (Hoganson et al, 2002): 20 mM Tris pH 8, 25 mM NaCl, 2.5% glycerol; or 20 mM Tris, 2 mM MgCl2, 25 mM NaCl, sucrose 10% w/v, polysorbate-80 0.02% w/v; or 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Many other buffers can be used, and examples of suitable formulations for the storage and for pharmaceutical administration of purified pharmaceutical preparations are known.

The composition may comprise one or more adjuvants. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g. polyarginine or polylysine). Other non-limiting examples of adjuvants include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that may be used include lectins, growth factors, cytokines, and lymphokines such as alpha-interferon, gamma interferon, platelet derived growth factor (PDGF), granulocyte-colony stimulating factor (GCSF), granulocyte macrophage colony stimulating factor (GMCSF), tumor necrosis factor (TNF), epidermal growth factor (EGF), IL-1, IL-2, IL-4, IL-6, IL-8, IL-10, IL-12 or TLR agonists, and particulate adjuvants (e g immunostimulatory complexes (ISCOMS).

Methods of Treatment or Use

Provided herein are methods for treating a subject with the polypeptides, polynucleotides, vectors, or pharmaceutical compositions disclosed herein. The methods and uses provided herein comprise administering any of the polynucleotides, polypeptides, vectors, and compositions of the disclosure. The polynucleotides, polypeptides, vectors, compositions and administration regimens of the disclosure may be used to treat, prevent or reduce the risk of a clinical condition. The polynucleotides, polypeptides, vectors, compositions and administration regimens of the disclosure may be used to induce an immune response in a subject.

In certain embodiments the clinical condition is cancer. In certain embodiments, the cancer is characterized by expression of a neoantigen. In certain embodiments, the neoantigen is a polypeptide comprising an amino acid substitution, a frame shift mutation, a fusion, an in-frame deletion, or an insertion. In certain embodiments the neoantigen arises from overexpression of a polypeptide.

In certain embodiments, the clinical condition is characterized by expression of a CIC mutant. In some embodiments, the CIC mutant comprises an arginine to tryptophan amino acid substitution at a position corresponding to position 215 of SEQ ID NO: 102 (R215W).

In certain embodiments, the clinical condition is characterized by expression of a CTNNB1 mutant. In some embodiments, the CTNNB1 mutant comprises a serine to cysteine amino acid substitution at a position corresponding to position 33 of SEQ ID NO: 103 (S33C). In some embodiments, the CTNNB1 mutant comprises a serine to phenylalanine amino acid substitution at a position corresponding to position 37 of SEQ ID NO: 103 (S37F).

In certain embodiments, the clinical condition is characterized by expression of an ERBB2 mutant. In some embodiments, the ERBB2 mutant comprises a valine to isoleucine amino acid substitution at a position corresponding to position 842 of SEQ ID NO: 104 (V842I).

In certain embodiments, the clinical condition is characterized by expression of a KRAS mutant. In some embodiments, the KRAS mutant comprises a glycine to alanine amino acid substitution at a position corresponding to position 12 of SEQ ID NO: 105 (G12A). In some embodiments, the KRAS mutant comprises a glycine to cysteine amino acid substitution at a position corresponding to position 12 of SEQ ID NO: 105 (G12C). In some embodiments, the KRAS mutant comprises a glycine to valine amino acid substitution at a position corresponding to at position 12 of SEQ ID NO: 105 (G12V).

In certain embodiments, the clinical condition is characterized by expression of a PIK3CA mutant. In some embodiments, the PIK3CA mutant comprises a glutamic acid to lysine amino acid substitution at a position corresponding to position 453 of SEQ ID NO: 106 (E453K). In some embodiments, the PIK3CA mutant comprises a glycine to aspartic acid amino acid substitution at a position corresponding to position 118 of SEQ ID NO: 106 (G118D).

In certain embodiments, the clinical condition is characterized by expression of a PTEN mutant. In some embodiments, the PTEN mutant comprises an arginine to cysteine amino acid substitution at a position corresponding to position 173 of SEQ ID NO: 107 (R173C).

In certain embodiments, the clinical condition is characterized by expression of an SF3B1 mutant. In some embodiments, the SF3B1 mutant comprises an arginine to histidine amino acid substitution at a position corresponding to position 625 of SEQ ID NO: 108 (R625H).

In certain embodiments, the clinical condition is characterized by expression of a SOX17 mutant. In some embodiments, the SOX17 mutant comprises a serine to isoleucine amino acid substitution at a position corresponding to position 403 of SEQ ID NO: 109 (S403I).

In certain embodiments, the clinical condition is characterized by expression of a TP53 mutant. In some embodiments, the TP53 mutant comprises an arginine to leucine amino acid substitution at a position corresponding to position 110 of SEQ ID NO: 110 (R110L). In some embodiments, the TP53 mutant comprises a serine to phenylalanine amino acid substitution at a position corresponding to position 127 of SEQ ID NO: 110 (S127F). In some embodiments, the TP53 mutant comprises a lysine to asparagine amino acid substitution at a position corresponding to position 132 of SEQ ID NO: 110 (K132N). In some embodiments, the TP53 mutant comprises a cysteine to tyrosine amino acid substitution at a position corresponding to position 141 of SEQ ID NO: 110 (C141Y). In some embodiments, the TP53 mutant comprises a proline to leucine amino acid substitution at a position corresponding to position 152 of SEQ ID NO: 110 (P152L). In some embodiments, the TP53 mutant comprises a histidine to leucine amino acid substitution at a position corresponding to position 193 of SEQ ID NO: 110 (H193L). In some embodiments, the TP53 mutant comprises a histidine to tyrosine amino acid substitution at a position corresponding to position 193 of SEQ ID NO: 110 (H193Y). In some embodiments, the TP53 mutant comprises a tyrosine to cysteine amino acid substitution at a position corresponding to position 220 of SEQ ID NO: 110 (Y220C). In some embodiments, the TP53 mutant comprises a valine to methionine amino acid substitution at a position corresponding to position 272 of SEQ ID NO: 110 (V272M).

Described herein are methods of inducing an immune response or methods of treating, preventing, reducing a risk of onset or delaying the onset of a clinical condition characterized by expression of CIC mutant comprising an arginine to tryptophan amino acid substitution at a position corresponding to position 215 of SEQ ID NO: 102 (R215W) in a subject, the method comprising administering to the subject in need thereof a) a polynucleotide encoding a polypeptide fragment comprising SEQ ID NO: 1, b) a polynucleotide encoding a polypeptide fragment comprising SEQ ID NO: 25, SEQ ID NO: 26, OR SEQ ID NO: 27, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of CIC mutant comprising an arginine to tryptophan amino acid substitution at a position corresponding to position 215 of SEQ ID NO: 102 (R215W) in a subject, the method comprising administering to the subject in need thereof a) a polynucleotide encoding a polypeptide fragment comprising SEQ ID NO: 1, b) a polynucleotide encoding a polypeptide fragment comprising SEQ ID NO: 225, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of CTNNB1 mutant comprising a serine to cysteine amino acid substitution at a position corresponding to position 33 of SEQ ID NO: 103 (S33C) in a subject, the method comprising administering to the subject in need thereof a) a polynucleotide encoding a polypeptide fragment comprising SEQ ID NO: 2, b) a polynucleotide encoding a polypeptide fragment comprising SEQ ID NO: 28, SEQ ID NO: 29, SEQ ID NO: 30, or SEQ ID NO: 80, or c) a combination thereof in an amount effective to treat, prevent, reduce the risk of onset or delay the onset of the clinical condition. In certain embodiments, described herein are methods of inducing an immune response or methods treating, preventing, reducing a risk of onset or delaying the onset of a clinical condition characterized by expression of CTNNB1 mutant comprising a serine to cysteine amino acid substitution at a position corresponding to position 33 of SEQ ID NO: 103 (S33C) in a subject, the method comprising administering to the subject in need thereof a) a polynucleotide encoding a polypeptide fragment comprising SEQ ID NO: 2, b) a polynucleotide encoding a polypeptide fragment comprising SEQ ID NO: 29, or c) a combination thereof in an amount effective to treat, prevent, reduce the risk of onset or delay the onset of the clinical condition. In certain embodiments, described herein are methods of inducing an immune response or methods treating, preventing, reducing a risk of onset or delaying the onset of a clinical condition characterized by expression of CTNNB1 mutant comprising a serine to cysteine amino acid substitution at a position corresponding to position 33 of SEQ ID NO: 103 (S33C) in a subject, the method comprising administering to the subject in need thereof a) a polynucleotide encoding a polypeptide fragment comprising SEQ ID NO: 2, b) a polynucleotide encoding a polypeptide fragment comprising SEQ ID NO: 226, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a CTNNB1 mutant comprising a serine to phenylalanine amino acid substitution at a position corresponding to position 37 of SEQ ID NO: 103 (S37F) in a subject, the method comprising administering to the subject in need thereof a) a polynucleotide encoding a polypeptide fragment comprising SEQ ID NO: 3, b) a polynucleotide encoding a polypeptide fragment comprising SEQ ID NO: 31, SEQ ID NO: 32, SEQ ID NO: 33, or SEQ ID NO: 81, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a catenin beta 1 (CTNNB1) mutant comprising a serine to phenylalanine amino acid substitution at a position corresponding to position 37 of SEQ ID NO: 103 (S37F) in a subject, the method comprising administering to the subject in need thereof a) a polynucleotide encoding a polypeptide fragment comprising SEQ ID NO: 3, b) a polynucleotide encoding a polypeptide fragment comprising SEQ ID NO: 32, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a catenin beta 1 (CTNNB1) mutant comprising a serine to phenylalanine amino acid substitution at a position corresponding to position 37 of SEQ ID NO: 103 (S37F) in a subject, the method comprising administering to the subject in need thereof a) a polynucleotide encoding a polypeptide fragment comprising SEQ ID NO: 3, b) a polynucleotide encoding a polypeptide fragment comprising SEQ ID NO: 227, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a KRAS mutant comprising a glycine to alanine amino acid substitution at a position corresponding to position 12 of SEQ ID NO: 105 (G12A) in a subject, the method comprising administering to the subject in need thereof a) a polynucleotide encoding a polypeptide fragment comprising SEQ ID NO: 5, b) a polynucleotide encoding a polypeptide fragment comprising SEQ ID NO: 37, or SEQ ID NO: 38, or c) a combination thereof in an amount effective to treat, prevent, reduce the risk of onset or delay the onset of the clinical condition. Described herein are methods of inducing an immune response or methods of treating, preventing, reducing a risk of onset or delaying the onset of a clinical condition characterized by expression of a KRAS mutant comprising a glycine to alanine amino acid substitution at a position corresponding to position 12 of SEQ ID NO: 105 (G12A) in a subject, the method comprising administering to the subject in need thereof a) a polynucleotide encoding a polypeptide fragment comprising SEQ ID NO: 5, b) a polynucleotide encoding a polypeptide fragment comprising SEQ ID NO: 228, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a KRAS mutant comprising a glycine to cysteine amino acid substitution at a position corresponding to position 12 of SEQ ID NO: 105 (G12C) in a subject, the method comprising administering to the subject in need thereof a) a polynucleotide encoding a polypeptide fragment comprising SEQ ID NO: 6, b) a polynucleotide encoding a polypeptide fragment comprising SEQ ID NO: 39, or SEQ ID NO: 40, or c) a combination thereof in an amount effective to treat, prevent, reduce the risk of onset or delay the onset of the clinical condition. Described herein are methods of inducing an immune response or methods of treating, preventing, reducing a risk of onset or delaying the onset of a clinical condition characterized by expression of a KRAS mutant comprising a glycine to cysteine amino acid substitution at a position corresponding to position 12 of SEQ ID NO: 105 (G12C) in a subject, the method comprising administering to the subject in need thereof a) a polynucleotide encoding a polypeptide fragment comprising SEQ ID NO: 6, b) a polynucleotide encoding a polypeptide fragment comprising SEQ ID NO: 229, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a KRAS mutant comprising a glycine to valine amino acid substitution at a position corresponding to at position 12 of SEQ ID NO: 105 (G12V) in a subject, the method comprising administering to the subject in need thereof a) a polynucleotide encoding a polypeptide fragment comprising SEQ ID NO: 7, b) a polynucleotide encoding a polypeptide fragment comprising SEQ ID NO: 41, or SEQ ID NO: 42, or c) a combination thereof in an amount effective to treat, prevent, reduce the risk of onset or delay the onset of the clinical condition. Described herein are methods of inducing an immune response or methods of treating, preventing, reducing a risk of onset or delaying the onset of a clinical condition characterized by expression of a KRAS mutant comprising a glycine to valine amino acid substitution at a position corresponding to at position 12 of SEQ ID NO: 105 (G12V) in a subject, the method comprising administering to the subject in need thereof a) a polynucleotide encoding a polypeptide fragment comprising SEQ ID NO: 7, b) a polynucleotide encoding a polypeptide fragment comprising SEQ ID NO: 230, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a PIK3CA mutant comprising a glutamic acid to lysine amino acid substitution at a position corresponding to position 453 of SEQ ID NO: 106 (E453K) in a subject, the method comprising administering to the subject in need thereof a) a polynucleotide encoding a polypeptide fragment comprising SEQ ID NO: 8, b) a polynucleotide encoding a polypeptide fragment comprising SEQ ID NO: 43, or SEQ ID NO: 44, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a PIK3CA mutant comprising a glutamic acid to lysine amino acid substitution at a position corresponding to position 453 of SEQ ID NO: 106 (E453K) in a subject, the method comprising administering to the subject in need thereof a) a polynucleotide encoding a polypeptide fragment comprising SEQ ID NO: 8, b) a polynucleotide encoding a polypeptide fragment comprising SEQ ID NO: 231, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a PIK3CA mutant comprising a glycine to aspartic acid amino acid substitution at a position corresponding to position 118 of SEQ ID NO: 106 (G118D) in a subject, the method comprising administering to the subject in need thereof a) a polynucleotide encoding a polypeptide fragment comprising SEQ ID NO: 9, b) a polynucleotide encoding a polypeptide fragment comprising SEQ ID NO: 45, SEQ ID NO: 46, or SEQ ID NO: 47, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a PIK3CA mutant comprising a glycine to aspartic acid amino acid substitution at a position corresponding to position 118 of SEQ ID NO: 106 (G118D) in a subject, the method comprising administering to the subject in need thereof a) a polynucleotide encoding a polypeptide fragment comprising SEQ ID NO: 9, b) a polynucleotide encoding a polypeptide fragment comprising SEQ ID NO: 45, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a PIK3CA mutant comprising a glycine to aspartic acid amino acid substitution at a position corresponding to position 118 of SEQ ID NO: 106 (G118D) in a subject, the method comprising administering to the subject in need thereof a) a polynucleotide encoding a polypeptide fragment comprising SEQ ID NO: 9, b) a polynucleotide encoding a polypeptide fragment comprising SEQ ID NO: 232, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a PTEN mutant comprising an arginine to cysteine amino acid substitution at a position corresponding to position 173 of SEQ ID NO: 107 (R173C) in a subject, the method comprising administering to the subject in need thereof a) a polynucleotide encoding a polypeptide fragment comprising SEQ ID NO: 10, b) a polynucleotide encoding a polypeptide fragment comprising SEQ ID NO: 48, SEQ ID NO: 49, SEQ ID NO: 50, SEQ ID NO: 87, SEQ ID NO: 88, or SEQ ID NO: 89 or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a PTEN mutant comprising an arginine to cysteine amino acid substitution at a position corresponding to position 173 of SEQ ID NO: 107 (R173C) in a subject, the method comprising administering to the subject in need thereof a) a polynucleotide encoding a polypeptide fragment comprising SEQ ID NO: 10, b) a polynucleotide encoding a polypeptide fragment comprising SEQ ID NO: 233 or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a SF3B1 mutant comprising an arginine to histidine amino acid substitution at a position corresponding to position 625 of SEQ ID NO: 108 (R625H) in a subject, the method comprising administering to the subject in need thereof a) a polynucleotide encoding a polypeptide fragment comprising SEQ ID NO: 11, b) a polynucleotide encoding a polypeptide fragment comprising SEQ ID NO: 51, SEQ ID NO: 52, SEQ ID NO: 53, SEQ ID NO: 90, SEQ ID NO: 91, or SEQ ID NO: 92 or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a SF3B1 mutant comprising an arginine to histidine amino acid substitution at a position corresponding to position 625 of SEQ ID NO: 108 (R625H) in a subject, the method comprising administering to the subject in need thereof a) a polynucleotide encoding a polypeptide fragment comprising SEQ ID NO: 11, b) a polynucleotide encoding a polypeptide fragment comprising SEQ ID NO: 234 or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a SOX10 mutant comprising a serine to isoleucine amino acid substitution at a position corresponding to position 403 of SEQ ID NO: 109 (S403I) in a subject, the method comprising administering to the subject in need thereof a) a polynucleotide encoding a polypeptide fragment comprising SEQ ID NO: 12, b) a polynucleotide encoding a polypeptide fragment comprising SEQ ID NO: 54, SEQ ID NO: 55, SEQ ID NO: 56, SEQ ID NO: 93, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a SOX10 mutant comprising a serine to isoleucine amino acid substitution at a position corresponding to position 403 of SEQ ID NO: 109 (S403I) in a subject, the method comprising administering to the subject in need thereof a) a polynucleotide encoding a polypeptide fragment comprising SEQ ID NO: 12, b) a polynucleotide encoding a polypeptide fragment comprising SEQ ID NO: 235, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a cysteine to tyrosine amino acid substitution at a position corresponding to position 141 of SEQ ID NO: 110 (C141Y) in a subject, the method comprising administering to the subject in need thereof a) a polynucleotide encoding a polypeptide fragment comprising SEQ ID NO: 13, b) a polynucleotide encoding a polypeptide fragment comprising SEQ ID NO: 57, SEQ ID NO: 58, SEQ ID NO: 59, or SEQ ID NO: 94, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a cysteine to tyrosine amino acid substitution at a position corresponding to position 141 of SEQ ID NO: 110 (C141Y) in a subject, the method comprising administering to the subject in need thereof a) a polynucleotide encoding a polypeptide fragment comprising SEQ ID NO: 13, b) a polynucleotide encoding a polypeptide fragment comprising SEQ ID NO: 59, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a cysteine to tyrosine amino acid substitution at a position corresponding to position 141 of SEQ ID NO: 110 (C141Y) in a subject, the method comprising administering to the subject in need thereof a) a polynucleotide encoding a polypeptide fragment comprising SEQ ID NO: 13, b) a polynucleotide encoding a polypeptide fragment comprising SEQ ID NO: 244, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a histidine to leucine amino acid substitution at a position corresponding to position 193 of SEQ ID NO: 110 (H193L) in a subject, the method comprising administering to the subject in need thereof a) a polynucleotide encoding a polypeptide fragment comprising SEQ ID NO: 14, b) a polynucleotide encoding a polypeptide fragment comprising SEQ ID NO: 60, or SEQ ID NO: 61, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a histidine to leucine amino acid substitution at a position corresponding to position 193 of SEQ ID NO: 110 (H193L) in a subject, the method comprising administering to the subject in need thereof a) a polynucleotide encoding a polypeptide fragment comprising SEQ ID NO: 14, b) a polynucleotide encoding a polypeptide fragment comprising SEQ ID NO: 245, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a histidine to tyrosine amino acid substitution at a position corresponding to position 193 of SEQ ID NO: 110 (H193Y) in a subject, the method comprising administering to the subject in need thereof a) a polynucleotide encoding a polypeptide fragment comprising SEQ ID NO: 15, b) a polynucleotide encoding a polypeptide fragment comprising SEQ ID NO: 62, or SEQ ID NO: 63, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a histidine to tyrosine amino acid substitution at a position corresponding to position 193 of SEQ ID NO: 110 (H193Y) in a subject, the method comprising administering to the subject in need thereof a) a polynucleotide encoding a polypeptide fragment comprising SEQ ID NO: 15, b) a polynucleotide encoding a polypeptide fragment comprising SEQ ID NO: 236, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a lysine to asparagine amino acid substitution at a position corresponding to position 132 of SEQ ID NO: 110 (K132N) in a subject, the method comprising administering to the subject in need thereof a) a polynucleotide encoding a polypeptide fragment comprising SEQ ID NO: 16, b) a polynucleotide encoding a polypeptide fragment comprising SEQ ID NO: 64, or SEQ ID NO: 66, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a lysine to asparagine amino acid substitution at a position corresponding to position 132 of SEQ ID NO: 110 (K132N) in a subject, the method comprising administering to the subject in need thereof a) a polynucleotide encoding a polypeptide fragment comprising SEQ ID NO: 16, b) a polynucleotide encoding a polypeptide fragment comprising SEQ ID NO: 64, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a lysine to asparagine amino acid substitution at a position corresponding to position 132 of SEQ ID NO: 110 (K132N) in a subject, the method comprising administering to the subject in need thereof a) a polynucleotide encoding a polypeptide fragment comprising SEQ ID NO: 16, b) a polynucleotide encoding a polypeptide fragment comprising SEQ ID NO: 237, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a proline to leucine amino acid substitution at a position corresponding to position 152 of SEQ ID NO: 110 (P152L) in a subject, the method comprising administering to the subject in need thereof a) a polynucleotide encoding a polypeptide fragment comprising SEQ ID NO: 18, b) a polynucleotide encoding a polypeptide fragment comprising SEQ ID NO: 67, or SEQ ID NO: 68, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a proline to leucine amino acid substitution at a position corresponding to position 152 of SEQ ID NO: 110 (P152L) in a subject, the method comprising administering to the subject in need thereof a) a polynucleotide encoding a polypeptide fragment comprising SEQ ID NO: 18, b) a polynucleotide encoding a polypeptide fragment comprising SEQ ID NO: 68, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a proline to leucine amino acid substitution at a position corresponding to position 152 of SEQ ID NO: 110 (P152L) in a subject, the method comprising administering to the subject in need thereof a) a polynucleotide encoding a polypeptide fragment comprising SEQ ID NO: 18, b) a polynucleotide encoding a polypeptide fragment comprising SEQ ID NO: 239, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising an arginine to leucine amino acid substitution at a position corresponding to position 110 of SEQ ID NO: 110 (R110L) in a subject, the method comprising administering to the subject in need thereof a) a polynucleotide encoding a polypeptide fragment comprising SEQ ID NO: 20, b) a polynucleotide encoding a polypeptide fragment comprising SEQ ID NO: 70, or SEQ ID NO: 71, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising an arginine to leucine amino acid substitution at a position corresponding to position 110 of SEQ ID NO: 110 (R110L) in a subject, the method comprising administering to the subject in need thereof a) a polynucleotide encoding a polypeptide fragment comprising SEQ ID NO: 20, b) a polynucleotide encoding a polypeptide fragment comprising SEQ ID NO: 241, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a serine to phenylalanine amino acid substitution at a position corresponding to position 127 of SEQ ID NO: 110 (S127F) in a subject, the method comprising administering to the subject in need thereof a) a polynucleotide encoding a polypeptide fragment comprising SEQ ID NO: 21, b) a polynucleotide encoding a polypeptide fragment comprising SEQ ID NO: 72, SEQ ID NO: 73, SEQ ID NO: 74, SEQ ID NO: 95, or SEQ ID NO: 96 or c) a combination thereof in an amount effective to treat, prevent, reduce the risk of onset or delay the onset of the clinical condition. Also described herein are methods of inducing an immune response or methods of treating, preventing, reducing a risk of onset or delaying the onset of a clinical condition characterized by expression of a TP53 mutant comprising a serine to phenylalanine amino acid substitution at a position corresponding to position 127 of SEQ ID NO: 110 (S127F) in a subject, the method comprising administering to the subject in need thereof a) a polynucleotide encoding a polypeptide fragment comprising SEQ ID NO: 21, b) a polynucleotide encoding a polypeptide fragment comprising SEQ ID NO: 242 or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a valine to methionine amino acid substitution at a position corresponding to position 272 of SEQ ID NO: 110 (V272M) in a subject, the method comprising administering to the subject in need thereof a) a polynucleotide encoding a polypeptide fragment comprising SEQ ID NO: 22, b) a polynucleotide encoding a polypeptide fragment comprising SEQ ID NO: 75, or SEQ ID NO: 76 or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a valine to methionine amino acid substitution at a position corresponding to position 272 of SEQ ID NO: 110 (V272M) in a subject, the method comprising administering to the subject in need thereof a) a polynucleotide encoding a polypeptide fragment comprising SEQ ID NO: 22, b) a polynucleotide encoding a polypeptide fragment comprising SEQ ID NO: 75, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a valine to methionine amino acid substitution at a position corresponding to position 272 of SEQ ID NO: 110 (V272M) in a subject, the method comprising administering to the subject in need thereof a) a polynucleotide encoding a polypeptide fragment comprising SEQ ID NO: 22, b) a polynucleotide encoding a polypeptide fragment comprising SEQ ID NO: 246, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a TP53 mutant comprising a tyrosine to cysteine amino acid substitution at a position corresponding to position 220 of SEQ ID NO: 110 (Y220C) in a subject, the method comprising administering to the subject in need thereof a) a polynucleotide encoding a polypeptide fragment comprising SEQ ID NO: 23, b) a polynucleotide encoding a polypeptide fragment comprising SEQ ID NO: 78, or SEQ ID NO: 79, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a tyrosine to cysteine amino acid substitution at a position corresponding to position 220 of SEQ ID NO: 110 (Y220C) in a subject, the method comprising administering to the subject in need thereof a) a polynucleotide encoding a polypeptide fragment comprising SEQ ID NO: 23, b) a polynucleotide encoding a polypeptide fragment comprising SEQ ID NO: 78, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a TP53 mutant comprising a tyrosine to cysteine amino acid substitution at a position corresponding to position 220 of SEQ ID NO: 110 (Y220C) in a subject, the method comprising administering to the subject in need thereof a) a polynucleotide encoding a polypeptide fragment comprising SEQ ID NO: 23, b) a polynucleotide encoding a polypeptide fragment comprising SEQ ID NO: 243, or c) a combination thereof in an amount effective to treat, prevent, reduce the risk of onset or delay the onset of the clinical condition.

Described herein are methods of inducing an immune response or methods of treating, preventing, reducing a risk of onset or delaying the onset of a clinical condition characterized by expression of a ERBB2 mutant comprising a valine to isoleucine amino acid substitution at a position corresponding to position 842 of SEQ ID NO: 104 (V842I) in a subject, the method comprising administering to the subject in need thereof a) a polynucleotide encoding a polypeptide fragment comprising SEQ ID NO: 24, b) a polynucleotide encoding a polypeptide fragment comprising SEQ ID NO: 84, SEQ ID NO: 85, or SEQ ID NO: 86, or c) a combination thereof in an amount effective to treat, prevent, reduce the risk of onset or delay the onset of the clinical condition. In certain embodiments, described herein are methods of inducing an immune response or methods of treating, preventing, reducing a risk of onset or delaying the onset of a clinical condition characterized by expression of a ERBB2 mutant comprising a valine to isoleucine amino acid substitution at a position corresponding to position 842 of SEQ ID NO: 104 (V842I) in a subject, the method comprising administering to the subject in need thereof a) a polynucleotide encoding a polypeptide fragment comprising SEQ ID NO: 24, b) a polynucleotide encoding a polypeptide fragment comprising SEQ ID NO: 247, or c) a combination thereof in an amount effective to treat, prevent, reduce the risk of onset or delay the onset of the clinical condition.

In certain embodiments the methods of treatment comprise administering the polynucleotide in part a) prior to administering the polynucleotide in part b). In certain embodiments the methods of treatment comprise administering the polynucleotide in part b) prior to administering the polynucleotide in part a). In certain embodiments the methods of treatment comprise administering the polynucleotide in part a) concurrently with the polynucleotide in part b).

In certain embodiments, the time between administration of the polynucleotide in part a) and the polynucleotide in part b) is about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In certain embodiments the methods of treatment comprise administering a vector encoding the polynucleotide of part a) and a vector encoding the polynucleotide of part b). In some embodiments, the vectors are independently selected from an adenovirus vector, an alphaviral vector, a poxvirus vector, an adeno-associated virus vector, a retrovirus vector, and a self-replicating RNA molecule. In further embodiments, the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3. In further embodiments, the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Also provided herein are methods of treating cancer in a subject comprising administering to the subject in need thereof a pharmaceutical composition comprising a TCR described herein. In certain embodiments, the TCR comprises an alpha chain and a beta chain, wherein: (a) the alpha chain comprises a complementarity determining region 3 (CDR3) comprising an amino acid sequence provided in Table 14, Table 15, Table 16, Table 17 or Table 18, and the beta chain comprises a CDR3 comprising a corresponding amino acid sequence provided in Table 14, Table 15, Table 16, Table 17 or Table 18. An alpha chain CDR3 corresponds to a beta chain CDR3 if they appear in the same row in Table 14, Table 15, Table 16, Table 17 or Table 18.

In further embodiments, the TCR comprises an alpha chain and a beta chain, wherein: (a) the alpha chain comprises a CDR1 comprising an amino acid sequence provided in Table 19, Table 20, Table 21, Table 22, or Table 23, a CDR2 comprising an amino acid sequence provided in Table 19, Table 20, Table 21, Table 22, or Table 23, and a CDR3 comprising an amino acid sequence provided in Table 14, Table 15, Table 16, Table 17, or Table 18, and (b) the beta chain comprises a CDR1 comprising an amino acid sequence provided in Table 19, Table 20, Table 21, Table 22, or Table 23, a CDR2 comprising an amino acid sequence provided in Table 19, Table 20, Table 21, Table 22, or Table 23, and a CDR3 comprising a corresponding amino acid sequence provided in Table 14, Table 15, Table 16, Table 17 or Table 18. An alpha chain CDR1 or CDR2 corresponds to a beta chain CDR1 or CDR2 if they appear in the same row in Table 19, Table 20, Table 21, Table 22, or Table 23. An alpha chain CDR3 corresponds to a beta chain CDR3 if they appear in the same row in Table 14, Table 15, Table 16, Table 17, or Table 18. An alpha and beta chain CDR1 and CDR2 provided in Table 19, Table 20, Table 21, Table 22, or Table 23 correspond to and alpha and beta chain CDR3 provided in the same row in Table 14, Table 15, Table 16, Table 17 or Table 18.

Also provided herein are methods of inducing an immune response in a subject comprising administering to the subject in need thereof a pharmaceutical composition comprising a TCR described herein.

Described herein are methods of inducing an immune response or treating, preventing, reducing a risk of onset or delaying the onset of a clinical condition characterized by expression of a PIK3CA mutant comprising a glycine to aspartic acid amino acid substitution at a position corresponding to position 118 of SEQ ID NO: 106 (G118D) in a subject comprising administering to the subject in need thereof a TCR described herein. In certain embodiments, the TCR comprises an alpha chain and a beta chain, wherein: (a) the alpha chain comprises a CDR3 comprising an amino acid sequence provided in Table 14, and (b) the beta chain comprises a CDR3 comprising a corresponding amino acid sequence provided in Table 14. In certain embodiments, the TCR comprises an alpha chain and a beta chain, wherein: (a) the alpha chain comprises a CDR1 comprising an amino acid sequence provided in Table 19, a CDR2 comprising an amino acid sequence provided in Table 19, and a CDR3 comprising an amino acid sequence provided in Table 14, and (b) the beta chain comprises a CDR1 comprising an amino acid sequence provided in Table 19, a CDR2 comprising an amino acid sequence provided in Table 19, and a CDR3 comprising a corresponding amino acid sequence provided in Table 14.

Described herein are methods of inducing an immune response or treating, preventing, reducing a risk of onset or delaying the onset of a clinical condition characterized by expression of a TP53 mutant comprising a cysteine to tyrosine amino acid substitution at a position corresponding to position 141 of SEQ ID NO: 110 (C141Y) in a subject comprising administering to the subject in need thereof a TCR described herein. In certain embodiments, the TCR comprises an alpha chain and a beta chain, wherein: (a) the alpha chain comprises a CDR3 comprising an amino acid sequence provided in Table 15, and (b) the beta chain comprises a CDR3 comprising a corresponding amino acid sequence provided in Table 15. In certain embodiments, the TCR comprises an alpha chain and a beta chain, wherein: (a) the alpha chain comprises a CDR1 comprising an amino acid sequence provided in Table 20, a CDR2 comprising an amino acid sequence provided in Table 20, and a CDR3 comprising an amino acid sequence provided in Table 15, and (b) the beta chain comprises a CDR1 comprising an amino acid sequence provided in Table 20, a CDR2 comprising an amino acid sequence provided in Table 20, and a CDR3 comprising a corresponding amino acid sequence provided in Table 15.

Described herein are methods of inducing an immune response or treating, preventing, reducing a risk of onset or delaying the onset of a clinical condition characterized by expression of a TP53 mutant comprising a proline to leucine amino acid substitution at a position corresponding to position 152 of SEQ ID NO: 110 (P152L) in a subject comprising administering to the subject in need thereof a TCR described herein. In certain embodiments, the TCR comprises an alpha chain and a beta chain, wherein: (a) the alpha chain comprises a CDR3 comprising an amino acid sequence provided in Table 16, and (b) the beta chain comprises a CDR3 comprising a corresponding amino acid sequence provided in Table 16. In certain embodiments, the TCR comprises an alpha chain and a beta chain, wherein: (a) the alpha chain comprises a CDR1 comprising an amino acid sequence provided in Table 21, a CDR2 comprising an amino acid sequence provided in Table 21, and a CDR3 comprising an amino acid sequence provided in Table 16, and (b) the beta chain comprises a CDR1 comprising an amino acid sequence provided in Table 21, a CDR2 comprising an amino acid sequence provided in Table 21, and a CDR3 comprising a corresponding amino acid sequence provided in Table 16.

Described herein are methods of inducing an immune response or treating, preventing, reducing a risk of onset or delaying the onset of a clinical condition characterized by expression of a CTNNB1 mutant comprising a serine to phenylalanine amino acid substitution at a position corresponding to position 37 of SEQ ID NO: 103 (S37F) in a subject comprising administering to the subject in need thereof a TCR described herein. In certain embodiments, the TCR comprises an alpha chain and a beta chain, wherein: (a) the alpha chain comprises a CDR3 comprising an amino acid sequence provided in Table 17, and (b) the beta chain comprises a CDR3 comprising a corresponding amino acid sequence provided in Table 17. In certain embodiments, the TCR comprises an alpha chain and a beta chain, wherein: (a) the alpha chain comprises a CDR1 comprising an amino acid sequence provided in Table 22, a CDR2 comprising an amino acid sequence provided in Table 22, and a CDR3 comprising an amino acid sequence provided in Table 17, and (b) the beta chain comprises a CDR1 comprising an amino acid sequence provided in Table 22, a CDR2 comprising an amino acid sequence provided in Table 22, and a CDR3 comprising a corresponding amino acid sequence provided in Table 17.

Described herein are methods of inducing an immune response or treating, preventing, reducing a risk of onset or delaying the onset of a clinical condition characterized by expression of a TP53 mutant comprising a tyrosine to cysteine amino acid substitution at a position corresponding to position 220 of SEQ ID NO: 110 (Y220C) in a subject comprising administering to the subject in need thereof a TCR described herein. In certain embodiments, the TCR comprises an alpha chain and a beta chain, wherein: (a) the alpha chain comprises a CDR3 comprising an amino acid sequence provided in Table 18, and (b) the beta chain comprises a CDR3 comprising a corresponding amino acid sequence provided in Table 18. In certain embodiments, the TCR comprises an alpha chain and a beta chain, wherein: (a) the alpha chain comprises a CDR1 comprising an amino acid sequence provided in Table 23, a CDR2 comprising an amino acid sequence provided in Table 23, and a CDR3 comprising an amino acid sequence provided in Table 18, and (b) the beta chain comprises a CDR1 comprising an amino acid sequence provided in Table 23, a CDR2 comprising an amino acid sequence provided in Table 23, and a CDR3 comprising a corresponding amino acid sequence provided in Table 18.

Kits/Articles of Manufacture

For use in the methods or uses described herein, kits and articles of manufacture are also described. Such kits include a package or container that is compartmentalized to receive one or more dosages of the pharmaceutical compositions disclosed herein. Suitable containers include, for example, bottles. In one embodiment, the containers are formed from a variety of materials such as glass or plastic.

Described herein are kits of parts comprising a pair of polypeptide fragments selected from the group consisting of: (a) SEQ ID NO: 2 and SEQ ID NO: 29; (b) SEQ ID NO: 3 and SEQ ID NO: 32; (c) SEQ ID NO: 9 and SEQ ID NO: 45; (d) SEQ ID NO: 13 and SEQ ID NO: 59; (e) SEQ ID NO: 16 and SEQ ID NO: 64; (f) SEQ ID NO: 18 and SEQ ID NO 68; (g) SEQ ID NO: 22 and SEQ ID NO: 75; and (h) SEQ ID NO: 23 and SEQ ID NO: 78.

Described herein are kits of parts comprising a pair of polypeptide fragments selected from the group consisting of: (a) SEQ ID NO: 9 and SEQ ID NO: 45; (b) SEQ ID NO: 13 and SEQ ID NO: 59; and (c) SEQ ID NO: 18 and SEQ ID NO: 68.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert.

In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Methods of Generating CD8+ T-Cells

Described herein are methods for generating CD8+ T-cells that are positive for an HLA-A*02:01-restricted polypeptide fragment and a cognate native polypeptide fragment. In certain embodiments, said methods comprise exposing CD8+ T-cells to the HLA-A*02:01-restricted polypeptide fragment and cognate native polypeptide fragment selected from the group consisting of: (a) SEQ ID NO: 2 or a sequence having 90% identity to SEQ ID NO: 2 and SEQ ID NO: 29 or a sequence having 90% identity to SEQ ID NO: 29; (b) SEQ ID NO: 3 or a sequence having 90% identity to SEQ ID NO: 3 and SEQ ID NO: 32 or a sequence having 90% identity to SEQ ID NO: 32; (c) SEQ ID NO: 9 or a sequence having 90% identity to SEQ ID NO: 9 and SEQ ID NO: 45 or a sequence having 90% identity to SEQ ID NO: 45; (d) SEQ ID NO: 13 or a sequence having 90% identity to SEQ ID NO: 13 and SEQ ID NO: 59 or a sequence having 90% identity to SEQ ID NO: 59; (e) SEQ ID NO: 16 or a sequence having 90% identity to SEQ ID NO: 16 and SEQ ID NO: 64 or a sequence having 90% identity to SEQ ID NO: 64; (f) SEQ ID NO: 18 or a sequence having 90% identity to SEQ ID NO: 18 and SEQ ID NO 68 or a sequence having 90% identity to SEQ ID NO: 68; (g) SEQ ID NO: 22 or a sequence having 90% identity to SEQ ID NO: 22 and SEQ ID NO: 75 or a sequence having 90% identity to SEQ ID NO: 75; and (h) SEQ ID NO: 23 or a sequence having 90% identity to SEQ ID NO: 23 and SEQ ID NO: 78 or a sequence having 90% identity to SEQ ID NO: 78, and selecting CD8+ T cells that are positive to both the HLA-A*02:01-restricted polypeptide fragment and a cognate neoantigen polypeptide fragment.

Described herein are methods for generating CD8+ T-cells that are positive for an HLA-A*02:01-restricted polypeptide fragment and a cognate native polypeptide fragment. In certain embodiments, said methods comprise exposing CD8+ T-cells to the HLA-A*02:01-restricted polypeptide fragment and cognate native polypeptide fragment selected from the group consisting of: (a) SEQ ID NO: 9 or a sequence having 90% identity to SEQ ID NO: 9 and SEQ ID NO: 45 or a sequence having 90% identity to SEQ ID NO: 45; (b) SEQ ID NO: 13 or a sequence having 90% identity to SEQ ID NO: 13 and SEQ ID NO: 59 or a sequence having 90% identity to SEQ ID NO: 59; and (c) SEQ ID NO: 18 or a sequence having 90% identity to SEQ ID NO: 18 and SEQ ID NO 68 or a sequence having 90% identity to SEQ ID NO: 68; and selecting CD8+ T cells that are positive to both the HLA-A*02:01-restricted polypeptide fragment and a cognate neoantigen polypeptide fragment.

EXAMPLES

These examples are provided for illustrative purposes only and not to limit the scope of the claims provided herein.

Example 1. Peptide Mimic Design

Selection of Cancer Driver Mutations

A list of cancer driver mutations compiled from 9176 cancer patients was examined as described in Marty R, et al. Cell. 2017; 171(6):1272-1283, and driver mutations were prioritized based on their recurrence. HLA binding predictions using the NetMHCpan4.0 suite of prediction algorithms were performed as described in Jurtz V., et al., *J Immunol.* 2017; 199(9):3360-3368, and antigens were prioritized on the basis of their predicted binding affinities to HLA-A*02:01. The HLA-A*02:01 allele was chosen for mimic design due to its high allele frequency (~40%) in North American and European populations, and because there is abundant experimental binding data of different antigens bound to HLA-A*02:01. Finally, mimic antigens were designed as follows.

Prioritization of Mutations and Mimic Design

Driver mutations in cancer are expected to be present in most of the tumor cells (i.e. they have high clonality). The mutant proteins can be processed into 9- or 10-mer neoantigen epitopes that contain the mutation and are presented by the class I MHC complex of these tumor cells. Neoepitopes that have very weak binding affinity to MHC molecules are not presented since they are unable to stabilize the peptide-MHC complex, while epitopes with intermediate or strong binding affinity to the MHC I protein could be presented on the surface of tumor cells. Furthermore, the stability of the peptide-MHC complex can determine the number and duration of the complex on the cell surface. As a result, the immunogenicity of a given antigen is related to its binding affinity to MHC I proteins.

Cancer driver mutations arise early in the process of malignant transformation of cells into cancers, and they are subject to surveillance by the immune system. Hence, cells with mutations that can result in highly immunogenic antigens are likely to be recognized and killed by the immune system. As a consequence, early cancer driver mutations are expected to be weakly immunogenic and to have moderate binding to the host MHC proteins. On the other hand, due to their high clonality, driver mutations are an attractive target for therapies that redirect the immune system to specifically recognize and attack cancer cells. Thus, an approach has been developed based on molecular mimicry, wherein synthetic mimic peptide antigens are designed with enhanced MHC binding affinity relative to the driver mutant antigens, but with sufficient sequence similarity that they elicit an immune response that can also recognize and attack the mutant antigens presented on cancer cells.

Methods 9-mer and 10-mer epitopes containing a cancer mutation were identified, and mimics were designed against those candidate epitopes that exhibited intermediate (weak) predicted binding affinities to the HLA-A*02:01 allele. To analyze the predicted binding affinities, NetMHCpan4.0 was used, which ranks epitopes according to their predicted affinity to a given HLA allele, with lower ranks being indicative of a higher binding affinity. The ranks of epitopes are allowed to vary across a range from 0 to 100. Most natural peptide epitopes were identified as predicted to bind at a rank <2. Motivated by this feature of the algorithm, the predicted binding was classified as intermediate if the rank of the binding affinity was >0.5 and predicted binding affinity was <4, and strong if the rank was <0.5. Mimics were designed by allowing amino acid substitutions at amino acid positions 2 and 9 (P2 and P9) of the binding 9mer epitope. To generate rules for amino acid substitutions, the set of known 9mer epitope binders to HLA-A*02:01 was obtained from the IEDB database (Vita R, et al. Nucleic Acids Res. 2018 Oct. 24), and the frequencies of occurrence of different amino acids at positions P2 and P9 estimated.

The Shannon entropy was estimated for each amino acid substitution at P2 and P9 as a measure of amino acid conservation. To generate mimic peptides, amino acids at P2 and P9 were ranked by degree of conservation and substitutions by replacing the wild type amino acid by other amino acid residues according to their degree of conservation. Amino acid conservation at P2 in the order L>M>I and at P9 in the order V>L>I was used. Finally, mimics for antigens with the cancer driver mutation present at either of P2 or P9 (the anchor positions on a 9mer epitope) were designed by altering amino acids at the anchor position which did not contain the mutation, thus retaining the cancer driver mutation.

The mimic peptides were then again examined for their predicted binding affinity with netMHCpan4.0 and ranked accordingly. A list of 90 peptides (23 cancer driver mutation+66 mimic epitopes, excluding controls, for an average of 3 mimics/mutant) was created by ranking cancer mutant 9- and 10-mer epitopes and their corresponding mimic pairs according to the ratio of their predicted affinities. Mutant and mimic sequences are provided in Table 1. Mutant peptide substitutions relative to wild-type 9- or 10-mer epitopes are identified with bold font and mimic peptide amino acid substitutions relative to the mutant peptides are identified with underlining.

TABLE 1

| Name | Type | Gene | Variant | Sequence | SEQ ID NO |
|---|---|---|---|---|---|
| M010 | mutant | CIC | CIC.R215W | MIFSKRHWA | 1 |
| M011 | mimic | CIC | CIC_R215W15 | MMFSKRHWI | 25 |
| M012 | mimic | CIC | CIC_R215W6 | MLFSKRHWV | 26 |
| M013 | mimic | CIC | CIC_R215W7 | MMFSKRHWV | 27 |
| M020 | mutant | CTNNB1 | CTNNB1.S33C | YLDCGIHSG | 2 |
| M021 | mimic | CTNNB1 | CTNNB1_S33C10 | YMDCGIHSL | 28 |
| M022 | mimic | CTNNB1 | CTNNB1_S33C5 | YLDCGIHSV | 29 |
| M023 | mimic | CTNNB1 | CTNNB1_S33C6 | YMDCGIHSV | 30 |
| M030 | mutant | CTNNB1 | CTNNB1.S37F | YLDSGIHFG | 3 |
| M031 | mimic | CTNNB1 | CTNNB1_S37F14 | YMDSGIHFI | 31 |
| M032 | mimic | CTNNB1 | CTNNB1_S37F5 | YLDSGIHFV | 32 |
| M033 | mimic | CTNNB1 | CTNNB1_S37F6 | YMDSGIHFV | 33 |
| M034 | mimic | CTNNB1 | CTNNB1.S33C9 | YLDCGIHSL | 80 |
| M035 | mimic | CTNNB1 | CTNNB1.S37F10 | YMDSGIHFL | 81 |
| M040 | control | Control | N/A | YLSTDVGFA | 4 |
| M041 | mimic | Control | N/A | YLSTDVGFV | 34 |
| M042 | mimic | Control | N/A | YMSTDVGFV | 35 |
| M043 | mimic | Control | N/A | YLSTDVGFL | 36 |
| M044 | mimic | Control | N/A | YMSTDVGFL | 82 |
| M045 | mimic | Control | N/A | YLSTDVGFI | 83 |
| M050 | mutant | KRAS | KRAS.G12A | LVVVGAAGV | 5 |
| M051 | mimic | KRAS | KRAS_G12A2 | LLVVGAAGV | 37 |
| M052 | mimic | KRAS | KRAS_G12A3 | LMVVGAAGV | 38 |

TABLE 1-continued

| Name | Type | Gene | Variant | Sequence | SEQ ID NO |
|---|---|---|---|---|---|
| M060 | mutant | KRAS | KRAS.G12C | LVVVGACGV | 6 |
| M061 | mimic | KRAS | KRAS_G12C2 | LLVVGACGV | 39 |
| M062 | mimic | KRAS | KRAS_G12C3 | LMVVGACGV | 40 |
| M070 | mutant | KRAS | KRAS.G12V | LVVVGAVGV | 7 |
| M071 | mimic | KRAS | KRAS_G12V2 | LLVVGAVGV | 41 |
| M072 | mimic | KRAS | KRAS_G12V3 | LMVVGAVGV | 42 |
| M080 | mutant | PIK3CA | PIK3CA.E453K | GLKDLLNPI | 8 |
| M081 | mimic | PIK3CA | PIK3CA_E453K5 | GLKDLLNPV | 43 |
| M082 | mimic | PIK3CA | PIK3CA_E453K6 | GMKDLLNPV | 44 |
| M090 | mutant | PIK3CA | PIK3CA.G118D | ILNREIDFA | 9 |
| M091 | mimic | PIK3CA | PIK3CA_G118D5 | ILNREIDFV | 45 |
| M092 | mimic | PIK3CA | PIK3CA_G118D6 | IMNREIDFV | 46 |
| M093 | mimic | PIK3CA | PIK3CA_G118D9 | ILNREIDFL | 47 |
| M100 | mutant | PTEN | PTEN.R173C | CYVYYYSYLL | 10 |
| M101 | mimic | PTEN | PTEN.R173C2 | CYLYYYSYLL | 48 |
| M102 | mimic | PTEN | PTEN.R173C6 | CYLYYYSYLV | 49 |
| M103 | mimic | PTEN | PTEN.R173C7 | CYMYYYSYLV | 50 |
| M104 | mimic | PTEN | PTEN.R173C3 | CYMYYYSYLL | 87 |
| M105 | mimic | PTEN | PTEN.R173C10 | CYLYYYSYLI | 88 |
| M106 | mimic | PTEN | PTEN.R173C11 | CYMYYYSYLI | 89 |
| M110 | mutant | SF3B1 | SF3B1.R625H | NMDEYVHNT | 11 |
| M111 | mimic | SF3B1 | SF3B1_R625H5 | NMDEYVHNV | 51 |
| M112 | mimic | SF3B1 | SF3B1_R625H6 | NLDEYVHNV | 52 |
| M113 | mimic | SF3B1 | SF3B1_R625H9 | NMDEYVHNL | 53 |
| M114 | mimic | SF3B1 | SF3B1.R625H10 | NLDEYVHNL | 90 |
| M115 | mimic | SF3B1 | SF3B1.R625H13 | NMDEYVHNI | 91 |
| M116 | mimic | SF3B1 | SF3B1.R625H14 | NLDEYVHNI | 92 |
| M120 | mutant | SOX17 | SOX17.S4031 | VVSDAISAV | 12 |
| M121 | mimic | SOX17 | SOX17_S40312 | VLSDAISAV | 54 |
| M122 | mimic | SOX17 | SOX17_S40313 | VMSDAISAV | 55 |
| M123 | mimic | SOX17 | SOX17_S40316 | VLSDAISAL | 56 |
| M124 | mimic | SOX17 | SOX17.S40317 | VMSDAISAL | 93 |
| M130 | mutant | TP53 | TP53.C141Y | KTYPVQLWV | 13 |
| M131 | mimic | TP53 | TP53_C141Y2 | KLYPVQLWV | 57 |
| M132 | mimic | TP53 | TP53_C141Y3 | KMYPVQLWV | 58 |
| M133 | mimic | TP53 | TP53_C141Y8 | KMYPVQLWL | 59 |
| M134 | mimic | TP53 | TP53.C141Y12 | KLYPVQLWI | 94 |
| M140 | mutant | TP53 | TP53.H193L | GLAPPQLLI | 14 |
| M141 | mimic | TP53 | TP53_H193L5 | GLAPPQLLV | 60 |
| M142 | mimic | TP53 | TP53_H193L6 | GMAPPQLLV | 61 |
| M150 | mutant | TP53 | TP53.H193Y | GLAPPQYLI | 15 |
| M151 | mimic | TP53 | TP53_H193Y5 | GLAPPQYLV | 62 |
| M152 | mimic | TP53 | TP53_H193Y6 | GMAPPQYLV | 63 |
| M160 | mutant | TP53 | TP53.K132N | ALNNMFCQL | 16 |
| M161 | mimic | TP53 | TP53_K132N5 | ALNNMFCQV | 64 |
| M162 | mimic | TP53 | TP53_K132N6 | AMNNMFCQV | 66 |
| M170 | mutant | TP53 | TP53.K132N | NMFCQLAKT | 17 |
| M171 | mimic | TP53 | TP53_K132N6 | NLFCQLAKV** | 65 |
| M180 | mutant | TP53 | TP53.P152L | QLWVDSTPL | 18 |
| M181 | mimic | TP53 | TP53_P152L3 | QLWVDSTPI | 67 |
| M182 | mimic | TP53 | TP53_P152L4 | QLWVDSTPV | 68 |
| M190 | mutant | TP53 | TP53.P250L | RLILTIITL | 19 |
| M191 | mimic | TP53 | TP53_P250L4 | RLILTIITV | 69 |
| M200 | mutant | TP53 | TP53.R110L | YQGSYGFLL | 20 |
| M201 | mimic | TP53 | TP53_R110L3 | YQGSYGFLI | 70 |
| M202 | mimic | TP53 | TP53_R110L4 | YQGSYGFLV | 71 |
| M210 | mutant | TP53 | TP53.S127F | SVTCTYFPA | 21 |
| M211 | mimic | TP53 | TP53_S127F11 | SMTCTYFPL | 72 |
| M212 | mimic | TP53 | TP53_S127F6 | SLTCTYFPV | 73 |
| M213 | mimic | TP53 | TP53_S127F7 | SMTCTYFPV | 74 |
| M214 | mimic | TP53 | TP53_S127F8 | SLTCTYFPL | 95 |
| M215 | mimic | TP53 | TP53_S127F12 | SMTCTYFPI | 96 |
| M220 | mutant | TP53 | TP53.V272M | LLGRNSFEM | 22 |
| M221 | mimic | TP53 | TP53_V272M2 | LLGRNSFEL | 75 |
| M222 | mimic | TP53 | TP53_V272M3 | LLGRNSFEI | 76 |
| M223 | Wild type | TP53 | TP53_V272M4 | LLGRNSFEV | 77 |
| M230 | mutant | TP53 | TP53.Y220C | VVPCEPPEV | 23 |
| M231 | mimic | TP53 | TP53_Y220C2 | VLPCEPPEV | 78 |
| M232 | mimic | TP53 | TP53_Y220C3 | VMPCEPPEV | 79 |
| M240 | mutant | ERBB2 | ERBB2.V842I | RLIHRDLAA | 24 |
| M241 | mimic | ERBB2 | ERBB2_V842I10 | RMIHRDLAL | 84 |
| M242 | mimic | ERBB2 | ERBB2_V842I5 | RLIHRDLAV | 85 |
| M243 | mimic | ERBB2 | ERBB2_V842I6 | RMIHRDLAV | 86 |

TABLE 1-continued

| Name | Type | Gene | Variant | Sequence | SEQ ID NO |
|---|---|---|---|---|---|
| M250 | wild type control | CMV | CMV.pp65 | NLVPMVATV | 97 |
| M251 | mimic | CMV | CMV.pp651 | NMVPMVATV | 98 |
| M252 | mimic | CMV | CMV.pp652 | NLVPMVATL | 99 |
| M253 | mimic | CMV | CMV.pp653 | NMVPMVATL | 100 |

The wild-type amino acid sequences for each of the genes identified in Table 1 are provided in Table 2.

TABLE 2

| Gene | Amino Acid Sequence | SEQ ID NO | Protein Database No. |
|---|---|---|---|
| CIC | MYSAHRPLMPASSAASRGLGMFVWTNVEPRSVAVFPWHSLVPFLA PSQPDPSVQPSEAQQPASHPVASNQSKEPAESAAVAHERPPGGTG SADPERPPGATCPESPGPGPPHPLGVVESGKGPPPTTEEEASGPP GEPRLDSETESDHDDAFLSIMSPEIQLPLPPGKRRTQSLSALPKE RDSSSEKDGRSPNKREKDHIRRPMNAFMIFSKRHRALVHQRHPNQ DNRTVSKILGEWWYALGPKEKQKYHDLAFQVKEAHFKAHPDWKWC NKDRKKSSSEAKPTSLGLAGGHKETRERSMSETGTAAAPGVSSEL LSVAAQTLLSSDTKAPGSSSCGAERLHTVGGPGSARPRAFSHSGV HSLDGGEVDSQALQELTQMVSGPASYSGPKPSTQYGAPGPFAAPG EGGALAATGRPPLLPTRASRSQRAASEDMTSDEERMVICEEEGDD DVIADDGFGTTDIDLKCKERVTDSESGDSSGEDPEGNKGFGRKVF SPVIRSSFTHCRPPLDPEPPGPPDPPVAFGKGYGSAPSSSASSPA SSSASAATSFSLGSGTFKAQESGQGSTAGPLRPPPPGAGGPATPS KATRFLPMDPATFRRKRPESVGGLEPPGPSVIAAPPSGGGNILQT LVLPPNKEEQEGGGARVPSAPAPSLAYGAPAAPLSRPAATMVTNV VRPVSSTPVPIASKPFPTSGRAEASPNDTAGARTEMGTGSRVPGG SPLGVSLVYSDKKSAAATSPAPHLVAGPLLGTVGKAPATVTNLLV GTPGYGAPAPPAVQFIAQGAPGGGTTAGSGAGAGSGPNGPVPLGI LQPGALGKAGGITQVQYILPTLPQQLQVAPAPAPAPGTKAAAPSG PAPTTSIRFTLPPGTSTNGKVLAATAPTPGIPILQSVPSAPPPKA QSVSPVQAPPPGGSAQLLPGKVLVPLAAPSMSVRGGGAGQPLPLV SPPPFSVPVQNGAQPPSKIIQLTPVPVSTPSGLVPPLSPATLPGPT SQPQKVLLPSSTRITYVQSAGGHALPLGTSPASSQAGTVTSYGPT SSVALGFTSLGPSGPAFVQPLLSAGQAPLLAPGQVGVSPVPSPQL PPACAAPGGPVITAFYSGSPAPTSSAPLAQPSQAPPSLVYTVATS TTPPAATILPKGPPAPATATPAPTSPFPSATAGSMTYSLVAPKAQ RPSPKAPQKVKAAIASIPVGSFEAGASGRPGPAPRQPLEPGPVRE PTAPESELEGQPTPPAPPPLPETWTPTARSSPPLPPPAEERTSAK GPETMASKFPSSSSDWRVPGQGLENRGEPPTPPSPAPAPAVAPGG SSESSSGRAAGDTPERKEAAGTGKKVKVRPPPLKKTFDSVDNRVL SEVDFEERFAELPEFRPEEVLPSPTLQSLATSPRAILGSYRKKRK NSTDLDSAPEDPTSPKRKMRRRSSCSSEPNTPKSAKCEGDIFTFD RTGTEAEDVLGELEYDKVPYSSLRRTLDQRRALVMQLFQDHGFFP SAQATAAFQARYADIFPSKVCLQLKIREVRQKIMQAATPTEQPPG AEAPLVPPPTGTAAAPAPTPSPAGGPDPTSPSSDSGTAQAAPPL PPPPESGPGQPGWEGAPQPSPPPGPSTAATGR | 102 | Q96RK0 |
| CTNNB1 | MATQADLMELDMAMEPDRKAAVSHWQQQSYLDSGIHSGATTTAPS LSGKGNPEEEDVDTSQVLYEWEQGFSQSFTQEQVADIDGQYAMTR AQRVRAAMFPETLDEGMQIPSTQFDAAHPTNVQRLAEPSQMLKHA VVNLINYQDDAELATRAIPELTKLLNDEDQVVVNKAAVMVHQLSK KEASRHAIMRSPQMVSAIVRTMQNTNDVETARCTAGTLHNLSHHR EGLLAIFKSGGIPALVKMLGSPVDSVLFYAITTLHNLLLHQEGAK MAVRLAGGLQKMVALLNKTNVKFLAITTDCLQILAYGNQESKLII LASGGPQALVNIMRTYTYEKLLWTTSRVLKVLSVCSSNKPAIVEA GGMQALGLHLTDPSQRLVQNCLWTLRNLSDAATKQEGMEGLLGTL VQLLGSDDINVVTCAAGILSNLTCNNYKNKMMVCQVGGIEALVRT VLRAGDREDITEPAICALRHLTSRHQEAEMAQNAVRLHYGLPVVV KLLHPPSHWPLIKATVGLIRNLALCPANHAPLREQGAIPRLVQLL VRAHQDTQRRTSMGGTQQQFVEGVRMEEIVEGCTGALHILARDVH NRIVIRGLNTIPLFVQLLYSPIENIQRVAAGVLCELAQDKEAAEA IEAEGATAPLTELLHSRNEGVATYAAAVLFRMSEDKPQDYKKRLS VELTSSLFRTEPMAWNETADLGLDIGAQGEPLGYRQDDPSYRSFH SGGYGQDALGMDPMMEHEMGGHHPGADYPVDGLPDLGHAQDLMDG LPPGDSNQLAWFDTDL | 103 | P35222 |

TABLE 2-continued

| Gene | Amino Acid Sequence | SEQ ID NO | Protein Database No. |
|---|---|---|---|
| ERBB2 | MELAALCRWGLLLALLPPGAASTQVCTGTDMKLRLPASPETHLDM LRHLYQGCQVVQGNLELTYLPTNASLSFLQDIQEVQGYVLIAHNQ VRQVPLQRLRIVRGTQLFEDNYALAVLDNGDPLNNFIPVTGASPG GLRELQLRSLTEILKGGVLIQRNPQLCYQDTILWKDIFHKNNQLA LTLIDTNRSRACHPCSPMCKGSRCWGESSEDCQSLTRTVCAGGCA RCKGPLPTDCCHEQCAAGCTGPKHSDCLACLHFNHSGICELHCPA LVTYNTDTFESMPNPEGRYTFGASCVTACPYNYLSTDVGSCTLVC PLHNQEVTAEDGTQRCEKCSKPCARVCYGLGMEHLREVRAVTSAN IQEFAGCKKIFGSLAFLPESFDGDPASNTAPLQPEQLQVFETLEE ITGYLYISAWPDSLPDLSVFQNLQVIRGRILHNGAYSLTLQGLGI SWLGLRSLRELGSGLALIHHNTHLCFVHTVPWDQLFRNPHQALLH TANRPEDECVGEGLACHQLCARGHCWGPGPTQCVNCSQFLRGQEC VEECRVLQGLPREYVNARHCLPCHPECQPQNGSVTCFGPEADQCV ACAHYKDPPFCVARCPSGVKPDLSYMPIWKFPDEEGACQPCPINC THSCVDLDDKGCPAEQRASPLTSIISAVVGILLVVVLGVVFGILI KRRQQKIRKYTMRRLLQETELVEPLTPSGAMPNQAQMRILKETEL RKVKVLGSGAFGTVYKGIWIPDGENVKIPVAIKVLRENTSPKANK EILDEAYVMAGVGSPYVSRLLGICLTSTVQLVTQLMPYGCLLDHV RENRGRLGSQDLLNWCMQIAKGMSYLEDVRLVHRDLAARNVLVKS PNHVKITDFGLARLLDIDETEYHADGGKVPIKWMALESILRRRFT HQSDVWSYGVTVWELMTFGAKPYDGIPAREIPDLLEKGERLPQPP ICTIDVYMIMVKCWMIDSECRPRFRELVSEFSRMARDPQRFVVIQ NEDLGPASPLDSTFYRSLLEDDDMGDLVDAEEYLVPQQGFFCPDP APGAGGMVHHRHRSSSTRSGGGDLTLGLEPSEEEAPRSPLAPSEG AGSDVFDGDLGMGAAKGLQSLPTHDPSPLQRYSEDPTVPLPSETD GYVAPLTCSPQPEYVNQPDVRPQPPSPREGPLPAARPAGATLERP KTLSPGKNGVVKDVFAFGGAVENPEYLTPQGGAAPQPHPPPAFSP AFDNLYYWDQDPPERGAPPSTFKGTPTAENPEYLGLDVPV | 104 | P04626 |
| KRAS | MTEYKLVVVGAGGVGKSALTIQLIQNHFVDEYDPTIEDSYRKQVV IDGETCLLDILDTAGQEEYSAMRDQYMRTGEGFLCVFAINNTKSF EDIHHYREQIKRVKDSEDVPMVLVGNKCDLPSRTVDTKQAQDLAR SYGIPFIETSAKTRQRVEDAFYTLVREIRQYRLKKISKEEKTPGC VKIKKCIIM | 105 | P01116 |
| PIK3CA | MPPRPSSGELWGIHLMPPRILVECLLPNGMIVTLECLREATLITI KHELFKEARKYPLHQLLQDESSYIFVSVTQEAEREEFFDETRRLC DLRLFQPFLKVIEPVGNREEKILNREIGFAIGMPVCEFDMVKDPE VQDFRRNILNVCKEAVDLRDLNSPHSRAMYVYPPNVESSPELPKH IYNKLDKGQIIVVIWVIVSPNNDKQKYTLKINHDCVPEQVIAEAI RKKTRSMLLSSEQLKLCVLEYQGKYILKVCGCDEYFLEKYPLSQY KYIRSCIMLGRMPNLMLMAKESLYSQLPMDCFTMPSYSRRISTAT PYMNGETSTKSLWVINSALRIKILCATYVNVN1RDIDKIYVRTGI YHGGEPLCDNVNTQRVPCSNPRWNEWLNYDIYIPDLPRAARLCLS ICSVKGRKGAKEEHCPLAWGNINLFDYTDTLVSGKMALNLWPVPH GLEDLLNPIGVTGSNPNKETPCLELEFDWFSSVVKFPDMSVIEEH ANWSVSREAGFSYSHAGLSNRLARDNELRENDKEQLKAISTRDPL SEITEQEKDFLWSHRHYCVTIPEILPKLLLSVKWNSRDEVAQMYC LVKDWPPIKPEQAMELLDCNYPDPMVRGFAVRCLEKYLTDDKLSQ YLIQLVQVLKYEQYLDNLLVRFLLKKALTNQRIGHFFFWHLKSEM ENKTVSQRFGLLLESYCRACGMYLKHLNRQVEAMEKLINLTDILK QEKKDETQKVQMKFLVEQMRRPDFMDALQGFLSPLNPAHQLGNLR LEECRIMSSAKRPLWLNWENPDIMSELLFQNNEI1FKNGDDLRQD MLTLQIIRIMENIWQNQGLDRMLPYGCLSIGDCVGLIEVVRNSH TIMQICKGGLKGALQFNSHTLHQWLKDKNKGEIYDAAIDLFTRS CAGYCVATFILGIGDRHNSNIMVKDDGQLFHIDFGHFLDHKKKKF GYKRERVPFVLTQDFLIVISKGAQECTKTREFERFQEMCYKAYLA IRQHANLFINLFSMMLGSGMPELQSFDDIAYIRKTLALDKTEQEA LEYFMKQMNDAHHGGWTTKMDWIFHTIKQHALN | 106 | P42336 |
| PTEN | MTAIIKEIVSRNKRRYQEDGFDLDLTYIYPNIIAMGFPAERLEGV YRNNIDDVVRFLDSKHKNHYKIYNLCAERHYDTAKFNCRVAQYPF EDHNPPQLELIKPFCEDLDQWLSEDDNHVAAIHCKAGKGRTGVMI CAYLLHRGKFLKAQEALDFYGEVRTRDKKGVTIPSQRRYVYYYSY LLKNHLDYRPVALLFHKMMFETIPMFSGGTCNPQFVVCQLKVKIY SSNSGPTRREDKFMYFEFPQPLPVCGDIKVEFFHKQNKMLKKDKM FHFWVNTFFIPGPEETSEKVENGSLCDQEIDSICSIERADNDKEY LVLTLTKNDLDKANKDKANRYFSPNFKVKLYFTKTVEEPSNPEAS SSTSVTPDVSDNEPDHYRYSDTTDSDPENEPFDEDQHTQITKV | 107 | P60484 |
| SF3B1 | MAKIAKTHEDIEAQIREIQGKKAALDEAQGVLDSTGYYDQEIYG GSDSRFAGYVTSIAATELEDDDDDYSSSTSLLGQKKPGYHAPVAL LNDIPQSTEQYDPFAEHRPPKIADREDEYKKHRRTMIISPERLDP FADGGKTPDPKMNARTYMDVMREQHLTKEEREIRQQLAEKAKAGE | 108 | O75333 |

TABLE 2-continued

| Gene | Amino Acid Sequence | SEQ ID NO | Protein Database No. |
|------|---------------------|-----------|----------------------|
| | LKVVNGAAASQPPSKRKRRWDQTADQTPGATPKKLSSWDQAETPG<br>HTPSLRWDETPGRAKGSETPGATPGSKIWDPTPSHTPAGAATPGR<br>GDTPGHATPGHGGATSSARKNRWDETPKTERDTPGHGSGWAETPR<br>TDRGGDSIGETPTPGASKRKSRWDETPASQMGGSTPVLTPGKTPI<br>GTPAMNMATPTPGHIMSMTPEQLQAWRWEREIDERNRPLSDEELD<br>AMFPEGYKVLPPPAGYVPIRTPARKLTATPTPLGGMTGFHMQTED<br>RTMKSVNDQPSGNLPFLKPDDIQYFDKLLVDVDESTLSPEEQKER<br>KIMKLLLKINGTPPMRKAALRQITDKAREFGAGPLFNQILPLLM<br>SPTLEDQERHLLVKVIDRILYKLDDLVRPYVHKILVVIEPLLIDE<br>DYYARVEGREIISNLAKAAGLATMISTMRPDIDNMDEYVRNTTAR<br>AFAVVASALGIPSLLPFLKAVCKSKKSWQARHTGIKIVQQIAILM<br>GCAILPHLRSLVEIIEHGLVDEQQKVRTISALAIAALAEAATPYG<br>IESFDSVLKPLWKGIRQHRGKGLAAFLKAIGYLIPLMDAEYANYY<br>TREVMLILIREFQSPDEEMKKIVLKVVKQCCGTDGVEANYIKTEI<br>LPPFFKHFWQHRMALDRRNYRQLVDTTVELANKVGAAEIISRIVD<br>DLKDEAEQYRKMVMETIEKIMGNLGAADIDHKLEEQLIDGILYAF<br>QEQTTEDSVMLNGFGTVVNALGKRVKPYLPQICGTVLWRLNNKSA<br>KVRQQAADLISRTAVVMKTCQEEKLMGHLGVVLYEYLGEEYPEVL<br>GSILGALKAIVNVIGMHKMTPPIKDLLPRLTPILKNRHEKVQENC<br>IDLVGRIADRGAEYVSAREWMRICFELLELLKAHKKAIRRATVNT<br>FGYIAKAIGPHDVLATLLNNLKVQERQNRVCTTVAIAIVAETCSP<br>FTVLPALMNEYRVPELNVQNGVLKSLSFLFEYIGEMGKDYIYAVT<br>PLLEDALMDRDLVHRQTASAVVQHMSLGVYGFGCEDSLNHLLNYV<br>WPNVFETSPHVIQAVMGALEGLRVAIGPCRMLQYCLQGLFHPARK<br>VRDVYWKIYNSIYIGSQDALIAHYPRIYNDDKNTYIRYELDYIL | | |
| SOX17 | MSSPDAGYASDDQSQTQSALPAVMAGLGPCPWAESLSPIGDMKVK<br>GEAPANSGAPAGAAGRAKGESRIRRPMNAFMVWAKDERKRLAQQN<br>PDLHNAELSKMLGKSWKALTLAEKRPFVEEAERLRVQHMQDHPNY<br>KYRPRRRKQVKRLKRVEGGFLHGLAEPQAAALGPEGGRVAMDGLG<br>LQFPEQGFPAGPPLLPPHMGGHYRDCQSLGAPPLDGYPLPTPDTS<br>PLDGVDPDPAFFAAPMPGDCPAAGTYSYAQVSDYAGPPEPPAGPM<br>HPRLGPEPAGPSIPGLLAPPSALHVYYGAMGSPGAGGGRGFQMQP<br>QHQHQHQHQHPPGPGQPSPPPEALPCRDGTDPSQPAELLGEVDR<br>TEFEQYLHFVCKPEMGLPYQGHDSGVNLPDSHGAISSVVSDASSA<br>VYYCNYPDV | 109 | Q9H6I2 |
| TP53 | MEEPQSDPSVEPPLSQETFSDLWKLLPENNVLSPLPSQAMDDLML<br>SPDDIEQWFTEDPGPDEAPRMPEAAPPVAPAPAAPTPAAPAPAPS<br>WPLSSSVPSQKTYQGSYGFRLGFLHSGTAKSVTCTYSPALNKMFC<br>QLAKTCPVQLWVDSTPPPGTRVRAMAIYKQSQHMTEVVRRCPHHE<br>RCSDSDGLAPPQHLIRVEGNLRVEYLDDRNTFRHSVVVPYEPPEV<br>GSDCTTIHYNYMCNSSCMGGMNRRPILTIITLEDSSGNLLGRNSF<br>EVRVCACPGRDRRTEEENLRKKGEPHHELPPGSTKRALPNNTSSS<br>PQPKKKPLDGEYFTLQIRGRERFEMFRELNEALELKDAQAGKEPG<br>GSRAHSSHLKSKKGQSTSRHKKLMFKTEGPDSD | 110 | P04637 |
| CMV | MESRGRRCPEMISVLGPISGHVLKAVFSRGDTPVLPHETRLLQTG<br>IHVRVSQPSLILVSQYTPDSTPCHRGDNQLQVQHTYFTGSEVENV<br>SVNVHNPTGRSICPSQEPMSIYVYALPLKMLNIPSINVHHYPSAA<br>ERKHRHLPVADAVIHASGKQMWQARLTVSGLAWTRQQNQWKEPDV<br>YYTSAFVFPTKDVALRHVVCAHELVCSMENTRATKMQVIGDQYVK<br>VYLESFCEDVPSGKLFMHVTLGSDVEEDLTMTRNPQPFMRPHERN<br>GFTVLCPKNMIIKPGKISHIMLDVAFTSHEHFGLLCPKSIPGLSI<br>SGNLLMNGQQIFLEVQAIRETVELRQYDPVAALFFFDIDLLLQRG<br>PQYSEHPTFTSQYRIQGKLEYRHTWDRHDEGAAQGDDDVWTSGSD<br>SDEELVTTERKTPRVTGGGAMAGASTSAGRKRKSASSATACTSGV<br>MTRGRLKAESTVAPEEDTDEDSDNEIHNPAVFTWPPWQAGILARN<br>LVPMVATVQGQNLKYQEFFWDANDIYRIFAELEGVWQPAAQPKRR<br>RHRQDALPGPCIASTPKKHRG | 111 | P06725 |

Example 2. Screen for Best Binders to HLA-A*02:01

The 9- or 10-mer peptides from Table 1 were synthesized and MHC binding assays were performed to experimentally evaluate their binding to HLA-A*02:01 as follows.

UV-Mediated Peptide Exchange Overview

HLA-bound peptides are critical for the stability of the HLA complex. A conditional HLA class I complex is stabilized by an UV-labile peptide (p*). Through UV irradiation this peptide can be cleaved in the HLA-bound state. Because the obtained peptide fragments no longer meet the strict length requirement for high-affinity HLA class I binding, these fragments dissociate from the HLA class I complex and the complex disintegrates. Under the conditions in which peptide cleavage is performed (neutral pH, on melting ice), the resulting peptide-free HLA complex is stable, and when cleavage is performed in the presence of another HLA class I peptide, this reaction results in net exchange of the cleaved peptide, yielding an HLA class I complex with an epitope of choice. The peptide exchange efficiency can be analyzed using an HLA class I ELISA. The combined technologies allow the identification of ligands for an HLA molecule of interest which are potentially immunogenic.

Exchange control peptide Pos is a high affinity binder to the relevant HLA class I allele while exchange control peptide Neg is a non-binder. The UV control represents UV-irradiation of conditional HLA class I complex in the absence of a rescue peptide. The binding of exchange control peptide Neg and all experimental peptides were evaluated relative to that of exchange control peptide Pos. The absorption of the latter peptide is put to 100%. This procedure results in a range of different percentages depending on the affinities of the different experimental peptides for the HLA allele that is used. An arbitrary cut off value was chosen as a positive cut off for binders.

Assay Procedure

All reagents were brought to 0° C. by putting them on melting ice. The concentrated p*HLA*02:01 (1.5 mg/mL) class I solution was kept in the dark to ensure stability. All vials were centrifuged at 3000 g for 1 minute before use.

Preparation of the peptides of choice: 459 µL sterile phosphate buffered saline pH 7.4 (PBS) and 5 µL of peptide (10 mg/mL) were pipetted in 1.4 mL Micronic tubes (Micronic #MP32022). Then, using a multichannel pipetting device, 10 µL of diluted peptide was added to a 384-well PP microtiter plate.

P*HLA class I solution: The concentrated p*HLA*02:01 (1.5 mg/mL) class I solution was diluted in an amber safe lock tube to 50 µg/mL in PBS and kept on melting ice in the dark.

Preparation of change controls: A stock solution of change control positive (abbreviated "pos") for p*HLA*02:01 (NLVPMVATV) (SEQ ID NO: 97) was prepared at 10 mg/mL in 100% dimethyl sulfoxide (DMSO). A stock solution of change control negative (abbreviated "neg") for p*HLA*02:01 (IVTDFSVIK) (SEQ ID NO: 101) was prepared at 10 mg/mL in 100% DMSO. The positive and negative stock solutions were diluted to 100 µM using 5 µL peptide and 495 µL PBS. Three tubes were labeled for each mixture: 'Pos,' 'Neg,' and 'UV.' The following reagents were added per tube:

TABLE 3

| Reagent | Pos | Neg | UV |
| --- | --- | --- | --- |
| PBS | — | — | 12.5 µL |
| Change control Pos (100 µM) | 12.5 µL | — | — |
| Change control Neg (100 µM) | — | 12.5 µL | — |
| Diluted p*HLA class I solution | 12.5 µL | 12.5 µL | 12.5 µL |

20 µL of the controls were mixed and transferred to the 384-well plate.

UV-induced peptide exchange: 10 µL of the diluted p*HLA class I solution was pipetted into the 384-well PP microtiter plate using a multichannel pipetting device into each well, and the solution was mixed thoroughly using the multichannel pipetting device. The plate was sealed and centrifuged at 3300 g for 2 minutes at 4° C. The seal was removed, and the plate was placed on ice and under the ultraviolet (UV) lamp for 30 minutes with the UV lamp at a distance of 2-5 cm from the sample. The plate was sealed and incubated for 30 minutes at 37° C. The plate was centrifuged at 3300 g for 5 minutes at 4° C. Two UV-induced peptide exchanges were performed ("exchange I" and "exchange II").

Screening: The outcome of the UV-mediated HLA peptide exchange was evaluated by HLA class I ELISA.

Enzyme Immunoassay for the Determination of the Presence of Intact HLA Class I Complexes Overview The HLA class I ELISA is an enzyme immunoassay based on the detection of beta2-microglobulin (B2M) of (peptide-stabilized) HLA class I complexes. To this end streptavidin is bound onto polystyrene microtiter wells. After washing and blocking, HLA complex present in exchange reaction mixtures or ELISA controls is captured by the streptavidin on the microtiter plate via its biotinylated heavy chain. Non-bound material is removed by washing. Subsequently, horseradish peroxidase (HRP)-conjugated antibody to human B2M is added. This antibody binds only to an intact HLA complex present in the microtiter well because unsuccessful peptide exchange results in disintegration of the original UV-sensitive HLA complex upon UV illumination. In the latter case B2M is removed during the washing step. After removal of non-bound HRP conjugate by washing, a substrate solution is added to the wells. A colored product is formed in proportion to the amount of intact HLA complex present in the samples. After the reaction has been terminated by the addition of a stop solution, absorbance is measured in a microtiter plate reader. The absorbance is normalized to the absorbance of an exchange control peptide (represents 100%). Also, suboptimal HLA binding of peptides with a moderate to low affinity for HLA class I molecules can be detected by this ELISA technique Assay Procedure Before use, all reagents were brought to room temperature (18-25° C.) with the exception of anti-human beta2-microglobulin-HRP conjugate and a screen control (2.7 µM HLA complex), which were kept on melting ice to ensure stability. All vials were centrifuged before use (1 minute 3000 g).

Coating wells of two NUNC MaxiSorp™ 96-well ELISA plates: only the contents of one coating buffer capsule were dissolved in 100 mL of distilled water (0.05 M carbonate-bicarbonate buffer, pH 9.6 at 25° C.). 46 µL of Streptavidin stock solution were added to 23 mL coating buffer. 100 µL of the Streptavidin stock solution were added to all wells. Each microtiter plate was covered with an adhesive seal and incubated overnight at room temperature (18-25° C.).

Dilution buffer (Sanquin): The exchange reaction mixtures and controls were diluted in working-strength Dilution buffer.

Washing procedure (Sanquin): Fresh Washing buffer was prepared. Supernatants were discarded from wells and the wells were filled with Washing buffer (300 µL per well) and tipped out. This was repeated three times.

Blocking procedure: 300 µL of working-strength Dilution buffer was added to all wells. The microtiter plate(s) were covered with adhesive seal or lid and incubated for 30 minutes at room temperature (18-25° C.).

Preparation of ELISA HLA controls: From the Screen control three HLA controls were generated by serial dilution in Dilution buffer. The controls were prepared fresh and kept on melting ice until usage. Specifically, 4 tubes were labeled, one tube for each dilution: '1:500', 'H', 'M' and 'L'. 1.5 mL of working-strength Dilution buffer was pipetted into the tube '1:500' and 500 µL into the other tubes. 3 µL of the Screen control was transferred into the first tube labeled '1:500', mixed well, and 500 µL of this dilution was transferred into the second tube labeled 'H'. The serial dilution was repeated twice by adding 500 µL of the previous tube of diluted control to the 500 µL of working-strength Dilution buffer.

Dilution of exchange reaction mixtures: To evaluate the outcome of UV-mediated HLA peptide exchange, a small aliquot of the exchange reaction mixture was diluted in working-strength Dilution buffer (the proper dilution factor was p*HLA lot-dependent). The exchange reaction mixture was diluted in working-strength Dilution buffer.

Incubation step (controls and exchange reaction mixtures): Dilution buffer was tipped out from the wells. 100 μL of working-strength Dilution buffer was pipetted into the blank wells and 100 μL of the HLA controls was pipetted into in the appropriate wells. 100 μL of the prepared exchange reaction mixture dilutions was transferred into the appropriate wells. The plates were covered with adhesive seal and incubated for 1 hour at 37° C.

Wash step: supernatant was discarded from the wells and the microtiter plates were washed as described in 'Washing procedure' above.

Incubation step (HRP-conjugated antibody): Per microtiter plate, 11 μL of concentrated HRP-conjugated antibody was added to 11 mL of working-strength Dilution buffer just before use. 100 μL of diluted HRP-conjugated antibody was added to all wells. The plates were covered with adhesive seal and incubate for 1 hour at 37° C.

Wash step: The supernatant was discarded from the wells and the microtiter plates were washed as described in 'Washing procedure' above.

Incubation step (enzymatic color development): Approximately 10 minutes before use, the substrate solution was prepared as follows per microtiter plate: 9.57 mL of distilled water; 1.1 mL of Substrate buffer stock solution; 220 μL of ABTS stock solution; and 110 μL of Hydrogen peroxide stock solution.

The substrate solution was at room temperature (18-25° C.). 100 μL of substrate solution was added to all wells and the wells were incubated for 8 minutes at room temperature (18-25° C.) in the dark on a plate shaker at 400-500 rpm.

Stop enzymatic reaction: 50 μL of Stop buffer (Sanquin) was added to all wells.

Plate read-out: plates were read at 414 nm in an ELISA reader within 30 minutes.

Results

The results from the two UV-mediated HLA peptide exchanges (abbreviated 'Exch I' and 'Exch II') are provided in Table 4. "SD" stands for standard deviation.

TABLE 4

| SEQ ID NO | Sequence | Exch I (%) | Exch II (%) | Average % | SD |
|---|---|---|---|---|---|
| Pos (97) | NLVPMVATV | 100.0 | 100.0 | 100.0 | 0.0000 |
| Neg (101) | IVTDFSVIK | 7.0 | 6.9 | 6.9 | 0.0081 |
| UV | No peptide | 7.9 | 7.6 | 7.8 | 0.2293 |
| 1 | MIFSKRHWA | 6.2 | 6.1 | 6.2 | 0.0842 |
| 2 | YLDCGIHSG | 34.8 | 33.0 | 33.9 | 1.2804 |
| 3 | YLDSGIHFG | 53.7 | 53.2 | 53.4 | 0.4031 |
| 5 | LVVVGAAGV | 6.6 | 6.2 | 6.4 | 0.2337 |
| 6 | LVVVGACGV | 6.5 | 7.5 | 7.0 | 0.7515 |
| 7 | LVVVGAVGV | 4.3 | 4.6 | 4.5 | 0.2227 |
| 8 | GLKDLLNPI | 73.8 | 84.9 | 79.4 | 7.7994 |
| 9 | ILNREIDFA | 53.1 | 47.8 | 50.4 | 3.7270 |
| 10 | CYVYYYSYL | 38.2 | 38.5 | 38.4 | 0.2562 |
| 11 | NMDEYVHNT | 9.2 | 7.3 | 8.3 | 1.3162 |
| 12 | VVSDAISAV | 88.5 | 83.8 | 86.2 | 3.2840 |
| 13 | KTYPVQLWV | 66.6 | 71.2 | 68.9 | 3.2688 |
| 14 | GLAPPQLLI | 9.2 | 7.2 | 8.2 | 1.4007 |
| 15 | GLAPPQYLI | 13.5 | 13.1 | 13.3 | 0.2875 |
| 16 | ALNNMFCQL | 39.6 | 43.1 | 41.3 | 2.4847 |
| 18 | QLWVDSTPL | 84.3 | 88.1 | 86.2 | 2.6915 |
| 20 | YQGSYGFLL | 14.3 | 9.6 | 11.9 | 3.3633 |
| 21 | SVTCTYFPA | 7.7 | 9.4 | 8.6 | 1.1462 |
| 22 | LLGRNSFEM | 58.8 | 42.9 | 50.9 | 11.2708 |
| 23 | VVPCEPPEV | 29.4 | 37.5 | 33.5 | 5.7534 |
| 24 | RLIHRDLAA | 6.8 | 7.7 | 7.2 | 0.6221 |
| 25 | MMFSKRHWI | 40.4 | 45.3 | 42.8 | 3.4162 |
| 26 | MLFSKRHWV | 74.8 | 73.8 | 74.3 | 0.6809 |
| 27 | MMFSKRHWV | 76.2 | 72.6 | 74.4 | 2.5217 |
| 28 | YMDCGIHSL | 107.9 | 103.3 | 105.6 | 3.2934 |
| 29 | YLDCGIHSV | 100.4 | 103.5 | 101.9 | 2.2217 |
| 30 | YMDCGIHSV | 100.8 | 115.1 | 108.0 | 10.0855 |
| 31 | YMDSGIHFI | 97.6 | 115.8 | 106.7 | 12.8512 |
| 32 | YLDSGIHFV | 99.3 | 108.7 | 104.0 | 6.6311 |
| 33 | YMDSGIHFV | 104.1 | 95.5 | 99.8 | 6.0739 |
| 37 | LLVVGAAGV | 34.1 | 32.5 | 33.3 | 1.1431 |
| 38 | LMVVGAAGV | 51.0 | 51.5 | 51.3 | 0.3763 |
| 39 | LLVVGACGV | 36.4 | 33.1 | 34.8 | 2.3173 |
| 40 | LMVVGACGV | 47.1 | 50.4 | 48.7 | 2.3509 |
| 41 | LLVVGAVGV | 31.8 | 40.1 | 35.9 | 5.8591 |
| 42 | LMVVGAVGV | 39.0 | 33.3 | 36.1 | 4.0013 |
| 43 | GLKDLLNPV | 73.5 | 76.3 | 74.9 | 1.9449 |
| 44 | GMKDLLNPV | 74.7 | 80.4 | 77.5 | 4.0472 |
| 45 | ILNREIDFV | 62.1 | 78.7 | 70.4 | 11.7708 |
| 46 | IMNREIDFV | 68.6 | 64.9 | 66.7 | 2.5838 |
| 47 | ILNREIDFL | 51.1 | 61.3 | 56.2 | 7.1945 |
| 48 | CYLYYYSYL | 16.1 | 20.6 | 18.3 | 3.1585 |
| 49 | CYLYYYSYLV | 10.4 | 10.9 | 10.7 | 0.3435 |

TABLE 4-continued

| SEQ ID NO | Sequence | Exch I (%) | Exch II (%) | Average % | SD |
|---|---|---|---|---|---|
| 51 | NMDEYVHNV | 86.6 | 80.6 | 83.6 | 4.2367 |
| 52 | NLDEYVHNV | 88.1 | 88.4 | 88.2 | 0.1818 |
| 53 | NMDEYVHNL | 62.0 | 54.3 | 58.1 | 5.4566 |
| 54 | VLSDAISAV | 89.3 | 90.9 | 90.1 | 1.1771 |
| 55 | VMSDAISAV | 96.9 | 87.9 | 92.4 | 6.3778 |
| 56 | VLSDAISAL | 91.9 | 82.6 | 87.3 | 6.5884 |
| 57 | KLYPVQLWV | 84.1 | 79.8 | 81.9 | 3.0527 |
| 58 | KMYPVQLWV | 72.7 | 81.0 | 76.9 | 5.8253 |
| 59 | KMYPVQLWL | 122.1 | 102.8 | 112.5 | 13.6215 |
| 60 | GLAPPQLLV | 40.3 | 44.1 | 42.2 | 2.6661 |
| 61 | GMAPPQLLV | 13.9 | 13.9 | 13.9 | 0.0076 |
| 62 | GLAPPQYLV | 48.8 | 47.6 | 48.2 | 0.8672 |
| 63 | GMAPPQYLV | 22.5 | 20.3 | 21.4 | 1.5723 |
| 64 | ALNNMFCQV | 69.7 | 68.8 | 69.3 | 0.6662 |
| 66 | AMNNMFCQV | 69.4 | 70.8 | 70.1 | 1.0420 |
| 67 | QLWVDSTPI | 62.0 | 73.8 | 67.9 | 8.3729 |
| 68 | QLWVDSTPV | 95.6 | 95.7 | 95.7 | 0.0913 |
| 70 | YQGSYGFLI | 7.1 | 10.8 | 8.9 | 2.6418 |
| 71 | YQGSYGFLV | 53.6 | 45.6 | 49.6 | 5.6164 |
| 72 | SMTCTYFPL | 56.4 | 50.6 | 53.5 | 4.0810 |
| 73 | SLTCTYFPV | 93.7 | 97.2 | 95.5 | 2.4364 |
| 74 | SMTCTYFPV | 83.4 | 93.3 | 88.4 | 7.0148 |
| 75 | LLGRNSFEL | 101.2 | 95.7 | 98.4 | 3.9238 |
| 76 | LLGRNSFEI | 75.3 | 58.0 | 66.7 | 12.2339 |
| 78 | VLPCEPPEV | 66.3 | 73.7 | 70.0 | 5.1976 |
| 79 | VMPCEPPEV | 62.9 | 58.9 | 60.9 | 2.8611 |
| 80 | YLDCGIHSL | 102.8 | 110.9 | 106.8 | 5.7387 |
| 81 | YMDSGIHFL | 101.5 | 107.8 | 104.7 | 4.4311 |
| 84 | RMIHRDLAL | 51.5 | 55.8 | 53.7 | 3.0145 |
| 85 | RLIHRDLAV | 69.9 | 77.3 | 73.6 | 5.2146 |
| 86 | RMIHRDLAV | 56.7 | 58.5 | 57.6 | 1.2275 |
| 87 | CYMYYYSYLL | 8.3 | 8.7 | 8.5 | 0.2510 |
| 88 | CYLYYYSYLI | 27.8 | 18.9 | 23.3 | 6.3290 |
| 89 | CYMYYYSYLI | 4.9 | 4.8 | 4.9 | 0.0760 |
| 90 | NLDEYVHNL | 57.2 | 53.0 | 55.1 | 2.9456 |
| 91 | NMDEYVHNI | 73.6 | 63.1 | 68.4 | 7.4102 |
| 92 | NLDEYVHNI | 71.1 | 69.0 | 70.1 | 1.4997 |
| 93 | VMSDAISAL | 75.3 | 79.5 | 77.4 | 2.9691 |
| 94 | KLYPVQLWI | 81.3 | 66.4 | 73.9 | 10.5149 |
| 95 | SLTCTYFPL | 69.9 | 71.6 | 70.8 | 1.2464 |
| 96 | SMTCTYFPI | 32.2 | 22.7 | 27.5 | 6.7081 |
| 97 | NLVPMVATV | 99.4 | 89.1 | 94.3 | 7.2778 |
| 98 | NMVPMVATV | 77.6 | 66.2 | 71.9 | 8.0381 |
| 99 | NLVPMVATL | 26.8 | 20.4 | 23.6 | 4.5505 |
| 100 | NMVPMVATL | 26.4 | 22.0 | 24.2 | 3.0889 |

CONCLUSIONS

Peptides having SEQ ID NOs: 28-32, 59, 80, and 81 showed binding of more than 100% as compared to the positive peptide control (average relative binding to HLA-A*02:01 in the range of 102-113%). Peptides having SEQ ID NOs: 33, 54, 55, 68, 73, 75, and 97 showed an average binding in the range of 90-100%. The average binding of peptides having SEQ ID NOs: 12, 18, 51, 52, 56, 57, and 74 was in the range of 80-88%. Peptides having SEQ ID NOs: 8, 26, 27, 43-45, 58, 66, 78, 85, 92-95, and 98 demonstrated an average binding in the range of 70-79%. The average binding of peptides having SEQ ID NOs: 13, 46, 64, 67, 76, 79, and 91 was in the range of 61-69%. Peptides having SEQ ID NOs: 3, 9, 22, 38, 47, 53, 71, 72, 84, 86, and 90 demonstrated an average relative binding to HLAA*02:01 in the range of 50-58%. Peptides having SEQ ID NOs: 16, 25, 40, 60, and 62 showed an average binding in the range of 41-49%. The average binding of peptides having SEQ ID NOs: 2, 10, 23, 37, 39, 41, and 42 was in the range of 33-38%. Peptides having SEQ ID NOs: 48, 63, 88, 96, 99, and 100 showed an average binding in the range of 18-28%. The average binding of all other peptides was found to be below 15%.

The experimental values of binding were used to prioritize 8 mutant-mimic pairs for further experimental validation (Table 5) based on two criteria—i) the mutant epitopes have moderate binding to HLA-A*0201 (>10% in comparison to CMV pp65 antigen) and ii) the ratio of mimic binding to mutant binding was as high as possible (a ratio of >1).

TABLE 5

| Mutant | SEQ ID NO | Mutation | No. patients out of 9176 patients[1] | Mutant Binding | Mimic | SEQ ID NO | Mimic Binding |
|---|---|---|---|---|---|---|---|
| YLDCGIHSG | 2 | CTNNB1.S33C | 13 | 34.8 | YLDCGIHSV | 29 | 101.9 |
| YLDSGIHFG | 3 | CTNNB1.S37F | 21 | 53.7 | YLDSGIHFV | 32 | 104.0 |
| ILNREIDFA | 9 | PIK3CA.G118D | 19 | 50.4 | ILNREIDFV | 45 | 70.4 |
| KTYPVQLWV | 13 | TP53.C141Y | 14 | 68.9 | KMYPVQLWL | 59 | 112.5 |
| ALNNMFCQL | 16 | TP53.K132N | 19 | 41.3 | ALNNMFCQV | 64 | 69.3 |
| QLWVDSTPL | 18 | TP53.P152L | 10 | 86.2 | QLWVDSTPV | 68 | 95.7 |
| LLGRNSFEM | 22 | TP53.V272M | 19 | 50.9 | LLGRNSFEL | 75 | 98.4 |
| VVPCEPPEV | 23 | TP53.Y220C | 62 | 33.5 | VLPCEPPEV | 78 | 70.0 |

[1]Marty R, et al. Cell. 2017;171(6):1272-1283

Example 3: TCRs that Recognize Mutant Peptides are Cross-Reactive to Mimic Peptides Determination of Frequency of Double Positive T Cells for Mimic and Mutant Tetramers from HLA-02:01+Primary Peripheral Blood Mononuclear Cells (PBMCs)

Protocol

Preparation of PBMCs: Vials of HLA-02:01+ PBMCs frozen from donors (Hemacare) were removed from $LN_2$ storage and rapidly thawed in a 37° C. water bath. The cells were transferred to a 50 mL conical tube containing 40 mL warm media (RPMI 1640 medium+10% fetal bovine serum (FBS)+1% Penicillin streptomycin solution), spun at 1300 rpm for 5 minutes at room temperature. The cell pellet was resuspended in 2 mL EASYSEP™ buffer and cells were counted using trypan blue live dead marker using a haemocytometer.

Enrichment of CD8+ T cells: To enrich the CD8+ T cells from the PBMCs, EASYSEP™ Human CD8+ T Cell Isolation Kit was used as per the manufacturer's instructions. Post enrichment, the cell pellet was resuspended in Dulbecco's phosphate-buffered saline (DPBS) and cells were counted as above. To determine the viability, LIVE/DEAD™ Fixable Violet Dead Cell Stain Kit was used at 0.5 µL/1×10⁶/100 µL cell suspension and incubated at room temperature for 20 minutes. At the end of incubation period, FACS buffer (DPBS+2% FBS) was added and the cells were spun at 1300 rpm for 5 minutes at room temperature. The cell pellet was resuspended in FACS buffer, trypan blue was added, and the cell count was determined using a haemocytometer. The cell density was maintained at 1×10⁶/50 µL FACS buffer. 3 µL Fc block was added per 1×10⁶ cells and incubated for 10 minutes at room temperature in the dark. At the end of the incubation, mimic tetramer and the corresponding mutant tetramers were added at 3 µL tetramer/1×10⁶ cells. The sequences of the peptides used for tetramer synthesis is provided in Table 6.

TABLE 6

| Mutated peptide sequence | SEQ ID NO mutant sequence | Tetramer Conjugate for mutant sequence | Mimic peptide sequence | SEQ ID NO mimic seq. | Tetramer Conjugate for mimic seq. |
|---|---|---|---|---|---|
| ILNREIDFA | 9 | PE | ILNREIDFV | 45 | APC |
| KTYPVQLWV | 13 | APC | KMYPVQLWL | 59 | PE |
| QLWVDSTPL | 18 | APC | QLWVDSTPV | 68 | PE |
| YLDCGIHSG | 2 | APC | YLDCGIHSV | 29 | PE |
| YLDSGIHFG | 3 | APC | YLDSGIHFV | 32 | PE |
| ALNNMFCQL | 16 | PE | ALNNMFCQV | 64 | APC |
| LLGRNSFEM | 22 | PE | LLGRNSFEL | 75 | APC |
| VVPCEPPEV | 23 | PE | VLPCEPPEV | 78 | APC |

For frequency determination, 2×10⁶ cells were used for test samples and 1×10⁶ cells were used for control samples where negative tetramers were added in place of the mimic or mutant tetramers. A sample where no tetramers were added was kept as unstained control. The samples were incubated at room temperature for 30 minutes in dark. At the end of incubation period, CD8 antibody was added at 2 µL/1×10⁶ cells and the samples were incubated for another 30 minutes at room temperature in dark. At the end of incubation, FACS buffer was added to the samples and the samples were spun at 1300 rpm for 5 minutes. The pellet was resuspended in 5 mL FACS buffer and the cells were spun at 1300 rpm for 5 minutes. The pellet was resuspended in 200 µL FACS buffer and events were acquired using the Novocyte flow cytometer.

Gating Strategy and Data Analysis

The cells were acquired on the Novocyte flow cytometer and gated on forward scatter height (FSC-H) versus side scatter height (SSC-H). The cells high on FSC-H versus SSC-H were gated as lymphocytes. From the lymphocytes, live cells were gated by selecting the pacific blue negative cells on an FSC-H versus Pacific Blue-H plot. From the live cells, single cells were gated on FSC-H versus forward scatter area (FSC-A). CD8+ T cells were gated from the singlets as Alexa Fluor 700 positive cells. For gating phycoerythrin (PE) conjugated tetramer positive cells, the CD8+ cells were gated on Alexa Fluor 700-H versus PE-H and the double positive cells were considered as CD8+ tetramer+. For gating allophycocyanin (APC) conjugated tetramer positive cells, the CD8+ cells were gated on Alexa Fluor 700-H versus APC-H and the double positive cells were considered as CD8+tetramer+. All gates were set using the negative tetramers to eliminate non-specific binding. The dual positive cells that were mimic and mutant tetramer positive cells were gated by plotting PE-H versus APC-H within the CD8+ cells. The percentage of double positive cells for APC and PE is the frequency of mimic and mutant positive tetramer cells displayed in the gate.

Sorting of Double Positive Cells for Mimic and Mutant Tetramers Specific to Peptide Sequences from HLA-02:01+ PBMCs Protocol PBMCs were prepared and CD8+ T cells were enriched following the protocol described above. At the end of the 10 minute room temperature incubation in 3 µL Fc block, mimic tetramer and the corresponding mutant tetramers were added.

For sorting, a minimum of 5×10$^6$ cells were used for test samples. 1×10$^6$ cells were used for control samples where negative tetramers were added in place of the mimic or mutant tetramers and a sample where no tetramers were added was kept as unstained control. 3 µL tetramer/1×10$^6$cells were added and the samples were incubated at room temperature for 30 minutes in dark. At the end of incubation period, CD8 antibody was added at 2 µL/1×10$^6$ cells and the samples were incubated for another 30 minutes at room temperature in dark. At the end of incubation, FACS buffer was added to the samples and the samples were spun at 1300 rpm for 5 minutes. The pellet was resuspended in 5 mL FACS buffer and the cells were spun at 1300 rpm for 5 minutes. The pellet was resuspended at a density of 3×10$^6$/1 mL FACS buffer for the sorting.

Gating Strategy and Data Analysis

The cells were acquired on the BD FACS ARIA III flow cytometer and gated on FSC-A versus side scatter area (SSC-A). The cells high on FSC-A versus SSC-A were gated as lymphocytes. From the lymphocytes, single cells were gated on FSC-W versus FSC-H. Live cells were gated as brilliant violet 421 area (BV421-A) negative cells on the SSC-A versus BV421-A plot. The live cells were gated on SSC-A versus allophycocyanin-cyanine 7 area (APC-Cy7-A) and the positive cells on APC-Cy7 channel were marked as CD8+ cells. The dual mimic and mutant tetramer positive cells were gated by plotting PE-A versus APC-A within the CD8+ cells. The percentage of double positive cells for APC and PE is the frequency of mimic and mutant positive tetramer cells displayed in the gate. All gates were set using unstained samples and negative tetramers to eliminate non-specific binding. Mimic and mutant tetramers specific double positive were sorted into single cell/well in a 96 well plate containing cell lysis buffer for m-RNA preparation for NGS.

A summary of the CD8+ T cells (Table 7 and Table 8) positive for mimic and mutant tetramers for various donors is provided below.

TABLE 7

Frequency (%) of double positive T cells within CD8+ compartment of donors

| Donor ID | Mutant (SEQ ID NO: 9) Mimic (SEQ ID NO: 45) | Mutant (SEQ ID NO: 13) Mimic (SEQ ID NO: 59) | Mutant (SEQ ID NO: 18) Mimic (SEQ ID NO 68) |
|---|---|---|---|
| 17042765 | 0.14 | 0.13 | 0 |
| 19054445 | 0.24 | 0.38 | 0.01 |
| 19053796 | 0.1 | 0.06 | 0 |
| 17042380 | 0.05 | 0.04 | 0.01 |
| 19054456 | 0.01 | 0 | 0 |
| 19054141 | 0.03 | 0.02 | 0 |
| 19054183 | 0.01 | 0.01 | 0 |
| 18047563 | 0.01 | 0.01 | 0 |

TABLE 8

Frequency (%) of double positive T cells within CD8+ compartment of donors

| Donor ID | Mutant (SEQ ID NO: 2) Mimic (SEQ ID NO: 29) | Mutant (SEQ ID NO: 3) Mimic (SEQ ID NO: 32) | Mutant (SEQ ID NO: 16) Mimic (SEQ ID NO: 64) | Mutant (SEQ ID NO: 22) Mimic (SEQ ID NO: 75) | Mutant (SEQ ID NO: 23) Mimic (SEQ ID NO: 78) |
|---|---|---|---|---|---|
| 20061357 | 0.095 | 0.007 | 0.002 | 0.004 | 0.006 |
| 20001476 | 0.075 | 0.051 | 0.021 | 0.000 | 0.153 |
| 20062384 | 0.000 | 0.023 | 0.000 | 0.000 | 0.023 |
| 20062224 | 0.000 | 0.000 | 0.016 | 0.015 | 0.000 |
| 20061661 | 0.000 | 0.000 | 0.000 | 0.000 | 0.000 |
| 20001487 | 0.000 | 0.000 | 0.000 | 0.000 | 0.000 |
| 20061599 | 0.000 | 0.000 | 0.000 | 0.000 | 0.000 |

Figure 10:
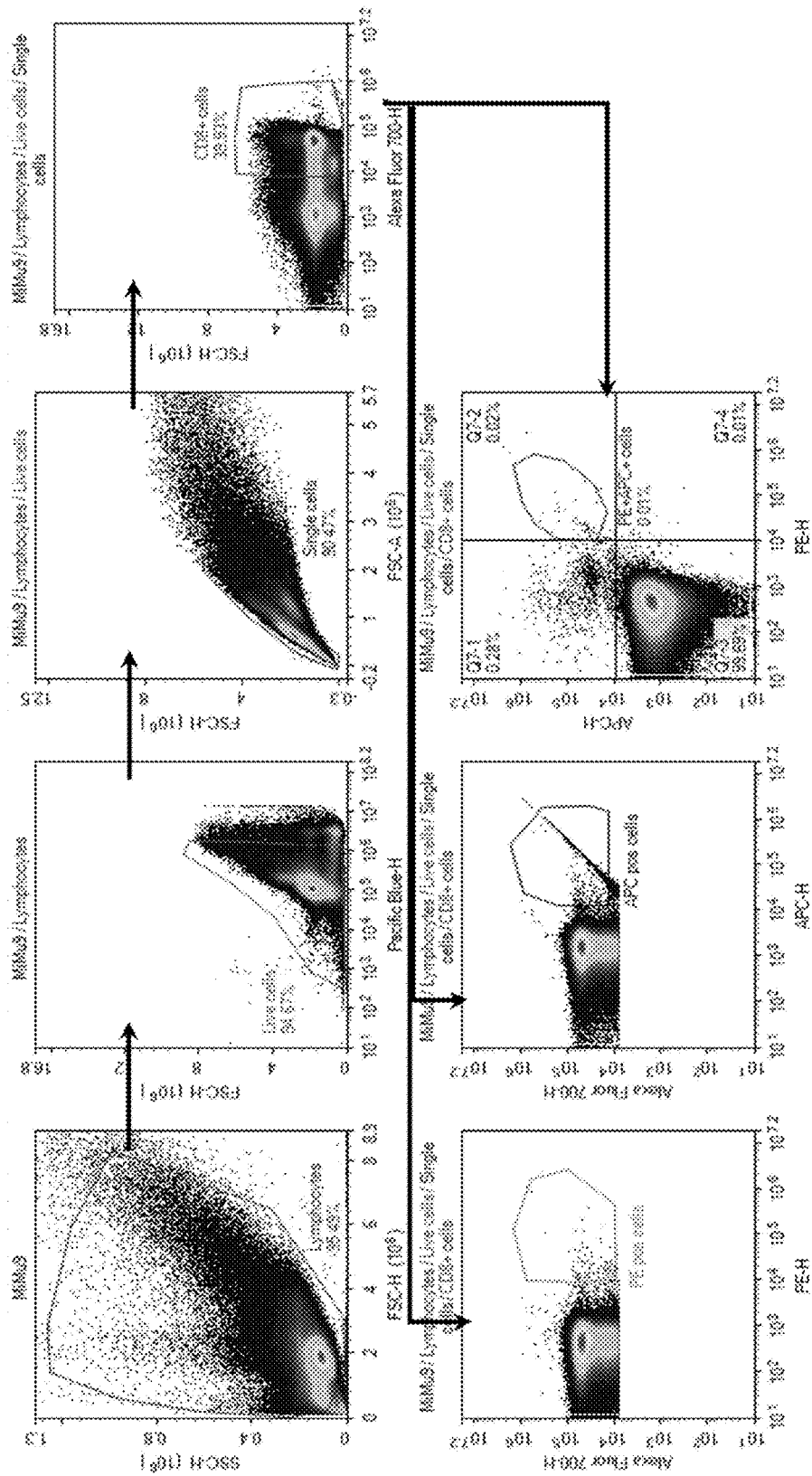
FIG. 10 illustrates exemplary FACS plots used to determine the frequency of dual positive T cells for tetramers specific for mutant and mimic peptides represented by SEQ ID NO: 22 and SEQ ID NO: 75. The donor used was Lot #20062224 from Hemacare. The gating strategy is mentioned in the figure. Lymphocytes derived from the donor were gated to remove dead cells. Live cells were further gated to remove doublets and other cell aggregates. Finally, CD8+ T cells were gated and the frequency of cells staining positive for both mutant and mimic peptide loaded tetramers (PE+/APC+) was determined. mi_mu refers to a sample in which both mimic and mutant tetramers specific to the peptide were used for staining.

FIG. 1-FIG. 10 depict FACS plots used to determine the frequency of dual positive cells for mimic and mutant tetramers specific for mutant and mimic peptides represented by SEQ ID NO: 9 and SEQ ID NO: 45 (FIG. 1), mutant and mimic peptides represented by SEQ ID NO: 13 and SEQ ID NO: 59 (FIG. 2), mutant and mimic peptides represented by SEQ ID NO: 18 and SEQ ID NO: 68 (FIG. 3), negative APC tetramer (FIG. 4), negative PE tetramer (FIG. 5), mutant and mimic peptides represented by SEQ ID NO: 2 and SEQ ID NO: 29 (FIG. 6), mutant and mimic peptides represented by SEQ ID NO: 3 and SEQ ID NO: 32 (FIG. 7), mutant and mimic peptides represented by SEQ ID NO: 16 and SEQ ID NO: 64 (FIG. 8), mutant and mimic peptides represented by SEQ ID NO: 23 and SEQ ID NO: 78 (FIG. 9), and mutant and mimic peptides represented by SEQ ID NO: 22 and SEQ ID NO: 75 (FIG. 10).

Example 4: Identification of TCR Sequences that are Cross Reactive to Both Mutant and Mimic Peptides The following donors were selected for individual single cell TCR sequencing based on a frequency of double positive T cells that was at least 2-fold higher than the background (negative tetramers): T-cells cells from donor 17042765 that were positive for mutant-mimic pairs a) SEQ ID NO: 9 and 45 and b) SEQ ID NO: 13 and 59; T-cells from donor 19054445 that were positive for mutant-mimic pairs a) SEQ ID NO: 9 and 45 and b) SEQ ID NO: 13 and 59. Also, T-cells from donor 19053796 were positive for following mutant-mimic pairs: a) SEQ ID NO: 9 and 45 b) SEQ ID NO: 13 and 59 and c) SEQ ID NO: 18 and 68.

Single cell TCR profiling was performed according to the methods described in the Takara Bio USA, SMARTer® Human scTCR a/b Profiling Kit User Manual, the entirety of which is incorporated herein by reference. In brief, single T cells were sorted into a 96-well plate. The cells were lysed, and first-strand synthesis was performed. cDNA was amplified by polymerase chain reaction (PCR) (16 cycles). The resultant cDNA was pooled and purified using Agencourt® AMPure® XP beads. Semi-nested PCR was used for TCR a/b amplification and sequencing library generation. The first TCR-specific PCR reaction was performed using 16 cycles and the second TCR-specific PCR reaction was performed using 14 cycles. The resultant cDNA was pooled and purified using Agencourt® AMPure® XP beads.

Library quality control was performed using Qubit quantification and TapeStation quality control. Libraries were pooled and sequencing was performed on 2×300 cycles V3 chemistry flow-cell on Illumina MiSeq.

Data analysis was performed by de-multiplexing using MiSeq Reported and checked for quality. TCR analysis was performed using Lymanalyzer and the results from individual single cell data were summarized by taking the best hit for TCR a/b for each cell data file.

Table 9 provides the donor number, sample name and the V(J) or V(D)J genes for the alpha and beta chains for TCRs positive for mutant-mimic pair SEQ ID NO: 9 and 45 tetramers. Each row represents an individual well in a 96 well plate.

TABLE 9

|  | Row | Sample | TCR1 V_Gene | TCR1 J_Gene | TCRB V_Gene | TCRB D_Gene | TCRB J_Gene |
|---|---|---|---|---|---|---|---|
| Donor 19054445 | 1 | S17 | TRAV26-2*01 | TRAJ37*01 | TRBV12-3*01 | TRBD2*02 | TRBJ1-2*01 |
|  | 2 | S19 | TRAV26-2*01 | TRAJ37*01 | TRBV12-3*01 | TRBD2*02 | TRBJ1-2*01 |
|  | 3 | S20 | TRAV26-2*01 | TRAJ37*01 | TRBV12-3*01 | TRBD2*02 | TRBJ1-2*01 |
|  | 4 | S21 | TRAV5*01 | TRAJ41*01 | TRBV12-3*01 | TRBD2*02 | TRBJ1-2*01 |
|  | 5 | S22 | TRAV26-2*01 | TRAJ37*01 | TRBV12-3*01 | TRBD2*02 | TRBJ1-2*01 |
|  | 6 | S24 | TRAV9-2*01 | TRAJ18*01 | TRBV12-3*01 | TRBD2*02 | TRBJ1-2*01 |
|  | 7 | S24 | TRAV26-2*01 | TRAJ37*01 | TRBV12-3*01 | TRBD2*02 | TRBJ1-2*01 |
|  | 8 | S25 | TRAV26-2*01 | TRAJ37*01 | TRBV12-3*01 | TRBD2*02 | TRBJ1-2*01 |
| Donor 19053796 | 9 | S39 | TRAV12-2*01 | TRAJ15*01 | TRBV12-3*01 | TRBD2*02 | TRBJ1-2*01 |
|  | 10 | S41 | TRAV16*01 | TRAJ41*01 | TRBV20-1*05 | TRBD2*02 | TRBJ2-7*01 |
|  | 11 | S41 | TRAV16*01 | TRAJ41*01 | TRBV20-1*05 | TRBD2*02 | TRBJ2-7*01 |
|  | 12 | S41 | TRAV16*01 | TRAJ41*01 | TRBV20-1*05 | TRBD2*02 | TRBJ2-7*01 |
|  | 13 | S41 | TRAV16*01 | TRAJ41*01 | TRBV12-3*01 | TRBD2*02 | TRBJ1-2*01 |
|  | 14 | S42 | TRAV5*01 | TRAJ41*01 | TRBV11-1*01 | TRBD2*02 | TRBJ2-7*01 |
|  | 15 | S42 | TRAV22*01 | TRAJ37*01 | TRBV15*02 | TRBD2*02 | TRBJ1-2*01 |
|  | 16 | S44 | TRAV5*01 | TRAJ41*01 | TRBV12-3*01 | TRBD2*02 | TRBJ1-2*01 |
|  | 17 | S44 | TRAV16*01 | TRAJ41*01 | TRBV12-3*01 | TRBD2*02 | TRBJ1-2*01 |
|  | 18 | S45 | TRAV5*01 | TRAJ41*01 | TRBV11-1*01 | TRBD2*02 | TRBJ2-7*01 |
|  | 19 | S45 | TRAV5*01 | TRAJ41*01 | TRBV11-1*01 | TRBD2*02 | TRBJ2-7*01 |
|  | 20 | S45 | TRAV5*01 | TRAJ41*01 | TRBV12-3*01 | TRBD2*02 | TRBJ1-2*01 |
|  | 21 | S45 | TRAV5*01 | TRAJ41*01 | TRBV11-1*01 | TRBD2*02 | TRBJ2-7*01 |
|  | 22 | S46 | TRAV22*01 | TRAJ37*01 | TRBV5-6*01 | TRBD2*02 | TRBJ2-7*01 |
|  | 23 | S48 | TRAV16*01 | TRAJ41*01 | TRBV15*02 | TRBD2*02 | TRBJ1-2*01 |
|  | 24 | S50 | TRAV22*01 | TRAJ37*01 | TRBV12-4*01 | TRBD2*02 | TRBJ1-2*01 |

Table 10 provides the donor number, sample name and the V(J) or V(D)J genes for the alpha and beta chains for TCRs positive for mutant-mimic pair SEQ ID NO: 13 and 59 tetramers. Each row represents an individual well in 96 well plate.

TABLE 10

|  | Row | Sample | TCRA V_Gene | TCRA J_Gene | TCRB V_Gene | TCRB D_Gene | TCRB J_Gene |
|---|---|---|---|---|---|---|---|
| Donor 19054445 | 1 | S27 | TRAV24*01 | TRAJ49*01 | TRBV2*01 | TRBD1*01 | TRBJ2-4*01 |
|  | 2 | S28 | TRAV4*01 | TRAJ4*01 | TRBV12-3*01 | TRBD2*02 | TRBJ1-2*01 |
|  | 3 | S29 | TRAV9-2*01 | TRAJ18*01 | TRBV7-8*01 | TRBD2*02 | TRBJ1-5*01 |
|  | 4 | S29 | TRAV22*01 | TRAJ37*01 | TRBV7-8*01 | TRBD2*02 | TRBJ1-5*01 |
|  | 5 | S29 | TRAV24*01 | TRAJ49*01 | TRBV12-3*01 | TRBD2*02 | TRBJ1-2*01 |
|  | 6 | S29 | TRAV24*01 | TRAJ49*01 | TRBV7-8*01 | TRBD2*02 | TRBJ1-5*01 |
|  | 7 | S30 | TRAV13-1*01 | TRAJ45*01 | TRBV6-6*01 | TRBD2*02 | TRBJ1-4*01 |
|  | 8 | S30 | TRAV22*01 | TRAJ37*01 | TRBV12-4*01 | TRBD2*02 | TRBJ2-7*01 |
|  | 9 | S30 | TRAV8-4*01 | TRAJ3*01 | TRBV12-3*01 | TRBD2*02 | TRBJ1-2*01 |
|  | 10 | S31 | TRAV9-2*01 | TRAJ18*01 | TRBV12-3*01 | TRBD2*02 | TRBJ1-2*01 |
|  | 11 | S31 | TRAV22*01 | TRAJ37*01 | TRBV12-3*01 | TRBD2*02 | TRBJ1-2*01 |
|  | 12 | S32 | TRAV9-2*01 | TRAJ18*01 | TRBV12-3*01 | TRBD2*02 | TRBJ1-2*01 |
|  | 13 | S32 | TRAV9-2*01 | TRAJ18*01 | TRBV7-8*01 | TRBD2*02 | TRBJ1-5*01 |
|  | 14 | S32 | TRAV9-2*01 | TRAJ18*01 | TRBV12-3*01 | TRBD2*02 | TRBJ1-2*01 |
|  | 15 | S32 | TRAV4*01 | TRAJ4*01 | TRBV12-3*01 | TRBD2*02 | TRBJ1-2*01 |
|  | 16 | S32 | TRAV9-2*01 | TRAJ18*01 | TRBV12-3*01 | TRBD2*02 | TRBJ1-2*01 |
|  | 17 | S32 | TRAV9-2*01 | TRAJ18*01 | TRBV12-3*01 | TRBD2*02 | TRBJ1-2*01 |

TABLE 10-continued

|  | Row | Sample | TCRA V_Gene | TCRA J_Gene | TCRB V_Gene | TCRB D_Gene | TCRB J_Gene |
|---|---|---|---|---|---|---|---|
|  | 18 | S33 | TRAV13-1*01 | TRAJ45*01 | TRBV6-6*01 | TRBD2*02 | TRBJ1-4*01 |
|  | 19 | S33 | TRAV13-1*01 | TRAJ45*01 | TRBV6-6*01 | TRBD2*02 | TRBJ1-4*01 |
|  | 20 | S33 | TRAV13-1*01 | TRAJ45*01 | TRBV12-3*01 | TRBD2*02 | TRBJ1-2*01 |
|  | 21 | S33 | TRAV9-2*01 | TRAJ18*01 | TRBV7-8*01 | TRBD2*02 | TRBJ1-5*01 |
|  | 22 | S33 | TRAV22*01 | TRAJ37*01 | TRBV12-3*01 | TRBD2*02 | TRBJ1-2*01 |
|  | 23 | S33 | TRAV13-1*01 | TRAJ45*01 | TRBV12-3*01 | TRBD2*02 | TRBJ1-2*01 |
|  | 24 | S33 | TRAV8-4*01 | TRAJ3*01 | TRBV12-3*01 | TRBD2*02 | TRBJ1-2*01 |
|  | 25 | S34 | TRAV4*01 | TRAJ4*01 | TRBV6-2*01, TRBV6-3*01 | TRBD2*02 | TRBJ2-2*01 |
|  | 26 | S34 | TRAV4*01 | TRAJ4*01 | TRBV6-2*01, TRBV6-3*01 | TRBD2*02 | TRBJ2-2*01 |
|  | 27 | S34 | TRAV9-2*01 | TRAJ18*01 | TRBV12-3*01 | TRBD2*02 | TRBJ1-2*01 |
|  | 28 | S34 | TRAV4*01 | TRAJ4*01 | TRBV6-2*01, TRBV6-3*01 | TRBD2*02 | TRBJ2-2*01 |
|  | 29 | S34 | TRAV4*01 | TRAJ4*01 | TRBV12-3*01 | TRBD2*02 | TRBJ1-2*01 |
|  | 30 | S36 | TRAV22*01 | TRAJ37*01 | TRBV27*01 | TRBD1*01 | TRBJ2-1*01 |
|  | 31 | S38 | TRAV22*01 | TRAJ37*01 | TRBV12-4*01 | TRBD2*02 | TRBJ2-7*01 |
|  | 32 | S38 | TRAV22*01 | TRAJ37*01 | TRBV12-4*01 | TRBD2*02 | TRBJ2-7*01 |
|  | 33 | S38 | TRAV22*01 | TRAJ37*01 | TRBV12-4*01 | TRBD2*02 | TRBJ2-7*01 |
|  | 34 | S38 | TRAV22*01 | TRAJ37*01 | TRBV12-4*01 | TRBD2*02 | TRBJ2-7*01 |
| Donor 19053796 | 35 | S14 | TRAV10*01 | TRAJ40*01 | TRBV7-9*03 | TRBD2*01 | TRBJ2-2*01 |
|  | 36 | S14 | TRAV12-2*01 | TRAJ43*01 | TRBV18*01 | TRBD1*01 | TRBJ1-1*01 |
|  | 37 | S14 | TRAV13-2*01 | TRAJ9*01 | TRBV7-9*03 | TRBD2*01 | TRBJ2-2*01 |
|  | 38 | S15 | TRAV13-2*01 | TRAJ15*01 | TRBV11-2*01 | TRBD1*01 | TRBJ1-2*01 |
|  | 39 | S15 | TRAV13-2*01 | TRAJ15*01 | TRBV5-1*01 | TRBD2*02 | TRBJ2-7*01 |
|  | 40 | S15 | TRAV8-4*01 | TRAJ3*01 | TRBV12-3*01 | TRBD2*02 | TRBJ1-2*01 |
|  | 41 | S15 | TRAV13-2*01 | TRAJ15*01 | TRBV5-1*01 | TRBD2*02 | TRBJ2-7*01 |
|  | 42 | S16 | TRAV10*01 | TRAJ40*01 | TRBV12-3*01 | TRBD1*01 | TRBJ2-1*01 |
|  | 43 | S16 | TRAV10*01 | TRAJ40*01 | TRBV12-3*01 | TRBD1*01 | TRBJ2-1*01 |
|  | 44 | S16 | TRAV10*01 | TRAJ40*01 | TRBV12-3*01 | TRBD1*01 | TRBJ2-1*01 |
|  | 45 | S16 | TRAV10*01 | TRAJ40*01 | TRBV29-1*01 | TRBD2*02 | TRBJ2-7*01 |
|  | 46 | S16 | TRAV10*01 | TRAJ40*01 | TRBV29-1*01 | TRBD2*02 | TRBJ2-7*01 |
|  | 47 | S17 | TRAV10*01 | TRAJ11*01 | TRBV12-3*01 | TRBD2*02 | TRBJ1-2*01 |
|  | 48 | S17 | TRAV10*01 | TRAJ40*01 | TRBV12-3*01 | TRBD2*02 | TRBJ1-2*01 |
|  | 49 | S17 | TRAV12-2*01 | TRAJ9*01 | TRBV12-3*01 | TRBD2*02 | TRBJ1-2*01 |
|  | 50 | S18 | TRAV10*01 | TRAJ11*01 | TRBV14*01 | TRBD2*02 | TRBJ2-5*01 |
|  | 51 | S18 | TRAV10*01 | TRAJ11*01 | TRBV14*01 | TRBD2*02 | TRBJ2-5*01 |
|  | 52 | S18 | TRAV10*01 | TRAJ11*01 | TRBV14*01 | TRBD2*02 | TRBJ2-5*01 |
|  | 53 | S18 | TRAV25*01 | TRAJ12*01 | TRBV6-5*01 | TRBD2*02 | TRBJ2-7*01 |
|  | 54 | S18 | TRAV10*01 | TRAJ11*01 | TRBV12-3*01 | TRBD2*02 | TRBJ1-2*01 |
|  | 55 | S19 | TRAV8-4*01 | TRAJ3*01 | TRBV12-3*01 | TRBD2*02 | TRBJ1-2*01 |
|  | 56 | S19 | TRAV8-4*01 | TRAJ3*01 | TRBV12-3*01 | TRBD2*02 | TRBJ1-2*01 |
|  | 57 | S20 | TRAV10*01 | TRAJ11*01 | TRBV12-3*01 | TRBD2*02 | TRBJ1-2*01 |
|  | 58 | S20 | TRAV10*01 | TRAJ40*01 | TRBV12-3*01 | TRBD1*01 | TRBJ2-1*01 |
|  | 59 | S22 | TRAV10*01 | TRAJ40*01 | TRBV7-9*03 | TRBD2*01 | TRBJ2-2*01 |
|  | 60 | S23 | TRAV10*01 | TRAJ40*01 | TRBV6-5*01 | TRBD1*01 | TRBJ2-3*01 |
|  | 61 | S38 | TRAV12-2*01 | TRAJ43*01 | TRBV13*01 | TRBD1*01 | TRBJ2-2*01 |
|  | 62 | S38 | TRAV13-2*01 | TRAJ9*01 | TRBV12-3*01 | TRBD2*02 | TRBJ1-2*01 |
|  | 63 | S38 | TRAV12-2*01 | TRAJ43*01 | TRBV12-3*01 | TRBD2*02 | TRBJ1-2*01 |
|  | 64 | S38 | TRAV12-2*01 | TRAJ43*01 | TRBV12-3*01 | TRBD2*02 | TRBJ1-2*01 |
|  | 65 | S38 | TRAV12-2*01 | TRAJ43*01 | TRBV12-3*01 | TRBD2*02 | TRBJ1-2*01 |
|  | 66 | S39 | TRAV26-1*01 | TRAJ48*01 | TRBV11-2*01 | TRBD1*01 | TRBJ2-7*01 |
|  | 67 | S40 | TRAV13-1*01 | TRAJ37*01 | TRBV12-3*01 | TRBD2*02 | TRBJ1-2*01 |
|  | 68 | S42 | TRAV8-4*01 | TRAJ3*01 | TRBV12-3*01 | TRBD2*02 | TRBJ1-2*01 |
|  | 69 | S42 | TRAV8-4*01 | TRAJ3*01 | TRBV12-3*01 | TRBD2*02 | TRBJ1-2*01 |
|  | 70 | S43 | TRAV8-4*01 | TRAJ3*01 | TRBV12-3*01 | TRBD2*02 | TRBJ1-2*01 |
|  | 71 | S44 | TRAV12-2*01 | TRAJ43*01 | TRBV12-3*01 | TRBD2*02 | TRBJ1-2*01 |
|  | 72 | S45 | TRAV12-2*01 | TRAJ9*01 | TRBV12-3*01 | TRBD2*02 | TRBJ1-2*01 |
|  | 73 | S46 | TRAV8-4*01 | TRAJ3*01 | TRBV12-3*01 | TRBD2*02 | TRBJ1-2*01 |
|  | 74 | S46 | TRAV8-4*01 | TRAJ3*01 | TRBV12-3*01 | TRBD2*02 | TRBJ1-2*01 |
|  | 75 | S46 | TRAV8-4*01 | TRAJ3*01 | TRBV12-3*01 | TRBD2*02 | TRBJ1-2*01 |
|  | 76 | S46 | TRAV12-2*01 | TRAJ43*01 | TRBV12-3*01 | TRBD2*02 | TRBJ1-2*01 |
|  | 77 | S46 | TRAV9-2*01 | TRAJ18*01 | TRBV12-3*01 | TRBD2*02 | TRBJ1-2*01 |
|  | 78 | S46 | TRAV9-2*01 | TRAJ56*01 | TRBV12-3*01 | TRBD2*02 | TRBJ1-2*01 |
|  | 79 | S46 | TRAV8-4*01 | TRAJ3*01 | TRBV12-3*01 | TRBD2*02 | TRBJ1-2*01 |
|  | 80 | S46 | TRAV8-4*01 | TRAJ3*01 | TRBV12-3*01 | TRBD2*02 | TRBJ1-2*01 |
|  | 81 | S47 | TRAV9-2*01 | TRAJ18*01 | TRBV12-3*01 | TRBD2*02 | TRBJ1-2*01 |
|  | 82 | S47 | TRAV26-2*01 | TRAJ37*01 | TRBV12-3*01 | TRBD2*02 | TRBJ1-2*01 |
|  | 83 | S48 | TRAV8-4*01 | TRAJ8*01 | TRBV12-3*01 | TRBD2*02 | TRBJ1-2*01 |
|  | 84 | S48 | TRAV8-4*01 | TRAJ3*01 | TRBV12-3*01 | TRBD1*01 | TRBJ1-2*01 |
|  | 85 | S48 | TRAV9-2*01 | TRAJ18*01 | TRBV12-3*01 | TRBD2*02 | TRBJ1-2*01 |
|  | 86 | S48 | TRAV9-2*01 | TRAJ56*01 | TRBV12-3*01 | TRBD2*02 | TRBJ1-2*01 |
|  | 87 | S48 | TRAV8-4*01 | TRAJ3*01 | TRBV12-3*01 | TRBD2*02 | TRBJ1-2*01 |

Table 11 provides the donor number, sample name and the V(J) or V(D)J genes for the alpha and beta chains for TCRs positive for mutant-mimic pair SEQ ID NO: 18 and 68 tetramers. Each row represents an individual well in a 96 well plate.

TABLE 11

|  | Row | Sample | TCRA | | TCRB | | |
|---|---|---|---|---|---|---|---|
|  |  |  | V_Gene | J_Gene | V_Gene | D_Gene | J_Gene |
| Donor 19053796 | 1 | S26 | TRAV13-2*01 | TRAJ9*01 | TRBV3-1*01 | TRBD1*01 | TRBJ1-1*01 |
|  | 2 | S26 | TRAV12-2*01 | TRAJ43*01 | TRBV18*01 | TRBD1*01 | TRBJ1-1*01 |
|  | 3 | S26 | TRAV13-2*01 | TRAJ9*01 | TRBV3-1*01 | TRBD1*01 | TRBJ1-1*01 |
|  | 4 | S26 | TRAV13-2*01 | TRAJ9*01 | TRBV18*01 | TRBD1*01 | TRBJ1-1*01 |
|  | 5 | S27 | TRAV21*01 | TRAJ26*01 | TRBV12-3*01 | TRBD2*02 | TRBJ1-2*01 |
|  | 6 | S29 | TRAV13-2*01 | TRAJ9*01 | TRBV12-3*01 | TRBD2*02 | TRBJ1-2*01 |
|  | 7 | S30 | TRAV29/DV5*01 | TRAJ26*01 | TRBV12-3*01 | TRBD2*02 | TRBJ1-2*01 |
|  | 8 | S30 | TRAV8-4*01 | TRAJ3*01 | TRBV12-3*01 | TRBD2*02 | TRBJ1-2*01 |
|  | 9 | S32 | TRAV13-2*01 | TRAJ9*01 | TRBV12-3*01 | TRBD2*02 | TRBJ1-2*01 |
|  | 10 | S32 | TRAV12-3*01 | TRAJ37*01 | TRBV12-3*01 | TRBD2*02 | TRBJ1-2*01 |
|  | 11 | S34 | TRAV13-2*01 | TRAJ9*01 | TRBV3-1*01 | TRBD1*01 | TRBJ1-1*01 |
|  | 12 | S34 | TRAV12-3*01 | TRAJ37*01 | TRBV14*01 | TRBD2*02 | TRBJ2-7*01 |
|  | 13 | S35 | TRAV12-3*01 | TRAJ37*01 | TRBV14*01 | TRBD2*02 | TRBJ2-7*01 |
|  | 14 | S35 | TRAV6*01 | TRAJ32*01 | TRBV14*01 | TRBD2*02 | TRBJ2-7*01 |
|  | 15 | S35 | TRAV13-2*01 | TRAJ9*01 | TRBV3-1*01 | TRBD1*01 | TRBJ1-1*01 |
|  | 16 | S35 | TRAV12-3*01 | TRAJ37*01 | TRBV14*01 | TRBD2*02 | TRBJ2-7*01 |
|  | 17 | S35 | TRAV12-3*01 | TRAJ37*01 | TRBV14*01 | TRBD2*02 | TRBJ2-7*01 |

Table 12 provides the donor number, sample name and the V(J) or V(D)J genes for the alpha and beta chains for TCRs positive for mutant-mimic pair SEQ ID NO: 3 and 32 tetramers. Each row represents an individual well in a 96 well plate.

TABLE 12

|  | Row | TCRA | | TCRB | | |
|---|---|---|---|---|---|---|
|  |  | V_Gene | J_Gene | V_Gene | D_Gene | J_Gene |
| Donor 20001476 | 1 | TRAV26-2*01 | TRAJ43*01 | TRBV7-6*01 | TRBD2*02 | TRBJ1-4*01 |
|  | 2 | TRAV26-2*01 | TRAJ43*01 | TRBV7-6*01 | TRBD2*02 | TRBJ1-4*01 |
|  | 3 | TRAV8-4*01 | TRAJ3*01 | TRBV15*01 | TRBD2*01 | TRBJ2-1*01 |
|  | 4 | TRAV8-4*01 | TRAJ3*01 | TRBV12-3*01 | TRBD2*02 | TRBJ1-2*01 |
|  | 5 | TRAV4*01 | TRAJ20*01 | TRBV4-1*01 | TRBD1*01 | TRBJ1-1*01 |
|  | 6 | TRAV4*01 | TRAJ20*01 | TRBV12-3*01 | TRBD2*02 | TRBJ1-2*01 |
|  | 7 | TRAV26-2*01 | TRAJ43*01 | TRBV5-1*01 | TRBD1*01 | TRBJ1-6*02 |
|  | 8 | TRAV12-3*01 | TRAJ54*01 | TRBV4-1*01 | TRBD1*01 | TRBJ2-1*01 |
|  | 9 | TRAV29/DV5*03 | TRAJ41*01 | TRBV5-4*04 | TRBD1*01 | TRBJ1-1*01 |
|  | 10 | TRAV26-2*01 | TRAJ43*01 | TRBV7-6*01 | TRBD2*02 | TRBJ1-4*01 |
|  | 11 | TRAV22*01 | TRAJ32*01 | TRBV2*01 | TRBD1*01 | TRBJ1-1*01 |
|  | 12 | TRAV22*01 | TRAJ32*01 | TRBV5-6*01 | TRBD2*02 | TRBJ2-7*01 |
|  | 13 | TRAV8-4*01 | TRAJ3*01 | TRBV12-3*01 | TRBD2*02 | TRBJ1-2*01 |
|  | 14 | TRAV1-2*01 | TRAJ28*01 | TRBV6-2*01, TRBV6-3*01 | TRBD1*01 | TRBJ1-6*02 |
|  | 15 | TRAV12-2*01 | TRAJ10*01 | TRBV6-2*01, TRBV6-3*01 | TRBD2*02 | TRBJ2-7*01 |
|  | 16 | TRAV8-4*01, TRAV8-2*01 | TRAJ3*01 | TRBV12-3*01 | TRBD2*02 | TRBJ1-2*01 |
|  | 17 | TRAV8-4*01, TRAV8-2*01 | TRAJ3*01 | TRBV12-4*01, TRBV12-3*01 | TRBD2*02 | TRBJ1-2*01 |
|  | 18 | TRAV23/DV6*01 | TRAJ31*01 | TRBV7-2*01 | TRBD1*01 | TRBJ2-1*01 |
|  | 19 | TRAV12-3*01 | TRAJ24*01 | TRBV12-4*01 | TRBD2*02 | TRBJ2-5*01 |
|  | 20 | TRAV26-2*01 | TRAJ43*01 | TRBV7-6*01 | TRBD2*02 | TRBJ1-4*01 |
|  | 21 | TRAV26-2*01 | TRAJ43*01 | TRBV7-6*01 | TRBD2*02 | TRBJ1-4*01 |

Table 13 provides the donor number, sample name and the V(J) or V(D)J genes for the alpha and beta chains for TCRs positive for mutant-mimic pair SEQ ID NO: 23 and 78 tetramers. Each row represents an individual well in a 96 well plate.

TABLE 13

| | | TCRA | | TCRB | | |
|---|---|---|---|---|---|---|
| | Row | V_Gene | J_Gene | V_Gene | D_Gene | J_Gene |
| Donor 20001476 | 1 | TRAV26-2*01 | TRAJ43*01 | TRBV12-3*01 | TRBD2*02 | TRBJ1-2*01 |
| | 2 | TRAV29/DV5*01 | TRAJ8*01 | TRBV14*01 | TRBD1*01 | TRBJ2-1*01 |
| | 3 | TRAV29/DV5*01 | TRAJ8*01 | TRBV14*01 | TRBD1*01 | TRBJ2-1*01 |
| | 4 | TRAV29/DV5*01 | TRAJ8*01 | TRBV12-4*01, TRBV12-3*01 | TRBD2*02 | TRBJ1-2*01 |
| | 5 | TRAV29/DV5*01 | TRAJ8*01 | TRBV12-3*01 | TRBD2*02 | TRBJ1-2*01 |

Table 14, Table 15, Table 16, Table 17 and Table 18 provide the CDR3 amino acid (aa) sequence, CDR3 nucleotide (nt) sequence and SEQ ID NOs for the mutant-mimic pair SEQ ID NO: 9 and SEQ ID NO: 45 tetramer positive TCRs identified in Table 9, the mutant-mimic pair SEQ ID NO: 13 and SEQ ID NO: 59 tetramer positive TCRs identified in Table 10, the mutant-mimic pair SEQ ID NO: 18 and SEQ ID NO: 68 tetramer positive TCRs identified in Table 11, the mutant-mimic pair SEQ ID NO: 3 and SEQ ID NO: 32 TCRs identified in Table 12, and the mutant-mimic pair SEQ ID NO: 23 and SEQ ID NO: 78 tetramer positive TCRs identified in Table 13, respectively. Each row in Table 14, Table 15, Table 16, Table 17 and Table 18 corresponds to the matching row in Table 9, Table 10, Table 11, Table 12 and Table 13, respectively, e.g. the V(J) or V(D)J genes in row 1 of Table 9 correspond to the CDR3 sequences in row 1 of Table 14, and so on.

TABLE 14

| | | | TCRA | | | | TCRB | | |
|---|---|---|---|---|---|---|---|---|---|
| | Row | Sample | CDR3 (aa) | SEQ ID NO | CDR3 (nt) | SEQ ID NO | CDR3 (aa) | SEQ ID NO | CDR3 (nt) | SEQ ID NO |
| Donor 19054445 | 1 | S17 | CVLLHKKTTGKLIF | 112 | TGTGTACTACTGCATAAAAAAACAACAGGCAAACTAATCTTT | 113 | CASSFSTCSANYGYTF | 114 | TGTGCCAGCAGTTTCTCGACCTGTTCGGCTAACTATGGCTACACCTTC | 115 |
| | 2 | S19 | CVLLHKKTTGKLIF | 112 | TGTGTACTACTGCATAAAAAAACAACAGGCAAACTAATCTTT | 113 | CASSFSTCSANYGYTF | 114 | TGTGCCAGCAGTTTCTCGACCTGTTCGGCTAACTATGGCTACACCTTC | 115 |
| | 3 | S20 | CVLLHKKTTGKLIF | 112 | TGTGTACTACTGCATAAAAAAACAACAGGCAAACTAATCTTT | 113 | CASSFSTCSANYGYTF | 114 | TGTGCCAGCAGTTTCTCGACCTGTTCGGCTAACTATGGCTACACCTTC | 115 |
| | 4 | S21 | CAESPSGYALNF | 116 | TGTGCAGAGAGTCCTTCCGGGTATGCACTCAACTTC | 117 | CASSFSTCSANYGYTF | 114 | TGTGCCAGCAGTTTCTCGACCTGTTCGGCTAACTATGGCTACACCTTC | 115 |
| | 5 | S22 | CVLLHKKTTGKLIF | 112 | TGTGTACTACTGCATAAAAAAACAACAGGCAAACTAATCTTT | 113 | CASSFSTCSANYGYTF | 114 | TGTGCCAGCAGTTTCTCGACCTGTTCGGCTAACTATGGCTACACCTTC | 115 |
| | 6 | S24 | CALSEDRGSTLGRLYF | 118 | TGTGCTCTGAGTGAAGACAGAGGCTCAACCCTGGGGAGGCTATACTTT | 119 | CASSFSTCSANYGYTF | 114 | TGTGCCAGCAGTTTCTCGACCTGTTCGGCTAACTATGGCTACACCTTC | 115 |
| | 7 | S24 | CVLLHKKTTGKLIF | 112 | TGTGTACTACTGCATAAAAAAACAACAGGCAAACTAATCTTT | 113 | CASSFSTCSANYGYTF | 114 | TGTGCCAGCAGTTTCTCGACCTGTTCGGCTAACTATGGCTACACCTTC | 115 |
| | 8 | S25 | CVLLHKKTTGKLIF | 112 | TGTGTACTACTGCATAAAAAAACAACAGGCAAACTAATCTTT | 113 | CASSFSTCSANYGYTF | 114 | TGTGCCAGCAGTTTCTCGACCTGTTCGGCTAACTATGGCTACACCTTC | 115 |

TABLE 14-continued

|  |  | TCRA | | | TCRB | | |
| --- | --- | --- | --- | --- | --- | --- | --- |
| Row | Sample | CDR3 (aa) | SEQ ID NO | CDR3 (nt) | SEQ ID NO | CDR3 (aa) | SEQ ID NO | CDR3 (nt) | SEQ ID NO |
| Donor 19053796 | 9 S39 | CAGLIGTALIF | 120 | TGTGCCGGGTTAATAGGAACTGCTCTGATCTTT | 121 | CASSFSTCSANYGYTF | 114 | TGTGCCAGCAGTTTCTCGACCTGTTCGGCTAACTATGGCTACACCTTC | 115 |
|  | 10 S41 | CALSRDSGYALNF | 122 | TGTGCTCTAAGTAGGGATTCCGGGTATGCACTCAACTTC | 123 | CSAQGLAGEPIYEQYF | 124 | TGCAGTGCCCAGGGACTAGCGGGTGAACCAATCTACGAGCAGTACTTC | 125 |
|  | 11 S41 | CALSRDSGYALNF | 122 | TGTGCTCTAAGTAGGGATTCCGGGTATGCACTCAACTTC | 123 | CSAQGLAGEPIYEQYF | 124 | TGCAGTGCCCAGGGACTAGCGGGTGAACCAATCTACGAGCAGTACTTC | 125 |
|  | 12 S41 | CALSRDSGYALNF | 122 | TGTGCTCTAAGTAGGGATTCCGGGTATGCACTCAACTTC | 123 | CSAQGLAGEPIYEQYF | 124 | TGCAGTGCCCAGGGACTAGCGGGTGAACCAATCTACGAGCAGTACTTC | 125 |
|  | 13 S41 | CAQSRDSGYALNF | 126 | TGTGCTCAAAGTAGGGATTCCGGGTATGCACTCAACTTC | 127 | CASSFSTCSANYGYTF | 114 | TGTGCCAGCAGTTTCTCGACCTGTTCGGCTAACTATGGCTACACCTTC | 115 |
|  | 14 S42 | CAESPSGYALNF | 116 | TGTGCAGAGAGTCCTTCCGGGTATGCACTCAACTTC | 117 | CASSLKLAPYEQYF | 128 | TGTGCCAGCAGTTGAAACTAGCCCCCTACGAGCAGTACTTC | 129 |
|  | 15 S42 | CTFPLPRPQTQAFISVLSRTSASNTGKLIF | 130 | TGTACATTTCCTCTTCCCAGACCACAGACTCAGGCGTTTATTTCTGTGCTGTCCCGAACTTCAGCTAGCAACACAGGCAAACTAATCTTT | 131 | CATSFPDLYGYTF | 134 | TGTGCCACCAGCTTCCCCGGACCTCTATGGCTACACCTTC | 135 |
|  | 16 S44 | CAESPSGYALNF | 116 | TGTGCAGAGAGTCCTTCCGGGTATGCACTCAACTTC | 117 | CASSFSTCSANYGYTF | 114 | TGTGCCAGCAGTTTCTCGACCTGTTCGGCT17AACTATGGCTACACCTTC | 115 |
|  | 17 S44 | CALSRDSGYALNF | 122 | TGTGCTCTAAGTAGGGATTCCGGGTATGCACTCAACTTC | 123 | CASSFSTCSANYGYTF | 114 | TGTGCCAGCAGTTTCTCGACCTGTTCGGCTAACTATGGCTACACCTTC | 115 |
|  | 18 S45 | CAESPSGYALNF | 116 | TGTGCAGAGAGTCCTTCCGGGTATGCACTCAACTTC | 117 | CASSLKLAPYEQYF | 128 | TGTGCCAGCAGTTGAAACTAGCCCCCTACGAGCAGTACTTC | 129 |
|  | 19 S45 | CAESPSGYALNF | 116 | TGTGCAGAGAGTCCTTCCGGGTATGCACTCAACTTC | 117 | CASSLKLAPYEQYF | 128 | TGTGCCAGCAGTTGAAACTAGCCCCCTACGAGCAGTACTTC | 129 |
|  | 20 S45 | CAESPSGYALNF | 116 | TGTGCAGAGAGTCCTTCCGGGTATGCACTCAACTTC | 117 | CASSFSTCSANYGYTF | 114 | TGTGCCAGCAGTTTCTCGACCTGTTCGGCTAACTATGGCTACACCTTC | 115 |
|  | 21 S45 | CAESPSGYALNF | 116 | TGTGCAGAGAGTCCTTCCGGGTATGCACTCAACTTC | 117 | CASSLKLAPYEQYF | 128 | TGTGCCAGCAGTTGAAACTAGCCCCCTACGAGCAGTACTTC | 129 |
|  | 22 S46 | CTFPLPRPQTQAFISVLSRTSASNTGKLIF | 130 | TGTACATTTCCTCTTCCCAGACCACAGACTCAGGCGTTTATTTCTGTGCTGTCCCGAACTTCAGCTAGCAACACAGGCAAACTAATCTTT | 131 | CASSESTYEQYF | 132 | TGTGCCAGCAGCGAGAGTACCTACGAGCAGTACTTC | 133 |
|  | 23 S48 | CALSRDSGYALNF | 122 | TGTGCTCTAAGTAGGGATTCCGGGTATGCACTCAACTTC | 123 | CATSFPDLYGYTF | 134 | TGTGCCACCAGCTTCCCCGGACCTCTATGGCTACACCTTC | 135 |

TABLE 14-continued

|  |  | TCRA | | | | TCRB | | | |
| --- | --- | --- | --- | --- | --- | --- | --- | --- | --- |
| Row | Sample | CDR3 (aa) | SEQ ID NO | CDR3 (nt) | SEQ ID NO | CDR3 (aa) | SEQ ID NO | CDR3 (nt) | SEQ ID NO |
| 24 | S50 | CTFPLPRPQTQAFISVLSRTSASNTGKLIF | 130 | TGTACATTTCCTCTTCCCAGACCACAGACTCAGGCGTTTATTTCTGTGCTGTCCCGAACTTCAGCTAGCAACACAGGCAAACTAATCTTT | 131 | CASSFSTCSANYGYTF | 114 | TGTGCCAGCAGTTTCTCGACCTGTTCGGCTAACTATGGCTACACCTTC | 115 |

TABLE 15

|  |  |  | TCRA | | | | TCRB | | | |
| --- | --- | --- | --- | --- | --- | --- | --- | --- | --- | --- |
|  | Row | Sample | CDR3 (aa) | SEQ ID NO | CDR3 (nt) | SEQ ID NO | CDR3 (aa) | SEQ ID NO | CDR3 (nt) | SEQ ID NO |
| Donor 19054445 | 1 | S27 | CARNTGNQFYF | 136 | TGTGCCCGGAACACCGGTAACCAGTTCTATTTT | 137 | CASRSGVLLAKNIQYF | 138 | TGTGCCAGCAGATCGGGTGTACTACTAGCCAAAAACATTCAGTACTTC | 139 |
|  | 2 | S28 | CLVGDRGLMFSGGYNKLIF | 140 | TGCCTCGTGGGTGACAGGGGACTCATGTTTCTGGTGGCTACAATAAGCTGATTTTT | 141 | CASSFSTCSANYGYTF | 114 | TGTGCCAGCAGTTTCTCGACCTGTTCGGCTAACTATGGCTACACCTTC | 115 |
|  | 3 | S29 | CALSEDRGSTLGRLYF | 118 | TGTGCTCTGAGTGAAGACAGAGGCTCAACCCTGGGGAGGCTATACTTT | 119 | CASSSLSNPQHF | 142 | TGTGCCAGCAGCTCGTTGAGCAATCAGCCCCAGCATTTT | 143 |
|  | 4 | S29 | CTFPLPRPQTQAFISVLSRTSASNTGKLIF | 130 | TGTACATTTCCTCTTCCCAGACCACAGACTCAGGCGTTTATTTCTGTGCTGTCCCGAACTTCAGCTAGCAACACAGGCAAACTAATCTTT | 131 | CASSSLSNPQHF | 142 | TGTGCCAGCAGCTCGTTGAGCAATCAGCCCCAGCATTTT | 143 |
|  | 5 | S29 | CARNTGNQFYF | 136 | TGTGCCCGGAACACCGGTAACCAGTTCTATTTT | 137 | CASSFSTCSANYGYTF | 114 | TGTGCCAGCAGTTTCTCGACCTGTTCGGCTAACTATGGCTACACCTTC | 115 |
|  | 6 | S29 | CARNTGNQFYF | 136 | TGTGCCCGGAACACCGGTAACCAGTTCTATTTT | 137 | CASSSLSNPQHF | 142 | TGTGCCAGCAGCTCGTTGAGCAATCAGCCCCAGCATTTT | 143 |
|  | 7 | S30 | CAARGGADGLTF | 144 | TGTGCAGCACGAGGAGGTGTGACGGACTCACCTTT | 145 | CASSYYGQGGEKLFF | 146 | TGTGCCAGCAGTTACTATGGACAGGGGGAGAAAAACTGTTTTTT | 147 |
|  | 8 | S30 | CTFPLPRPQTQAFISVLSRTAASNTGKLIF | 148 | TGTACATTTCCTCTTCCCAGACCACAGACTCAGGCGTTTATTTCTGTGCTGTCCCGAACTGCAGCTAGCAACACAGGCAAACTAATCTTT | 149 | CASSSDRVYEQYF | 150 | TGTGCCAGCAGTTCCGACCGAGTTTACGAGCAGTACTTC | 151 |

TABLE 15-continued

| | | TCRA | | | | TCRB | | | |
|---|---|---|---|---|---|---|---|---|---|
| Row | Sample | CDR3 (aa) | SEQ ID NO | CDR3 (nt) | SEQ ID NO | CDR3 (aa) | SEQ ID NO | CDR3 (nt) | SEQ ID NO |
| 9 | S30 | CAVSDLEPNSSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 10 | S31 | CALSEDRGSTLGRLYF | 118 | TGTGCTCTGAGTGAAGACAGAGGCTCAACCCTGGGGAGGCTATACTTT | 119 | CASSFSTCSANYGYTF | 114 | TGTGCCAGCAGTTTCTCGACCTGTTCGGCTAACTATGGCTACACCTTC | 115 |
| 11 | S31 | CTFPLPRPQTQAFISVLSRTSASNTGKLIF | 130 | TGTACATTTCCTCTTCCCAGACCACAGACTCAGGCGTTTATTTCTGTGCTGTCCCGAACTTCAGCTAGCAACACAGGCAAACTAATCTTT | 131 | CASSFSTCSANYGYTF | 114 | TGTGCCAGCAGTTTCTCGACCTGTTCGGCTAACTATGGCTACACCTTC | 115 |
| 12 | S32 | CALSEDRGSTLGRLYF | 118 | TGTGCTCTGAGTGAAGACAGAGGCTCAACCCTGGGGAGGCTATACTTT | 119 | CASSFSTCSANYGYTF | 114 | TGTGCCAGCAGTTTCTCGACCTGTTCGGCTAACTATGGCTACACCTTC | 115 |
| 13 | S32 | CALSEDRGSTLGRLYF | 118 | TGTGCTCTGAGTGAAGACAGAGGCTCAACCCTGGGGAGGCTATACTTT | 119 | CASSSLSNQPQHF | 142 | TGTGCCAGCAGCTCGTTGAGCAATCAGCCCCAGCATTTT | 143 |
| 14 | S32 | CALSEDRGSTLGRLYF | 118 | TGTGCTCTGAGTGAAGACAGAGGCTCAACCCTGGGGAGGCTATACTTT | 119 | CASSFSTCSANYGYTF | 114 | TGTGCCAGCAGTTTCTCGACCTGTTCGGCTAACTATGGCTACACCTTC | 115 |
| 15 | S32 | CLVGDRGLMFSGGYNKLIF | 140 | TGCCTCGTGGGTGACAGGGGACTCATGTTTTCTGGTGGCTACAATAAGCTGATTTTT | 141 | CASSFSTCSANYGYTF | 114 | TGTGCCAGCAGTTTCTCGACCTGTTCGGCTAACTATGGCTACACCTTC | 115 |
| 16 | S32 | CALREDRGSTLGRLYF | 154 | TGTGCTCTGCGTGAAGACAGAGGCTCAACCCTGGGGAGGCTATACTTT | 155 | CKPISGHNSLFWYRQTMMRGLELLIYFNNNVPIDDSGMPEDRFSAKMPNASFSTLKIQPSEPRDSAVYFYASSFSTCSANYGYTF | 156 | TGTAAACCAATTTCAGGCCACAACTCCCTTTTCTGGTACAGACAGACCATGATGCGGGGACTGGAGTTGCTCATTTACTTTAACAACAACGTTCCGATAGATGATTCAGGGGATGCCCGAGGATCGATTCTCAGCTAAGATGCCTAATGCATCATTCTCCACTCTGAAGATCCAGCCCTCAGAACCCAGGGACTCAGCTGTGTACTTCTATGCCAGCAGTTTCTCGACCTGTTCGGCTAACTATGGCTACACCTTC | 157 |

TABLE 15-continued

| | | TCRA | | | | TCRB | | | |
|---|---|---|---|---|---|---|---|---|---|
| Row | Sample | CDR3 (aa) | SEQ ID NO | CDR3 (nt) | SEQ ID NO | CDR3 (aa) | SEQ ID NO | CDR3 (nt) | SEQ ID NO |
| 17 | S32 | CALSEDRGST LGRLYF | 118 | TGTGCTCTGA GTGAAGACAG AGGCTCAACC CTGGGGAGGC TATACTTT | 119 | CASSFSTCSA NYGYTF | 114 | TGTGCCAGCA GTTTCTCGAC CTGTTCGGCT AACTATGGCT ACACCTTC | 115 |
| 18 | S33 | CAARGGADGL TF | 144 | TGTGCAGCAC GAGGAGGTGC TGACGGACTC ACCTTT | 145 | CASSYYGQGG EKLFF | 146 | TGTGCCAGCA GTTACTATGG ACAGGGGGGA GAAAAACTGT TTTTT | 147 |
| 19 | S33 | CAARGGADGL TF | 144 | TGTGCAGCAC GAGGAGGTGC TGACGGACTC ACCTTT | 145 | CASSYYGQGG EKLFF | 146 | TGTGCCAGCA GTTACTATGG ACAGGGGGGA GAAAAACTGT TTTTT | 147 |
| 20 | S33 | CAARGGADGL TF | 144 | TGTGCAGCAC GAGGAGGTGC TGACGGACTC ACCTTT | 145 | CASSFSTCSA NYGYTF | 114 | TGTGCCAGCA GTTTCTCGAC CTGTTCGGCT AACTATGGCT ACACCTTC | 115 |
| 21 | S33 | CALSEDRGST LGRLYF | 118 | TGTGCTCTGA GTGAAGACAG AGGCTCAACC CTGGGGAGGC TATACTTT | 119 | CASSSLSNQP QHF | 142 | TGTGCCAGCA GCTCGTTGAG CAATCAGCCC CAGCATTTT | 143 |
| 22 | S33 | CTFPLPRPQT QAFISVLSRT AASNTGKLIF | 148 | TGTACATTTC CTCTTCCCAG ACCACAGACT CAGGCGTTTA TTTCTGTGCT GTCCCGAACT GCAGCTAGCA ACACAGGCAA ACTAATCTTT | 149 | CASSFSTCSA NYGYTF | 114 | TGTGCCAGCA GTTTCTCGAC CTGTTCGGCT AACTATGGCT ACACCTTC | 115 |
| 23 | S33 | CAARGGADGL TF | 144 | TGTGCAGCAC GAGGAGGTGC TGACGGACTC ACCTTT | 145 | CKPISGHNSL FWYRQTMMRG LELLIYFNNN VPIDDSGMPE DRFSAKMPNA SFSTLKIQPS EPRDSAVYFG ASSFSTCSAN YGYTF | 158 | TGTAAACCAA TTTCAGGCCA CAACTCCCTT TTCTGGTACA GACAGACCAT GATGCGGGGA CTGGAGTTGC TCATTTACTT TAACAACAAC GTTCCGATAG ATGATTCAGG GATGCCCGAG GATCGATTCT CAGCTAAGAT GCCTAATGCA TCATTCTCCA CTCTGAAGAT CCAGCCCTCA GAACCCAGGG ACTCAGCTGT GTACTTCGGT GCCAGCAGTT TCTCGACCTG TTCGGCTA ACTATGGCTA CACCTTC | 159 |
| 24 | S33 | CAVSDLEPNS SASKIIF | 152 | TGTGCTGTGA GTGATCTCGA ACCGAACAGC AGTGCTTCCA AGATAATCTT T | 153 | CASSFSTCSA NYGYTF | 114 | TGTGCCAGCA GTTTCTCGAC CTGTTCGGCT AACTATGGCT ACACCTTC | 115 |

TABLE 15-continued

| | | TCRA | | | | TCRB | | | |
|---|---|---|---|---|---|---|---|---|---|
| Row | Sample | CDR3 (aa) | SEQ ID NO | CDR3 (nt) | SEQ ID NO | CDR3 (aa) | SEQ ID NO | CDR3 (nt) | SEQ ID NO |
| 25 | S34 | CLVGDRGLMF SGGYNKLIF | 140 | TGCCTCGTGG GTGACAGGGG ACTCATGTTT TCTGGTGGCT ACAATAAGCT GATTTTT | 141 | CATLAGSTNT GELFF | 160 | TGTGCCACCC TTGCCGGGTC TACGAACACC GGGGAGCTGT TTTTT | 161 |
| 26 | S34 | CLVGDRGLMF SGGYNKLIF | 140 | TGCCTCGTGG GTGACAGGGG ACTCATGTTT TCTGGTGGCT ACAATAAGCT GATTTTT | 141 | CATLAGSTNT GELFF | 160 | TGTGCCACCC TTGCCGGGTC TACGAACACC GGGGAGCTGT TTTTT | 161 |
| 27 | S34 | CALSEDRGST LGRLYF | 118 | TGTGCTCTGA GTGAAGACAG AGGCTCAACC CTGGGGAGGC TATACTTT | 119 | CASSFSTCSA NYGYTF | 114 | TGTGCCAGCA GTTTCTCGAC CTGTTCGGCT AACTATGGCT ACACCTTC | 115 |
| 28 | S34 | CLVGDRGLMF SGGYNKLIF | 140 | TGCCTCGTGG GTGACAGGGG ACTCATGTTT TCTGGTGGCT ACAATAAGCT GATTTTT | 141 | CATLAGSTNT GELFF | 160 | TGTGCCACCC TTGCCGGGTC TACGAACACC GGGGAGCTGT TTTTT | 161 |
| 29 | S34 | CLVGDRGLMF SGGYNKLIF | 140 | TGCCTCGTGG GTGACAGGGG ACTCATGTTT TCTGGTGGCT ACAATAAGCT GATTTTT | 141 | CASSFSTCSA NYGYTF | 114 | TGTGCCAGCA GTTTCTCGAC CTGTTCGGCT AACTATGGCT ACACCTTC | 115 |
| 30 | S36 | CTFPLPRPQT QAFISVLSRT SASNTGKLIF | 130 | TGTACATTTC CTCTTCCCAG ACCACAGACT CAGGCGTTTA TTTCTGTGCT GTCCCGAACT TCAGCTAGCA ACACAGGCAA ACTAATCTTT | 131 | CASSLSMNRV KNEQFF | 162 | TGTGCCAGCA GTTTATCCAT GAACAGGGTT AAGAATGAGC AGTTCTTC | 163 |
| 31 | S38 | CTFPLPRPQT QAFISVLSRT SASNTGKLIF | 130 | TGTACATTTC CTCTTCCCAG ACCACAGACT CAGGCGTTTA TTTCTGTGCT GTCCCGAACT TCAGCTAGCA ACACAGGCAA ACTAATCTTT | 131 | CASSSDRVYE QYF | 150 | TGTGCCAGCA GTTCCGACCG AGTTTACGAG CAGTACTTC | 151 |
| 32 | S38 | CTFPLPRPQT QAFISVLSRT SASNTGKLIF | 130 | TGTACATTTC CTCTTCCCAG ACCACAGACT CAGGCGTTTA TTTCTGTGCT GTCCCGAACT TCAGCTAGCA ACACAGGCAA ACTAATCTTT | 131 | CASSSDRVYE QYF | 150 | TGTGCCAGCA GTTCCGACCG AGTTTACGAG CAGTACTTC | 151 |
| 33 | S38 | CTFPLPRPQT QAFISVLSRT SASNTGKLIF | 130 | TGTACATTTC CTCTTCCCAG ACCACAGACT CAGGCGTTTA TTTCTGTGCT GTCCCGAACT TCAGCTAGCA ACACAGGCAA ACTAATCTTT | 131 | CASSSDRVYE QYF | 150 | TGTGCCAGCA GTTCCGACCG AGTTTACGAG CAGTACTTC | 151 |

TABLE 15-continued

| | Row | Sample | TCRA CDR3 (aa) | SEQ ID NO | CDR3 (nt) | SEQ ID NO | TCRB CDR3 (aa) | SEQ ID NO | CDR3 (nt) | SEQ ID NO |
|---|---|---|---|---|---|---|---|---|---|---|
| | 34 | S38 | CTFPLPRPQT QAFISVLSRT SASNTGKLIF | 130 | TGTACATTTC CTCTTCCCAG ACCACAGACT CAGGCGTTTA TTTCTGTGCT GTCCCGAACT TCAGCTAGCA ACACAGGCAA ACTAATCTTT | 131 | CASSSDRVYE QYF | 150 | TGTGCCAGCA GTTCCGACCG AGTTTACGAG CAGTACTTC | 151 |
| Donor 19053796 | 35 | S14 | CVVSERTSGT YKYIF | 164 | TGTGTGGTGA GCGAAAGGAC CTCAGGAACC TACAAATACA TCTTT | 165 | CASSLGGPGE LFF | 166 | TGTGCCAGCA GCCTAGGGGG ACCCGGGGAG CTGTTTTTT | 167 |
| | 36 | S14 | CREHGDDMRF | 168 | TGCCGTGAAC ATGGCGATGA CATGCGCTTT | 169 | CASSPLRDNT EAFF | 170 | TGTGCCAGCT CACCACTTCG GGACAACACC GAAGCTTTCT TT | 171 |
| | 37 | S14 | CKLQLLNLET QLSTFVPENT GGFKTIF | 172 | TGCAAATTGC AGCTACTCAA CCTGGAGACT CAGCTGTCTA CTTTT GTGCCTGAAA ATACTGGAGG CTTCAAAACT ATCTTT | 173 | CASSLGGPGE LFF | 166 | TGTGCCAGCA GCCTAGGGGG ACCCGGGGAG CTGTTTTTT | 167 |
| | 38 | S15 | CKLQLLNLET QLSTFVQRQT QNQAGTALIF | 174 | TGCAAATTGC AGCTACTCAA CCTGGAGACT CAGCTGTCTA CTTTTGTGCA GAGACAAACG CAAAACCAGG CAGGAACTGC TCTGATCTTT | 175 | CASHLGTGAY NEQFF | 176 | TGTGCCAGCC ATTTAGGGAC AGGGGCTTAC AATGAGCAGT TCTTC | 177 |
| | 39 | S15 | CKLQLLNLET QLSTFVQRQT QNQAGTALIF | 174 | TGCAAATTGC AGCTACTCAA CCTGGAGACT CAGCTGTCTA CTTTTGTGCA GAGACAAACG CAAAACCAGG CAGGAACTGC TCTGATCTTT | 175 | CASSLDPESW GPSYEQYF | 178 | TGCGCCAGCA GCTTGGATCC CGAGAGCTGG GGACCCTCCT ACGAGCAGTA CTTC | 179 |
| | 40 | S15 | CAVSDLEPNS SASKIIF | 152 | TGTGCTGTGA GTGATCTCGA ACCGAACAGC AGTGCTTCCA AGATAATCTT T | 153 | CASSFSTCSA NYGYTF | 114 | TGTGCCAGCA GTTTCTCGAC CTGTTCGGCT AACTATGGCT ACACCTTC | 115 |
| | 41 | S15 | CKLQLLNLET QLSTFVQRQT QNQAGTALIF | 174 | TGCAAATTGC AGCTACTCAA CCTGGAGACT CAGCTGTCTA CTTTTGTGCA GAGACAAACG CAAAACCAGG CAGGAACTGC TCTGATCTTT | 175 | CASSLDPESW GPSYEQYF | 178 | TGCGCCAGCA GCTTGGATCC CGAGAGCTGG GGACCCTCCT ACGAGCAGTA CTTC | 179 |

TABLE 15-continued

| | | TCRA | | | | TCRB | | | |
|---|---|---|---|---|---|---|---|---|---|
| Row | Sample | CDR3 (aa) | SEQ ID NO | CDR3 (nt) | SEQ ID NO | CDR3 (aa) | SEQ ID NO | CDR3 (nt) | SEQ ID NO |
| 42 | S16 | CVVSERTSGT YKYIF | 164 | TGTGTGGTGA GCGAAAGGAC CTCAGGAACC TACAAATACA TCTTT | 165 | CASSFGSYHN EQFF | 180 | TGTGCCAGCA GTTTTGGCTC TTATCACAAT GAGCAGTTCT TC | 181 |
| 43 | S16 | CWSERTSGTY KYIF | 164 | TGTGTGGTGA GCGAAAGGAC CTCAGGAACC TACAAATACA TCTTT | 165 | CASSFGSYHN EQFF | 180 | TGTGCCAGCA GTTTTGGCTC TTATCACAAT GAGCAGTTCT TC | 181 |
| 44 | S16 | CVVSERTSGT YKYIF | 164 | TGTGTGGTGA GCGAAAGGAC CTCAGGAACC TACAAATACA TCTTT | 165 | CASSFGSYHN EQFF | 180 | TGTGCCAGCA GTTTTGGCTC TTATCACAAT GAGCAGTTCT TC | 181 |
| 45 | S16 | CVVSERTSGTY KYIF | 164 | TGTGTGGTGA GCGAAAGGAC CTCAGGAACC TACAAATACA TCTTT | 165 | CSVVGGVTYE QYF | 182 | TGCAGCGTTG TAGGGGGCGT TACCTACGAG CAGTACTTC | 183 |
| 46 | S16 | CVVSERTSGT YKYIF | 164 | TGTGTGGTGA GCGAAAGGAC CTCAGGAACC TACAAATACA TCTTT | 165 | CSVVGGVTYE QYF | 182 | TGCAGCGTTG TAGGGGGCGT TACCTACGAG CAGTACTTC | 183 |
| 47 | S17 | CGERRNSGYS TLTF | 184 | TGTGGTGAGC GCAGGAATTC AGGATACAGC ACCCTCACCT TT | 185 | CASSFSTCSA NYGYTF | 114 | TGTGCCAGCA GTTTCTCGAC CTGTTCGGCT AACTATGGCT ACACCTTC | 115 |
| 48 | S17 | CVVSERTSGT YKYIF | 164 | TGTGTGGTGA GCGAAAGGAC CTCAGGAACC TACAAATACA TCTTT | 165 | CASSFSTCSA NYGYTF | 114 | TGTGCCAGCA GTTTCTCGAC CTGTTCGGCT AACTATGGCT ACACCTTC | 115 |
| 49 | S17 | CALGGFKTIF | 186 | TGTGCCTTGG GAGGCTTCAA AACTATCTTT | 187 | CASSFSTCSA NYGYTF | 114 | TGTGCCAGCA GTTTCTCGAC CTGTTCGGCT AACTATGGCT ACACCTTC | 115 |
| 50 | S18 | CGERRNSGYS TLTF | 184 | TGTGGTGAGC GCAGGAATTC AGGATACAGC ACCCTCACCT TT | 185 | CASSQDRETQ YF | 188 | TGTGCCAGCA GCCAAGATAG GGAGACCCAG TACTTC | 189 |
| 51 | S18 | CGERRNSGYS TLTF | 184 | TGTGGTGAGC GCAGGAATTC AGGATACAGC ACCCTCACCT | 185 | CASSQDRETQ YF | 188 | TGTGCCAGCA GCCAAGATAG GGAGACCCAG TACTTC | 189 |
| 52 | S18 | CGERRNSGYS TLTF | 184 | TGTGGTGAGC GCAGGAATTC AGGATACAGC ACCCTCACCT TT | 185 | CASSQDRETQ YF | 188 | TGTGCCAGCA GCCAAGATAG GGAGACCCAG TACTTC | 189 |
| 53 | S18 | CAGHAITRPM DSSYKLIF | 190 | TGTGCAGGGC ACGCGATAAC CCGACCGATG GATAGCAGCT ATAAATTGAT CTTC | 191 | CASSYGSPAQ DEQYF | 192 | TGTGCCAGCA GTTACGGGTC CCCCGCTCAG GACGAGCAGT ACTTC | 193 |

TABLE 15-continued

|  | Row | Sample | TCRA CDR3 (aa) | SEQ ID NO | CDR3 (nt) | SEQ ID NO | TCRB CDR3 (aa) | SEQ ID NO | CDR3 (nt) | SEQ ID NO |
|---|---|---|---|---|---|---|---|---|---|---|
|  | 54 | S18 | CGERRNSGYSNLTF | 194 | TGTGGTGAGCGCAGGAATTCAGGATACAGCAACCTCACCTTT | 195 | CASSFSTCSANYGYTF | 114 | TGTGCCAGCAGTTTCTCGACCTGTTCGGCTAACTATGGCTACACCTTC | 115 |
|  | 55 | S19 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
|  | 56 | S19 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
|  | 57 | S20 | out_of_frame | N/A | TGTTTCCCTGACAATCATGACTTTCAGTGAGAACACAAAGTCGAACGGAAGAGATACAGCAACACTGGAGGAAGACACAAAGCAAAGATCAAGGCACAACACAGCCTCCCAGCTCAGCGATAGAGCCTCCTACATCTGGGTGATGAGCGAAGGAATAGAGGGTACAGCAACCTCATCTTT | 196 | CASSFSTCSANYGYTF | 114 | TGTGCCAGCAGTTTCTCGACCTGTTCGGCTAACTATGGCTACACCTTC | 115 |
|  | 58 | S20 | CVVSERTSGTYKYIF | 164 | TGTGTGGTGAGCGAAAGGACCTCAGGAACCTACAAATACATCTTT | 165 | CASSFGSYHNEQFF | 180 | TGTGCCAGCAGTTTTGGCTCTTATCACAATGAGCAGTTCTTC | 181 |
|  | 59 | S22 | CVVSERTSGTYKYIF | 164 | TGTGTGGTGAGCGAAAGGACCTCAGGAACCTACAAATACATCTTT | 165 | CASSLGGPGELFF | 166 | TGTGCCAGCAGCCTAGGGGGACCCGGGGAGCTGTTTTTT | 167 |
|  | 60 | S23 | CVVSERTSGTYKYIF | 164 | TGTGTGGTGAGCGAAAGGACCTCAGGAACCTACAAATACATCTTT | 165 | CASSYGQLADTQYF | 197 | TGTGCCAGCAGTTACGGCCAGTTGGCCGATACGCAGTATTTT | 198 |
| Donor 17042765 | 61 | S38 | CREHGDDMRF | 168 | TGCCGTGAACATGGCGATGACATGCGCTTT | 169 | CASSSTGTGNTGELFF | 199 | TGTGCCAGCAGTTCAACCGGGACAGGGAACACCGGGGAGCTGTTTTTT | 200 |
|  | 62 | S38 | CKLQLLNLETQLSTFVPENTGGFKTIF | 172 | TGCAAATTGCAGCTACTCAACCTGGAGACTCAGCTGTCTACTTTTGTGCCTGAAAATACTGGAGGCTTCAAAACTATCTTT | 173 | CASSFSTCSANYGYTF | 114 | TGTGCCAGCAGTTTCTCGACCTGTTCGGCTAACTATGGCTACACCTTC | 115 |

TABLE 15-continued

| | | TCRA | | | | TCRB | | | |
|---|---|---|---|---|---|---|---|---|---|
| Row | Sample | CDR3 (aa) | SEQ ID NO | CDR3 (nt) | SEQ ID NO | CDR3 (aa) | SEQ ID NO | CDR3 (nt) | SEQ ID NO |
| 63 | S38 | CREHGDDMRF | 168 | TGCCGTGAACATGGCGATGACATGCGCTTT | 169 | CASSFSTCSANYGYTF | 114 | TGTGCCAGCAGTTTCTCGACCTGTTCGGCTAACTATGGCTACACCTTC | 115 |
| 64 | S38 | CREHGDDMRF | 168 | TGCCGTGAACATGGCGATGACATGCGCTTT | 169 | CASSFSTCSANYGYTF | 114 | TGTGCCAGCAGTTTCTCGACCTGTTCGGCTAACTATGGCTACACCTTC | 115 |
| 65 | S38 | CREHGDDMRF | 168 | TGCCGTGAACATGGCGATGACATGCGCTTT | 169 | CASSFSTCSANYGYTF | 114 | TGTGCCAGCAGTTTCTCGACCTGTTCGGCTAACTATGGCTACACCTTC | 115 |
| 66 | S39 | CIVGRDFGNEKLTF | 201 | TGCATCGTGGGCCGGGACTTTGGAAATGAGAAATTAACCTTT | 202 | CASSLERAGAYEQYF | 203 | TGTGCCAGCAGCTTAGAGCGGGGCAGGGGCCTACGAGCAGTACTTC | 204 |
| 67 | S40 | CAASIPARSNTGKLIF | 205 | TGTGCAGCAAGTATACCCGCCAGGAGCAACACAGGCAAACTAATCTTT | 206 | CASSFSTCSANYGYTF | 114 | TGTGCCAGCAGTTTCTCGACCTGTTCGGCTAACTATGGCTACACCTTC | 115 |
| 68 | S42 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 69 | S42 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 70 | S43 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 71 | S44 | CREHGDDMRF | 168 | TGCCGTGAACATGGCGATGACATGCGCTTT | 169 | CASSFSTCSANYGYTF | 114 | TGTGCCAGCAGTTTCTCGACCTGTTCGGCTAACTATGGCTACACCTTC | 115 |
| 72 | S45 | CALGGFKTIF | 186 | TGTGCCTTGGGAGGCTTCAAAACTATCTTT | 187 | CASSFSTCSANYGYTF | 114 | TGTGCCAGCAGTTTCTCGACCTGTTCGGCTAACTATGGCTACACCTTC | 115 |
| 73 | S46 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |

TABLE 15-continued

| | | TCRA | | | | TCRB | | |
|---|---|---|---|---|---|---|---|---|
| Row | Sample | CDR3 (aa) | SEQ ID NO | CDR3 (nt) | SEQ ID NO | CDR3 (aa) | SEQ ID NO | CDR3 (nt) | SEQ ID NO |
| 74 | S46 | CAVSDLEPNSSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 75 | S46 | CAVSDLEPNSSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 76 | S46 | CREHGDDMRF | 168 | TGCCGTGAACATGGCGATGACATGCGCTTT | 169 | CASSFSTCSANYGYTF | 114 | TGTGCCAGCAGTTTCTCGACCTGTTCGGCTAACTATGGCTACACCTTC | 115 |
| 77 | S46 | CALSEDRGSTLGRLYF | 118 | TGTGCTCTGAGTGAAGACAGAGGCTCAACCCTGGGGAGGCTATACTTT | 119 | CASSFSTCSANYGYTF | 114 | TGTGCCAGCAGTTTCTCGACCTGTTCGGCTAACTATGGCTACACCTTC | 115 |
| 78 | S46 | CALQAGGGANSKLTF | 207 | TGTGCTCTGCAAGCGGGAGGTGGAGCCAATAGTAAGCTGACATTT | 208 | CASSFSTCSANYGYTF | 114 | TGTGCCAGCAGTTTCTCGACCTGTTCGGCTAACTATGGCTACACCTTC | 115 |
| 79 | S46 | CAVSDLEPNSSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 80 | S46 | CAVSDLEPNSSASKIIF | 152 | TGTGCTGTGAGTGATCTGAACCGAACAGCAGTGCTTCCAAGATAATCTTT | 209 | CASSFSTCSANYGYTF | 114 | TGTGCCAGCAGTTTCTCGACCTGTTCGGCTAACTATGGCTACACCTTC | 115 |
| 81 | S47 | CALSEDRGSTLGRLYF | 118 | TGTGCTCTGAGTGAAGACAGAGGCTCAACCCTGGGGAGGCTATACTTT | 119 | CASSFSTCSANYGYTF | 114 | TGTGCCAGCAGTTTCTCGACCTGTTCGGCTAACTATGGCTACACCTTC | 115 |
| 82 | S47 | CVLLHKKTTGKLIF | 112 | TGTGTACTACTGCATAAAAAAACAACAGGCAAACTAATCTTT | 113 | CASSFSTCSANYGYTF | 114 | TGTGCCAGCAGTTTCTCGACCTGTTCGGCTAACTATGGCTACACCTTC | 115 |
| 83 | S48 | CAVSDEDTGFQKLVF | 210 | TGTGCTGTGAGTGACGAGGACACAGGCTTTCAGAAACTTGTATTT | 211 | CASSFSTCSANYGYTF | 114 | TGTGCCAGCAGTTTCTCGACCTGTTCGGCTAACTATGGCTACACCTTC | 115 |
| 84 | S48 | out_of_frame | N/A | TGCAATACCCCAACCAAGGACTCCAGCTTCTCCTGAAGTACACATCAGCGGCCACCCTGGTTAAAGGCATCAACGGTTTTGAGGCTGAAT | 212 | CASSFSTCSANYGYTF | 114 | TGTGCCAGCAGTTTCTCGACCTGTTCGGCTAACTATGGCTACACCTTC | 115 |

TABLE 15-continued

| | | TCRA | | | | TCRB | | | |
|---|---|---|---|---|---|---|---|---|---|
| Row | Sample | CDR3 (aa) | SEQ ID NO | CDR3 (nt) | SEQ ID NO | CDR3 (aa) | SEQ ID NO | CDR3 (nt) | SEQ ID NO |
| | | | | TTAAGAAGAGTGAAACCTCCTTCCACCTGACGAAACCCTCAGCCCATATGAGCGACGCGGCTGAGTACTTCTGTGCTGAGTGATCTCGAACCGAACAGCAGTGCTTCCAAGATAATCTTT | | | | | |
| 85 | S48 | CALSEDRGSTLGRLYF | 118 | TGTGCTCTGAGTGAAGACAGAGGCTCAACCCTGGGGAGGCTATACTTT | 119 | CASSFSTCSANYGYTF | 114 | TGTGCCAGCAGTTTCTCGACCTGTTCGGCTAACTATGGCTACACCTTC | 115 |
| 86 | S48 | CALQAGGGANSKLTF | 207 | TGTGCTCTGCAAGCGGGAGGTGGAGCCAATAGTAAGCTGACATTT | 208 | CASSFSTCSANYGYTF | 114 | TGTGCCAGCAGTTTCTCGACCTGTTCGGCTAACTATGGCTACACCTTC | 115 |
| 87 | S48 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |

TABLE 16

| | | | TCRA | | | | TCRB | | |
|---|---|---|---|---|---|---|---|---|---|
| | Row | Sample | CDR3 (aa) | SEQ ID NO | CDR3 (nt) | SEQ ID NO | CDR3 (aa) | SEQ ID NO | CDR3 (nt) | SEQ ID NO |
| Donor 19053796 | 1 | S26 | CKLQLLNLETQLSTFVPENTGGFKTIF | 172 | TGCAAATTGCAGCTACTCAACCTGGAGACTCAGCTGTCTACTTTTGTGCCTGAAAATACTGGAGGCTTCAAAACTATCTTT | 173 | CASSQGDRGPSNTEAFF | 213 | TGTGCCAGCAGCCAAGGGGACAGGGGGCCGTCGAACACTGAAGCTTTCTTT | 214 |
| | 2 | S26 | CREHGDDMRF | 168 | TGCCGTGAACATGGCGATGACATGCGCTTT | 169 | CASSPLRDNTEAFF | 170 | TGTGCCAGCTCACCACTTCGGGACAACACCGAAGCTTTCTTTT | 171 |
| | 3 | S26 | CKLQLLNLETQLSTF | 172 | TGCAAATTGCAGCTA | 173 | CASSQGDRGPSNTEA | 213 | TGTGCCAGCAGCCAA | 214 |

TABLE 16-continued

| Row | Sample | TCRA CDR3 (aa) | SEQ ID NO | TCRA CDR3 (nt) | SEQ ID NO | TCRB CDR3 (aa) | SEQ ID NO | TCRB CDR3 (nt) | SEQ ID NO |
|---|---|---|---|---|---|---|---|---|---|
| | | VPENTGGFKTIF | | CTCAACCTGGAGACTCAGCTGTCTACTTTTGTGCCTGAAAATACTGGAGGCTTCAAAACTATCTTT | | FF | | GGGGACAGGGGGCCGTCGAACACTGAAGCTTTCTTT | |
| 4 | S26 | CKLQLLNLETQLSTFVPENTGGFKTIF | 172 | TGCAAATTGCAGCTACTCAACCTGGAGACTCAGCTGTCTACTTTTGTGCCTGAAAATACTGGAGGCTTCAAAACTATCTTT | 173 | CASSPLRDNTEAFF | 170 | TGTGCCAGCTCACCACTTCGGGACAACACCGAAGCTTTTCTTT | 171 |
| 5 | S27 | CAPEENYGKNFVF | 215 | TGTGCTCCCGAGGAGAACTATGGTAAGAATTTTGTCTTT | 216 | CASSFSTCSANYGYTF | 114 | TGTGCCAGCAGTTTCTCGACCTGTTCGGCTAACTATGGCTACACCTTC | 115 |
| 6 | S29 | CKLQLLNLETQLSTFVPENTGGFKTIF | 172 | TGCAAATTGCAGCTACTCAACCTGGAGACTCAGCTGTCTACTTTTGTGCCTGAAAATACTGGAGGCTTCAAAACTATCTTT | 173 | CASSFSTCSANYGYTF | 114 | TGTGCCAGCAGTTTCTCGACCTGTTCGGCTAACTATGGCTACACCTTC | 115 |
| 7 | S30 | CAAIGYGENFVF | 217 | TGTGCAGCAATCGGCTATGGTGAGAATTTTGTCTTT | 218 | CASSFSTCSANYGYTF | 114 | TGTGCCAGCAGTTTCTCGACCTGTTCGGCTAACTATGGCTACACCTTC | 115 |

TABLE 16-continued

| Row | Sample | TCRA CDR3 (aa) | SEQ ID NO | TCRA CDR3 (nt) | SEQ ID NO | TCRB CDR3 (aa) | SEQ ID NO | TCRB CDR3 (nt) | SEQ ID NO |
|---|---|---|---|---|---|---|---|---|---|
| 8 | S30 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 9 | S32 | CKLQLLNLETQLSTFVPENTGGFKTIF | 172 | TGCAAATTGCAGCTACTCAACCTGGAGACTCAGCTGTCTACTTTTGTGCCTGAAAATACTGGAGGCTTCAAAACTATCTTT | 173 | CASSFSTCSANYGYTF | 114 | TGTGCCAGCAGTTTCTCGACCTGTTCGGCTAACTATGGCTACACCTTC | 115 |
| 10 | S32 | CAMTRSSNTGKLIF | 219 | TGTGCAATGACCCGTTCTAGCAACACAGGCAAAACTAATCTTTT | 220 | CASSFSTCSANYGYTF | 114 | TGTGCCAGCAGTTTCTCGACCTGTTCGGCTAACTATGGCTACACCTTC | 115 |
| 11 | S34 | CKLQLLNLETQLSTFVPENTGGFKTIF | 172 | TGCAAATTGCAGCTACTCAACCTGGAGACTCAGCTGTCTACTTTTGTGCCTGAAAATACTGGAGGCTTCAAAACTATCTTT | 173 | CASSQGDRGPSNTEAFF | 213 | TGTGCCAGCAGCCAAGGGGACAGGGGGCCGTCGAACACTGAAGCTTTCTTT | 214 |
| 12 | S34 | CAMTRSSNTGKLIF | 219 | TGTGCAATGACCCGTTCTAGCAACACAGGCAAAACTAATCTTTT | 220 | CASSRDRVGQYF | 221 | TGTGCCAGCAGCCGGGACAGGGTCGGGCAGTACTTC | 222 |
| 13 | S35 | CAMTRSSNTGKLIF | 219 | TGTGCAATGACCCGTTCTAG | 220 | CASSRDRVGQYF | 221 | TGTGCCAGCAGCCGGGACAG | 222 |

TABLE 16-continued

| Row | Sample | TCRA CDR3 (aa) | SEQ ID NO | TCRA CDR3 (nt) | SEQ ID NO | TCRB CDR3 (aa) | SEQ ID NO | TCRB CDR3 (nt) | SEQ ID NO |
|---|---|---|---|---|---|---|---|---|---|
| | | | | CAACACAGGCAAACTAATCTTT | | | | GGTCGGGCAGTACTTC | |
| 14 | S35 | CALDMNYGGATNKLIF | 223 | TGTGCTCTAGACATGAATTATGGTGGTGCTACAAACAAGCTCATCTTT | 224 | CASSRDRVGQYF | 221 | TGTGCCAGCAGCCGGGACAGGGTCGGGCAGTACTTC | 222 |
| 15 | S35 | CKLQLLNLETQLSTFVPENTGGFKTIF | 172 | TGCAAATTGCAGCTACTCAACCTGGAGACTCAGCTGTCTACTTTTGTGCCTGAAAATACTGGAGGCTTCAAAACTATCTTT | 173 | CASSQGDRGPSNTEAFF | 213 | TGTGCCAGCAGCCAAGGGGACAGGGGGCCGTCGAACACTGAAGCTTTCTTT | 214 |
| 16 | S35 | CAMTRSSNTGKLIF | 219 | TGTGCAATGACCCGTTCTAGCAACACAGGCAAACTAATCTTT | 220 | CASSRDRVGQYF | 221 | TGTGCCAGCAGCCGGGACAGGGTCGGGCAGTACTTC | 222 |
| 17 | S3 5 | CAMTRSSNTGKLIF | 219 | TGTGCAATGACCCGTTCTAGCAACACAGGCAAACTAATCTTT | 220 | CASSRDRVGQYF | 221 | TGTGCCAGCAGCCGGGACAGGGTCGGGCAGTACTTC | 222 |

TABLE 17

| | Row | Well | TCRA CDR3 (aa) | SEQ ID NO | TCRA CDR3 (nt) | SEQ ID NO | TCRB CDR3 (aa) | SEQ ID NO | TCRB CDR3 (nt) | SEQ ID NO |
|---|---|---|---|---|---|---|---|---|---|---|
| Donor 2001476 | 1 | B1 | CILDNNNDMRF | 248 | TGCATCCTTGACAATAACAATGACATGCGCTTT | 249 | CASSLAPGATNEKLF | 250 | TGTGCCAGCAGCTTAGCGCCGGGTGCAACTAATGA | 251 |

TABLE 17-continued

| | | TCRA | | | | TCRB | | | |
|---|---|---|---|---|---|---|---|---|---|
| Row | Well | CDR3 (aa) | SEQ ID NO | CDR3 (nt) | SEQ ID NO | CDR3 (aa) | SEQ ID NO | CDR3 (nt) | SEQ ID NO |
| | | | | | | | | AAAACTGTTTTTT | |
| 2 | C1 | CILDNNNDMRF | 248 | TGCATCCTTGACAATAACAATGACATGCGCTTT | 249 | CASSLAPGATNEKLFF | 250 | TGTGCCAGCAGCTTAGCGCCGGGTGCAACTAATGAAAACTGTTTTTT | 251 |
| 3 | D1 | CAVSDLEPNSSASKIIF | 152 | TGTGCTGTGAGTGATCTCGAACCGAACAGCAGTGCTTCCAAGATAATCTTT | 153 | CATSRDLPLAGGRGEQFF | 252 | TGTGCCACCAGCAGAGATCTCCCGCTAGCGGGGGGCGAGTGAGCAGTTCTTC | 253 |
| 4 | E1 | CAVSDLEPNSSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 5 | F1 | CLVVYDYKLSF | 254 | TGCCTCGTGGTCTACGACTACAAGCTCAGCTTT | 255 | CASSHLTGLAEAFF | 256 | TGCGCCAGCAGCCATCTGACAGGGTTGGCTGAAGCTTTCTTT | 257 |
| 6 | H1 | CLVVYDYKLSF | 254 | TGCCTCGTGGTCTACGACTACAAGCTCAGCTTT | 255 | CASSFSTCSANYGYTF | 114 | TGTGCCAGCAGTTTCTCGACCTGTTCGGCTAACTATGGCTACACCTTC | 115 |
| 7 | C2 | CILDNNNDMRF | 248 | TGCATCCTTGACAATAACAATGACATGCGCTTT | 249 | CASSLLGNSPLHF | 258 | TGCGCCAGCAGTCTGCTGGGTAATTCACCCCTCCACTTT | 259 |
| 8 | D2 | out_of_frame | | TGTTCATCAGAGACTCACAGCCCAG | 260 | CASSGLAGAYNEQFF | 261 | TGCGCCAGCAGCGGGCTAGCGGGGG | 262 |

TABLE 17-continued

| Row | Well | TCRA CDR3 (aa) | SEQ ID NO | TCRA CDR3 (nt) | SEQ ID NO | TCRB CDR3 (aa) | SEQ ID NO | TCRB CDR3 (nt) | SEQ ID NO |
|---|---|---|---|---|---|---|---|---|---|
| | | | | TGATTCAGCCACCTACCTCTGTGCAATGACCTGCCACTGACCTTCAGGGAGCCCAGAAGCTGGTATTT | | | | CCTACAATGAGCAGTCTTC | |
| 9 | E2 | CAATHSKSGYALNF | 263 | TGTGCAGCAACCCACTCAAATTCCGGGTATGCACTCAACTTC | 264 | CASSLWVMNTEAFF | 265 | TGTGCCAGCAGCTTGTGGGTATGAACACTGAAGCTTTCTT | 266 |
| 10 | E3 | CELDNNNDMRF | 248 | TGCATCCTTGACAATAACAATGACATGCGCTTT | 249 | CASSLAPGATNEKLF | 250 | TGTGCCAGCAGCTTAGCGCCGGGTGCAACTAATGAAAAACTGTTTTTT | 251 |
| 11 | D6 | CAVYGATKKLIF | 267 | TGTGCTGTTTATGGTGGTGCTACAAACAAGCTCATCTTT | 268 | CASSIGEAFF | 269 | TGTGCCAGCAGTATTGGGGAAGCTTTCTTT | 270 |
| 12 | H6 | CAVYGATKKLIF | 267 | TGTGCTGTTTATGGTGGTGCTACAAACAAGCTCATCTTT | 268 | CASTPGTGAYEQYF | 271 | TGTGCCAGCACCCCCGGGACAGGGGCGTACGAGCAGTACTTC | 272 |
| 13 | E7 | CAVSDLEPNSSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACTGTTCGGCTAACTATGGCTACACCTTC | 115 |
| 14 | F7 | CAVRALVPGAGSYQLTF | 273 | TGTGCTGTGAGAGCCCTCGTCCCTGGGGCTGGGAG | 274 | CASNDYSSPLHF | 275 | TGTGCCAGCAACGACTATAGTTCACCCCTCCACTT | 276 |

TABLE 17-continued

| Row | Well | TCRA CDR3 (aa) | SEQ ID NO | TCRA CDR3 (nt) | SEQ ID NO | TCRB CDR3 (aa) | SEQ ID NO | TCRB CDR3 (nt) | SEQ ID NO |
|---|---|---|---|---|---|---|---|---|---|
| | | | | TTACCAACTCACTTTC | | | | T | |
| 15 | B8 | CAVNRGGGNKLTF | 277 | TGTGCCGTGAACCGGGGAGGAGGAACAAACTCACCTTT | 278 | CASSYGGAYEQYF | 279 | TGTGCCAGCAGTTATGGGGGAGCCTACGAGCAGTACTTC | 280 |
| 16 | D8 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 17 | F8 | CAVSDLEPNSASKIIF | 152 | TGTGCTGTGAGTGATCTCGAACCGAACAGCAGTGCTTCCAAGATAATCTTT | 153 | CASSFSTCSANYGYTF | 114 | TGTGCCAGCAGTTTCTCGACCTGTTCGGCTAACTATGGCTACACCTTC | 115 |
| 18 | E9 | CISWIPSLETQPPPLRSQLIF | 281 | TGCATATCATGGATTCCCAGCCTGGAGACTCAGCCACCCCCCTTGAGGTCGCAACTCATCTTT | 282 | CASSPVQGVYNEQFF | 283 | TGTGCCAGCAGCCCAGTCCAGGGGGTTTACAATGAGCAGTCTTC | 284 |
| 19 | F9 | CATPRYF | 285 | TGTGCAACCCCGCGCTATTTT | 286 | CASSLAGETQYF | 287 | TGTGCCAGCAGCCTCGCGGGAGAGACCCAGTACTTC | 288 |
| 20 | B10 | CILDNNNDMRF | 248 | TGCATCCTTGACAATAACAATGACATGCGCTTT | 249 | CASSLAPGATNEKLF | 250 | TGTGCCAGCAGCTTAGCGCCGGGTGCAACTAATGAAAAACTGTTTTTT | 251 |

TABLE 17-continued

|  |  |  | TCRA | | | | TCRB | | | |
| --- | --- | --- | --- | --- | --- | --- | --- | --- | --- | --- |
| Row | Well | CDR3 (aa) | SEQ ID NO | CDR3 (nt) | SEQ ID NO | CDR3 (aa) | SEQ ID NO | CDR3 (nt) | SEQ ID NO |
|  | 21 | C10 | CILDNNDMRF | 248 | TGCATCCTTGACAATAACAATGACATGCGCTTT | 249 | CASSLAPGATNEKLF | 250 | TGTGCCAGCAGCTTAGCGCCGGGTGCAACTAATGAAAACTGTTTTTT | 251 |

TABLE 18

|  |  |  | TCRA | | | | TCRB | | | |
| --- | --- | --- | --- | --- | --- | --- | --- | --- | --- | --- |
|  | Row | Well | CDR3 (aa) | SEQ ID NO | CDR3 (nt) | SEQ ID NO | CDR3 (aa) | SEQ ID NO | CDR3 (nt) | SEQ ID NO |
| Donor 2001476 | 1 | E3 | CILDNNDMRF | 248 | TGCATCCTTGACAATAACAATGACATGCGCTTT | 249 | CASSFSTCSANYGYTF | 114 | TGTGCCAGCAGTTTCTCGACCTGTTCGGCTAACTATGGCTACACCTTC | 115 |
|  | 2 | B4 | CAASLIGKJLTF | 289 | TGTGCAGCAAGCCTTATAGGGAAACTGACATTT | 290 | CASSQLQSSYNEQFF | 291 | TGTGCCAGCAGCCAATTACAGAGCTCCTACAATGAGCAGTTCTTC | 292 |
|  | 3 | C4 | CAASLIGKLTF | 289 | TGTGCAGCAAGCCTTATAGGGAAACTGACATTT | 290 | CASSQLQSSYNEQFF | 291 | TGTGCCAGCAGCCAATTACAGAGCTCCTACAATGAGCAGTTCTTC | 292 |
|  | 4 | E4 | CAASLIGKLTF | 289 | TGTGCAGCAAGCCTTATAGGGAAACTGACATTT | 290 | CASSFSTCSANYGYTF | 114 | TGTGCCAGCAGTTTCTCGACCTGTTCGGCTAACTATGGCTACACCTTC | 115 |
|  | 5 | F4 | CAASLIGKLTF | 289 | TGTGCAGCAAGCCTTATAGGGAAACTGACATTT | 290 | CASSFSTCSANYGYTF | 114 | TGTGCCAGCAGTTTCTCGACCTGTTCGGCTAACTATGGCTACACCTTC | 115 |

Table 19, Table 20, Table 21, Table 22 and Table 23 provide the CDR1 and CDR2 amino acid (aa) sequences and the CDR1 and CDR2 nucleotide (nt) sequences and SEQ ID NOs for select mutant-mimic pair SEQ ID NO: 9 and SEQ ID NO: 45 tetramer positive TCRs identified in Table 9, the mutant-mimic pair SEQ ID NO: 13 and SEQ ID NO: 59 tetramer positive TCRs identified in Table 10, the mutant-mimic pair SEQ ID NO: 18 and SEQ ID NO: 68 tetramer positive TCRs identified in Table 11, the mutant-mimic pair SEQ ID NO: 3 and SEQ ID NO: 32 tetramer positive TCRs identified in Table 12, and the mutant-mimic pair SEQ ID NO: 23 and SEQ ID NO: 78 tetramer positive TCRs identified in Table 13, respectively. Each row in Table 19, Table 20, Table 21, Table 22, and Table 23 corresponds to the matching row in Table 9, Table 10, Table 11, Table 12 and Table 13, respectively, e.g., the V(J) or V(D)J genes in row 1 of Table 9 correspond to the CDR1 and CDR2 sequences in row 1 of Table 19, and so on.

TABLE 19

| | | | TCRA | | | | | | | TCRB | | | | | | |
|---|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| Donor 19054445 1 | S17 | — | — | — | — | — | — | — | — | — | — | — | — | — | — | — | — |
| 2 | S19 | — | — | — | — | — | — | — | — | — | — | — | — | — | — | — | — |
| 3 | S20 | — | — | — | — | — | — | — | — | SGHNS | 293 | TCAGGCCACAACTCC | 294 | FNNNVP | 295 | TTTAACAACAACGTTCCG | 296 |
| 4 | S21 | — | — | — | — | — | — | — | — | SGHNS | 293 | TCAGGCCACAACTCC | 294 | FNNNVP | 295 | TTTAACAACAACGTTCCG | 296 |
| 5 | S22 | — | — | — | — | — | — | — | — | SGHNS | 293 | TCAGGCCACAAC | 294 | FNNNVP | 295 | TTTAACAACAACGTTCCG | 296 |
| 6 | S24 | — | — | — | — | — | — | — | — | — | — | — | — | — | — | — | — |
| 7 | S24 | — | — | — | — | — | — | — | — | — | — | — | — | — | — | — | — |
| 8 | S25 | — | — | — | — | — | — | — | — | SGHNS | 293 | TCAGGCCACAACTCC | 294 | FNNNVP | 295 | TTTAACAACAACGTTCCG | 296 |
| Donor 19063796 9 | S39 | — | — | — | — | — | — | — | — | — | — | — | — | — | — | — | — |
| 10 | S41 | — | — | — | — | — | — | — | — | DFQATT | 297 | GACTTTCAGGCCACAACT | 298 | SNEGSKA | 299 | TCCAATGAGGGCTCCAAGGCC | 300 |
| 11 | S41 | YSGSPE | 301 | TATTCTGGGAGTCCTGAA | 302 | HISR | 303 | CACATCTCTAGA | 304 | DFQATT | 297 | GACTTTCAGGCCACAACT | 298 | SNEGSKA | 299 | TCCAATGAGGGCTCCAAGGCC | 300 |
| 12 | S41 | — | — | — | — | — | — | — | — | — | — | — | — | — | — | — | — |
| 13 | S41 | — | — | — | — | — | — | — | — | SGHAT | 305 | TCTGGCCATGCT | 306 | FQDESV | 307 | TTTCAGGATGAGA | 308 |

TABLE 19-continued

| | | TCRA | | | | | | | | TCRB | | | | | | |
|---|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| | | | | | | | | | | | | ACC | | | | GTG TA | |
| 14 | S42 | DSSS TY | 309 | GAC AGC TCC TCC ACC TAC | 310 | IFSN MDM | 311 | ATT TTTT CAA ATA TGG ACA TG | 312 | — | — | — | — | — | — | — | — |
| 15 | S42 | — | — | — | — | — | — | — | — | SGH NS | 293 | TCA GGC CAC AAC TCC | 294 | FNN NVP | 295 | TTT AAC AAC AAC GTT CCG | 296 |
| 16 | S44 | — | — | — | — | — | — | — | — | — | — | — | — | — | — | — | — |
| 17 | S44 | — | — | — | — | — | — | — | — | SGH AT | 305 | TCT GGC CAT GCT ACC | 306 | FQD ESV | 307 | TTTC AGG ATG AGA GTG TA | 308 |
| 18 | S45 | DSSS TY | 309 | GAC AGC TCC TCC ACC TAC | 310 | IFSN MDM | 311 | ATT TTTT CAA ATA TGG ACA TG | 312 | SGH AT | 305 | TCT GGC CAT GCT ACC | 306 | FQD ESV | 307 | TTTC AGG ATG AGA GTG TA | 308 |
| 19 | S45 | DSSS TY | 309 | GAC AGC TCC TCC ACC TAC | 310 | IFSN MDM | 311 | ATT TTTT CAA ATA TGG ACA TG | 312 | SGH AT | 305 | TCT GGC CAT GCT ACC | 306 | FQD ESV | 307 | TTTC AGG ATG AGA GTG TA | 308 |
| 20 | S45 | DSSS TY | 309 | GAC AGC TCC TCC ACC TAC | 310 | IFSN MDM | 311 | ATT TTTT CAA ATA TGG ACA TG | 312 | SGH AT | 305 | TCT GGC CAT GCT ACC | 306 | FQD ESV | 307 | TTTC AGG ATG AGA GTG TA | 308 |
| 21 | S45 | DSSS TY | 309 | GAC AGC TCC TCC ACC TAC | 310 | IFSN MDM | 311 | ATT TTTT CAA ATA TGG ACA TG | 312 | SGH DT | 313 | TCT GGG CAT GAC ACT | 314 | YYE EEE | 315 | TAT TAT GAG GAG GAA GAG | 316 |
| 22 | S46 | — | — | — | — | — | — | — | — | LNH NV | 317 | TTG AAC CAT AAC GTC | 318 | YYD KDF | 319 | TAC TAT GAC AAA GAT TTT | 320 |
| 23 | S48 | — | — | — | — | — | — | — | — | — | — | — | — | — | — | — | — |
| 24 | S50 | — | — | — | — | — | — | — | — | — | — | — | — | — | — | — | — |

TABLE 20

| | | | TCRA | | | | | | TCRB | | | | | | |
|---|---|---|---|---|---|---|---|---|---|---|---|---|---|---|---|
| Row | Sample | CDR1 (aa) | SEQ ID NO | CDR1 (nt) | SEQ ID NO | CDR2 (aa) | SEQ ID NO | CDR2 (nt) | SEQ ID NO | CDR1 (aa) | SEQ ID NO | CDR1 (nt) | SEQ ID NO | CDR2 (aa) | SEQ ID NO | CDR2 (nt) | SEQ ID NO |
| Donor 19054445 1 | S27 | SSNFYA | 321 | TCCAGCAATTTTATGCC | 322 | MTLNGDE | 323 | ATGACTTTAAATGGGGATGAA | 324 | SNHLY | 325 | TCTAATCACTTATAC | 326 | FYNEI | 327 | TTTTATAATGAAATC | 328 |
| 2 | S28 | — | — | — | — | — | — | — | — | | | | | | | | |
| 3 | S29 | — | — | — | — | — | — | — | — | SGHVS | 329 | TCGGGTCATGTATCC | 330 | FQNEAQ | 331 | TTCCAGAATGAAGCTCAA | 332 |
| 4 | S29 | — | — | — | — | — | — | — | — | | | | | | | | |
| 5 | S29 | SSNFYA | 321 | TCCAGCAATTTTATGCC | 322 | MTLNGDE | 323 | ATGACTTTAAATGGGGATGAA | 324 | — | — | — | — | — | — | — | — |
| 6 | S29 | SSNFYA | 321 | TCCAGCAATTTTATGCC | 322 | MTLNGDE | 323 | ATGACTTTAAATGGGGATGAA | 324 | — | — | — | — | — | — | — | — |
| 7 | S30 | — | — | — | — | — | — | — | — | — | — | — | — | — | — | — | — |
| 8 | S30 | — | — | — | — | — | — | — | — | | | | | | | | |
| 9 | S30 | SSVPPY | 333 | TCGTCTGTTCCACCATAT | 334 | YTSAATLV | 335 | TACACATCAGCGGCCACCCTGGTT | 336 | SGHNS | 293 | TCAGGCCACAACTCC | 294 | FNNVP | 295 | TTTAACAACAACGTTCCG | 296 |
| 10 | S31 | — | — | — | — | — | — | — | — | — | — | — | — | — | — | — | — |
| 11 | S31 | — | — | — | — | — | — | — | — | | | | | | | | |
| 12 | S32 | — | — | — | — | — | — | — | — | | | | | | | | |
| 13 | S32 | — | — | — | — | — | — | — | — | | | | | | | | |
| 14 | S32 | ATGYPS | 337 | GCCACAGGATACCCTTCC | 338 | ATKADDK | 339 | GCCACGAAGGCTGATGACAAG | 340 | — | — | — | — | — | — | — | — |
| 15 | S32 | — | — | — | — | — | — | — | — | | | | | | | | |
| 16 | S32 | — | — | — | — | — | — | — | — | | | | | | | | |
| 17 | S32 | ATGYPS | 337 | GCCACAGGATACCCTTCC | 338 | ATKADDK | 339 | GCCACGAAGGCTGATGACAAG | 340 | SGHNS | 293 | TCAGGCCACAACTCC | 294 | FNNVP | 295 | TTTAACAACAACGTTCCG | 296 |
| 18 | S33 | DSASNY | 341 | GACAGTGCCTCAAACTAC | 342 | IRSNVGE | 343 | ATTCGTTCAAATGTGGGCGAA | 344 | MNHNY | 345 | ATGAACCATAACTAC | 346 | SVGAGI | 347 | TCAGTTGGTGCTGGTATC | 348 |
| 19 | S33 | — | — | — | — | — | — | — | — | | | | | | | | |
| 20 | S33 | SSVPPY | 333 | TCGTCTGTTCCA | 334 | YTSAATLV | 335 | TACACATCAGCG | 336 | — | — | — | — | — | — | — | — |

TABLE 20-continued

| | | TCRA | | | | | | | | TCRB | | | | | | | |
|---|---|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| | | | | CCA TAT | | | | GCC ACC CTG GTT | | | | | | | | | |
| 21 | S33 | — | | — | | — | | — | | — | | — | | — | | — | |
| 22 | S33 | SSVP PY | 333 | TCG TCT GTT CCA CCA TAT | 334 | YTS AAT LA | 349 | TAC ACA TCA GCG GCC ACC CTG GCT | 350 | — | | — | | — | | — | |
| 23 | S33 | — | | — | | — | | — | | — | | — | | — | | — | |
| 24 | S33 | — | | — | | — | | — | | — | | — | | — | | — | |
| 25 | S34 | NIAT NDY | 351 | AAC ATT GCT ACA AAT GAT TAT | 352 | GYK TK | 353 | GGA TAC AAG ACA AAA | 354 | — | | — | | — | | — | |
| 26 | S34 | — | | — | | — | | — | | — | | — | | — | | — | |
| 27 | S34 | — | | — | | — | | — | | SGH NS | 293 | TCA GGC CAC AAC TCC | 294 | FNN NVP | 295 | TTT AAC AAC AAC GTT CCG | 296 |
| 28 | S34 | NIAT NDY | 351 | AAC ATT GCT ACA AAT GAT TAT | 352 | GYK TK | 353 | GGA TAC AAG ACA AAA | 354 | MNH EY | 355 | ATG AAC CAT GAA TAC | 356 | SVG EGT | 357 | TCA GTT GGT GAG GGT ACA | 358 |
| 29 | S34 | — | | — | | — | | — | | — | | — | | — | | — | |
| 30 | S36 | — | | — | | — | | — | | MNH EY | 355 | ATG AAC CAT GAG TAT | 359 | SMN VEV | 360 | TCA ATG AAT GTT GAG GTG | 361 |
| 31 | S38 | — | | — | | — | | — | | SGH DY | 362 | TCA GGA CAC GAC TAC | 363 | FNN NVP | 295 | TTT AAC AAC AAC GTT CCG | 296 |
| 32 | S38 | — | | — | | — | | — | | SGH DY | 362 | TCA GGA CAC GAC TAC | 363 | FNN NVP | 295 | TTT AAC AAC AAC GTT CCG | 29 |
| 33 | S38 | — | | — | | — | | — | | SGH DY | 362 | TCA GGA CAC GAC TAC | 363 | FNN NVP | 295 | TTT AAC AAC AAC GTT CCG | 296 |
| 34 | S38 | — | | — | | — | | — | | — | | — | | — | | — | |
| Donor 19053796 35 | S14 | — | | — | | — | | — | | SEH NR | 364 | TCT GAA CAC AAC CGC | 365 | FQN EAQ | 331 | TTC CAG AAT GAA GCT CAA | 332 |
| 36 | S14 | — | | — | | — | | — | | — | | — | | — | | — | |
| 37 | S14 | — | | — | | — | | — | | — | | — | | — | | — | |
| 38 | S15 | AQK VTQ AQS | 366 | ACA AGT TGG | 367 | QGS | 368 | CAG GGT TCT | 369 | SGH AT | 305 | TCT GGC CAT | 306 | FQN NGV | 370 | TTTC AGA ATA | 371 |

TABLE 20-continued

| | | TCRA | | | | | | | TCRB | | | | | | |
|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| | | SVSMPVRKAVTLNCLYE | | TGGTCATATTAT | | | | | | GCTACC | | | | ACGGTGTA | | | |
| 39 | S15 | AQKVTQAQSSVSMPVRKAVTLNCLYE | 366 | ACAAGTTGGTGGTCATATTAT | 367 | QGS | 368 | CAGGGTTCT | 369 | SGHRS | 372 | TCTGGGCATAGGAGT | 373 | YFSETQ | 374 | TACTTCAGTGAGACACAG | 375 |
| 40 | S15 | INAEYQIGSHVSVSEGALVLLRCNYS | 376 | TCGTCTGTTCCACCATAT | 334 | YTSAATLV | 335 | TACACATCAGCGGCCACCCTGGTT | 336 | — | — | — | — | — | — | — | — |
| 41 | S15 | — | — | — | — | — | — | — | — | SGHAT | 305 | TCTGGCCATGCTACC | 306 | FQNNGV | 370 | TTTCAGAATAACGGTGTA | 37 |
| 42 | S16 | KNQVEQSPQSLIILEGKNCTLQCNYT | 377 | GTGAGCCCCTTCAGCAAC | 378 | MTFSENT | 379 | ATGACTTTCAGTGAGAACACA | 380 | — | — | — | — | — | — | — | — |
| 43 | S16 | KNQVEQSPQSLIILEGKNCTLQCNYT | 377 | GTGAGCCCCTTCAGCAAC | 378 | MTFSENT | 379 | ATGACTTTCAGTGAGAACACA | 380 | SGHNS | 293 | TCAGGCCACAACTCC | 294 | FNNNVP | 295 | TTTAACAACGTTCCG | 296 |
| 44 | S16 | KNQVEQSPQSLIILEGKNCTLQCNYT | 377 | GTGAGCCCCTTCAGCAAC | 378 | MTFSENT | 379 | ATGACTTTCAGTGAGAACACA | 380 | SGHNS | 293 | TCAGGCCACAACTCC | 294 | FNNNVP | 295 | TTTAACAACGTTCCG | 296 |
| 45 | S16 | KNQVEQSPQSLIILEGKNCTLQCNYT | 377 | GTGAGCCCCTTCAGCAAC | 378 | MTFSENT | 379 | ATGACTTTCAGTGAGAACACA | 380 | — | — | — | — | — | — | — | — |
| 46 | S16 | KNQVEQSPQSLIILEGKNCTLQCNYT | 377 | GTGAGCCCCTTCAGCAAC | 378 | MTFSENT | 379 | ATGACTTTCAGTGAGAACACA | 380 | SQVTM | 381 | AGCCAAGTCACCATG | 382 | ANQGSEA | 383 | GCAAATCAGGGCTCTGAGGCC | 384 |
| 47 | S17 | — | — | — | — | — | — | — | — | SGHNS | 293 | TCAGGCCAC | 294 | FNNNVP | 295 | TTTAACAAC | 296 |

TABLE 20-continued

| | | TCRA | | | | | | | | TCRB | | | | | | | |
|---|---|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| 48 | S17 | — | — | — | — | — | — | — | — | SGHNS | 293 | TCAGGCCACAACTCC | 294 | FNNNVP | 295 | TTTAACAACAACGTTCCG | 296 |
| 49 | S17 | — | — | — | — | — | — | — | — | — | — | — | — | — | — | — | — |
| 50 | S18 | — | — | — | — | — | — | — | — | WSHSY | 385 | TGGAGCCACAGCTAT | 386 | SAAADI | 387 | TCAGCAGCTGCTGATATT | 388 |
| 51 | S18 | — | — | — | — | — | — | — | — | WSHSY | 385 | TGGAGCCACAGCTAT | 386 | SAAADI | 387 | TCAGCAGCTGCTGATATT | 388 |
| 52 | S18 | — | — | — | — | — | — | — | — | SGHNS | 293 | TCAGGCCACAACTCC | 294 | FNNNVP | 295 | TTTAACAACAACGTTCCG | 296 |
| 53 | S18 | GQQVMQIPQYQHVQEGEDFTYCNSS | 389 | ACTACTTTAAGCAAT | 390 | LVKSGEV | 391 | TTAGTGAAGAGTGGAGAAGTG | 392 | MNHEY | 355 | ATGAACCATGAATAC | 356 | SVGAGI | 347 | TCAGTTGGTGCTGGTATC | 348 |
| 54 | S18 | — | — | — | — | — | — | — | — | — | — | — | — | — | — | — | — |
| 55 | S19 | INAEYRCGSHVSVSEGALVLLRCNYS | 393 | TCGTCTGTTCCACCATAT | 334 | YTSAATLV | 335 | TACACATCAGCGGCCACCCTGGTT | 336 | — | — | — | — | — | — | — | — |
| 56 | S19 | INAEYQIGSHVSVSEGALVLLRCNYS | 376 | TCGTCTGTTCCACCATAT | 334 | YTSAATLV | 335 | TACACATCAGCGGCCACCCTGGTT | 336 | SGHNS | 293 | TCAGGCCACAACTCC | 294 | FNNNVP | 295 | TTTAACAACAACGTTCCG | 296 |
| 57 | S20 | — | — | — | — | — | — | — | — | SGHNS | 293 | TCAGGCCACAACTCC | 294 | FNNNVP | 295 | TTTAACAACAACGTTCCG | 296 |
| 58 | S20 | — | — | — | — | — | — | — | — | SGHNS | 293 | TCAGGCCACAACTCC | 294 | FNNNVP | 295 | TTTAACAACAACGTTCCG | 296 |

TABLE 20-continued

| | | TCRA | | | | | | | | TCRB | | | | | | |
|---|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| | 59 S22 | — | — | — | — | — | — | — | — | SEH NR | 364 | TCT GAA CAC AAC CGC | 365 | FQN EAQ | 331 | TTC CAG AAT GAA GCT CAA | 332 |
| | 60 S23 | — | — | — | — | — | — | — | — | — | — | — | — | — | — | — | — |
| Donor 17042765 | 61 S38 | TISG NEY | 394 | ACC ATC AGT GGA AAT GAG TAT | 395 | GLK NN | 396 | GGT CTA AAA AAC AAT | 397 | PRH DT | 398 | CCT AGA CAC GAC ACT | 399 | FYE KMQ | 400 | TTTT ATG AAA AGA TGC AG | 401 |
| | 62 S38 | ATG YPS | 337 | GCC ACA GGA TAC CCT TCC | 338 | ATK ADD K | 339 | GCC ACG AAG GCT GAT GAC AAG | 340 | SGH NS | 293 | TCA GGC CAC AAC TCC | 294 | FNN NVP | 295 | TTT AAC AAC AAC GTT CCG | 296 |
| | 63 S38 | — | — | — | — | — | — | — | — | SGH NS | 293 | TCA GGC CAC AAC TCC | 294 | FNN NVP | 295 | TTT AAC AAC AAC GTT CCG | 296 |
| | 64 S38 | — | — | — | — | — | — | — | — | — | — | — | — | — | — | — | — |
| | 65 S38 | — | — | — | — | — | — | — | — | SGH NS | 293 | TCA GGC CAC AAC TCC | 294 | FNN NVP | 295 | TTT AAC AAC AAC GTT CCG | 296 |
| | 66 S39 | — | — | — | — | — | — | — | — | SGH AT | 305 | TCT GGC CAT GCT ACC | 306 | FQN NGV | 370 | TTTC AGA ATA ACG GTG TA | 371 |
| | 67 S40 | — | — | — | — | — | — | — | — | SGH NS | 293 | TCA GGC CAC AAC TCC | 294 | FNN NVP | 295 | TTT AAC AAC AAC GTT CCG | 296 |
| | 68 S42 | — | — | — | — | — | — | — | — | — | — | — | — | — | — | — | — |
| | 69 S42 | — | — | — | — | — | — | — | — | SGH NS | 293 | TCA GGC CAC AAC TCC | 294 | FNN NVP | 295 | TTT AAC AAC AAC GTT CCG | 296 |
| | 70 S43 | — | — | — | — | — | — | — | — | SGH NS | 293 | TCA GGC CAC AAC TCC | 29 | FNN NVP | 295 | TTT AAC AAC AAC GTT CCG | 296 |
| | 71 S44 | — | — | — | — | — | — | — | — | SGH NS | 293 | TCA GGC CAC AAC TCC | 294 | FNN NVP | 295 | TTT AAC AAC AAC GTT CCG | 296 |
| | 72 S45 | — | — | — | — | — | — | — | — | — | — | — | — | — | — | — | — |
| | 73 S46 | SSVP PY | 333 | TCG TCT GTT CCA CCA TAT | 334 | YTS AAT LV | 335 | TAC ACA TCA GCG GCC ACC CTG | 336 | SGH NS | 293 | TCA GGC CAC AAC TCC | 294 | FNN NVP | 295 | TTT AAC AAC AAC GTT CCG | 296 |

TABLE 20-continued

| | | TCRA | | | | | | | TCRB | | | | | | |
|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| 74 | S46 | NIATNDY | 351 | AACATTGCTACAAATGATTAT | 352 | GYKTK | 353 | GTTGGATACAAGACAAAA | 354 | SGHNS | 293 | TCAGGCCACAACTCC | 294 | FNNVP | 295 | TTTAACAACAACGTTCCG | 296 |
| 75 | S46 | — | — | — | — | — | — | — | — | SGHNS | 293 | TCAGGCCACAACTCC | 294 | FNNVP | 295 | TTTAACAACAACGTTCCG | 296 |
| 76 | S46 | — | — | — | — | — | — | — | — | SGHNS | 293 | TCAGGCCACAACTCC | 294 | FNNVP | 295 | TTTAACAACAACGTTCCG | 296 |
| 77 | S46 | ATGYPS | 337 | GCCACAGGATACCCTTCC | 338 | ATKADDK | 339 | GCCACGAAGGCTGATGACAAG | 340 | SGHNS | 293 | TCAGGCCACAACTCC | 294 | FNNVP | 295 | TTTAACAACAACGTTCCG | 296 |
| 78 | S46 | ATGYPS | 337 | GCCACAGGATACCCTTCC | 338 | ATKADDK | 339 | GCCACGAAGGCTGATGACAAG | 340 | SGHNS | 293 | TCAGGCCACAACTCC | 294 | FNNVP | 295 | TTTAACAACAACGTTCCG | 296 |
| 79 | S46 | — | — | — | — | — | — | — | — | SGHNS | 293 | TCAGGCCACAACTCC | 294 | FNNVP | 295 | TTTAACAACAACGTTCCG | 296 |
| 80 | S46 | ATGYPS | 337 | GCCACAGGATACCCTTCC | 338 | ATKADDK | 339 | GCCACGAAGGCTGATGACAAG | 340 | SGHNS | 293 | TCAGGCCACAACTCC | 294 | FNNVP | 295 | TTTAACAACAACGTTCCG | 296 |
| 81 | S47 | ATGYPS | 337 | GCCACAGGATACCCTTCC | 338 | ATKADDK | 339 | GCCACGAAGGCTGATGACAAG | 340 | SGHNS | 293 | TCAGGCCACAACTCC | 294 | FNNVP | 295 | TTTAACAACAACGTTCCG | 296 |
| 82 | S47 | ATGYPS | 337 | GCCACAGGATACCCTTCC | 338 | ATKADDK | 339 | GCCACGAAGGCTGATGACAAG | 340 | SGHNS | 293 | TCAGGCCACAACTCC | 294 | FNNVS | 402 | TTTAACAACAACGTTCG | 403 |
| 83 | S48 | — | — | — | — | — | — | — | — | SGHNS | 293 | TCAGGCCACAACTCC | 294 | FNNVP | 295 | TTTAACAACAACGTTCCG | 296 |
| 84 | S48 | — | — | — | — | — | — | — | — | SGHNS | 293 | TCAGGCCACAACTCC | 294 | FNNVP | 295 | TTTAACAACAACGTTCCG | 296 |

TABLE 20-continued

| | | TCRA | | | | | | | | TCRB | | | | | | | |
|---|---|---|---|---|---|---|---|---|---|---|---|---|---|---|---|---|---|
| Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| 85 | S48 | — | — | — | — | — | — | — | — | SGHNS | 293 | TCAGGCCACAACTCC | 29 | FNNNVP | 295 | TTTAACAACAACGTTCCG | 296 |
| 86 | S48 | ATGYPS | 337 | GCCACAGGATACCCTTCC | 338 | ATKADDK | 339 | GCCACGAAGGCTGATGACAAG | 340 | SGHNS | 293 | TCAGGCCACAACTCC | 294 | FNNNVP | 295 | TTTAACAACAACGTTCCG | 296 |
| 87 | S48 | — | — | — | — | — | — | — | — | SGHNS | 293 | TCAGGCCACAACTCC | 294 | FNNNVP | 295 | TTTAACAACAACGTTCCG | 296 |

TABLE 21

| | | | TCRA | | | | | | | | TCRB | | | | | | | |
|---|---|---|---|---|---|---|---|---|---|---|---|---|---|---|---|---|---|---|
| | Row | Sample | CDR 1 (aa) | SEQ ID NO | CDR 1 (nt) | SEQ ID NO | CDR 2 (aa) | SEQ ID NO | CDR 2 (nt) | SEQ ID NO | CDR 1 (aa) | SEQ ID NO | CDR 1 (nt) | SEQ ID NO | CDR 2 (aa) | SEQ ID NO | CDR 2 (nt) | SEQ ID NO |
| 19053796 Donor | 1 | S26 | — | — | — | — | — | — | — | — | — | — | — | — | — | — | — | — |
| | 2 | S26 | — | — | — | — | — | — | — | — | — | — | — | — | — | — | — | — |
| | 3 | S26 | — | — | — | — | — | — | — | — | — | — | — | — | — | — | — | — |
| | 4 | S26 | — | — | — | — | — | — | — | — | — | — | — | — | — | — | — | — |
| | 5 | S27 | — | — | — | — | — | — | — | — | — | — | — | — | — | — | — | — |
| | 6 | S29 | — | — | — | — | — | — | — | — | — | — | — | — | — | — | — | — |
| | 7 | S30 | — | — | — | — | — | — | — | — | SGHNS | 293 | TCAGGCCACAACTCC | 294 | FNNNVP | 295 | TTTAACAACAACGTTCCG | 296 |
| | 8 | S30 | — | — | — | — | — | — | — | — | — | — | — | — | — | — | — | — |
| | 9 | S32 | — | — | — | — | — | — | — | — | — | — | — | — | — | — | — | — |
| | 10 | S32 | — | — | — | — | — | — | — | — | — | — | — | — | — | — | — | — |
| | 11 | S34 | — | — | — | — | — | — | — | — | LGHDT | 404 | CTGGGCCATGATACT | 405 | YNNKEL | 406 | TACAATAATAAGGAGCTC | 407 |
| | 12 | S34 | NSAFQY | 408 | AACAGTGCTTTTCAATAC | 409 | TYSSGN | 410 | ACATACTCCAGTGGTAAC | 411 | SGHDN | 412 | TCTGGACATGATAAT | 413 | FVKESK | 414 | TTTGTGAAAGAGTCTAAA | 415 |
| | 13 | S35 | — | — | — | — | — | — | — | — | — | — | — | — | — | — | — | — |
| | 14 | S35 | — | — | — | — | — | — | — | — | — | — | — | — | — | — | — | — |
| | 15 | S35 | — | — | — | — | — | — | — | — | SGHDN | 412 | TCTGGACATGATAAT | 413 | FVKESK | 414 | TTTGTGAAAGAGTCTAAA | 415 |
| | 16 | S35 | — | — | — | — | — | — | — | — | — | — | — | — | — | — | — | — |
| | 17 | S35 | — | — | — | — | — | — | — | — | SGHDN | 412 | TCTGGACATGATAAT | 413 | FVKESK | 414 | TTTGTGAAAGAGTCTAAA | 415 |

TABLE 22

| | Row | Well | TCRA CDR 1 (aa) | SEQ ID NO | CDR 1 (nt) | SEQ ID NO | CDR 2 (aa) | SEQ ID NO | CDR 2 (nt) | SEQ ID NO |
|---|---|---|---|---|---|---|---|---|---|---|
| Donor 2001476 | 1 | B1 | — | — | — | — | — | — | — | — |
| | 2 | C1 | — | — | — | — | — | — | — | — |
| | 3 | D1 | — | — | — | — | — | — | — | — |
| | 4 | E1 | — | — | — | — | — | — | — | — |
| | 5 | F1 | — | — | — | — | — | — | — | — |
| | 6 | H1 | — | — | — | — | — | — | — | — |
| | 7 | C2 | — | — | — | — | — | — | — | — |
| | 8 | D2 | — | — | — | — | — | — | — | — |
| | 9 | E2 | — | — | — | — | — | — | — | — |
| | 10 | E3 | TISGTDY | 424 | ACAATCAGTGGAACTGATTAC | 425 | GLTSN | 426 | GGTCTTACAAGCAAT | 427 |
| | 11 | D6 | DSVNN | 430 | GACTCTGTGAACAAT | 431 | IPSGT | 432 | ATTCCCTCAGGGACA | 433 |
| | 12 | H6 | DSVNN | 430 | GACTCTGTGAACAAT | 431 | IPSGT | 432 | ATTCCCTCAGGGACA | 433 |
| | 13 | E7 | SSVPPY | 333 | TCGTCTGTTCCACCGTAT | 434 | YTSAATLV | 335 | TACACATCAGCGGCCACCCTGGTT | 336 |
| | 14 | F7 | TSGFNG | 435 | ACATCTGGGTTCAACGGG | 436 | NVLDGL | 437 | AATGTTCTGGATGGTTTG | 438 |
| | 15 | B8 | DRGSQS | 439 | CGAGGTTCCCAGTCC | 440 | IYSNGD | 441 | TACTCCAATGGTGAC | 442 |
| | 16 | D8 | — | — | — | — | — | — | — | — |
| | 17 | F8 | — | — | — | — | — | — | — | — |
| | 18 | E9 | — | — | — | — | — | — | — | — |
| | 19 | F9 | NSAFQY | 408 | AACAGTGCTTTTCAATAC | 409 | TYSSGN | 410 | ACATACTCCAGTGGTAAC | 411 |

TABLE 22-continued

| Row | Well | CDR 1 (aa) | SEQ ID NO | CDR 1 (nt) | SEQ ID NO | CDR 2 (aa) | SEQ ID NO | CDR 2 (nt) | SEQ ID NO |
|---|---|---|---|---|---|---|---|---|---|
| 20 | B10 | — | — | — | — | — | — | — | — |
| 21 | C10 | TISGTDY | 424 | ACAATCAGTGGAACTGATTAC | 425 | GLTSN | 426 | GGTCTTACAAGCAAT | 427 |

| | | TCRB |||||||
|---|---|---|---|---|---|---|---|---|
| Row | Well | CDR 1 (aa) | SEQ ID NO | CDR 1 (nt) | SEQ ID NO | CDR 2 (aa) | SEQ ID NO | CDR 2 (nt) | SEQ ID NO |
| Donor 2001476 | 1 | B1 | — | — | — | — | — | — | — |
| | 2 | C1 | — | — | — | — | — | — | — |
| | 3 | D1 | — | — | — | — | — | — | — |
| | 4 | E1 | LGHNA | 416 | CTGGGTCATAACGCT | 417 | YSLEER | 418 | TACAGTCTTGAAGAACGG | 419 |
| | 5 | F1 | DFQATT | 297 | GACTTTCAGGCCACAACT | 298 | SNEGSKA | 299 | TCCAATGAGGGCTCCAAGGCC | 300 |
| | 6 | H1 | — | — | — | — | — | — | — |
| | 7 | C2 | SGHRS | 372 | TCTGGGCATAGGAGT | 373 | YFSETQ | 374 | TACTTCAGTGAGACACAG | 375 |
| | 8 | D2 | MGHRA | 420 | ATGGGGCACAGGGCT | 421 | YSYEKL | 422 | TACAGCTATGAGAAACTC | 423 |
| | 9 | E2 | — | — | — | — | — | — | — |
| | 10 | E3 | SGHVS | 329 | TCGGGTCATGTATCC | 330 | FNYEAQ | 428 | TTCAATTATGAAGCCCAA | 429 |
| | 11 | D6 | SNHLY | 325 | TCTAATCACTTATAC | 326 | FYNNEI | 327 | TTTTATAATAATGAAATC | 328 |
| | 12 | H6 | SGHDT | 313 | TCTGGGCATGACACT | 314 | YYEEEE | 315 | TATTATGAGGAGGAAGAG | 316 |

TABLE 22-continued

| | | | | | | | | |
|---|---|---|---|---|---|---|---|---|
| 13 | E7 | SGH NS | 293 | TCA GGC CAC AAC TCC | 294 | FNN NVP | 295 | TTT AAC AAC AAC GTT CCG | 296 |
| 14 | F7 | MNH EY | 355 | ATG AAC CAT GAA TAC | 356 | SVG EGT | 357 | TCA GTT GGT GAG GGT ACA | 358 |
| 15 | B8 | — | — | — | — | — | — | — | — |
| 16 | D8 | — | — | — | — | — | — | — | — |
| 17 | F8 | SGH NS | 293 | TCA GGC CAC AAC TCC | 294 | FNN NVP | 295 | TTT AAC AAC AAC GTT CCG | 296 |
| 18 | E9 | SGH NS | 293 | TCA GGC CAC AAC TCC | 294 | FNN NVP | 295 | TTT AAC AAC AAC GTT CCG | 296 |
| 19 | F9 | SGH DY | 362 | TCA GGC CAC GAC TAC | 363 | FNN NVP | 295 | TTT AAC AAC AAC GTT CCG | 296 |
| 20 | B10 | — | — | — | — | — | — | — | — |
| 21 | C10 | SGH VS | 329 | TCG GGT CAT GTA TCC | 330 | FNY EAQ | 428 | TTC AAT TAT GAA GCC CAA | 429 |

TABLE 23

| | | TCRA | | | | | | |
|---|---|---|---|---|---|---|---|---|
| Row | Well | CDR 1 (aa) | SEQ ID NO | CDR 1 (nt) | SEQ ID NO | CDR 2 (aa) | SEQ ID NO | CDR 2 (nt) | SEQ ID NO |
| 1 | E3 | — | — | — | — | — | — | — |
| 2 | B4 | NSM FDY | 443 | AAC AGC ATG TTT GAT TAT | 444 | ISSIK DK | 445 | ATA AGT TCC ATT AAG GAT AAA | 446 |
| 3 | C4 | NSM FDY | 443 | AAC AGC ATG TTT GAT TAT | 444 | ISSIK DK | 445 | ATA AGT TCC ATT AAG GAT AAA | 446 |

TABLE 23-continued

| Row | Well | | | | | | | |
|---|---|---|---|---|---|---|---|---|
| 4 | E4 | — | — | — | — | — | — | — | — |
| 5 | F4 | — | — | — | — | — | — | — | — |

| | | TCRB | | | | | | |
|---|---|---|---|---|---|---|---|---|
| Row | Well | CDR 1 (aa) | SEQ ID NO | CDR 1 (nt) | SEQ ID NO | CDR 2 (aa) | SEQ ID NO | CDR 2 (nt) | SEQ ID NO |
| 1 | E3 | — | — | — | — | — | — | — |
| 2 | B4 | SGH DN | 412 | TCT GGA CAT GAT AAT | 413 | FVK ESK | 414 | TTT GTG AAA GAG TCT AAA | 415 |
| 3 | C4 | SGH DN | 412 | TCT GGA CAT GAT AAT | 413 | FVK ESK | 414 | TTT GTG AAA GAG TCT AAA | 415 |
| 4 | E4 | — | — | — | — | — | — | — |
| 5 | F4 | — | — | — | — | — | — | — |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The following list of embodiments is intended to complement, rather than displace or supersede, the previous descriptions:

Embodiment 1. A capicua transcriptional repressor (CIC) polypeptide fragment comprising an arginine to tryptophan amino acid substitution at a position corresponding to position 215 of SEQ ID NO: 102 (R215W), and an amino acid substitution at amino acid position 2 of the fragment, amino acid position 9 of the fragment, or both, wherein the fragment is at least nine amino acids in length, and wherein the fragment binds to HLA-A*02:01.

Embodiment 2. The CIC polypeptide fragment of embodiment 1, wherein the CIC polypeptide fragment has greater affinity for HLA-A*02:01 than a cognate native polypeptide fragment.

Embodiment 3. The CIC polypeptide fragment of embodiment 1 or 2, wherein the R215W substitution is at amino acid position 8 of the fragment.

Embodiment 4. The CIC polypeptide fragment of any one of embodiments 1-3, wherein the CIC polypeptide fragment is selected from the group consisting of SEQ ID NO: 25, SEQ ID NO: 26 and SEQ ID NO: 27.

Embodiment 5. A catenin beta 1 (CTNNB1) polypeptide fragment comprising: (a) a serine to cysteine amino acid substitution at a position corresponding to position 33 of SEQ ID NO: 103 (S33C), or (b) a serine to phenylalanine amino acid substitution at a position corresponding to position 37 of SEQ ID NO: 103 (S37F), and an amino acid substitution at amino acid position 2 of the fragment, amino acid position 9 of the fragment, or both, wherein the fragment is at least nine amino acids in length, and wherein the fragment binds to HLA-A*02:01.

Embodiment 6. The CTNNB1 polypeptide fragment of embodiment 5, wherein the CTNNB1 polypeptide fragment has greater affinity for HLA-A*02:01 than a cognate native polypeptide fragment.

Embodiment 7. The CTNNB1 polypeptide fragment of embodiment 5 or 6, wherein the S33C substitution is at amino acid position 4 of the fragment.

Embodiment 8. The CTNNB1 polypeptide fragment of embodiment 5 or 6, wherein the S37F substitution is at amino acid position 8 of the fragment.

Embodiment 9. The CTNNB1 polypeptide fragment of any one of embodiments 5-8, wherein the CTNNB1 polypeptide fragment is selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 80, and SEQ ID NO: 81.

Embodiment 10. An v-erb-b2 erythroblastic leukemia viral oncogene homolog B (ERBB2) polypeptide fragment comprising a valine to isoleucine amino acid substitution at a position corresponding to position 842 of SEQ ID NO: 104 (V842I), and an amino acid substitution at amino acid position 2 of the fragment, amino acid position 9 of the fragment, or both, wherein the fragment is at least nine amino acids in length, and wherein the fragment binds to HLA-A*02:01.

Embodiment 11. The ERBB2 polypeptide fragment of embodiment 10, wherein the ERBB2 polypeptide fragment has greater affinity for HLA-A*02:01 than a cognate native polypeptide fragment.

Embodiment 12. The ERBB2 polypeptide fragment of embodiment 10 or 11, wherein the V842I substitution at amino acid position 3 of the fragment.

Embodiment 13. The ERBB2 polypeptide fragment of any one of embodiments 10-13, wherein the ERBB2 polypeptide fragment is selected from the group consisting of SEQ ID NO: 84, SEQ ID NO: 85, and SEQ ID NO: 86.

Embodiment 14. A kirsten rat sarcoma (KRAS) polypeptide fragment comprising: (a) a glycine to alanine amino acid substitution at a position corresponding to position 12 of SEQ ID NO: 105 (G12A), (b) a glycine to cysteine amino acid substitution at a position corresponding to position 12 of SEQ ID NO: 105 (G12C), or (c) a glycine to valine amino acid substitution at a position corresponding to at position 12 of SEQ ID NO: 105 (G12V), and an amino acid substitution at amino acid position 2 of the fragment, amino acid position 9 of the fragment, or both, wherein the fragment is at least nine amino acids in length, and wherein the fragment binds to HLA-A*02:01.

Embodiment 15. The KRAS polypeptide fragment of embodiment 14, wherein the KRAS polypeptide fragment has greater affinity for HLA-A*02:01 than a cognate native polypeptide fragment.

Embodiment 16. The KRAS polypeptide fragment of embodiment 14 or 15, wherein the G12A substitution is at amino acid position 7 of the fragment.

Embodiment 17. The KRAS polypeptide fragment of embodiment 14 or 15, wherein the G12C substitution is at amino acid position 7 of the fragment.

Embodiment 18. The KRAS polypeptide fragment of embodiment 14 or 5, wherein the G12V substitution is at amino acid position 7 of the fragment.

Embodiment 19. The KRAS polypeptide fragment of any one of embodiments 14-18, wherein the KRAS polypeptide fragment is selected from the group consisting of SEQ ID NO: 37, SEQ ID NO: 38, SEQ ID NO: 39, SEQ ID NO: 40, SEQ ID NO: 41, and SEQ ID NO: 42.

Embodiment 20. A phosphatidylinositol-4,5-bisphosphate 3-kinase catalytic subunit alpha (PIK3CA) polypeptide fragment comprising: (a) a glutamic acid to lysine amino acid substitution at a position corresponding to position 453 of SEQ ID NO: 106 (E453K), or (b) a glycine to aspartic acid amino acid substitution at a position corresponding to position 118 of SEQ ID NO: 106 (G118D), and an amino acid substitution at amino acid position 2 of the fragment, amino acid position 9 of the fragment, or both, wherein the fragment is at least nine amino acids in length, and wherein the fragment binds to HLA-A*02:01.

Embodiment 21. The PIK3CA polypeptide fragment of embodiment 20, wherein the PIK3CA polypeptide fragment has greater affinity for HLA-A*02:01 than a cognate native polypeptide fragment.

Embodiment 22. The PIK3CA polypeptide fragment of embodiment 20 or 21, wherein the E453K substitution is at amino acid position 3 of the fragment.

Embodiment 23. The PIK3CA polypeptide fragment of embodiment 20 or 21, wherein the G118D substitution is at amino acid position 7 of the fragment.

Embodiment 24. The PIK3CA polypeptide fragment of any one of embodiments 20-23, wherein the PIK3CA polypeptide fragment is selected from the group consisting of SEQ ID NO: 43, SEQ ID NO: 44, SEQ ID NO: 45, SEQ ID NO: 46, and SEQ ID NO: 47.

Embodiment 25. A phosphatase and tensin homolog (PTEN) polypeptide fragment comprising an arginine to cysteine amino acid substitution at a position corresponding to position 173 of SEQ ID NO: 107 (R173C), and an amino acid substitution at amino acid position 3 of the fragment, amino acid position 10 of the fragment, or both, wherein the fragment is ten amino acids in length, and wherein the fragment binds to HLA-A*02:01.

Embodiment 26. The PTEN polypeptide fragment of embodiment 25, wherein the PTEN polypeptide fragment has greater affinity for HLA-A*02:01 than a cognate native polypeptide fragment.

Embodiment 27. The PTEN polypeptide fragment of embodiment 25 or 26, wherein the R173C substitution is at amino acid position 1 of the fragment.

Embodiment 28. The PTEN polypeptide fragment of any one of embodiments 25-27, wherein the PTEN polypeptide fragment is selected from the group consisting of SEQ ID NO: 48, SEQ ID NO: 49, and SEQ ID NO: 88.

Embodiment 29. A splicing factor 3b subunit 1 (SF3B1) polypeptide fragment comprising an arginine to histidine amino acid substitution at a position corresponding to position 625 of SEQ ID NO: 108 (R625H), and an amino acid substitution at amino acid position 2 of the fragment, amino acid position 9 of the fragment, or both, wherein the fragment is at least nine amino acids in length, and wherein the fragment binds to HLA-A*02:01.

Embodiment 30. The SF3B1 polypeptide fragment of embodiment 29, wherein the SF3B1 polypeptide fragment has greater affinity for HLA-A*02:01 than a cognate native epitope.

Embodiment 31. The SF3B1 polypeptide fragment of embodiment 29 or 30, wherein the R625H substitution is at amino acid position 7 of the fragment.

Embodiment 32. The SF3B1 polypeptide fragment of any one of embodiments 29-31, wherein the SF3B1 polypeptide fragment is selected from the group consisting of SEQ ID NO: 51, SEQ ID NO: 52, SEQ ID NO: 53, SEQ ID NO: 90, SEQ ID NO: 91 and SEQ ID NO: 92.

Embodiment 33. A SRY-box transcription factor 17 (SOX17) polypeptide fragment comprising a serine to isoleucine amino acid substitution at a position corresponding to position 403 of SEQ ID NO: 109 (S403I), and an amino acid substitution at amino acid position 2 of the fragment, amino acid position 9 of the fragment, or both, wherein the fragment is at least nine amino acids in length, and wherein the fragment binds to HLA-A*02:01.

Embodiment 34. The SOX17 polypeptide fragment of embodiment 33, wherein the SOX17 polypeptide fragment has greater affinity for HLA-A*02:01 than a cognate native polypeptide fragment.

Embodiment 35. The SOX17 polypeptide fragment of embodiment 33 or 34, wherein the S403I substitution is at amino acid position 6 of the fragment.

Embodiment 36. The SOX17 polypeptide fragment of any one of embodiments 33-35, wherein the SOX17 polypeptide fragment is selected from the group consisting of SEQ ID NO: 54, SEQ ID NO: 55, SEQ ID NO: 56, and SEQ ID NO: 93.

Embodiment 37. A tumor protein 53 (TP53) polypeptide fragment comprising: (a) an arginine to leucine amino acid substitution at a position corresponding to position 110 of SEQ ID NO: 110 (R110L), (b) a serine to phenylalanine amino acid substitution at a position corresponding to position 127 of SEQ ID NO: 110 (S127F), (c) a lysine to asparagine amino acid substitution at a position corresponding to position 132 of SEQ ID NO: 110 (K132N), (d) a cysteine to tyrosine amino acid substitution at a position corresponding to position 141 of SEQ ID NO: 110 (C141Y), (e) a proline to leucine amino acid substitution at a position corresponding to position 152 of SEQ ID NO: 110 (P152L), (f) a histidine to leucine amino acid substitution at a position corresponding to position 193 of SEQ ID NO: 110 (H193L), (g) a histidine to tyrosine amino acid substitution at a position corresponding to position 193 of SEQ ID NO: 110

(H193Y), (h) a tyrosine to cysteine amino acid substitution at a position corresponding to position 220 of SEQ ID NO: 110 (Y220C), or (i) a valine to methionine amino acid substitution at a position corresponding to position 272 of SEQ ID NO: 110 (V272M), and an amino acid substitution at amino acid position 2 of the fragment, amino acid position 9 of the fragment, or both, wherein the fragment is at least nine amino acids in length, and wherein the fragment binds to HLA-A*02:01.

Embodiment 38. The TP53 polypeptide fragment of embodiment 37, wherein the TP53 polypeptide fragment has greater affinity for HLA-A*02:01 than a cognate native polypeptide fragment.

Embodiment 39. The TP53 polypeptide fragment of embodiment 37 or 38, wherein the R110L substitution is at amino acid position 8 of the fragment.

Embodiment 40. The TP53 polypeptide fragment of embodiment 37 or 38, wherein the S127F substitution is at amino acid position 7 of the fragment.

Embodiment 41. The TP53 polypeptide fragment of embodiment 37 or 38, wherein the K132N substitution is at amino acid position 4 of the fragment.

Embodiment 42. The TP53 polypeptide fragment of embodiment 37 or 38, wherein the C141Y substitution is at amino acid position 3 of the fragment.

Embodiment 43. The TP53 polypeptide fragment of embodiment 37 or 38, wherein the P152L substitution is at amino acid position 9 of the fragment.

Embodiment 44. The TP53 polypeptide fragment of embodiment 37 or 38, wherein the H193L substitution is at amino acid position 7 of the fragment.

Embodiment 45. The TP53 polypeptide fragment of embodiment 37 or 38, wherein the Y220C substitution is at amino acid position 4 of the fragment.

Embodiment 46. The TP53 polypeptide fragment of embodiment 37 or 38, wherein the V272M substitution is at amino acid position 9 of the fragment.

Embodiment 47. The TP53 polypeptide fragment of any one of embodiments 37-46, wherein the TP53 polypeptide fragment is selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 66, SEQ ID NO: 67, SEQ ID NO: 68, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 94, SEQ ID NO: 95, and SEQ ID NO: 96.

Embodiment 48. A polypeptide fragment selected from the group consisting of SEQ ID NO: 25, SEQ ID NO: 26 and SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 66, SEQ ID NO: 67, SEQ ID NO: 68, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 78, SEQ ID NO: 79, SEQ ID NO: 80, SEQ ID NO: 81; SEQ ID NO: 84, SEQ ID NO: 85, and SEQ ID NO: 86, SEQ ID NO: 88, SEQ ID NO: 90, SEQ ID NO: 91, SEQ ID NO: 92, SEQ ID NO: 93, SEQ ID NO: 94, SEQ ID NO: 95, and SEQ ID NO: 96.

Embodiment 49. A polypeptide fragment selected from the group consisting of SEQ ID NO: 29, SEQ ID NO: 32, SEQ ID NO: 45, SEQ ID NO: 59, SEQ ID NO: 64, SEQ ID NO: 68, SEQ ID NO: 75 and SEQ ID NO: 78.

Embodiment 50. A polynucleotide encoding at least one or more polypeptide fragments according to any one of embodiment 1-49.

Embodiment 51. The polynucleotide of embodiment 50, wherein the polynucleotide is cDNA.

Embodiment 52. A vector comprising at least one or more polynucleotides of embodiment 50 or 51.

Embodiment 53. The vector of embodiment 52, wherein the vector is selected from an adenovirus vector, an alphaviral vector, a poxvirus vector, an adeno-associated virus vector, a retrovirus vector, a self-replicating RNA molecule, and a combination thereof.

Embodiment 54. The vector of embodiment 53, wherein the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

Embodiment 55. The vector of embodiment 53, wherein the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Embodiment 56. The vector of embodiment 53, wherein the vector is the adenovirus vector comprising a polynucleotide encoding at least one or more polypeptide fragments according to any one of embodiment 1-55.

Embodiment 57. A pharmaceutical composition comprising at least one or more polypeptide fragments according to any one of embodiments 1-49.

Embodiment 58. A pharmaceutical composition comprising a polynucleotide according to embodiment 50 or 51.

Embodiment 59. A pharmaceutical composition comprising a vector according to any one of embodiments 52-56.

Embodiment 60. A method of treating cancer in a subject comprising administering to the subject in need thereof the polypeptide of any one of embodiments 1-49, the polynucleotide of embodiment 50 or 51, the vector of any one of embodiments 52-56, or the pharmaceutical composition of any one of embodiments 57-59.

Embodiment 61. A method of inducing an immune response in a subject comprising administering to the subject in need thereof the polypeptide of any one of embodiments 1-49, the polynucleotide of embodiment 50 or 51, the vector of any one of embodiments 52-56, or the pharmaceutical composition of any one of embodiments 57-59.

Embodiment 62. A method of treating, preventing, reducing a risk of onset or delaying the onset of a clinical condition characterized by expression of a catenin beta 1 (CTNNB1) mutant comprising a serine to cysteine amino acid substitution at a position corresponding to position 33 of SEQ ID NO: 103 (S33C) in a subject, the method comprising administering to the subject in need thereof (a) a polynucleotide encoding a polypeptide fragment comprising SEQ ID NO: 2, (b) a polynucleotide encoding a polypeptide fragment comprising SEQ ID NO: 29, or (c) a combination thereof in an amount effective to treat, prevent, reduce the risk of onset or delay the onset of the clinical condition.

Embodiment 63. A method of treating, preventing, reducing a risk of onset or delaying the onset of a clinical condition characterized by expression of a catenin beta 1 (CTNNB1) mutant comprising a serine to phenylalanine amino acid substitution at a position corresponding to position 37 of SEQ ID NO: 103 (S37F) in a subject, the method comprising administering to the subject in need thereof (a) a polynucleotide encoding a polypeptide fragment comprising SEQ ID NO: 3, (b) a polynucleotide encoding a polypeptide fragment comprising SEQ ID NO: 32, or (c) a combination thereof in an amount effective to treat, prevent, reduce the risk of onset or delay the onset of the clinical condition.

Embodiment 64. A method of treating, preventing, reducing a risk of onset or delaying the onset of a clinical condition characterized by expression of a phosphatidylinositol-4,5-bisphosphate 3-kinase catalytic subunit alpha (PIK3CA) mutant comprising a glycine to aspartic acid amino acid substitution at a position corresponding to position 118 of SEQ ID NO: 106 (G118D) in a subject, the method comprising administering to the subject in need thereof (a) a polynucleotide encoding a polypeptide fragment comprising SEQ ID NO: 9, (b) a polynucleotide encoding a polypeptide fragment comprising SEQ ID NO: 45, or (c) a combination thereof in an amount effective to treat, prevent, reduce the risk of onset or delay the onset of the clinical condition.

Embodiment 65. A method of treating, preventing, reducing a risk of onset or delaying the onset of a clinical condition characterized by expression of a tumor protein 53 (TP53) mutant comprising a cysteine to tyrosine amino acid substitution at a position corresponding to position 141 of SEQ ID NO: 110 (C141Y) in a subject, the method comprising administering to the subject in need thereof (a) a polynucleotide encoding a polypeptide fragment comprising SEQ ID NO: 13, (b) a polynucleotide encoding a polypeptide fragment comprising SEQ ID NO: 59, or (c) a combination thereof in an amount effective to treat, prevent, reduce the risk of onset or delay the onset of the clinical condition.

Embodiment 66. A method of treating, preventing, reducing a risk of onset or delaying the onset of a clinical condition characterized by expression of a tumor protein 53 (TP53) mutant comprising a lysine to asparagine amino acid substitution at a position corresponding to position 132 of SEQ ID NO: 110 (K132N) in a subject, the method comprising administering to the subject in need thereof (a) a polynucleotide encoding a polypeptide fragment comprising SEQ ID NO: 16, (b) a polynucleotide encoding a polypeptide fragment comprising SEQ ID NO: 64, or (c) a combination thereof in an amount effective to treat, prevent, reduce the risk of onset or delay the onset of the clinical condition.

Embodiment 67. A method of treating, preventing, reducing a risk of onset or delaying the onset of a clinical condition characterized by expression of a tumor protein 53 (TP53) mutant comprising a proline to leucine amino acid substitution at a position corresponding to position 152 of SEQ ID NO: 110 (P152L) in a subject, the method comprising administering to the subject in need thereof (a) a polynucleotide encoding a polypeptide fragment comprising SEQ ID NO: 18, (b) a polynucleotide encoding a polypeptide fragment comprising SEQ ID NO: 68, or (c) a combination thereof in an amount effective to treat, prevent, reduce the risk of onset or delay the onset of the clinical condition.

Embodiment 68. A method of treating, preventing, reducing a risk of onset or delaying the onset of a clinical condition characterized by expression of a tumor protein 53 (TP53) mutant comprising a valine to methionine amino acid substitution at a position corresponding to position 272 of SEQ ID NO: 110 (V272M) in a subject, the method comprising administering to the subject in need thereof (a) a polynucleotide encoding a polypeptide fragment comprising SEQ ID NO: 22, (b) a polynucleotide encoding a polypeptide fragment comprising SEQ ID NO: 75, or (c) a combination thereof in an amount effective to treat, prevent, reduce the risk of onset or delay the onset of the clinical condition.

Embodiment 69. A method of treating, preventing, reducing a risk of onset or delaying the onset of a clinical condition characterized by expression of a tumor protein 53 (TP53) mutant comprising a tyrosine to cysteine amino acid substitution at a position corresponding to position 220 of SEQ ID NO: 110 (Y220C) in a subject, the method comprising administering to the subject in need thereof (a) a polynucleotide encoding a polypeptide fragment comprising SEQ ID NO: 23, (b) a polynucleotide encoding a polypeptide fragment comprising SEQ ID NO: 78, or (c) a combination thereof in an amount effective to treat, prevent, reduce the risk of onset or delay the onset of the clinical condition.

Embodiment 70. The method of any one of embodiments 62-69, comprising administering the polynucleotide in part a) prior to administering the polynucleotide in part b).

Embodiment 71. The method of any one of embodiments 62-69, comprising administering the polynucleotide in part b) prior to administering the polynucleotide in part a).

Embodiment 72. The method of any one of embodiments 62-71, comprising administering the polynucleotide in part a) concurrently with the polynucleotide in part b).

Embodiment 73. The method of any one of embodiments 62-69, comprising administering a vector encoding the polynucleotide of part a) and a vector encoding the polynucleotide of part b).

Embodiment 74. The method of embodiment 73, wherein the vectors are independently selected from an adenovirus vector, an alphaviral vector, a poxvirus vector, an adeno-associated virus vector, a retrovirus vector, and a self-replicating RNA molecule.

Embodiment 75. The method of embodiment 74, wherein the adenovirus vector is selected from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, and PanAd3.

Embodiment 76. The method of embodiment 74, wherein the poxvirus vector is selected from smallpox virus vector, vaccinia virus vector, cowpox virus vector, monkeypox virus vector, Copenhagen vaccinia virus (W) vector, New York Attenuated Vaccinia Virus (NYVAC) vector, and Modified Vaccinia Ankara (MVA) vector.

Embodiment 77. A kit of parts comprising a pair of polypeptide fragments selected from the group consisting of: (a) SEQ ID NO: 2 and SEQ ID NO: 29; (b) SEQ ID NO: 3 and SEQ ID NO: 32; (c) SEQ ID NO: 9 and SEQ ID NO: 45; (d) SEQ ID NO: 13 and SEQ ID NO: 59; (e) SEQ ID NO: 16 and SEQ ID NO: 64; (f) SEQ ID NO: 18 and SEQ ID NO 68; (g) SEQ ID NO: 22 and SEQ ID NO: 75; and (h) SEQ ID NO: 23 and SEQ ID NO: 78.

Embodiment 78. A kit of parts comprising a pair of polypeptide fragments selected from the group consisting of: (a) SEQ ID NO: 9 and SEQ ID NO: 45 (b) SEQ ID NO: 13 and SEQ ID NO: 59; and (c) SEQ ID NO: 18 and SEQ ID NO 68.

Embodiment 79. A method for generating CD8+ T-cells that are positive for an HLA-A*02:01-restricted polypeptide fragment and a cognate native polypeptide fragment, comprising exposing CD8+ T-cells to the HLA-A*02:01-restricted polypeptide fragment and cognate native polypeptide fragment selected from the group consisting of: (a) SEQ ID NO: 2 and SEQ ID NO: 29; (b) SEQ ID NO: 3 and SEQ ID NO: 32; (c) SEQ ID NO: 9 and SEQ ID NO: 45; (d) SEQ ID NO: 13 and SEQ ID NO: 59; (e) SEQ ID NO: 16 and SEQ ID NO: 64; (f) SEQ ID NO: 18 and SEQ ID NO 68; (g) SEQ ID NO: 22 and SEQ ID NO: 75; and (h) SEQ ID NO: 23 and SEQ ID NO: 78; and selecting CD8+ T cells that are positive to both the HLA-A*02:01-restricted polypeptide fragment and a cognate neoantigen polypeptide fragment.

Embodiment 80. A method for generating CD8+ T-cells that are positive for an HLA-A*02:01-restricted polypeptide fragment and a cognate native polypeptide fragment, comprising exposing CD8+ T-cells to the HLA-A*02:01-restricted polypeptide fragment and cognate native polypeptide fragment selected from the group consisting of: (a) SEQ ID NO: 9 and SEQ ID NO: 45; (b) SEQ ID NO: 13 and SEQ ID NO: 59; and (c) SEQ ID NO: 18 and SEQ ID NO 68; and selecting CD8+ T cells that are positive to both the HLA-A*02:01-restricted polypeptide fragment and a cognate neoantigen polypeptide fragment.

Embodiment 81. A T-cell receptor (TCR) comprising an alpha chain and a beta chain, wherein: (a) the alpha chain comprises a complementarity determining region 3 (CDR3) comprising the amino acid sequence of SEQ ID NO: 120 and the beta chain comprises a CDR3 comprising the amino acid sequence of SEQ ID NO: 114; (b) the alpha chain comprises a CDR3 comprising the amino acid sequence of SEQ ID NO: 118 and the beta chain comprises a CDR3 comprising the amino acid sequence of SEQ ID NO: 114; (c) the alpha chain comprises a CDR3 comprising the amino acid sequence of SEQ ID NO: 122 and the beta chain comprises a CDR3 comprising the amino acid sequence of SEQ ID NO: 114; (d) the alpha chain comprises a CDR3 comprising the amino acid sequence of SEQ ID NO: 122 and the beta chain comprises a CDR3 comprising the amino acid sequence of SEQ ID NO: 124; (e) the alpha chain comprises a CDR3 comprising the amino acid sequence of SEQ ID NO: 122 and the beta chain comprises a CDR3 comprising the amino acid sequence of SEQ ID NO: 134; (f) the alpha chain comprises a CDR3 comprising the amino acid sequence of SEQ ID NO: 112 and the beta chain comprises a CDR3 comprising the amino acid sequence of SEQ ID NO: 114; (g) the alpha chain comprises a CDR3 comprising the amino acid sequence of SEQ ID NO: 116 and the beta chain comprises a CDR3 comprising the amino acid sequence of SEQ ID NO: 114; (h) the alpha chain comprises a CDR3 comprising the amino acid sequence of SEQ ID NO: 116 and the beta chain comprises a CDR3 comprising the amino acid sequence of SEQ ID NO: 128; (i) the alpha chain comprises a CDR3 comprising the amino acid sequence of SEQ ID NO: 126 and the beta chain comprises a CDR3 comprising the amino acid sequence of SEQ ID NO: 114; (j) the alpha chain comprises a CDR3 comprising the amino acid sequence of SEQ ID NO: 130 and the beta chain comprises a CDR3 comprising the amino acid sequence of SEQ ID NO: 114; (k) the alpha chain comprises a CDR3 comprising the amino acid sequence of SEQ ID NO: 130 and the beta chain comprises a CDR3 comprising the amino acid sequence of SEQ ID NO: 132; or (1) the alpha chain comprises a CDR3 comprising the amino acid sequence of SEQ ID NO: 130 and the beta chain comprises a CDR3 comprising the amino acid sequence of SEQ ID NO: 134.

Embodiment 82. A T-cell receptor (TCR) comprising an alpha chain and a beta chain, wherein: (a) the alpha chain comprises a complementarity determining region 3 (CDR3) comprising the amino acid sequence of SEQ ID NO: 118 and the beta chain comprises a CDR3 comprising the amino acid sequence of SEQ ID NO: 114; (b) the alpha chain comprises a CDR3 comprising the amino acid sequence of SEQ ID NO: 118 and the beta chain comprises a CDR3 comprising the amino acid sequence of SEQ ID NO: 142; (c) the alpha chain comprises a CDR3 comprising the amino acid sequence of SEQ ID NO: 207 and the beta chain comprises a CDR3 comprising the amino acid sequence of SEQ ID NO: 114; (d) the alpha chain comprises a CDR3 comprising the amino acid sequence of SEQ ID NO: 112 and the beta chain comprises a CDR3 comprising the amino acid sequence of SEQ ID NO: 114; (e) the alpha chain comprises a CDR3 comprising the amino acid sequence of SEQ ID NO: 205 and the beta chain comprises a CDR3 comprising the amino acid sequence of SEQ ID NO: 114; (f) the alpha chain comprises a CDR3 comprising the amino acid sequence of SEQ ID NO: 172 and the beta chain comprises a CDR3 comprising the amino acid sequence of SEQ ID NO: 114; (g) the alpha chain comprises a CDR3 comprising the amino acid sequence of SEQ ID NO: 172 and the beta chain comprises a CDR3 comprising the amino acid sequence of SEQ ID NO: 166; (h) the alpha chain comprises a CDR3 comprising the amino acid sequence of SEQ ID NO: 186 and the beta chain comprises a CDR3 comprising the amino acid sequence of SEQ ID NO: 114; (i) the alpha chain comprises a CDR3 comprising the amino acid sequence of SEQ ID NO: 152 and the beta chain comprises a CDR3 comprising the amino acid sequence of SEQ ID NO: 114; (j) the alpha chain comprises a CDR3 comprising the amino acid sequence of SEQ ID NO: 130 and the beta chain comprises a CDR3 comprising the amino acid sequence of SEQ ID NO: 114; (k) the alpha chain comprises a CDR3 comprising the amino acid sequence of SEQ ID NO: 130 and the beta chain comprises a CDR3 comprising the amino acid sequence of SEQ ID NO: 142; (1) the alpha chain comprises a CDR3 comprising the amino acid sequence of SEQ ID NO: 130 and the beta chain comprises a CDR3 comprising the amino acid sequence of SEQ ID NO: 150; (m) the alpha chain comprises a CDR3 comprising the amino acid sequence of SEQ ID NO: 130 and the beta chain comprises a CDR3 comprising the amino acid sequence of SEQ ID NO: 162; (n) the alpha chain comprises a CDR3 comprising the amino acid sequence of SEQ ID NO: 136 and the beta chain comprises a CDR3 comprising the amino acid sequence of SEQ ID NO: 114; (o) the alpha chain comprises a CDR3 comprising the amino acid sequence of SEQ ID NO: 136 and the beta chain comprises a CDR3 comprising the amino acid sequence of SEQ ID NO: 138; (p) the alpha chain comprises a CDR3 comprising the amino acid sequence of SEQ ID NO: 136 and the beta chain comprises a CDR3 comprising the amino acid sequence of SEQ ID NO: 142; (q) the alpha chain comprises a CDR3 comprising the amino acid sequence of SEQ ID NO: 140 and the beta chain comprises a CDR3 comprising the amino acid sequence of SEQ ID NO: 114; (r) the alpha chain comprises a CDR3 comprising the amino acid sequence of SEQ ID NO: 140 and the beta chain comprises a CDR3 comprising the amino acid sequence of SEQ ID NO: 160; (s) the alpha chain comprises a CDR3 comprising the amino acid sequence of SEQ ID NO: 144 and the beta chain comprises a CDR3 comprising the amino acid sequence of SEQ ID NO: 114; (t) the alpha chain comprises a CDR3 comprising the amino acid sequence of SEQ ID NO: 144 and the beta chain comprises a CDR3 comprising the amino acid sequence of SEQ ID NO: 146; (u) the alpha chain comprises a CDR3 comprising the amino acid sequence of SEQ ID NO: 144 and the beta chain comprises a CDR3 comprising the amino acid sequence of SEQ ID NO: 158; (v) the alpha chain comprises a CDR3 comprising the amino acid sequence of SEQ ID NO: 148 and the beta chain comprises a CDR3 comprising the amino acid sequence of SEQ ID NO: 114; (w) the alpha chain comprises a CDR3 comprising the amino acid sequence of SEQ ID NO: 148 and the beta chain comprises a CDR3 comprising the amino acid sequence of SEQ ID NO: 150; (x) the alpha chain comprises a CDR3 comprising the amino acid sequence of SEQ ID NO: 154 and the beta chain comprises a CDR3 comprising the amino acid sequence of SEQ ID NO: 156; (y) the alpha chain comprises a CDR3 comprising the amino acid sequence of SEQ ID NO: 164 and the beta chain comprises a CDR3 comprising the amino acid sequence of SEQ ID NO: 114; (z) the alpha chain comprises a CDR3 comprising the amino acid sequence of SEQ ID NO: 164 and the beta chain comprises a CDR3 comprising the amino acid sequence of SEQ ID NO: 166; (aa) the alpha chain comprises a CDR3 comprising the amino acid sequence of SEQ ID NO: 164 and the beta chain comprises a CDR3 comprising the amino acid sequence of SEQ ID NO: 180; (bb) the alpha chain comprises a CDR3 comprising the amino acid sequence of SEQ ID NO: 164 and the beta chain comprises a CDR3 comprising the amino acid sequence of SEQ ID NO: 182; (cc) the alpha chain comprises a CDR3 comprising the amino acid sequence of SEQ I) NO: 164 and the beta chain comprises a CDR3 comprising the amino acid sequence of SEQ ID NO: 197; (dd) the alpha chain comprises a CDR3 comprising the amino acid sequence of SEQ ID NO: 168 and the beta chain comprises a CDR3 comprising the amino acid sequence of SEQ ID NO: 114; (ee) the alpha chain comprises a CDR3 comprising the amino acid sequence of SEQ ID NO: 168 and the beta chain comprises a CDR3 comprising the amino acid sequence of SEQ ID NO: 170; (ff) the alpha chain comprises a CDR3 comprising the amino acid sequence of SEQ ID NO: 168 and the beta chain comprises a CDR3 comprising the amino acid sequence of SEQ ID NO: 199; (gg) the alpha chain comprises a CDR3 comprising the amino acid sequence of SEQ ID NO: 174 and the beta chain comprises a CDR3 comprising the amino acid sequence of SEQ ID NO: 176; (hh) the alpha chain comprises a CDR3 comprising the amino acid sequence of SEQ ID NO: 174 and the beta chain comprises a CDR3 comprising the amino acid sequence of SEQ ID NO: 178; (ii) the alpha chain comprises a CDR3 comprising the amino acid sequence of SEQ ID NO: 184 and the beta chain comprises a CDR3 comprising the amino acid sequence of SEQ ID NO: 114; (jj) the alpha chain comprises a CDR3 comprising the amino acid sequence of SEQ ID NO: 184 and the beta chain comprises a CDR3 comprising the amino acid sequence of SEQ ID NO: 188; (kk) the alpha chain comprises a CDR3 comprising the amino acid sequence of SEQ ID NO: 190 and the beta chain comprises a CDR3 comprising the amino acid sequence of SEQ ID NO: 192; (11) the alpha chain comprises a CDR3 comprising the amino acid sequence of SEQ ID NO: 194 and the beta chain comprises a CDR3 comprising the amino acid sequence of SEQ ID NO: 114; (mm) the alpha chain comprises a CDR3 comprising the amino acid sequence of SEQ ID NO: 201 and the beta chain comprises a CDR3 comprising the amino acid sequence of SEQ ID NO: 203; or (nn) the alpha chain comprises a CDR3 comprising the amino acid sequence of SEQ ID NO: 210 and the beta chain comprises a CDR3 comprising the amino acid sequence of SEQ ID NO: 114.

Embodiment 83. A T-cell receptor (TCR) comprising an alpha chain and a beta chain, wherein: (a) the alpha chain comprises a complementarity determining region 3 (CDR3) comprising the amino acid sequence of SEQ ID NO: 172 and the beta chain comprises a CDR3 comprising the amino acid sequence of SEQ ID NO: 114; (b) the alpha chain comprises a CDR3 comprising the amino acid sequence of SEQ ID NO: 172 and the beta chain comprises a CDR3 comprising the amino acid sequence of SEQ ID NO: 170; (c) the alpha chain comprises a CDR3 comprising the amino acid sequence of SEQ ID NO: 172 and the beta chain comprises a CDR3 comprising the amino acid sequence of SEQ ID NO: 213; (d) the alpha chain comprises a CDR3 comprising the amino acid sequence of SEQ ID NO: 152 and the beta chain comprises a CDR3 comprising the amino acid sequence of SEQ ID NO: 114; (e) the alpha chain comprises a CDR3 comprising the amino acid sequence of SEQ ID NO: 168 and the beta chain comprises a CDR3 comprising the amino acid sequence of SEQ ID NO: 170; (f) the alpha chain comprises a CDR3 comprising the amino acid sequence of SEQ ID NO: 215 and the beta chain comprises a CDR3 comprising the amino acid sequence of SEQ ID NO: 114; (g) the alpha chain comprises a CDR3 comprising the amino acid sequence of SEQ ID NO: 217 and the beta chain comprises a CDR3 comprising the amino acid sequence of SEQ ID NO: 114; (h) the alpha chain comprises a CDR3 comprising the amino acid sequence of SEQ ID NO: 219 and the beta chain comprises a CDR3 comprising the amino acid sequence of SEQ ID NO: 114; (i) the alpha chain comprises a CDR3 comprising the amino acid sequence of SEQ ID NO: 219 and the beta chain comprises a CDR3 comprising the amino acid sequence of SEQ ID NO: 221; or (j) the alpha chain comprises a CDR3 comprising the amino acid sequence of SEQ ID NO: 223 and the beta chain comprises a CDR3 comprising the amino acid sequence of SEQ ID NO: 221.

Embodiment 84. A T-cell receptor (TCR) comprising an alpha chain and a beta chain, wherein: (a) the alpha chain comprises a complementarity determining region 3 (CDR3) comprising the amino acid sequence of SEQ ID NO: 152 and the beta chain comprises a CDR3 comprising the amino acid sequence of SEQ ID NO: 252; (b) the alpha chain comprises a CDR3 comprising the amino acid sequence of SEQ ID NO: 152 and the beta chain comprises a CDR3 comprising the amino acid sequence of SEQ ID NO: 114; (c) the alpha chain comprises a CDR3 comprising the amino acid sequence of SEQ ID NO: 248 and the beta chain comprises a CDR3 comprising the amino acid sequence of SEQ ID NO: 250; (d) the alpha chain comprises a CDR3 comprising the amino acid sequence of SEQ ID NO: 248 and the beta chain comprises a CDR3 comprising the amino acid sequence of SEQ ID NO: 258; (e) the alpha chain comprises a CDR3 comprising the amino acid sequence of SEQ ID NO: 254 and the beta chain comprises a CDR3 comprising the amino acid sequence of SEQ ID NO: 256; (f) the alpha chain comprises a CDR3 comprising the amino acid sequence of SEQ ID NO: 254 and the beta chain comprises a CDR3 comprising the amino acid sequence of SEQ ID NO: 114; (g) the alpha chain comprises a CDR3 comprising the amino acid sequence of SEQ II) NO: 263 and the beta chain comprises a CDR3 comprising the amino acid sequence of SEQ ID NO: 265; (h) the alpha chain comprises a CDR3 comprising the amino acid sequence of SEQ ID NO: 267 and the beta chain comprises a CDR3 comprising the amino acid sequence of SEQ ID NO: 269; (i) the alpha chain comprises a CDR3 comprising the amino acid sequence of SEQ ID NO: 267 and the beta chain comprises a CDR3 comprising the amino acid sequence of SEQ ID NO: 271; (j) the alpha chain comprises a CDR3 comprising the amino acid sequence of SEQ ID NO: 273 and the beta chain comprises a CDR3 comprising the amino acid sequence of SEQ ID NO: 275; (k) the alpha chain comprises a CDR3 comprising the amino acid sequence of SEQ ID NO: 277 and the beta chain comprises a CDR3 comprising the amino acid sequence of SEQ ID NO: 279; (1) the alpha chain comprises a CDR3 comprising the amino acid sequence of SEQ ID NO: 281 and the beta chain comprises a CDR3 comprising the amino acid sequence of SEQ ID NO: 283; or (m) the alpha chain comprises a CDR3 comprising the amino acid sequence of SEQ ID NO: 285 and the beta chain comprises a CDR3 comprising the amino acid sequence of SEQ ID NO: 287.

Embodiment 85. A T-cell receptor (TCR) comprising an alpha chain and a beta chain, wherein: (a) the alpha chain comprises a complementarity determining region 3 (CDR3) comprising the amino acid sequence of SEQ ID NO: 248 and the beta chain comprises a CDR3 comprising the amino acid sequence of SEQ ID NO: 114; (b) the alpha chain comprises a CDR3 comprising the amino acid sequence of SEQ ID NO: 289 and the beta chain comprises a CDR3 comprising the amino acid sequence of SEQ ID NO: 291; or (c) the alpha chain comprises a CDR3 comprising the amino acid sequence of SEQ ID NO: 289 and the beta chain comprises a CDR3 comprising the amino acid sequence of SEQ ID NO: 114.

Embodiment 86. A polynucleotide encoding the TCR of any one of embodiments 81-85.

Embodiment 87. A vector comprising the polynucleotide of embodiment 86.

Embodiment 88. A cell transformed to express the polynucleotide of embodiment 86.

Embodiment 89. A cell comprising the vector of embodiment 87.

Embodiment 90. The cell of embodiment 88 or 89, wherein the cell is a CD8+ T cell.

Embodiment 91. A pharmaceutical composition comprising the TCR of any one of embodiment 82-85, the polynucleotide of embodiment 86, the vector of embodiment 87, or the cell of any one of embodiments 88-90.

Embodiment 92. A method of treating cancer in a subject comprising administering to the subject in need thereof a pharmaceutical composition of embodiment 91.

Embodiment 93. A method of inducing an immune response in a subject comprising administering to the subject in need thereof a pharmaceutical composition of embodiment 91.

Embodiment 94. A method of treating, preventing, reducing a risk of onset or delaying the onset of a clinical condition characterized by expression of a phosphatidylinositol-4,5-bisphosphate 3-kinase catalytic subunit alpha (PIK3CA) mutant comprising a glycine to aspartic acid amino acid substitution at a position corresponding to position 118 of SEQ ID NO: 106 (G118D) in a subject comprising administering to the subject in need thereof the TCR of embodiment 81.

Embodiment 95. A method of treating, preventing, reducing a risk of onset or delaying the onset of a clinical condition characterized by expression of a tumor protein 53 (TP53) mutant comprising a cysteine to tyrosine amino acid substitution at a position corresponding to position 141 of SEQ ID NO: 110 (C141Y) in a subject comprising administering to the subject in need thereof the TCR of embodiment 82.

Embodiment 96. A method of treating, preventing, reducing a risk of onset or delaying the onset of a clinical condition characterized by expression of a tumor protein 53 (TP53) mutant comprising a proline to leucine amino acid substitution at a position corresponding to position 152 of SEQ ID NO: 110 (P152L) in a subject comprising administering to the subject in need thereof the TCR of embodiment 83.

Embodiment 97. A method of treating, preventing, reducing a risk of onset or delaying the onset of a clinical condition characterized by expression of a catenin beta 1 (CTNNB1) mutant comprising a serine to phenylalanine amino acid substitution at a position corresponding to position 37 of SEQ ID NO: 103 (S37F) in a subject comprising administering to the subject in need thereof the TCR of embodiment 84.

Embodiment 98. A method of treating, preventing, reducing a risk of onset or delaying the onset of a clinical condition characterized by expression of a tumor protein 53 (TP53) mutant comprising a tyrosine to cysteine amino acid substitution at a position corresponding to position 220 of SEQ ID NO: 110 (Y220C) in a subject comprising administering to the subject in need thereof the TCR of embodiment 85.

The invention claimed is:

1. A polynucleotide encoding at least one or more polypeptide fragments selected from:
   a) a capicua transcriptional repressor (CIC) polypeptide fragment of nine amino acids in length comprising:
   an amino acid substitution at amino acid position 2 of the fragment, amino acid position 9 of the fragment, or both, and
   an arginine to tryptophan amino acid substitution at a position corresponding to position 215 (R215W) of SEQ ID NO: 102, wherein the R215W substitution is at amino acid position 8 of the fragment;
   b) a catenin beta 1 (CTNNB1) polypeptide fragment of nine amino acids in length comprising:
   an amino acid substitution at amino acid position 2 of the fragment, amino acid position 9 of the fragment, or both, and
   i. a serine to cysteine amino acid substitution at a position corresponding to position 33 (S33C) of SEQ ID NO: 103, wherein the S33C substitution is at amino acid position 4 of the fragment, or
   ii. a serine to phenylalanine amino acid substitution at a position corresponding to position 37 (S37F) of SEQ ID NO: 103, wherein the S37F substitution is at amino acid position 8 of the fragment;
   c) a v-erb-b2 erythroblastic leukemia viral oncogene homolog B (ERBB2) polypeptide fragment of nine amino acids in length comprising:
   an amino acid substitution at amino acid position 2 of the fragment, amino acid position 9 of the fragment, or both, and
   a valine to isoleucine amino acid substitution at a position corresponding to position 842 (V842I) of SEQ ID NO: 104, wherein the V842I substitution is at amino acid position 3 of the fragment;
   d) a kirsten rat sarcoma (KRAS) polypeptide fragment of nine amino acids in length comprising:
   an amino acid substitution at amino acid position 2 of the fragment, amino acid position 9 of the fragment, or both, and
   a glycine to alanine amino acid substitution at a position corresponding to position 12 (G12A) of SEQ ID NO: 105, wherein the G12A substitution is at amino acid position 7 of the fragment; or
   e) a phosphatase and tensin homolog (PTEN) polypeptide fragment of ten amino acids in length comprising:
   an amino acid substitution at amino acid position 3 of the fragment, amino acid position 10 of the fragment, or both, and
   an arginine to cysteine amino acid substitution at a position corresponding to position 173 (R173C) of SEQ ID NO: 107, wherein the R173C substitution is at amino acid position 1 of the fragment,
   wherein the one or more polypeptide fragment binds to HLA-A*02:01.

2. The polynucleotide of claim 1, wherein the polynucleotide is cDNA.

3. A vector comprising the polynucleotide of claim 1.

4. The vector of claim 3, wherein the vector is selected from the group consisting of an adenovirus vector, an alphaviral vector, a poxvirus vector, an adeno-associated virus vector, a retrovirus vector, a self-replicating RNA molecule, and a combination thereof.

5. A method of inducing an immune response in a subject, the method comprising administering a polynucleotide of claim 1 to the subject in need thereof in an amount effective to induce an immune response.

6. The method of claim 5, comprising administering to the subject a vector comprising the polynucleotide.

7. The method of claim 6, wherein the vector is selected from the group consisting of an adenovirus vector, an alphaviral vector, a poxvirus vector, an adeno-associated virus vector, a retrovirus vector, and a self-replicating RNA molecule.

8. The polynucleotide of claim 1 encoding at least one or more polypeptide fragments selected from SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 37, SEQ ID NO: 38, SEQ ID NO: 48, SEQ ID NO: 49, SEQ ID NO: 80, SEQ ID NO: 81; SEQ ID NO: 84, SEQ ID NO: 85, SEQ ID NO: 86, or SEQ ID NO: 88.

9. The polynucleotide of claim 8 encoding at least one or more polypeptide fragments selected from SEQ ID NO: 29 or SEQ ID NO: 32.

10. The method of claim 5, wherein the polynucleotide encodes at least one or more fragments selected from SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 37, SEQ ID NO: 38, SEQ ID NO: 48, SEQ ID NO: 49, SEQ ID NO: 80, SEQ ID NO: 81; SEQ ID NO: 84, SEQ ID NO: 85, SEQ ID NO: 86, or SEQ ID NO: 88.

11. The method of claim 10, wherein the polynucleotide encodes at least one or more polypeptide fragments selected from SEQ ID NO: 29 or SEQ ID NO: 32.

12. A method of treating cancer in a subject, the method comprising administering a polynucleotide of claim 1 to the subject in need thereof in an amount effective to treat the cancer.

13. The method of claim 12, comprising administering to the subject a vector comprising the polynucleotide.

14. The method of claim 13, wherein the vector is selected from the group consisting of an adenovirus vector, an alphaviral vector, a poxvirus vector, an adeno-associated virus vector, a retrovirus vector, and a self-replicating RNA molecule.

* * * * *